United States Patent
Levy et al.

(10) Patent No.: US 7,115,741 B2
(45) Date of Patent: Oct. 3, 2006

(54) 4-THIENO[2,3-D]PYRIMIDIN-4-YL PIPERAZINE COMPOUNDS

(76) Inventors: Daniel E. Levy, 2035 Carmelita Dr., San Carlos, CA (US) 94070; Mark S. Smyth, 860 Pollux Dr., Foster City, CA (US) 94404; Robert M. Scarborough, 22 Greenbrier Ct., Half Moon Bay, CA (US) 94019

( * ) Notice: Subject to any disclaimer, the term of this patent is extended or adjusted under 35 U.S.C. 154(b) by 339 days.

(21) Appl. No.: 10/237,153

(22) Filed: Sep. 6, 2002

(65) Prior Publication Data
US 2003/0153556 A1    Aug. 14, 2003

Related U.S. Application Data

(60) Provisional application No. 60/317,192, filed on Sep. 6, 2001.

(51) Int. Cl.
C07D 495/04    (2006.01)
A61K 31/519    (2006.01)
A61P 7/02      (2006.01)

(52) U.S. Cl. .................. 544/278; 514/252.16
(58) Field of Classification Search ........... 514/252.16; 544/278

See application file for complete search history.

(56) References Cited

U.S. PATENT DOCUMENTS 4,459,296 A    7/1984    Ancher et al.
5,057,517 A    10/1991   Johnston et al.
2003/0225097 A1 *  12/2003  Block et al. ........... 514/252.01

FOREIGN PATENT DOCUMENTS

DE    2200764 A1 *    7/1973
WO    WO 2001/046200 A1 *    6/2001

* cited by examiner

Primary Examiner—Thomas C. McKenzie
(74) Attorney, Agent, or Firm—Townsend and Townsend and Crew LLP

(57) ABSTRACT

Compounds of formula II are provided:

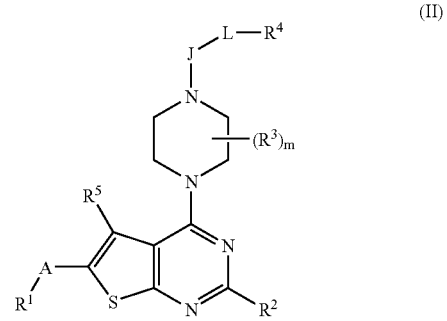

wherein A, J and L are independently a direct link or a divalent linking group. The compounds are useful in the treatment of thrombosis.

19 Claims, No Drawings

4-THIENO[2,3-D]PYRIMIDIN-4-YL PIPERAZINE COMPOUNDS

CROSS-REFERENCES TO RELATED APPLICATIONS

This application claims the benefit of U.S. Provisional Application Ser. No. 60/317,192, filed Sep. 6, 2001, the disclosure of which is incorporated herein by reference.

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK.

Not Applicable

BACKGROUND OF THE INVENTION

The invention relates to novel piperazine and homopiperazine derivatives which are effective platelet ADP receptor inhibitors. These derivatives may be used in various pharmaceutical compositions. In particular, the derivatives may be used in pharmaceutical compositions effective for the prevention and/or treatment of cardiovascular diseases, particularly those diseases related to thrombosis.

Thrombotic complications are a major cause of death in the industrialized world. Examples of these complications include acute myocardial infarction, unstable angina, chronic stable angina, transient ischemic attacks, strokes, peripheral vascular disease, preeclampsia/eclampsia, deep venous thrombosis, embolism, disseminated intravascular coagulation and thrombotic cytopenic purpura. Thrombotic and restenotic complications also occur following invasive procedures, e.g., angioplasty, carotid endarterectomy, post CABG (coronary artery bypass graft) surgery, vascular graft surgery, stent placements and insertion of endovascular devices and protheses. It is generally thought that platelet aggregates play a critical role in these events. Blood platelets, which normally circulate freely in the vasculature, become activated and aggregate to form a thrombus with disturbed blood flow caused by ruptured atherosclerotic lesions or by invasive treatments such as angioplasty, resulting in vascular occlusion. Platelet activation can be initiated by a variety of agents, e.g., exposed subendothelial matrix molecules such as collagen, or by thrombin which is formed in the coagulation cascade.

An important mediator of platelet activation and aggregation is ADP (adenosine 5'-diphosphate) which is released from blood platelets in the vasculature upon activation by various agents, such as collagen and thrombin, and from damaged blood cells, endothelium or tissues. Activation by ADP results in the recruitment of more platelets and stabilization of existing platelet aggregates. Platelet ADP receptors mediating aggregation are activated by ADP and some of its derivatives and antagonized by ATP (adenosine 5'-triphosphate) and some of its derivatives (Mills, D. C. B. (1996) Thromb. Hemost. 76:835–856). Therefore, platelet ADP receptors are members of the family of P2 receptors activated by purine and/or pyrimidine nucleotides (King, B. F., Townsend-Nicholson, A. & Burnstock, G. (1998) Trends Pharmacol. Sci. 19:506–514).

Recent pharmacological data using selective antagonists suggests that ADP-dependent platelet aggregation requires activation of at least two ADP receptors (Kunapuli, S. P. (1998), Trends Pharmacol. Sci. 19:391–394; Kunapuli, S. P. & Daniel, J. L. (1998) Biochem. J. 336:513–523; Jantzen, H. M. et al. (1999) Thromb. Hemost. 81:111–117). One receptor appears to be identical to the cloned P2Y$_1$ receptor, mediates phospholipase C activation and intracellular calcium mobilization and is required for platelet shape change. The second platelet ADP receptor important for aggregation mediates inhibition of adenylyl cyclase. Molecular cloning of the gene or cDNA for this receptor (P2Y$_{12}$) has recently been reported (Hollopeter, G. et. al. (2001) Nature 409: 202–207.) Based on its pharmacological and signaling properties this receptor has been previously termed P2Y$_{ADP}$ (Fredholm, B. B. et al. (1997) TIPS 18:79–82), P2T$_{AC}$ (Kunapuli, S. P. (1998), Trends Pharmacol. Sci. 19:391–394) or P2Ycyc (Hechler, B. et al. (1998) Blood 92, 152–159).

Various directly or indirectly acting synthetic inhibitors of ADP-dependent platelet aggregation with antithrombotic activity have been reported. The orally active antithrombotic thienopyridines ticlopidine and clopidogrel inhibit ADP-induced platelet aggregation, binding of radiolabeled ADP receptor agonist 2-methylthioadenosine 5'-diphosphate to platelets, and other ADP-dependent events indirectly, probably via formation of an unstable and irreversible acting metabolite (Quinn, M. J. & Fitzgerald, D. J. (1999) Circulation 100:1667–1667). Some purine derivatives of the endogenous antagonist ATP, e.g., AR-C (formerly FPL or ARL) 67085MX and AR-C69931MX, are selective platelet ADP receptor antagonists which inhibit ADP-dependent platelet aggregation and are effective in animal thrombosis models (Humphries et al. (1995), Trends Pharmacol. Sci. 16, 179; Ingall, A. H. et al. (1999) J. Med. Chem. 42, 213–230). Novel triazolo [4,5-d] pyrimidine compounds have been disclosed as P$_{2T}$-antagonists (WO 99/05144). Tricyclic compounds as platelet ADP receptor inhibitors have been disclosed in WO 99/36425. More recently, sulfonylureas and related compounds have also been disclosed as specific ADP receptor inhibitors in WO 01/57037. The target of these antithrombotic compounds appears to be the platelet ADP receptor mediating inhibition of adenylyl cyclase.

Despite these compounds, there exists a need for more effective platelet ADP receptor inhibitors. In particular, there is a need for platelet ADP receptor inhibitors having antithrombotic activity that are useful in the prevention and/or treatment of cardiovascular diseases, particularly those related to thrombosis.

BRIEF SUMMARY OF THE INVENTION

In one aspect, the present invention provides compounds of formula I:

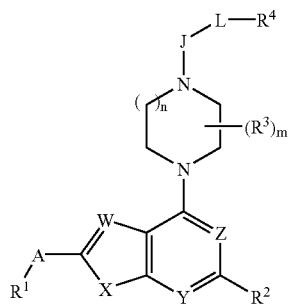

(I)

wherein the subscript n is 1 or 2; the subscript m is an integer of from 0 to 4; W is selected from N and C—$R^5$; X is selected from S, O and N—$R^6$; Y is selected from N and C—$R^7$; Z is selected from N and C—$R^8$; wherein each of $R^5$, $R^6$, $R^7$ and $R^8$ is independently selected from H, $(C_1$–$C_6)$ alkyl, $(C_3$–$C_7)$cycloalkyl and —$(CH_2)_{n1}$—$R^{11}$ wherein the subscript n1 is an integer of from 0 to 3 and $R^{11}$ is selected from $(C_1$–$C_6)$alkoxy, $(C_1$–$C_6)$alkylthio, mono- or di-$(C_1$–$C_6)$alkylamino, amino, phenyl, pyridyl, furanyl, pyrrolyl, imidazolyl, oxazolyl, isoxazolyl, triazolyl, tetrazolyl, thiazolyl, pyrazolyl, and thienyl, wherein each of the rings is optionally substituted with from 1 to 3 substituents selected from halogen, $N_3$, $NO_2$, CN, $(C_1$–$C_6)$alkyl, $OR^{12}$, $N(R^{12})_2$, $CO_2R^{12}$ and $CON(R^{12})_2$, wherein each $R^{12}$ is independently H or $(C_1$–$C_6)$alkyl.

Returning to formula I, the letter J represents a direct link, C(O), C(S), C($NR^9$), S(O) or $S(O)_2$, wherein $R^9$ is selected from H, CN, $NO_2$ and $(C_1$–$C_6)$alkyl; and the letter A represents a direct link, O, S, N—$R^{10}$, C(O) and CH(OH), wherein $R^{10}$ is selected from H, $(C_1$–$C_6)$alkyl and C(O)—$(C_1$–$C_6)$alkyl.

The symbol $R^1$ represents H, halo, CN, $NO_2$, $N_3$, $(C_1$–$C_6)$ alkyl, $(C_3$–$C_7)$cycloalkyl, —C($R^{13}$)=C($R^{13})_2$, —C≡C$R^{13}$ or —$(CH_2)_{n2}$—$R^{14}$; wherein each $R^{13}$ is independently selected from H, F, Cl, Br, CN, $(C_1$–$C_6)$alkyl, $(C_3$–$C_7)$ cycloalkyl, $(CH_2)_{n2}$—$R^{14}$ and C(O)—$(CH_2)_{n2}$—$R^{14}$; and wherein each subscript n2 is independently an integer of from 0 to 3 and each $R^{14}$ is independently selected from $(C_1$–$C_6)$alkoxy, $(C_1$–$C_6)$alkylthio, mono- or di-$(C_1$–$C_6)$alkylamino, amino, phenyl, pyridyl, furanyl, pyrrolyl, imidazolyl, oxazolyl, isoxazolyl, triazolyl, tetrazolyl, thiazolyl, pyrazolyl, and thienyl, wherein each of the rings is optionally substituted with from 1 to 3 substituents selected from halogen, $NO_2$, $N_3$, CN, $(C_1$–$C_6)$alkyl, $OR^5$, $N(R^5)_2$, $CO_2R^{15}$ and $CON(R^5)_2$, wherein each $R^{15}$ is independently H or $(C_1$–$C_6)$alkyl; and wherein any alkyl or cycloalkyl portions of $R^1$ are optionally substituted with from one to five F substituents.

The symbol $R^2$ represents H, halo, CN, $NO_2$, $N_3$, $(C_1$–$C_6)$ alkyl, $(C_3$–$C_7)$cycloalkyl, —C($R^{16}$)=C($R^{16})_2$, —C≡C$R^{16}$, —C(O)—$(CH^2)_{n3}$—$R^{17}$ or —$(CH_2)_{n3}$—$R^{17}$; wherein each $R^{16}$ is independently selected from H, F, Cl, Br, CN, $(C_1$–$C_6)$ alkyl, —$(CH_2)_{n3}$—$R^{17}$ and —$(CH_2)_{n3}$—C(O)—$R^{17}$; wherein each subscript n3 is independently an integer of from 0 to 3 and each $R^{17}$ is independently selected from $(C_1$–$C_6)$alkoxy, $(C_1$–$C_6)$alkylthio, mono- or di-$(C_1$–$C_6)$alkylamino, amino, hydroxy, phenyl, pyridyl, furanyl, pyrrolyl, imidazolyl, oxazolyl, isoxazolyl, triazolyl, tetrazolyl, thiazolyl, pyrazolyl, and thienyl, wherein each of the rings is optionally substituted with from 1 to 3 substituents selected from halogen, $N_3$, $NO_2$, CN, $(C_1$–$C_6)$alkyl, $OR^{18}$, $N(R^{18})_2$, $CO_2R^{18}$ and $CON(R^{18})_2$, wherein each $R^{18}$ is independently H or $(C_1$–$C_6)$alkyl; and wherein any alkyl or cycloalkyl portions of $R^2$ are optionally substituted with from one to five F substituents.

The symbol $R^3$, in each instance, represents a substituent independently selected from $(C_1$–$C_6)$alkyl, $(C_3$–$C_7)$cycloalkyl, —$(CH_2)_{n4}$—$R^{19}$ and —C(O)—$(CH_2)_{n4}$—$R^{19}$; wherein the subscript n4 is an integer of from 0 to 4 and each $R^{19}$ is independently selected from $(C_1$–$C_6)$alkoxy, $(C_1$–$C_6)$ alkylthio, mono- or di-$(C_1$–$C_6)$alkylamino, amino, phenyl, pyridyl, furanyl, pyrrolyl, imidazolyl, oxazolyl, isoxazolyl, triazolyl, tetrazolyl, thiazolyl, pyrazolyl, and thienyl, wherein each of the rings is optionally substituted with from 1 to 3 substituents selected from halogen, $N_3$, $NO_2$, CN, $(C_1$–$C_6)$alkyl, $OR^{20}$, $N(R^{20})_2$, $CO_2R^{20}$ and $CON(R^{20})_2$, wherein each $R^{20}$ is independently H or $(C_1$–$C_6)$alkyl; and wherein any alkyl or cycloalkyl portions of $R^3$ are optionally substituted with from one to five F substituents.

The letter L represents a direct link, or a divalent linking group having a formula selected from:

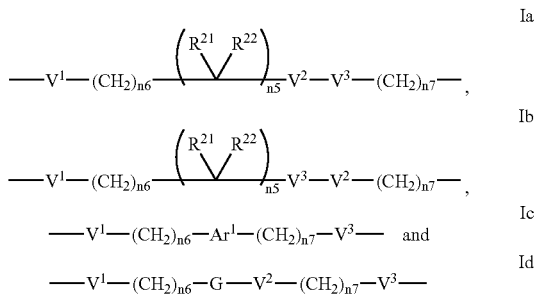

wherein the symbol $V^1$ represents a member selected from a direct link, O, S and $NR^{23}$; the symbol $V^2$ represents a member selected from a direct link, —$(CR^{24}$=$CR^{24})_{n8}$—, —(C≡C)$_{n8}$—, C(O), C(S), S(O), $S(O)_2$ and C($NR^{23}$); the symbol $V^3$ represents a member selected from a direct link, O, S and $NR^{23}$; the subscript n5 is an integer of from 0 to 2; the subscripts n6 and n7 are each independently an integer of from 0 to 7; the subscript n8 is an integer of from 1 to 2; each $R^{23}$ is independently selected from H and $(C_1$–$C_6)$ alkyl; each $R^{24}$ is independently selected from $(C_1$–$C_6)$alkyl, $(C_3$–$C_7)$ cycloalkyl, $(CH_2)_{n9}$—$R^{25}$ and —(CO)—$(CH^2)_{n9}$—$R^{25}$ wherein the subscript n9 is an integer of from 0 to 3 and $R^{25}$ is selected from $(C_1$–$C_6)$alkoxy, $(C_1$–$C_6)$alkylthio, mono- or di-$(C_1$–$C_6)$alkylamino, hydroxy, $NH_2$, phenyl, pyridyl, furanyl, pyrrolyl, imidazolyl, oxazolyl, isoxazolyl, triazolyl, tetrazolyl, thiazolyl, pyrazolyl, and thienyl, wherein each of the rings is optionally substituted with from 1 to 3 substituents selected from halogen, $N_3$, $NO_2$, CN, $(C_1$–$C_6)$alkyl, $OR^{26}$, $N(R^{26})_2$, $CO_2R^{26}$ and $CON(R^{26})_2$, wherein each $R^{26}$ is independently H or $(C_1$–$C_6)$alkyl; the symbol $Ar^1$ is a 5- or 6-membered heteroaryl or phenyl group, optionally substituted with from one to three substituents independently selected from halogen, $NO_2$, $N_3$, CN, $(C_1$–$C_6)$alkyl, $OR^{27}$, $N(R^{27})_2$, $CO_2R^{27}$ and $CON(R^{27})_2$, wherein each $R^{27}$ is independently H or $(C_1$–$C_6)$alkyl; the letter G represents a $(C_3$–$C_7)$heterocycloalkyl or $(C_3$–$C_7)$ cycloalkyl group, optionally substituted with from one to three substituents independently selected from halogen, =O, $N_3$, $NO_2$, CN, $(C_1$–$C_6)$alkyl, $OR^{28}$, $N(R^{28})_2$, $CO_2R^{28}$ and $CON(R^{28})_2$, wherein each $R^{28}$ is independently H or $(C_1$–$C_6)$alkyl; each $R^{21}$ and $R^{22}$ is (i) independently selected from H, $(C_1$–$C_6)$alkyl, phenyl, pyridyl, furanyl, pyrrolyl, imidazolyl, oxazolyl, isoxazolyl, triazolyl, tetrazolyl, thiazolyl, pyrazolyl, and thienyl, wherein each of the rings is optionally substituted with from 1 to 3 substituents selected from halogen, $N_3$, $NO_2$, CN, $(C_1–C_6)$alkyl, $OR^{29}$, $N(R^{29})_2$, $CO_2R^{29}$ and $CON(R^{29})_2$, wherein each $R^{29}$ is independently H or $(C_1–C_6)$alkyl; or (ii) combined to form —$CH_2$—$(CH_2)_{n10}$—$CH_2$—; wherein the subscript n10 is an integer of from 0 to 4.

Returning to formula I, the symbol $R^4$ represents a member selected from H, F, $CF_3$, CN, $N_3$, $NO_2$, $(C_1–C_6)$alkyl, amino, mono- or di-$(C_1–C_6)$alkylamino, $(C_3–C_7)$cycloalkyl, $(C_3–C_7)$heterocycloalkyl, heteroaryl, fused $(C_8–C_{10})$bicycloalkyl, fused $(C_8–C_{10})$bicycloalkaryl, aryl and fused bicycloaryl; wherein any alkyl group present in $R^4$ is unsubstituted, partially- or fully-substituted with F, and each of the rings is optionally substituted with from one to four substituents selected from halogen, $NO_2$, $N_3$, $SO_2NH_2$, CN, $(C_1–C_6)$alkyl, $OR^{30}$, $N(R^{30})_2$, $CO_2R^{30}$ and $CON(R^{30})_2$, wherein each $R^{30}$ is independently H or $(C_1–C_6)$alkyl.

In addition to the compounds recited above, the present invention is directed to all pharmaceutically acceptable salts or prodrugs of the noted compounds.

BRIEF DESCRIPTION OF THE DRAWINGS

Not applicable.

DETAILED DESCRIPTION OF THE INVENTION

Definitions

In accordance with the present invention and as used herein, the following terms are defined with the following meanings, unless explicitly stated otherwise.

The term "alkenyl" refers to a trivalent straight chain or branched chain unsaturated aliphatic radical. The term "alkynyl" refers to a straight or branched chain aliphatic radical that includes at least two carbons joined by a triple bond. If no number of carbons is specified alkenyl and alkynyl each refer to radicals having from 2–12 carbon atoms.

The term "alkyl" refers to saturated aliphatic groups including straight-chain, branched-chain and cyclic groups having the number of carbon atoms specified, or if no number is specified, having up to 12 carbon atoms. The term "cycloalkyl" as used herein refers to a mono-, bi-, or tricyclic aliphatic ring having 3 to 14 carbon atoms and preferably 3 to 7 carbon atoms.

The term "$C_1–C_6$ alkoxy" as used herein refers to an ether moiety whereby the oxygen is connected to a straight or branched chain of carbon atoms of the number indicated.

The term "mono-$C_1–C_6$ alkylamino" as used herein refers to an amino moiety whereby the nitrogen is substituted with one H and one $C_1–C_6$ alkyl substituent, the latter being defined as above.

The term "di-$C_1–C_6$ alkylamino" as used herein refers to an amino moiety whereby the nitrogen is substituted with two $C_1–C_6$ alkyl substituents as defined above.

The term "monoarylamino" as used herein refers to an amino moiety whereby the nitrogen is substituted with one H and one aryl substituent, such as a phenyl, the latter being defined as above.

The term "diarylamino" as used herein refers to an amino moiety whereby the nitrogen is substituted with two aryl substituents, such as phenyl, the latter being defined as above.

The term "$C_1–C_6$ alkylsulfonyl" as used herein refers to a dioxosulfur moiety with the sulfur atom also connected to one $C_1–C_6$ alkyl substituent, the latter being defined as above.

The term "$C_1–C_6$ alkoxycarbonyl" as used herein refers to a hydroxycarbonyl moiety whereby the hydrogen is replaced by a $C_1–C_6$ alkyl substituent, the latter being defined as above.

As used herein, the terms "carbocyclic ring structure" and "$C_{3-16}$ carbocyclic mono, bicyclic or tricyclic ring structure" or the like are each intended to mean stable ring structures having only carbon atoms as ring atoms wherein the ring structure is a substituted or unsubstituted member selected from the group consisting of: a stable monocyclic ring which is aromatic ring ("aryl") having six ring atoms ("phenyl"); a stable monocyclic non-aromatic ring having from 3 to 7 ring atoms in the ring; a stable bicyclic ring structure having a total of from 7 to 12 ring atoms in the two rings wherein the bicyclic ring structure is selected from the group consisting of ring structures in which both of the rings are aromatic, ring structures in which one of the rings is aromatic and ring structures in which both of the rings are non-aromatic; and a stable tricyclic ring structure having a total of from 10 to 16 atoms in the three rings wherein the tricyclic ring structure is selected from the group consisting of: ring structures in which three of the rings are aromatic, ring structures in which two of the rings are aromatic and ring structures in which three of the rings are non-aromatic. In each case, the non-aromatic rings when present in the monocyclic, bicyclic or tricyclic ring structure may independently be saturated, partially saturated or fully saturated. Examples of such carbocyclic ring structures include, but are not limited to, cyclopropyl, cyclobutyl, cyclopentyl, cyclohexyl, adamantyl, cyclooctyl, [3.3.0]bicyclooctane, [4.3.0]bicyclononane, [4.4.0]bicyclodecane (decalin), 2.2.2]bicyclooctane, fluorenyl, phenyl, naphthyl, indanyl, adamantyl, or tetrahydronaphthyl (tetralin). Moreover, the ring structures described herein may be attached to one or more indicated pendant groups via any carbon atom which results in a stable structure. The term "substituted" as used in conjunction with carbocyclic ring structures means that hydrogen atoms attached to the ring carbon atoms of ring structures described herein may be substituted by one or more of the substituents indicated for that structure if such substitution(s) would result in a stable compound.

The term "aryl" which is included with the term "carbocyclic ring structure" refers to an unsubstituted or substituted aromatic ring, substituted with one, two or three substituents selected from loweralkoxy, loweralkyl, loweralkylamino, hydroxy, halogen, cyano, hydroxyl, mercapto, nitro, thioalkoxy, carboxaldehyde, carboxyl, carboalkoxy and carboxamide, including but not limited to carbocyclic aryl, heterocyclic aryl, and biaryl groups and the like, all of which may be optionally substituted. Preferred aryl groups include phenyl, halophenyl, loweralkylphenyl, naphthyl, biphenyl, phenanthrenyl and naphthacenyl.

The term "arylalkyl" which is included with the term "carbocyclic aryl" refers to one, two, or three aryl groups having the number of carbon atoms designated, appended to an alkyl group having the number of carbon atoms designated. Suitable arylalkyl groups include, but are not limited to, benzyl, picolyl, naphthylmethyl, phenethyl, benzhydryl, trityl, and the like, all of which may be optionally substituted.

The term "phenyl" as used herein refers to a six carbon containing aromatic ring which can be variously mono- or poly-substituted with H, $C_1–C_6$ alkyl, hydroxyl, $C_1–C_6$ alkoxy, amino, mono-$C_1$–$C_6$ alkylamino, di-$C_1$–$C_6$ alkylamino, nitro, fluoro, chloro, bromo, iodo, hydroxycarbonyl, or $C_1$–$C_6$ alkoxycarbonyl.

As used herein, the term "heterocyclic ring" or "heterocyclic ring system" is intended to mean a substituted or unsubstituted member selected from the group consisting of stable monocyclic ring having from 3–7 members in the ring itself and having from 1 to 4 hetero ring atoms selected from the group consisting of N, O and S; a stable bicyclic ring structure having a total of from 7 to 12 atoms in the two rings wherein at least one of the two rings has from 1 to 4 hetero atoms selected from N, O and S, including bicyclic ring structures wherein any of the described stable monocyclic heterocyclic rings is fused to a hexane or benzene ring; and a stable tricyclic heterocyclic ring structure having a total of from 10 to 16 atoms in the three rings wherein at least one of the three rings has from 1 to 4 hetero atoms selected from the group consisting of N, O and S. Any nitrogen and sulfur atoms present in a heterocyclic ring of such a heterocyclic ring structure may be oxidized. Unless indicated otherwise the terms "heterocyclic ring" or "heterocyclic ring system" include aromatic rings, as well as non-aromatic rings which can be saturated, partially saturated or fully saturated non-aromatic rings. Also, unless indicated otherwise the "heterocyclic ring system" includes ring structures wherein all of the rings contain at least one hetero atom as well as structures having less than all of the rings in the ring structure containing at least one hetero atom, for example bicyclic ring structures wherein one ring is a benzene ring and one of the rings has one or more hetero atoms are included within the term "heterocyclic ring systems" as well as bicyclic ring structures wherein each of the two rings has at least one hetero atom. Moreover, the ring structures described herein may be attached to one or more indicated pendant groups via any hetero atom or carbon atom which results in a stable structure. Further, the term "substituted" means that one or more of the hydrogen atoms on the ring carbon atom(s) or nitrogen atom(s) of each of the rings in the ring structures described herein may be replaced by one or more of the indicated substituents if such replacement(s) would result in a stable compound. Nitrogen atoms in a ring structure may be quaternized, but such compounds are specifically indicated or are included within the term "a pharmaceutically acceptable salt" for a particular compound. When the total number of O and S atoms in a single heterocyclic ring is greater than 1, it is preferred that such atoms not be adjacent to one another. Preferably, there are no more than 1 O or S ring atoms in the same ring of a given heterocyclic ring structure.

Examples of monocylic and bicyclic heterocyclic ring systems, in alphabetical order, are acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pryidooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl. Preferred heterocyclic ring structures include, but are not limited to, pyridinyl, furanyl, thienyl, pyrrolyl, pyrazolyl, pyrrolidinyl, imidazolyl, indolyl, benzimidazolyl, 1H-indazolyl, oxazolinyl, or isatinoyl. Also included are fused ring and spiro compounds containing, for example, the above heterocyclic ring structures.

As used herein the term "aromatic heterocyclic ring system" has essentially the same definition as for the monocyclic and bicyclic ring systems except that at least one ring of the ring system is an aromatic heterocyclic ring or the bicyclic ring has an aromatic or non-aromatic heterocyclic ring fused to an aromatic carbocyclic ring structure.

The terms "halo" or "halogen" as used herein refer to Cl, Br, F or I substituents. The term "haloalkyl", and the like, refer to an aliphatic carbon radicals having at least one hydrogen atom replaced by a Cl, Br, F or I atom, including mixtures of different halo atoms. Trihaloalkyl includes trifluoromethyl and the like as preferred radicals, for example.

The term "methylene" refers to —$CH_2$—.

The term "($C_3$–$C_7$)heterocycloalkyl" refers to a 3–7 membered ring system containing 1–3 heteroatoms independently selected from N, O and S. Heterocycloalkyl groups may be selected from but not limited to the list containing aziridinyl, oxiranyl, oxetanyl, azetidinyl, pyrrolidinyl, tetrahydrofuranyl, isoxazolidinyl, piperidinyl, pyranyl, morpholinyl, thiomorpholinyl, piperazinyl, homopiperazinyl. Attachment points to the heterocycloalkyl groups are defined as any carbon or nitrogen atom in the ring system that contains a hydrogen atom when the heterocycloalkyl group is not attached. Up to 3 heterocycloalkyl ring hydrogens residing on carbon or nitrogen atoms may be independently substituted with groups selected from F, Cl, Br, benzyl, phenyl, pyridyl, pyrimidyl, pyrazinyl, triazyl, furyl, thienyl, pyrrolyl, thiazolyl, oxazolyl, imidazolyl, isoxazolyl, pyrazolyl, 1,2,3-triazolyl, 1,2,4-triazolyl, thiadiazolyl, tetrazolyl, benzyl, —O-phenyl, —S-phenyl, morpholino, thiomorpholino, CN, $NO_2$, branched or unbranched $C_1$–$C_6$ alkyl, $C_1$–$C_6$ alkoxy, $C_1$–$C_6$ alkylthio, and mono- or di-$C_1$–$C_6$ alkyl amino, where each carbon may be unsubstituted or partially substuted or fully substituted with F, or $C_3$–$C_7$ cycloalkyl where each carbon may be unsubstituted or partially substituted or fully substituted with F.

The term "bicycloalkaryl" ring refers to a 8–10 membered bicyclic ring system containing 1 aromatic ring fused to 1 non-aromatic ring collectively containing 0–5 heteroatoms independently selected from N, O and S. Bicycloalkaryl groups may be selected from, but not limited to, tetrahydronaphthyl, tetrahydroquinolyl, tetrahydroisoquinolyl, tetrahydroquinazolinyl, tetrahydrocinnolyl, tetrahydrophthalazyl, tetrahydroquinoxalyl, tetrahydroindolyl, tetrahydrothianaphthenyl, tetrahydrobenzofuranyl, tetrahydroazaindolyl, tetrahydroindazolyl, tetrahydrobenzimidazolyl, tetrahydroanthranilyl, tetrahydrobenzisoxazolyl, tetrahydrobenzoxazolyl, tetrahydrobenzothiazolyl, tetrahydroazabenzimidazolyl, tetrahydrobenzotriazolyl, indolinyl, isoindolinyl, phthalanyl, dihydrobenzofuranyl and piperonyl. Attachment points to the bicycloalkaryl groups are defined as any carbon or nitrogen atom in the ring system that contains a hydrogen atom when the bicycloalkaryl group is not attached. Up to 5 bicycloalkaryl ring hydrogens residing on carbon or nitrogen atoms may be independently substituted with groups selected from those described above with reference to the heterocycloalkyl groups.

The term "aryl" refers to a 5–6 membered ring containing 0–4 heteroatoms independently selected from N, O and S. Aryl groups may be selected from, but not limited to, phenyl, pyridyl, pyrimidyl, pyrazinyl, triazyl, furyl, thienyl, pyrrolyl, thiazolyl, oxazolyl, imidazolyl, isoxazolyl, pyrazolyl, 1,2,3-triazolyl, 1,2,4-triazolyl, thiadiazolyl and tetrazolyl. Attachment points to the aryl groups are defined as any carbon or nitrogen atom in the ring system that contains a hydrogen atom when the aryl group is not attached. Up to 3 aryl ring hydrogens residing on carbon or nitrogen atoms may be independently substituted with groups selected from those described above with reference to the heterocycloalkyl groups.

The term "bicycloaryl" refers to an 8–10 membered bicyclic ring system having two fused aromatic rings collectively containing 0–5 heteroatoms independently selected from N, O and S. Bicycloaryl groups can be selected from, but not limited to, naphthyl, quinolyl, isoquinolyl, quinazolyl, cinnolyl, phthalazyl, quinoxalyl, indolyl, thianaphthenyl, benzofuranyl, azaindolyl, indazolyl, benzimidazolyl, anthranilyl, benzisoxazolyl, benzoxazolyl, benzothiazolyl, azabenzimidazolyl, benzotriazolyl, purinyl, pyrazolopyrimidinyl, triazolopyrimidinyl. Attachment points to the bicycloaryl groups are defined as any carbon or nitrogen atom in the ring system that contains a hydrogen atom when the bicycloaryl group is not attached. Up to 5 aryl ring hydrogens residing on carbon or nitrogen atoms may be independently substituted with groups selected from those provided with reference to heterocycloalkyl groups, above.

The term "pharmaceutically acceptable salts" includes salts of compounds derived from the combination of a compound and an organic or inorganic acid. These compounds are useful in both free base and salt form. In practice, the use of the salt form amounts to use of the base form; both acid and base addition salts are within the scope of the present invention.

"Pharmaceutically acceptable acid addition salt" refers to salts retaining the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly preferred organic nontoxic bases are isopropylamine, diethylamine, ethanolamine, trimethamine, dicyclohexylamine, choline, and caffeine.

"Biological property" for the purposes herein means an in vivo effector or antigenic function or activity that is directly or indirectly performed by a compound of this invention that are often shown by in vitro assays. Effector functions include receptor or ligand binding, any enzyme activity or enzyme modulatory activity, any carrier binding activity, any hormonal activity, any activity in promoting or inhibiting adhesion of cells to an extracellular matrix or cell surface molecules, or any structural role. Antigenic functions include possession of an epitope or antigenic site that is capable of reacting with antibodies raised against it.

In the compounds of this invention, carbon atoms bonded to four non-identical substituents are asymmetric. Accordingly, the compounds may exist as diastereoisomers, enantiomers or mixtures thereof. The syntheses described herein may employ racemates, enantiomers or diastereomers as starting materials or intermediates. Diastereomeric products resulting from such syntheses may be separated by chromatographic or crystallization methods, or by other methods known in the art. Likewise, enantiomeric product mixtures may be separated using the same techniques or by other methods known in the art. Each of the asymmetric carbon atoms, when present in the compounds of this invention, may be in one of two configurations (R or S) and both are within the scope of the present invention.

Embodiments of the Invention

Compounds

In one aspect, the present invention provides compounds of formula I:

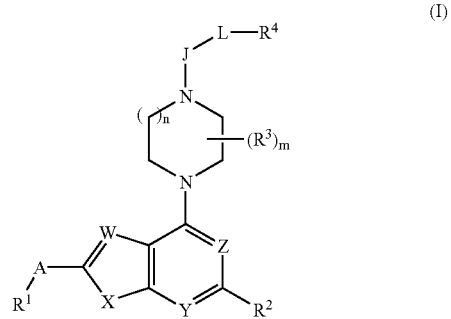

(I)

wherein the subscript n is 1 or 2; the subscript m is an integer of from 0 to 4; W is selected from N and C—$R^5$; X is selected from S, O and N—$R^6$; Y is selected from N and C—$R^7$; Z is selected from N and C—$R^8$; wherein each of $R^5$, $R^6$, $R^7$ and $R^8$ is independently selected from H, ($C_1$–$C_6$) alkyl, ($C_3$–$C_7$)cycloalkyl and —$(CH_2)_{n1}$—$R^{11}$ wherein the subscript n1 is an integer of from 0 to 3 and $R^{11}$ is selected from ($C_1$–$C_6$)alkoxy, ($C_1$–$C_6$)alkylthio, mono- or di-($C_1$–$C_6$)alkylamino, amino, phenyl, pyridyl, furanyl, pyrrolyl, imidazolyl, oxazolyl, isoxazolyl, triazolyl, tetrazolyl, thiazolyl, pyrazolyl, and thienyl, wherein each of the rings is optionally substituted with from 1 to 3 substituents selected from halogen, $N_3$, $NO_2$, CN, ($C_1$–$C_6$)alkyl, $OR^{12}$, $N(R^{12})_2$, $CO_2R^{12}$ and $CON(R^{12})_2$, wherein each $R^{12}$ is independently H or ($C_1$–$C_6$)alkyl.

Returning to formula I, the letter J represents a direct link, C(O), C(S), C(NR$^9$), S(O) or S(O)$_2$, wherein R$^9$ is selected from H, CN, NO$_2$ and (C$_1$–C$_6$)alkyl; and the letter A represents a direct link, O, S, N—R$^{10}$, C(O) and CH(OH), wherein R$^{10}$ is selected from H, (C$_1$–C$_6$)alkyl and C(O)— (C$_1$–C$_6$)alkyl.

The symbol R$^1$ represents H, halo, CN, NO$_2$, N$_3$, (C$_1$–C$_6$)alkyl, (C$_3$–C$_7$)cycloalkyl, —C(R$^{13}$)═C(R$^{13}$)$_2$, —C≡CR$^{13}$ or —(CH$_2$)$_{n2}$—R$^{14}$; wherein each R$^{13}$ is independently selected from H, F, Cl, Br, CN, (C$_1$–C$_6$)alkyl, (C$_3$–C$_7$)cycloalkyl, (CH$_2$)$_{n2}$—R$^{14}$ and C(O)—(CH$_2$)$_{n2}$—R$^{14}$; and wherein each subscript n2 is independently an integer of from 0 to 3 and each R$^{14}$ is independently selected from (C$_1$–C$_6$)alkoxy, (C$_1$–C$_6$)alkylthio, mono- or di-(C$_1$–C$_6$)alkylamino, amino, phenyl, pyridyl, furanyl, pyrrolyl, imidazolyl, oxazolyl, isoxazolyl, triazolyl, tetrazolyl, thiazolyl, pyrazolyl, and thienyl, wherein each of the rings is optionally substituted with from 1 to 3 substituents selected from halogen, NO$_2$, N$_3$, CN, (C$_1$–C$_6$)alkyl, OR$^{15}$, N(R$^{15}$)$_2$, CO$_2$R$^{15}$ and CON(R$^{15}$)$_2$, wherein each R$^{15}$ is independently H or (C$_1$–C$_6$)alkyl; and wherein any alkyl or cycloalkyl portions of R$^1$ are optionally substituted with from one to five F substituents.

The symbol R$^2$ represents H, halo, CN, NO$_2$, N$_3$, (C$_1$–C$_6$)alkyl, (C$_3$–C$_7$)cycloalkyl, —C(R$^{16}$)═C(R$^{16}$)$_2$, —C≡CR$^{16}$, —C(O)—(CH$_2$)$_{n3}$—R$^{17}$ or —(CH$_2$)$_{n3}$—R$^{17}$; wherein each R$^{16}$ is independently selected from H, F, Cl, Br, CN, (C$_1$–C$_6$)alkyl, —(CH$_2$)$_{n3}$—R$^{17}$ and —(CH$_2$)$_{n3}$—C(O)—R$^{17}$; wherein each subscript n3 is independently an integer of from 0 to 3 and each R$^{17}$ is independently selected from (C$_1$–C$_6$)alkoxy, (C$_1$–C$_6$)alkylthio, mono- or di-(C$_1$–C$_6$)alkylamino, amino, hydroxy, phenyl, pyridyl, furanyl, pyrrolyl, imidazolyl, oxazolyl, isoxazolyl, triazolyl, tetrazolyl, thiazolyl, pyrazolyl, and thienyl, wherein each of the rings is optionally substituted with from 1 to 3 substituents selected from halogen, N$_3$, NO$_2$, CN, (C$_1$–C$_6$)alkyl, OR$^{18}$, N(R$^{18}$)$_2$, CO$_2$R$^{18}$ and CON(R$^{18}$)$_2$, wherein each R$^{18}$ is independently H or (C$_1$–C$_6$)alkyl; and wherein any alkyl or cycloalkyl portions of R$^2$ are optionally substituted with from one to five F substituents.

The symbol R$^3$, in each instance, represents a substituent independently selected from (C$_1$–C$_6$)alkyl, (C$_3$–C$_7$)cycloalkyl, —(CH$_2$)$_{n4}$—R$^{19}$ and —C(O)—(CH$_2$)$_{n4}$—R$^{19}$; wherein the subscript n4 is an integer of from 0 to 4 and each R$^{19}$ is independently selected from (C$_1$–C$_6$)alkoxy, (C$_1$–C$_6$)alkylthio, mono- or di-(C$_1$–C$_6$)alkylamino, amino, phenyl, pyridyl, furanyl, pyrrolyl, imidazolyl, oxazolyl, isoxazolyl, triazolyl, tetrazolyl, thiazolyl, pyrazolyl, and thienyl, wherein each of the rings is optionally substituted with from 1 to 3 substituents selected from halogen, N$_3$, NO$_2$, CN, (C$_1$–C$_6$)alkyl, OR$^{20}$, N(R$^{20}$)$_2$, CO$_2$R$^{20}$ and CON(R$^{20}$)$_2$, wherein each R$^{20}$ is independently H or (C$_1$–C$_6$)alkyl; and wherein any alkyl or cycloalkyl portions of R$^3$ are optionally substituted with from one to five F substituents.

The letter L represents a direct link, or a divalent linking group having a formula selected from:

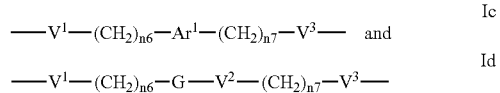

Ia

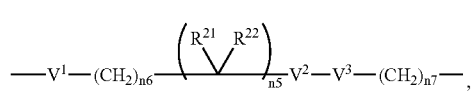

Ib

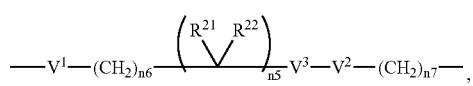

-continued

—V$^1$—(CH$_2$)$_{n6}$—Ar$^1$—(CH$_2$)$_{n7}$—V$^3$— and

Ic

—V$^1$—(CH$_2$)$_{n6}$—G—V$^2$—(CH$_2$)$_{n7}$—V$^3$—

Id wherein the symbol V$^1$ represents a member selected from a direct link, O, S and NR$^{23}$; the symbol V$^2$ represents a member selected from a direct link, —(CR$^{24}$═CR$^{24}$)$_{n8}$—, —(C≡C)$_{n8}$—, C(O), C(S), S(O), S(O)$_2$ and C(NR$^{23}$); the symbol V$^3$ represents a member selected from a direct link, O, S and NR$^{23}$; the subscript n5 is an integer of from 0 to 2; the subscripts n6 and n7 are each independently an integer of from 0 to 7; the subscript n8 is an integer of from 1 to 2; each R$^{23}$ is independently selected from H and (C$_1$–C$_6$)alkyl; each R$^{24}$ is independently selected from (C$_1$–C$_6$)alkyl, (C$_3$–C$_7$) cycloalkyl, (CH$_2$)$_{n9}$—R$^{25}$ and —(CO)—(CH$_2$)$_{n9}$—R$^{25}$ wherein the subscript n9 is an integer of from 0 to 3 and R$^{25}$ is selected from (C$_1$–C$_6$)alkoxy, (C$_1$–C$_6$)alkylthio, mono- or di-(C$_1$–C$_6$)alkylamino, hydroxy, NH$_2$, phenyl, pyridyl, furanyl, pyrrolyl, imidazolyl, oxazolyl, isoxazolyl, triazolyl, tetrazolyl, thiazolyl, pyrazolyl, and thienyl, wherein each of the rings is optionally substituted with from 1 to 3 substituents selected from halogen, N$_3$, NO$_2$, CN, (C$_1$–C$_6$)alkyl, OR$^{26}$, N(R$^{26}$)$_2$, CO$_2$R$^{26}$ and CON(R$^{26}$)$_2$, wherein each R$^{26}$ is independently H or (C$_1$–C$_6$)alkyl; the symbol Ar$^1$ is a 5- or 6-membered heteroaryl or phenyl group, optionally substituted with from one to three substituents independently selected from halogen, NO$_2$, N$_3$, CN, (C$_1$–C$_6$)alkyl, OR$^{27}$, N(R$^{27}$)$_2$, CO$_2$R$^{27}$ and CON(R$^{27}$)$_2$, wherein each R$^{27}$ is independently H or (C$_1$–C$_6$)alkyl; the letter G represents a (C$_3$–C$_7$)heterocycloalkyl or (C$_3$–C$_7$) cycloalkyl group, optionally substituted with from one to three substituents independently selected from halogen, ═O, N$_3$, NO$_2$, CN, (C$_1$–C$_6$)alkyl, OR$^{28}$, N(R$^{28}$)$_2$, CO$_2$R$^{28}$ and CON(R$^{28}$)$_2$, wherein each R$^{28}$ is independently H or (C$_1$–C$_6$)alkyl; each R$^{21}$ and R$^{22}$ is (i) independently selected from H, (C$_1$–C$_6$)alkyl, phenyl, pyridyl, furanyl, pyrrolyl, imidazolyl, oxazolyl, isoxazolyl, triazolyl, tetrazolyl, thiazolyl, pyrazolyl, and thienyl, wherein each of the rings is optionally substituted with from 1 to 3 substituents selected from halogen, N$_3$, NO$_2$, CN, (C$_1$–C$_6$)alkyl, OR$^{29}$, N(R$^{29}$)$_2$, CO$_2$R$^{29}$ and CON(R$^{29}$)$_2$, wherein each R$^{29}$ is independently H or (C$_1$–C$_6$)alkyl; or (ii) combined to form —CH$_2$—(CH$_2$)$_{n10}$—CH$_2$— wherein the subscript n10 is an integer of from 0 to 4.

Returning to formula I, the symbol R$^4$ represents a member selected from H, F, CF$_3$, CN, N$_3$, NO$_2$, (C$_1$–C$_6$)alkyl, amino, mono- or di-(C$_1$–C$_6$)alkylamino, (C$_3$–C$_7$)cycloalkyl, (C$_3$–C$_7$)heterocycloalkyl, heteroaryl, fused (C$_8$–C$_{10}$)bicycloalkyl, fused (C$_8$–C$_{10}$)bicycloalkaryl, aryl and fused bicycloaryl; wherein any alkyl group present in R$^4$ is unsubstituted, partially- or fully-substituted with F, and each of the rings is optionally substituted with from one to four substituents selected from halogen, NO$_2$, N$_3$, SO$_2$NH$_2$, CN, (C$_1$–C$_6$)alkyl, OR$^{30}$, N(R$^{30}$)$_2$, CO$_2$R$^{30}$ and CON(R$^{30}$)$_2$, wherein each R$^{30}$ is independently H or (C$_1$–C$_6$)alkyl.

In addition to the compounds recited above, the present invention is directed to all pharmaceutically acceptable salts or prodrugs of the noted compounds.

Each of the above letters and symbols includes certain generally preferred embodiments, or preferred embodiments when combined with other preferred groups. Accordingly, the subscript n is preferably 1. The subscript m is preferably 0 to 2, more preferably 0 to 1, and most preferably 0. W is preferably C—$R^5$, more preferably C—H. X is preferably S, O or NH, more preferably S or O and most preferably S. Y is preferably N or CH, more preferably N. Z is preferably N. Each of $R^5$, $R^6$, $R^7$ and $R^8$ is preferably H or ($C_1$–$C_6$)alkyl. J is preferably C(O), C(S), S(O), S(O)$_2$ or C(N$R^9$), wherein $R^9$ is H, CN, NO$_2$ or ($C_1$–$C_6$)alkyl; more preferably C(O) or C(S); and most preferably C(O). A is preferably a direct link, C(O) or CH(OH); more preferably a direct link or C(O); and most preferably a direct link. $R^1$ is preferably, H, halo, CN, NO$_2$, ($C_1$–$C_6$)alkyl, ($C_3$–$C_7$)cycloalkyl, —C($R^{13}$)=C($R^{13}$)$_2$, —C≡C$R^{13}$ or —(CH$_2$)$_{n2}$—$R^{14}$; wherein each $R^{13}$ is independently selected from H, F, Cl, Br, CN, ($C_1$–$C_6$)alkyl, ($C_3$–$C_7$)cycloalkyl, (CH$_2$)$_{n2}$—$R^{14}$ and C(O)—(CH$_2$)$_{n2}$—$R^{14}$; and wherein each subscript n2 is independently an integer of from 0 to 3 and each $R^{14}$ is independently selected from phenyl, pyridyl, furanyl, pyrrolyl, imidazolyl, oxazolyl, isoxazolyl, triazolyl, tetrazolyl, thiazolyl, pyrazolyl, and thienyl, wherein each of the rings is optionally substituted with from 1 to 3 substituents selected from halogen, NO$_2$, N$_3$, CN,($C_1$–$C_6$)alkyl, O$R^{15}$, N($R^{15}$)$_2$, CO$_2R^{15}$ and CON($R^{15}$)$_2$, wherein each $R^{15}$ is independently H or ($C_1$–$C_6$)alkyl; and wherein any alkyl or cycloalkyl portions of $R^1$ are optionally substituted with from one to five F substituents. More preferably, $R^1$ is H, ($C_1$–$C_6$)alkyl, —C($R^{13}$)=C($R^{13}$)$_2$, —C≡C$R^{13}$ or —(CH$_2$)$_{n2}$—$R^{14}$; wherein each $R^{13}$ is independently selected from H or ($C_1$–$C_6$)alkyl, and the subscript n2 is 0 to 3, more preferably 1 to 2, and each $R^{14}$ is independently selected from phenyl, pyridyl, furanyl, pyrrolyl, imidazolyl, oxazolyl, isoxazolyl, triazolyl, tetrazolyl, thiazolyl, pyrazolyl, and thienyl, wherein each of the rings is optionally substituted with from 1 to 3 substituents selected from halogen, NO$_2$, N$_3$, CN, ($C_1$–$C_6$)alkyl, O$R^{15}$, N($R^{15}$)$_2$, CO$_2R^{15}$ and CON($R^{15}$)$_2$, wherein each $R^{15}$ is independently H or ($C_1$–$C_6$)alkyl; and wherein any alkyl or cycloalkyl portions of $R^1$ are optionally substituted with from one to five F substituents. Most preferably, $R^1$ is H, ethyl, vinyl or acetylenyl. $R^2$ is preferably H, CN, N$_3$, ($C_1$–$C_6$)alkyl, —C($R^{16}$)=C($R^{16}$)$_2$, —C≡C$R^{16}$, —C(O)—(CH$_2$)$_{n3}$—$R^{17}$ or —(CH$_2$)$_{n3}$—$R^{17}$; wherein each $R^{16}$ is independently selected from H, F, Cl, Br, CN and ($C_1$–$C_6$)alkyl, wherein each subscript n3 is independently an integer of from 0 to 3, preferably 1 or 2, and each $R^{17}$ is independently selected from ($C_1$–$C_6$)alkoxy, ($C_1$–$C_6$)alkylthio, mono- or di-($C_1$–$C_6$)alkylamino, amino or hydroxy, and wherein any alkyl or cycloalkyl portions of $R^2$ are optionally substituted with from one to five F substituents. More preferably, $R^2$ is selected from H, ($C_1$–$C_6$)alkyl or ($C_3$–$C_7$)cycloalkyl. Most preferably, $R^2$ is selected from H and ($C_1$–$C_6$)alkyl. $R^3$, when present, is preferably ($C_1$–$C_6$) alkyl, ($C_3$–$C_7$)cycloalkyl, —(CH$_2$)$_{n4}$—$R^{19}$ and —C(O)—(CH$_2$)$_{n4}$—$R^{19}$; wherein the subscript n4 is an integer of from 0 to 4, more preferably 0 to 2, and each $R^{19}$ is independently selected from ($C_1$–$C_6$)alkoxy, ($C_1$–$C_6$)alkylthio, mono- or di-($C_1$–$C_6$)alkylamino, amino; and wherein any alkyl or cycloalkyl portions of $R^3$ are optionally substituted with from one to five F substituents. More preferably, $R^3$ is ($C_1$–$C_6$)alkyl, —(CH$_2$)$_{n4}$—$R^{19}$ and —C(O)—(CH$_2$)$_{n4}$—$R^{19}$; wherein the subscript n4 is an integer of from 0 to 2, and each $R^{19}$ is independently selected from ($C_1$–$C_6$)alkoxy, ($C_1$–$C_6$)alkylthio, mono- or di-($C_1$–$C_6$)alkylamino and amino. $R^4$ is preferably H, F, CF$_3$, CN, N$_3$, NO$_2$, ($C_1$–$C_6$) alkyl, ($C_3$–$C_7$)cycloalkyl, ($C_3$–$C_7$)heterocycloalkyl, heteroaryl, fused ($C_8$–$C_{10}$)bicycloalkyl, fused ($C_8$–$C_{10}$)bicycloalkaryl, aryl or fused bicycloaryl; wherein any alkyl group present in $R^4$ is unsubstituted, partially- or fully-substituted with F, and each of the rings is optionally substituted with from one to four substituents selected from halogen, NO$_2$, N$_3$, SO$_2$NH$_2$, CN, ($C_1$–$C_6$)alkyl, O$R^{30}$, N($R^{30}$)$_2$, CO$_2R^{30}$ and CON($R^{30}$)$_2$, wherein each $R^{30}$ is independently H or ($C_1$–$C_6$)alkyl. More preferably, $R^4$ is ($C_3$–$C_7$)cycloalkyl, ($C_3$–$C_7$)heterocycloalkyl, heteroaryl, fused ($C_8$–$C_{10}$)bicycloalkyl, fused ($C_8$–$C_{10}$)bicycloalkaryl, aryl or fused bicycloaryl, each of which is optionally substituted as noted above. Still more preferably, $R^4$ is heteroaryl, fused ($C_8$–$C_{10}$)bicycloalkaryl, aryl or fused bicycloaryl. Most preferably, $R^4$ is fused ($C_8$–$C_{10}$)bicycloalkaryl or fused bicycloaryl. Among the most preferred $R^4$ groups are benzotriazolyl, benzimidazolyl, benzoxazolyl, benzisoxazolyl, benzothiazolyl and indazolyl. As noted above, L can be a direct link or a divalent linking group of formula Ia, Ib, Ic or Id.

For those embodiments in which L has the formula Ia of Ib, $V^1$ and $V^2$ are preferably direct links and the subscripts n5 and n7 are preferably 0. More preferably, the subscript n6 is an integer of from 1 to 6. Still more preferably, $V^3$ is O, S or N$R^{23}$, more preferably $V^3$ is O. For those embodiments in which L is a divalent linking group of formula Ic, Ar$^1$ is preferably a benzene ring, which can be attached to its adjacent components in a 1,2-(ortho), 1,3-(meta) or 1,4-(para) configuration. More preferably, Ar$^1$ is a 1,2- or 1,4-phenylene group. For those embodiments in which L is a divalent linking group of formula Id, G is preferably a ($C_5$–$C_7$)cycloalkyl or ($C_3$–$C_7$)heterocycloalkyl group, more preferably a cyclopentane, cyclohexane, piperidine, pyrrolidine or piperazine group.

In a group of generally preferred embodiments, the compounds of the present invention are represented by formula I, wherein wherein the subscript n is 1 or 2; the subscript m is an integer of from 0 to 4; W is C—$R^5$; X is S; Y is N; Z is N; wherein $R^5$ is H; J is C(O); A is a direct link; $R^1$ is selected from halo, CN, NO$_2$, ($C_1$–$C_6$)alkyl, —C($R^{13}$)=C ($R^{13}$)$_2$, —C≡C$R^{13}$ and —(CH$_2$)$_{n2}$—$R^{14}$; wherein $R^{13}$ is H, and wherein each subscript n2 is independently an integer of from 0 to 3 and each $R^{14}$ is either phenyl or pyridyl,; and wherein any alkyl or cycloalkyl portions of $R^1$ are optionally substituted with from one to five F substituents; $R^2$ is selected from H, CN, N$_3$, ($C_1$–$C_6$)alkyl, —C(O)—(CH$^2$)$_{n3}$—$R^{17}$ and —(CH$_2$)$_{n3}$—$R^{17}$; wherein each subscript n3 is independently an integer of from 0 to 3 and each $R^{17}$ is independently selected from ($C_1$–$C_6$)alkoxy, ($C_1$–$C_6$)alkylthio, mono- or di-($C_1$–$C_6$)alkylamino, amino, and hydroxyl; and wherein any alkyl or cycloalkyl portions of $R^2$ are optionally substituted with from one to five F substituents; each $R^3$ is independently selected from ($C_1$–$C_6$)alkyl and ($C_3$–$C_7$)cycloalkyl; and wherein any alkyl or cycloalkyl portions of $R^3$ are optionally substituted with from one to five F substituents; L is a divalent linking group having a formula selected from:

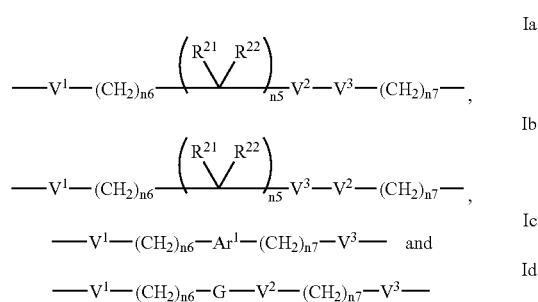

wherein V¹ is a direct link; V² is selected from a direct link and C(O); V³ is selected from a direct link and O; the subscript n5 is 0; the subscripts n6 and n7 are each independently an integer of from 0 to 4; Ar¹ is a 5- or 6-membered heteroaryl or phenyl group, optionally substituted with from one to three substituents independently selected from halogen, $NO_2$, $N_3$, CN, $(C_1–C_6)$alkyl, $OR^{27}$, $N(R^{27})_2$, $CO_2R^{27}$ and $CON(R^{27})_2$, wherein each $R^{27}$ is independently H or $(C_1–C_6)$alkyl; G is a $(C_3–C_7)$heterocycloalkyl or $(C_3–C_7)$cycloalkyl group, optionally substituted with from one to three substituents independently selected from halogen, =O, $N_3$, $NO_2$, CN, $(C_1–C_6)$alkyl, $OR^{28}$, $N(R^{28})_2$, $CO_2R^{28}$ and $CON(R^{28})_2$, wherein each $R^{28}$ is independently H or $(C_1–C_6)$alkyl; $R^4$ is a member selected from H, F, $CF_3$, CN, $N_3$, $NO_2$, $(C_1–C_6)$alkyl, amino, mono- or di-$(C_1–C_6)$alkylamino, $(C_3–C_7)$cycloalkyl, $(C_3–C_7)$heterocycloalkyl, heteroaryl, fused $(C_8–C_{10})$bicycloalkyl, fused $(C_8–C_{10})$bicycloalkaryl, aryl and fused bicycloaryl; wherein any alkyl group present in $R^4$ are unsubstituted, partially- or fully-substituted with F, and each of the rings is optionally substituted with from one to four substituents selected from halogen, $NO_2$, $N_3$, $SO_2NH_2$, CN, $(C_1–C_6)$alkyl, $OR^{30}$, $N(R^{30})_2$, $CO_2R^{30}$ and $CON(R^{30})_2$, wherein each $R^{30}$ is independently H or $(C_1–C_6)$alkyl; or a pharmaceutically acceptable salt or prodrug thereof.

One of skill in the art will appreciate that a number of other embodiments are particularly preferred within the above generic formula, having certain combinations of substituents or preferred substituents groups. In particular, preferred embodiments for the bicyclic framework which supports the piperazine and homopiperazine portions of the compound are those in which (i) W is C—$R^5$, X is S, Y is N and Z is N; (ii) W is C—$R^5$, X is O, Y is N and Z is N; (iii) W is N, X is N—$R^6$, Y is N and Z is N; (iv) W is C—$R^5$, X is S, Y is C—$R^7$ and Z is N; (v) W is N, X is O, Y is N and Z is N; and (vi) W is C—$R^5$, X is N—$R^6$, Y is N and Z is N. More preferably, the bicyclic framework is one in which (i) W is C—$R^5$, X is S, Y is N and Z is N; or (ii) W is C—$R^5$, X is O, Y is N and Z is N. Still more preferably, the compounds of the invention are those in which W is C—$R^5$, X is S, Y is N and Z is N.

In a first group of preferred embodiments, the subscript n is 1, W is C—$R^5$, X is S, Y is N and Z is N. Further preferred are those embodiments in which $R^5$ is H and $R^2$ is selected from H, halo, CN, $NO_2$, $N_3$, $(C_1–C_6)$alkyl, —C(O)—$(CH_2)_{n3}$—$R^{17}$ and —$(CH_2)_{n3}$—$R^7$; wherein each subscript n3 is independently an integer of from 0 to 2 and each $R^{17}$ is independently selected from $(C_1–C_6)$alkoxy, $(C_1–C_6)$alkylthio, mono- or di-$(C_1–C_6)$alkylamino, amino and hydroxy. More preferably, A is a direct link and $R^1$ is selected from the group consisting of H, halo, CN, $NO_2$, $N_3$, $(C_1–C_6)$alkyl, $(C_3–C_7)$cycloalkyl, —C($R^{13}$)=C($R^{13})_2$, —C≡C$R^3$ and —$(CH_2)_{n2}$—$R^{14}$; wherein each $R^{13}$ is independently selected from the group consisting of H, F, Cl, Br, CN, $(C_1–C_6)$alkyl, $(C_3–C_7)$cycloalkyl, $(CH_2)_{n2}$—$R^{14}$ and C(O)—$(CH_2)_{n2}$—$R^{14}$; wherein each subscript n2 is independently an integer of from 0 to 3 and each $R^{14}$ is independently selected from the group consisting of $(C_1–C_6)$alkoxy, $(C_1–C_6)$alkylthio, mono- or di-$(C_1–C_6)$alkylamino, amino; and wherein any alkyl or cycloalkyl portions of $R^1$ are optionally substituted with from one to five F substituents. Still more preferably, $R^1$ is selected from the group consisting of H, $(C_1–C_6)$alkyl, $(C_3–C_7)$cycloalkyl, —C($R^{13}$)=C($R^{13})_2$ and —C≡C$R^{13}$; wherein each $R^{13}$ is independently selected from the group consisting of H, $(C_1–C_6)$alkyl and $(C_3–C_7)$cycloalkyl; and wherein any alkyl or cycloalkyl portions of $R^1$ are optionally substituted with from one to five F substituents. Even further preferred are those embodiments in which $R^1$ is selected from ethyl, vinyl and acetylenyl. In each of the above groups of embodiments, the piperazine ring is optionally substituted, preferably with from 0 to 2 substituents selected from $(C_1–C_6)$alkyl. Attached to the piperazine ring is J, which in preferred embodiments is selected from C(O) and C(S), more preferably J is C(O).

Still further preferred in the first group of embodiments are those in which L is a divalent linking group of formula Ia, more preferably wherein V¹ and V² are direct links, the subscripts n5 and n7 are 0, and the subscript n6 is an integer of from 1 to 6. Still further preferred for the embodiments in which L is a divalent linking group of formula Ia, are those embodiments in which V³ is O, S or $NR^{23}$; more preferably V³ is O and $R^4$ is selected from fused $(C_8–C_{10})$bicycloalkaryl, aryl and fused bicycloaryl; and most preferably, $R^4$ is a fused bicycloaryl group selected from the group consisting of benzotriazolyl, benzimidazolyl, benzoxazolyl, benzisoxazolyl, benzothiazolyl and indazolyl. In one group of related, and preferred, embodiments, L is a divalent linking group of formula Ib. In another group of related, and preferred, embodiments, L is a divalent linking group of formula Ic, more preferably, wherein Ar¹ is phenyl and $R^4$ is a fused bicycloaryl group selected from the group consisting of benzotriazolyl, benzimidazolyl, benzoxazolyl, benzisoxazolyl, benzothiazolyl and indazolyl. In yet another group of related, and preferred, embodiments, L is a divalent linking group of formula Id, wherein G is preferably a $(C_3–C_7)$ heterocycloalkyl group, and $R^4$ is a fused bicycloaryl group selected from the group consisting of benzotriazolyl, benzimidazolyl, benzoxazolyl, benzisoxazolyl, benzothiazolyl and indazolyl. Particularly preferred $(C_3–C_7)$heterocycloalkyl groups are piperidine, pyrrolidine and piperazine.

In a second group of preferred embodiments, the subscript n is 2, indicating the presence of a homopiperazine ring. In this group of embodiments, preferred members for each of m, A, J, L, W, X, Y, Z, $R^1$, $R^2$, $R^3$ and $R^4$ are as described above for the preferred embodiments when n is 1.

Certain compounds of the present invention are among the most preferred, including:

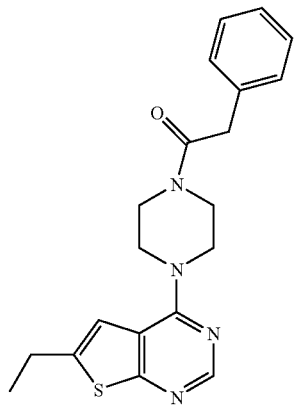

-continued
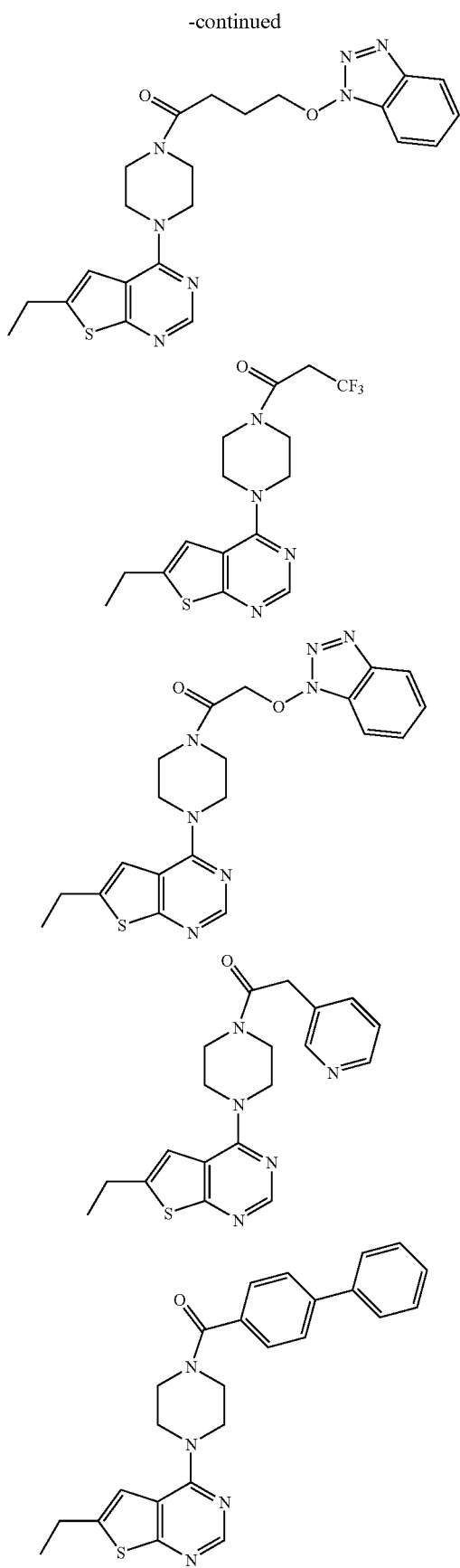
-continued
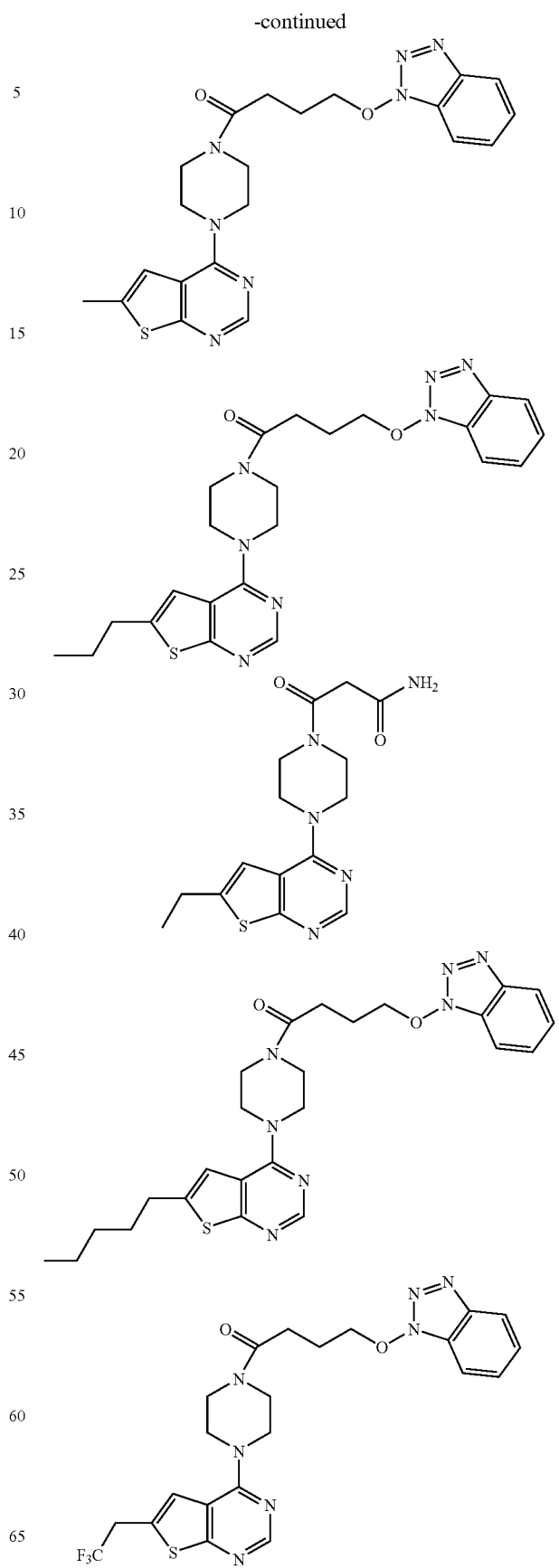

-continued
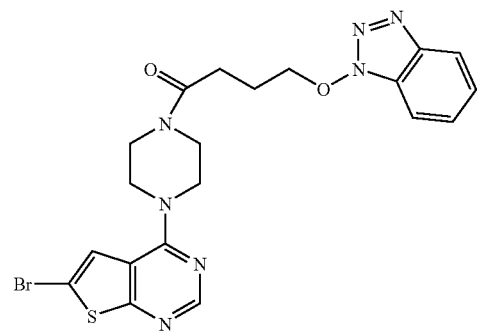
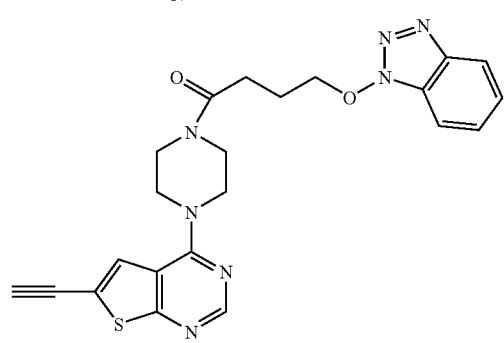
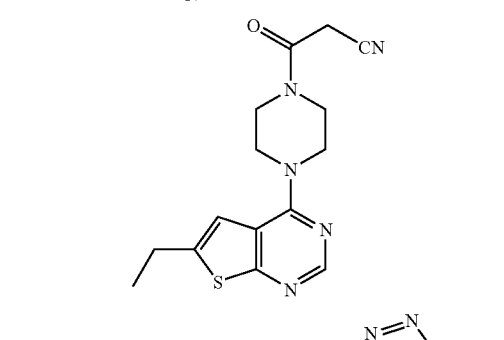
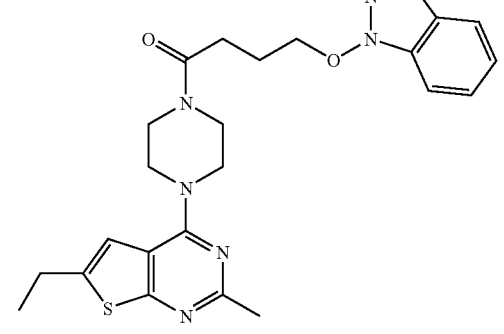
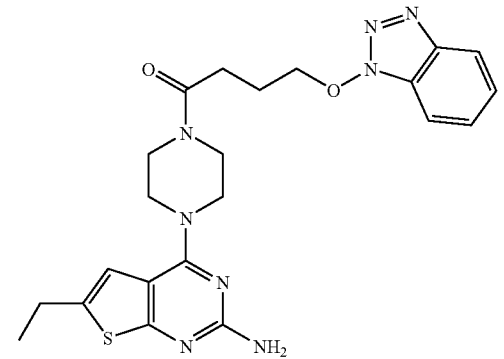
-continued
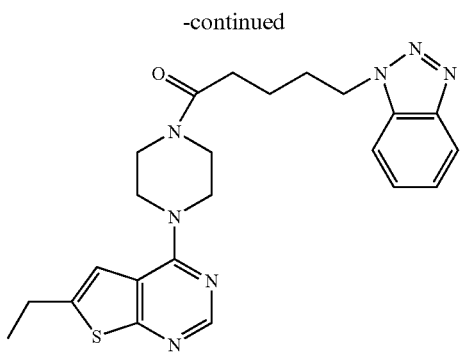
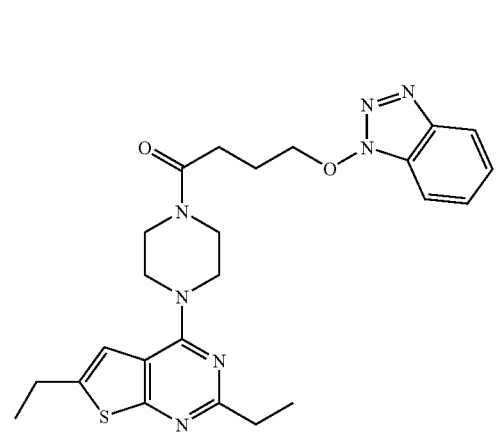
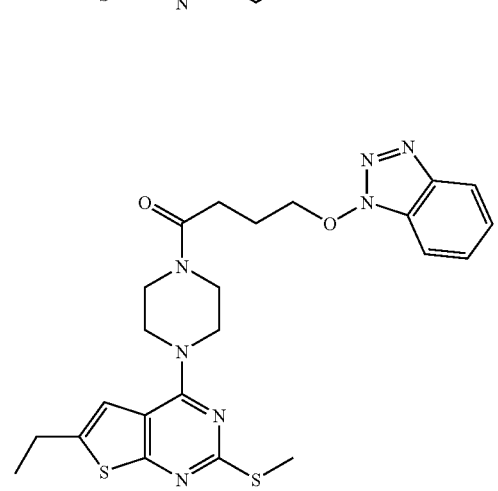
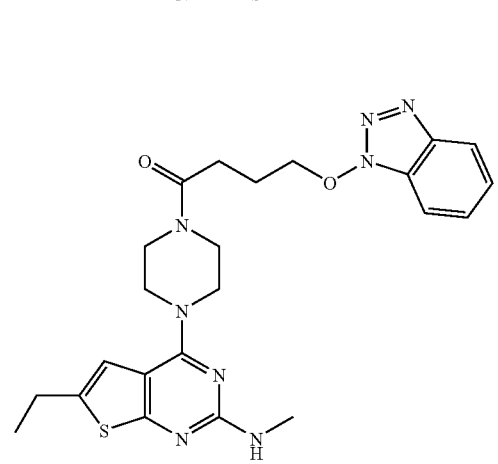

-continued
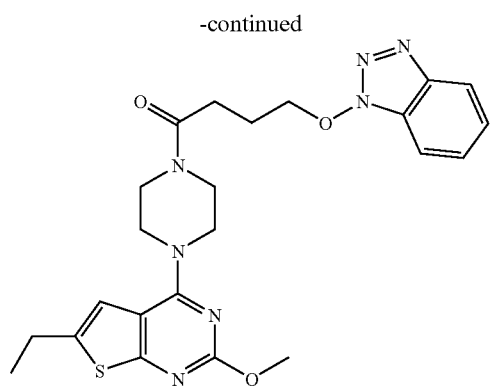
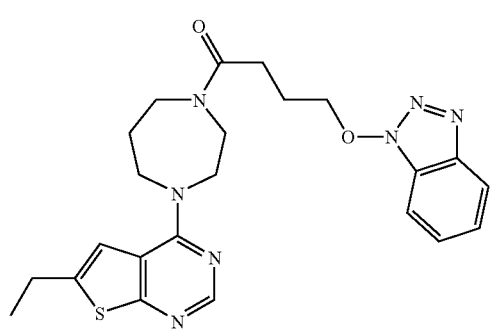
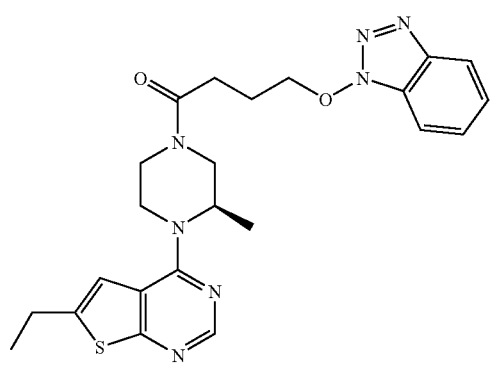
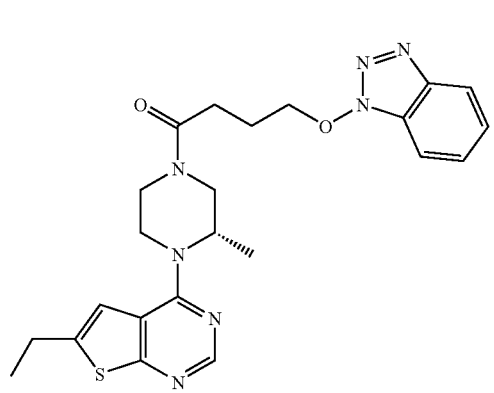
-continued
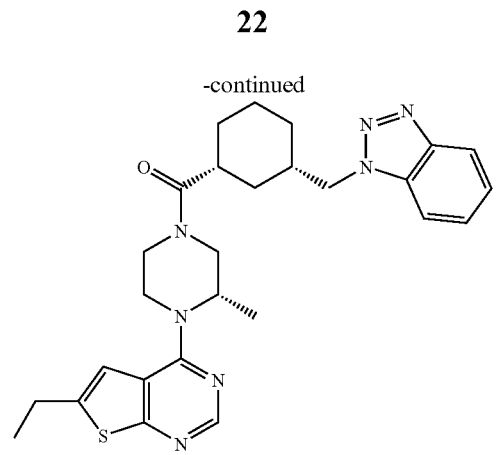
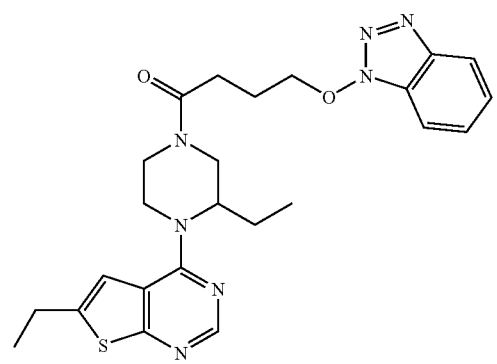
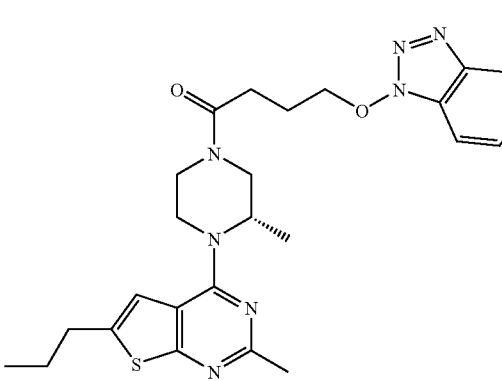
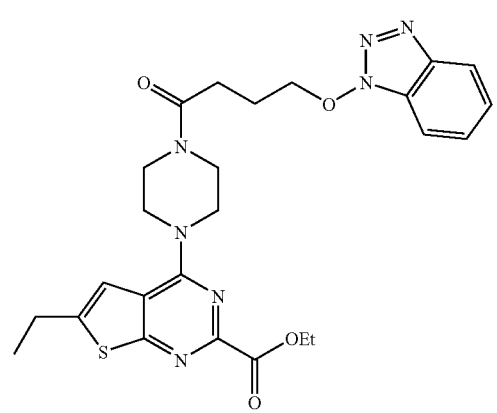

-continued
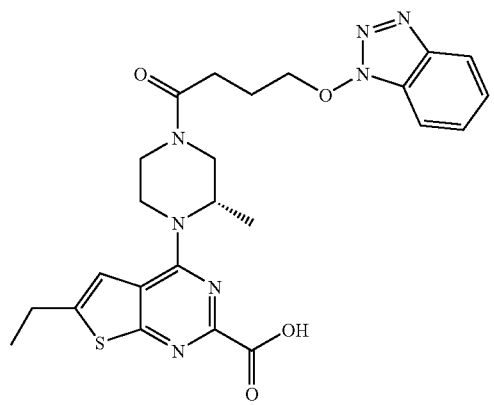
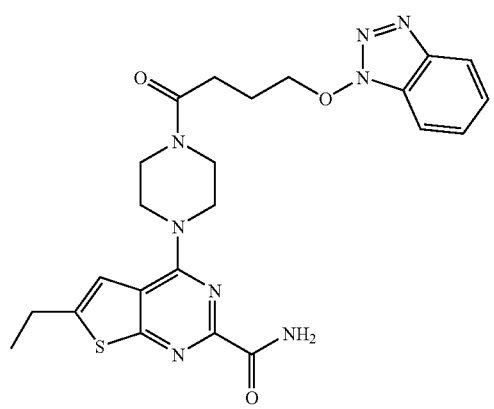
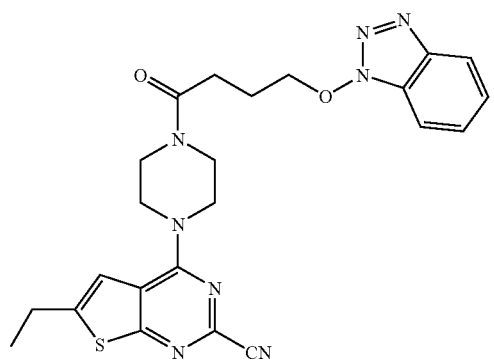
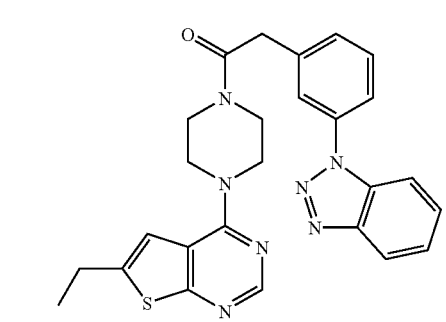
-continued
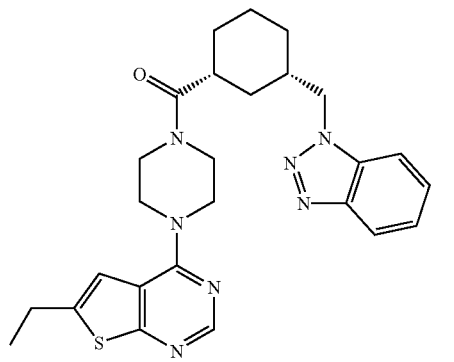
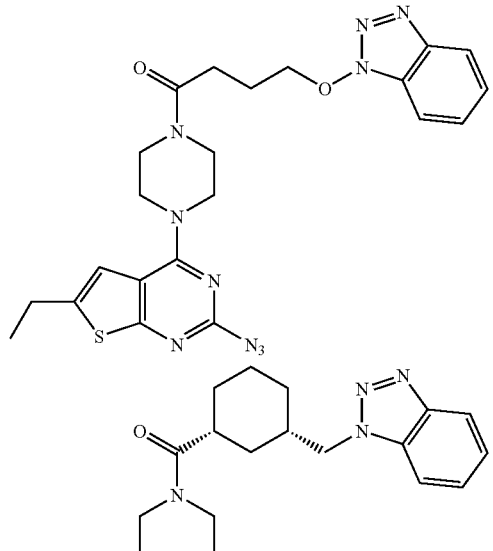
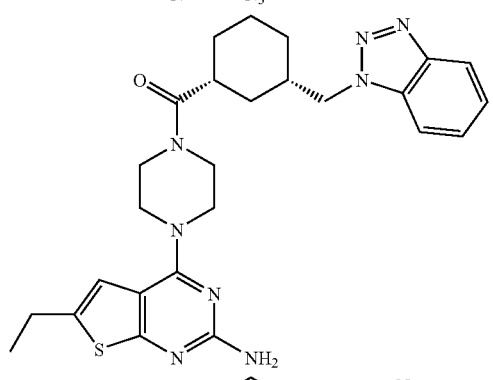
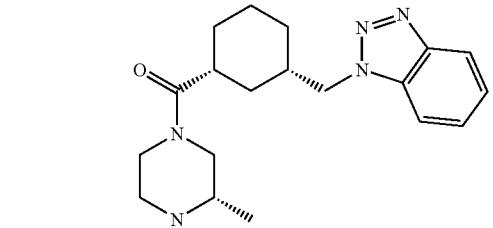
Preparation of Compounds of the Invention
Compounds of the present invention can be prepared utilizing methods outlined in the examples below, as well as certain general synthetic descriptions in one or more of the following documents: *J. Med. Chem.* 42, 5464–5474 (1999), *J. Med. Chem.* 38, 2763–2773 (1995), *J. Med. Chem.* 39, 2285–2292 (1996), WO-9962980, U.S. Pat. No. 5,948,911, WO-9817668, WO-9806722, *Tetrahedron*, 52, 1011–1026 (1996), WO-9519774, *J. Heterocycl. Chem.* 30, 1065–1072

(1993), *Pharmazie* 48, 192–194 (1993), which are incorporated herein in their entirety by reference. Other well-known heterocyclic and carbocyclic synthetic procedures as well as modification of the procedures that are incorporated above may be utilized.

Compounds of formula (I) may be isolated using typical isolation and purification techniques known in the art, including, for example, chromatographic and recrystallization methods.

In compounds of formula (I) of the invention, carbon atoms to which four non-identical substituents are bonded are asymmetric. Accordingly, a compound of formula (I) may exist as enantiomers, diastereomers or a mixture thereof. The enantiomers and diastereomers may be separated by chromatographic or crystallization methods, or by other methods known in the art. The asymmetric carbon atom when present in a compound of formula (I) of the invention, may be in one of two configurations (R or S) and both are within the scope of the invention. The presence of small amounts of the opposing enantiomer or diastereomer in the final purified product does not affect the therapeutic or diagnostic application of such compounds.

According to the invention, compounds of formula (I) may be further treated to form pharmaceutically acceptable salts. Treatment of a compound of the invention with an acid or base may form, respectively, a pharmaceutically acceptable acid addition salt and a pharmaceutically acceptable base addition salt, each as defined above. Various inorganic and organic acids and bases known in the art including those defined herein may be used to effect the conversion to the salt.

The invention also relates to pharmaceutically acceptable isomers, hydrates, and solvates of compounds of formula (I). Compounds of formula (I) may also exist in various isomeric and tautomeric forms including pharmaceutically acceptable salts, hydrates and solvates of such isomers and tautomers.

This invention also encompasses prodrug derivatives of the compounds of formula (I). The term "prodrug" refers to a pharmacologically inactive derivative of a parent drug molecule that requires biotransformation, either spontaneous or enzymatic, within the organism to release the active drug. Prodrugs are variations or derivatives of the compounds of formula (I) of this invention which have groups cleavable under metabolic conditions. Prodrugs become the compounds of the invention which are pharmaceutically active in vivo when they undergo solvolysis under physiological conditions or undergo enzymatic degradation. Prodrug compounds of this invention may be called single, double, triple, etc., depending on the number of biotransformation steps required to release the active drug within the organism, and indicating the number of functionalities present in a precursor-type form. Prodrug forms often offer advantages of solubility, tissue compatibility, or delayed release in the mammalian organism (Bundgard, *Design of Prodrugs*, pp. 7–9, 21–24, Elsevier, Amsterdam (1985); Silverman, *The Organic Chemistry of Drug Design and Drug Action*, pp. 352–401, Academic Press, San Diego, Calif. (1992)). Prodrugs commonly known in the art include acid derivatives well known to practitioners of the art, such as, for example, esters prepared by reaction of the parent acids with a suitable alcohol, or amides prepared by reaction of the parent acid compound with an amine, or basic groups reacted to form an acylated base derivative. Moreover, the prodrug derivatives of this invention may be combined with other features herein taught to enhance bioavailability.

Pharmaceutical Compositions and Methods of Treatment

A compound of formula (I) according to the invention may be formulated into pharmaceutical compositions. Accordingly, the invention also relates to a pharmaceutical composition for preventing or treating thrombosis in a mammal, particularly those pathological conditions involving platelet aggregation, containing a therapeutically effective amount of a compound of formula (I) or a pharmaceutically acceptable salt thereof, each as described above, and a pharmaceutically acceptable carrier or agent. Preferably, a pharmaceutical composition of the invention contains a compound of formula (I), or a salt thereof, in an amount effective to inhibit platelet aggregation, more preferably, ADP-dependent aggregation, in a mammal, in particular, a human. Pharmaceutically acceptable carriers or agents include those known in the art and are described below.

Pharmaceutical compositions of the invention may be prepared by mixing the compound of formula (I) with a physiologically acceptable carrier or agent. Pharmaceutical compositions of the invention may further include excipients, stabilizers, diluents and the like and may be provided in sustained release or timed release formulations. Acceptable carriers, agents, excipients, stabilizers, diluents and the like for therapeutic use are well known in the pharmaceutical field, and are described, for example, in *Remington's Pharmaceutical Sciences*, Mack Publishing Co., ed. A. R. Gennaro (1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine, proteins, such as serum albumin, gelatin, or immunoglobulins, hydrophilic polymers such as polyvinylpyrrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counterions such as sodium and/or nonionic surfactants such as TWEEN, or polyethyleneglycol.

Methods for treating thrombosis in a mammal embraced by the invention, include not only administering a therapeutically effective amount of a compound of formula (I) alone or as part of a pharmaceutical composition of the invention as described above to a mammal, in particular, a human to alleviate thromobosis or a thrombosis-related condition or disease, but also include administering the compound or composition prior to the onset of thrombosis or a thrombosis-related condition or disease. One of skill in the art will appreciate that thrombosis can occur as a result of surgical intervention and the prophylactic administration of a compound or composition of the invention can result in decreasing or the amount of thrombosis that occurs. As noted above, compounds of formula (I) and pharmaceutical compositions of the invention containing a compound of formula (I) of the invention are suitable for use alone or as part of a multi-component treatment regimen for the prevention or treatment of cardiovascular diseases, particularly those related to thrombosis. For example, a compound or pharmaceutical composition of the invention may be used as a drug or therapeutic agent for any thrombosis, particularly a platelet-dependent thrombotic indication, including, but not limited to, acute myocardial infarction, unstable angina, chronic stable angina, transient ischemic attacks, strokes, peripheral vascular disease, preeclampsia/eclampsia, deep venous thrombosis, embolism, disseminated intravascular coagulation and thrombotic cytopenic purpura, thrombotic and restenotic complications following invasive procedures, e.g., angioplasty, carotid endarterectomy, post CABG (coronary artery bypass graft) surgery, vascular graft surgery, stent placements and insertion of endovascular devices and protheses.

Compounds and pharmaceutical compositions of the invention may also be used as part of a multi-component treatment regimen in combination with other therapeutic or diagnostic agents in the prevention or treatment of thrombosis in a mammal. In certain preferred embodiments, compounds or pharmaceutical compositions of the invention may be coadministered along with other compounds typically prescribed for these conditions according to generally accepted medical practice such as anticoagulant agents, thrombolytic agents, or other antithrombotics, including platelet aggregation inhibitors, tissue plasminogen activators, urokinase, prourokinase, streptokinase, heparin, aspirin, or warfarin. Coadministration may also allow for application of reduced doses of the thrombolytic agents and therefore minimize potential hemorrhagic side-effects. Compounds and pharmaceutical compositions of the invention may also act in a synergistic fashion to prevent reocclusion following a successful thrombolytic therapy and/or reduce the time to reperfusion.

The compounds and pharmaceutical compositions of the invention may be utilized in vivo, ordinarily in mammals such as primates, (e.g., humans), sheep, horses, cattle, pigs, dogs, cats, rats and mice, or in vitro. The biological properties, as defined above, of a compound or a pharmaceutical composition of the invention can be readily characterized by methods that are well known in the art such as, for example, by in vivo studies to evaluate antithrombotic efficacy, and effects on hemostasis and hematological parameters.

Compounds and pharmaceutical compositions of the invention may be in the form of solutions or suspensions. In the management of thrombotic disorders the compounds or pharmaceutical compositions of the invention may also be in such forms as, for example, tablets, capsules or elixirs for oral administration, suppositories, sterile solutions or suspensions or injectable administration, and the like, or incorporated into shaped articles. Subjects (typically mammalian) in need of treatment using the compounds or pharmaceutical compositions of the invention may be administered dosages that will provide optimal efficacy. The dose and method of administration will vary from subject to subject and be dependent upon such factors as the type of mammal being treated, its sex, weight, diet, concurrent medication, overall clinical condition, the particular compound of formula (I) employed, the specific use for which the compound or pharmaceutical composition is employed, and other factors which those skilled in the medical arts will recognize.

Dosage formulations of compounds of formula (I), or pharmaceutical compositions contain a compound of the invention, to be used for therapeutic administration must be sterile. Sterility is readily accomplished by filtration through sterile membranes such as 0.2 micron membranes, or by other conventional methods. Formulations typically will be stored in a solid form, preferably in a lyophilized form. While the preferred route of administration is orally, the dosage formulations of compounds of formula (I) or pharmaceutical compositions of the invention may also be administered by injection, intravenously (bolus and/or infusion), subcutaneously, intramuscularly, colonically, rectally, nasally, transdermally or intraperitoneally. A variety of dosage forms may be employed as well including, but not limited to, suppositories, implanted pellets or small cylinders, aerosols, oral dosage formulations and topical formulations such as ointments, drops and dermal patches. The compounds of formula (I) and pharmaceutical compositions of the invention may also be incorporated into shapes and articles such as implants which may employ inert materials such biodegradable polymers or synthetic silicones as, for example, SILASTIC, silicone rubber or other polymers commercially available. The compounds and pharmaceutical compositions of the invention may also be administered in the form of liposome delivery systems, such as small unilamellar vesicles, large unilamellar vesicles and multilamellar vesicles. Liposomes can be formed from a variety of lipids, such as cholesterol, stearylamine or phosphatidylcholines.

Therapeutically effective dosages may be determined by either in vitro or in vivo methods. For each particular compound or pharmaceutical composition of the invention, individual determinations may be made to determine the optimal dosage required. The range of therapeutically effective dosages will be influenced by the route of administration, the therapeutic objectives and the condition of the patient. For injection by hypodermic needle, it may be assumed the dosage is delivered into the bodily fluids. For other routes of administration, the absorption efficiency must be individually determined for each compound by methods well known in pharmacology. Accordingly, it may be necessary for the therapist to titer the dosage and modify the route of administration as required to obtain the optimal therapeutic effect.

The determination of effective dosage levels, that is, the dosage levels necessary to achieve the desired result, i.e., platelet ADP receptor inhibition, will be readily determined by one skilled in the art. Typically, applications of a compound or pharmaceutical composition of the invention are commenced at lower dosage levels, with dosage levels being increased until the desired effect is achieved. The compounds and compositions of the invention may be administered orally in an effective amount within the dosage range of about 0.01 to 1000 mg/kg in a regimen of single or several divided daily doses. If a pharmaceutically acceptable carrier is used in a pharmaceutical composition of the invention, typically, about 5 to 500 mg of a compound of formula (I) is compounded with a pharmaceutically acceptable carrier as called for by accepted pharmaceutical practice including, but not limited to, a physiologically acceptable vehicle, carrier, excipient, binder, preservative, stabilizer, dye, flavor, etc. The amount of active ingredient in these compositions is such that a suitable dosage in the range indicated is obtained.

Typical adjuvants which may be incorporated into tablets, capsules and the like include, but are not limited to, binders such as acacia, corn starch or gelatin, and excipients such as microcrystalline cellulose, disintegrating agents like corn starch or alginic acid, lubricants such as magnesium stearate, sweetening agents such as sucrose or lactose, or flavoring agents. When a dosage form is a capsule, in addition to the above materials it may also contain liquid carriers such as water, saline, or a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

Pharmacological Assays

The pharmacological activity of each of the compounds according to the invention can be determined using in vitro assays as described below.

I. Inhibition of ADP-Mediated Platelet Aggregation in vitro

The effect of testing the compound according to the invention on ADP-induced human platelet aggregation is preferably assessed in 96-well microtiter assay (see generally the procedures in Jantzen, H. M. et al. (1999) *Thromb. Hemost.* 81:111–117). Human venous blood is collected from healthy, drug-free volunteers into ACD (85 mM sodium citrate, 111 mM glucose, 71.4 mM citric acid) containing $PGI_2$ (1.25 ml ACD containing 1.6 µM $PGI_2$/10 ml blood; $PGI_2$ was from Sigma, St. Louis, Mo.). Platelet-rich plasma (PRP) is prepared by centrifugation at 160×g for 20 minutes at room temperature. Washed platelets are prepared by centrifuging PRP for 10 minutes at 730×g and resuspending the platelet pellet in CGS (13 mM sodium citrate, 30 mM glucose, 120 mM NaCl; 2 ml CGS/10 ml original blood volume) containing 1 U/ml apyrase (grade V, Sigma, St. Louis, Mo.). After incubation at 37° C. for 15 minutes, the platelets are collected by centrifugation at 730×g for 10 minutes and resuspended at a concentration of $3×10^8$ platelets/ml in Hepes-Tyrode's buffer (10 mM Hepes, 138 mM NaCl, 5.5 mM glucose, 2.9 mM KCl, 12 mM $NaHCO_3$, pH 7.4) containing 0.1% bovine serum albumin, 1 mM $CaCl_2$ and 1 mM $MgCl_2$. This platelet suspension is kept >45 minutes at 37° C. before use in aggregation assays.

Inhibition of ADP-dependent aggregation is preferably determined in 96-well flat-bottom microtiter plates using a microtiter plate shaker and plate reader similar to the procedure described by Frantantoni et al., *Am. J. Clin. Pathol.* 94, 613 (1990). All steps are performed at room temperature. The total reaction volume of 0.2 ml/well includes in Hepes-Tyrodes buffer/0.1% BSA: $4.5×10^7$ apyrase-washed platelets, 0.5 mg/ml human fibrinogen (American Diagnostica, Inc., Greenwich, Conn.), serial dilutions of test compounds (buffer for control wells) in 0.6% DMSO. After about 5 minutes preincubation at room temperature, ADP is added to a final concentration of 2 µM which induces submaximal aggregation. Buffer is added instead of ADP to one set of control wells (ADP⁻ control). The OD of the samples is then determined at 490 nm using a microtiter plate reader (Softmax, Molecular Devices, Menlo Park, Calif.) resulting in the 0 minute reading. The plates are then agitated for 5 min on a microtiter plate shaker and the 5 minute reading is obtained in the plate reader. Aggregation is calculated from the decrease of OD at 490 nm at t=5 minutes compared to t=0 minutes and is expressed as % of the decrease in the ADP control samples after correcting for changes in the unaggregated control samples.

II. Inhibition of [³H]2-MeS-ADP Binding to Platelets

Having first determined that the compounds according to the invention inhibit ADP-dependent platelet aggregation with the above assay, a second assay is used to determine whether such inhibition is mediated by interaction with platelet ADP receptors. Utilizing the second assay the potency of inhibition of such compounds with respect to [³H]2-MeS-ADP binding to whole platelets is determined. [³H]2-MeS-ADP binding experiments are routinely performed with outdated human platelets collected by standard procedures at hospital blood banks. Apyrase-washed outdated platelets are prepared as follows (all steps at room temperature, if not indicated otherwise):

Outdated platelet suspensions are diluted with 1 volume of CGS and platelets pelleted by centrifugation at 1900×g for 45 minutes. Platelet pellets are resuspended at $3–6×10^9$ platelets/ml in CGS containing 1 U/ml apyrase (grade V, Sigma, St. Louis, Mo.) and incubated for 15 minutes at 37° C. After centrifugation at 730×g for 20 minutes, pellets are resuspended in Hepes-Tyrode's buffer containing 0.1% BSA (Sigma, St. Louis, Mo.) at a concentration of $6.66×10^8$ platelets/ml. Binding experiments are performed after >45 minutes resting of the platelets.

Alternatively, binding experiments are performed with fresh human platelets prepared as described in I.(Inhibition of ADP-Mediated Platelet Aggregation in vitro), except that platelets are resuspended in Hepes-Tyrode's buffer containing 0.1% BSA (Sigma, St. Louis, Mo.) at a concentration of $6.66×10^8$ platelets/ml. Very similar results are obtained with fresh and outdated platelets.

A platelet ADP receptor binding assay using the tritiated potent agonist ligand [³H]2-MeS-ADP (Jantzen, H. M. et al. (1999) *Thromb. Hemost.* 81:111–117) has been adapted to the 96-well microtiter format. In an assay volume of 0.2 ml Hepes-Tyrode's buffer with 0.1% BSA and 0.6% DMSO, $1×10^8$ apyrase-washed platelets are preincubated in 96-well flat bottom microtiter plates for 5 minutes with serial dilutions of test compounds before addition of 1 nM [³H]2-MeS-ADP ([³H]2-methylthioadenosine-5'-diphosphate, ammonium salt; specific activity 48–49 Ci/mmole, obtained by custom synthesis from Amersham Life Science, Inc., Arlington Heights, Ill., or NEN Life Science Products, Boston, Mass.). Total binding is determined in the absence of test compounds. Samples for nonspecific binding may contain $10^{-5}$ M unlabelled 2-MeS-ADP (RBI, Natick, Mass.). After incubation for 15 minutes at room temperature, unbound radioligand is separated by rapid filtration and two washes with cold (4–8° C.) Binding Wash Buffer (10 mM Hepes pH 7.4, 138 mM NaCl) using a 96-well cell harvester (Minidisc 96, Skatron Instruments, Sterling, Va.) and 8×12 GF/C glassfiber filtermats (Printed Filtermat A, for 1450 Microbeta, Wallac Inc., Gaithersburg, Md.). The platelet-bound radioactivity on the filtermats is determined in a scintillation counter (Microbeta 1450, Wallac Inc., Gaithersburg, Md.). Specific binding is determined by subtraction of non-specific binding from total binding, and specific binding in the presence of test compounds is expressed as % of specific binding in the absence of test compounds dilutions.

The table below provides an relative activities of selected compounds in the ARB binding assay (see, I. Inhibition of ADP-Mediated Platelet Aggregation in vitro, above).

Activity is set forth as follows: +>20 micromolar; ++10–20 micromolar; and +++<10 micromolar. The Example Number refers to the compound prepared as described in the noted Example.

TABLE

| Example Number | Relative Activity |
|---|---|
| 2 | +++ |
| 4 | +++ |
| 5 | +++ |
| 17 | +++ |
| 55 | +++ |
| 57 | ++ |
| 59 | + |
| 67 | ++ |
| 70 | + |
| 71 | +++ |
| 106 | ++ |
| 109 | + |

TABLE-continued

| Example Number | Relative Activity |
| --- | --- |
| 111 | ++ |
| 112 | +++ |
| 125 | +++ |
| 130 | ++ |
| 135 | +++ |
| 144 | ++ |
| 148 | +++ |
| 151 | +++ |
| 153 | +++ |
| 169 | +++ |
| 181 | +++ |
| 183 | + |
| 188 | +++ |
| 193 | +++ |
| 197 | ++ |
| 206 | + |
| 231 | +++ |
| 236 | +++ |
| 250 | ++ |
| 271 | ++ |
| 279 | +++ |
| 305 | +++ |
| 311 | + |
| 313 | ++ |
| 320 | + |
| 332 | ++ |
| 348 | + |
| 349 | + |
| 362 | + |
| 372 | ++ |
| 384 | + |
| 390 | + |
| 395 | + |
| 408 | ++ |
| 429 | + |
| 430 | + |
| 432 | + |
| 453 | + |

EXAMPLES

Example 1 tert-butyl 4-(6-ethylthiopheno[3,2-e]pyrimidin-4-yl)piperazinecarboxylate

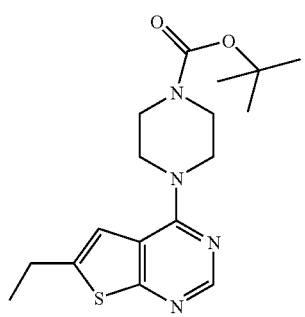

Step 1:

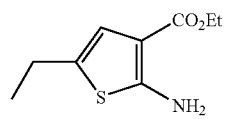

Ethyl 2-amino-5-Ethylthiophene-3-carboxylate was prepared according to the literature (J. Med. Chem. 1981, 24(7), 878–882.) in 65% yield. ES-MS: (M+H)+ 200

Step 2:

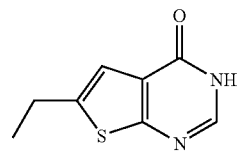

The compound from Step 1 (5.0 gm, 25.1 mmol) was suspended in formamide (15 mL, 377 mmol) under argon at rt. To this was added ammonium formate (2.36 gm, 37.5 mmol). The resulting suspension was warmed to 140° C. and stirred for 7.5 hrs. The solution was then cooled to rt and poured into ice cold H$_2$O (200 mL). After mixing thoroughly, the solid was filtered, rinsed with cold H$_2$O, air dried, and then further dried in vacuo to afford 3.76 gm (83%) of the desired 6-ethylthienopyrimidone. ES-MS: (M+H)+ 181

Step 3:

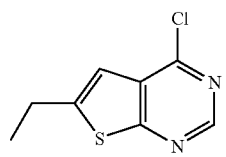

METHOD A: The compound from Step 2 (2.5 gm, 13.9 mmol) was placed into a dry round bottomed flask under argon at rt, and then POCl$_3$ (6.8 mL, 73 mmol) was carefully added and a reflux condenser was attached. The resulting suspension was warmed to 150° C. and stirred 3.5 hr. After cooling to rt, the mixture was carefully added to ice-cold KOH (11 gm in 50 mL H$_2$O) with vigorous stirring, and then washed with EtOAc (4×50 mL). The EtOAc was then washed with brine (50 mL), dried with MgSO$_4$, filtered, and concentrated in vacuo to afford 2.64 gm (96%) of the desired chloropyrimidine. ES-MS: (M+H)+ 198/200.

METHOD B: The compound from Step 2 (7 gm, 38.9 mmol) was placed into a dry round bottomed flask under argon at rt and a reflux condenser was attached. Then SOCl$_2$ (70 mL, 10 mL/gm) was carefully added followed by dropwise addition of DMF (2.1 mL, 3% Vol. of SOCl$_2$). The solution was then warmed to 80° C. and stirred for 1.25 hr. The SOCl$_2$ was then evaporated under reduced pressure. The resulting semi-solid was triturated with toluene (3×50 mL) with subsequent evaporation of the toluene each time to afford 9.3 gm (quantitative yield) of the desired chloropyrimidine. ES-MS: (M+H)+ 198/200.

Step 4. The compound from Step 3 (2.0 gm, 10.1 mmol) suspended in isopropanol (17 mL) and then Boc-piperazine (3.76 gm, 20.2 mmol) was added. After attaching a reflux condenser, the resulting solution was warmed to 80–85° C. and stirred for 3.5 hr at which time the majority of the solvent was evaporated in vacuo. To this residue was then added H$_2$O (50 mL) which was washed with EtOAc (2×30 mL). The EtOAc was then washed with brine (50 mL), dried with MgSO$_4$, filtered, and concentrated to afford 3.52 gm (quantitative) of the title compound. ES-MS: (M+H)+ 349.

Example 2

1-[4-(6-ethylthiopheno[3,2-e]pyrimidin-4-yl)piperazinyl]-2-phenylethan-1-one

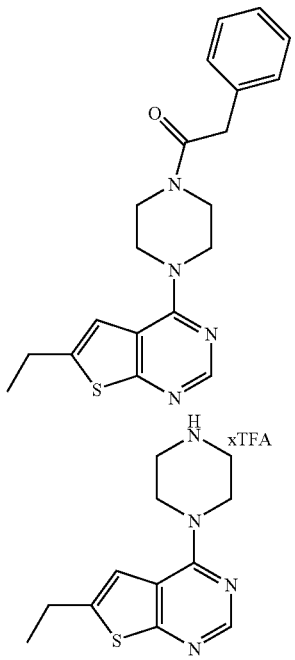

xTFA

Step 1: The compound of Example 1 (50 mg, 0.14 mmol) was treated with 40% TFA in DCM (0.5 mL) at rt under argon for 1 hr followed by evaporation of the solvent.

Step 2: The residue from Step 1 was next dissolved in DMF (0.5 mL). To this solution was then added HBTU (80 mg, 0.21 mmol), phenylacetic acid (23 mg, 0.17 mmol), and then DIEA (0.15 mL, 0.84 mmol). The resulting mixture was stirred at rt overnight, and the progress of the reaction was monitored using RP-HPLC. The crude mixture was then purified using prep RP-HPLC to provide 56 mg of pure title compound as a TFA salt. ES-MS: (M+H)$^+$ 367

Example 3

Phenyl 4-(6-ethylthiopheno[3,2-e]pyrimidin-4-yl)piperazinecarboxylate

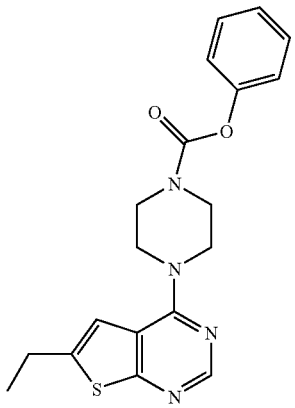

The compound from Example 1 (50 mg, 0.14 mmol) was treated with TFA in DCM as described in Example 2. To the resulting residue was added DCM (0.15 mL, 0.84 mmol) and DIEA (0.15 mL, 0.21 mmol) followed by slow addition of phenyl chloroformate (0.03 ml, 0.21 mmol), and this mixture was stirred over night. Purification was accomplished using prep RP-HPLC affording 53 mg of the title compound as a TEA salt. ES-MS: (M+H)$^+$ 369

Example 4

4-benzotriazolyloxy-1-[4-(6-ethylthiopheno[3,2-e]pyrimidin-4-yl)piperazinyl]butan-1-one

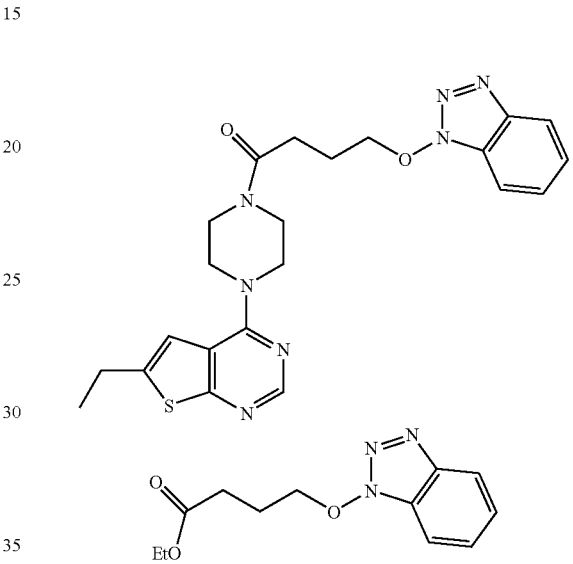

Step 1: To Ethyl 4-Br-butyrate (1.0 mL, 3.76 mmol) in DMF (4 mL) was added N(1)-hydroxybenzotriazole (559 mg, 4.14 mmol) followed by DIEA (2.0 mL, 11.3 mmol). The resulting solution was stirred for 3.5 hr and monitored by RP-HPLC. Brine (30 ml) was added and the mixture was washed with EtOAc (3×30 mL). The combined EtOAc was washed with brine, dried with MgSO$_4$, filtered and evaporated to afford 1.13 gm of crude ester.

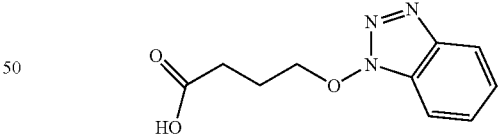

Step 2: The crude product from Step 1 was dissolved in MeOH (4 mL) and treated with 1M NaOH (5.6 mL). The reaction was stirred for 1.25 hr, and the MeOH was then removed in vacuo. After adding H$_2$O (20 mL), the mixture was washed with EtOAc (20 mL). The aqueous layer was acidified with 3M HCl (4 mL) which resulted in a white precipitate. This mixture was then washed with EtOAc (3×25 mL), and the combined extracts were washed with brine, dried with MgSO$_4$ and evaporated under reduced pressure to afford 710 mg (87%) of the desired acid. ES-MS: (M+H)$^+$ 222

Step 3: The title compound was obtained by essentially following Example 2 using the acid obtained in Step 2 of this example in place of phenylacetic acid to afford 65 mg of the desired product as a TFA salt. ES-MS: (M+H)⁺ 452, (M+Na)⁺ 474

Example 5

1-[4-(6-ethylthiopheno[3,2-e]pyrimidin-4-yl)piperazinyl]-3,3,3-trifluoropropan-1-one

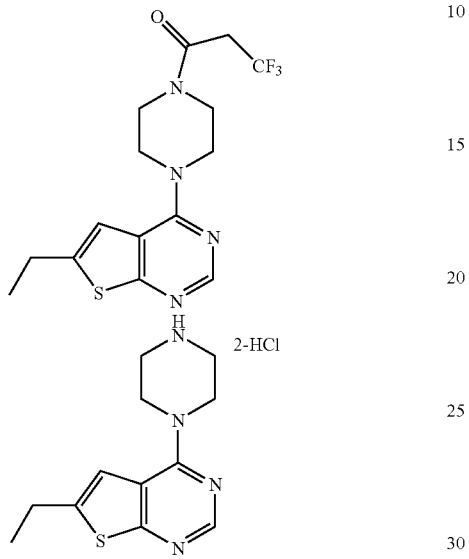

Step 1: The compound of Example 1 (500 mg, 1.4 mmol) was dissolved in DCM (5 mL) under argon at rt and then treated with anhydrous 4M HCl in dioxane (2.5 mL). The resulting mixture was stirred over night at rt, and then the solvents were evaporated under reduced pressure to afford 454 mg (100%) as an HCl salt.

Step 2: The title compound was obtained by essentially following Example 2 using the material obtained in Step 1 of this example (45 mg) and 3,3,3-trifluoropropionic acid (0.012 mL) in place of phenylacetic acid to afford 41 mg of the desired product as a TFA salt. ES-MS: (M+H)⁺ 359

Example 6

Phenylmethyl 4-(6-ethylthiopheno[3,2-e]pyrimidin-4-yl)piperazinecarboxylate

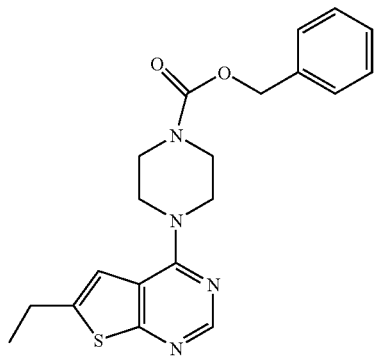

The title compound was prepared by essentially following Step 4 of Example 1 using N-carbobenzyloxy-piperazine in place of Boc-piperazine to afford after prep RP-HPLC purification a quantitative yield as the TFA salt. ES-MS: (M+H)⁺ 383

Example 7

6-ethyl-4-[4-benzylpiperazinyl]thiopheno[2,3-d]pyrimidine

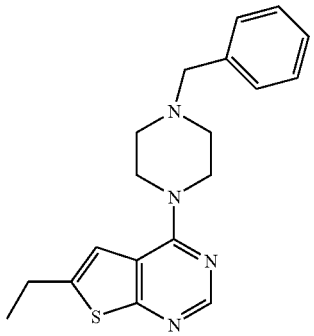

The title compound was prepared by essentially following Step 4 of Example 1 using N-benzyl-piperazine in place of Boc-piperazine to afford 214 mg as the TFA salt. ES-MS: (M+H)⁺ 383

Example 8

1-[4-(6-ethylthiopheno[3,2-e]pyrimidin-4-yl)piperazinyl]-5-indolylpentan-1-one

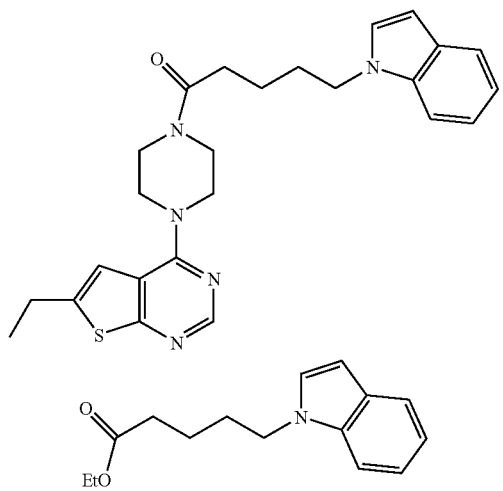

Step 1: To indole (500 mg, 4.27 mmol) in DMF (8.5 mL) at rt under argon was added K₂CO₃ (885 mg, 6.4 mmol) followed by ethyl 5-bromopentanoate (0.81 mL, 5.12 mmol). After stirring 2 days, the reaction had only gone to about 6% completion. Thus, Cs₂CO₃ (1.04 gm) was added and stirring continued for another day. RP-HPLC analysis indicated that the reaction proceeded to about 40% completion, so more ethyl 5-bromopentanoate (0.4 mL) was added followed by NaI (40 mg) 1 day later. After stirring for another 5 days, no further change was noted. The mixture was poured into brine (40 mL) and then 6M HCl (10 mL) was added at 0° C. This mixture was washed with EtOAc (3×50 mL). The EtOAc was dried with MgSO₄, filtered, and evaporated in vacuo to give 1.63 gm of crude ester mixed with indole.

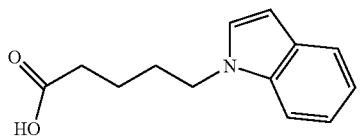

Step 2: The crude product from Step 1 was dissolved in MeOH (4 mL) at rt and then 1M NaOH (6.65 mL) was added followed by 3 mL H$_2$O. After stirring over night, 1M NaOH (3.5 mL) was added and stirring was maintained for 2 days. After evaporation of the MeOH, H$_2$O (15 mL) was added, and the mixture was washed with EtOAc (2×10 mL). The aqueous layer was then acidified with 3M HCl and washed with EtOAc (3×20 mL). The EtOAc was dried with MgSO$_4$, filtered, and evaporated to afford 780 mg (84%) of the desired acid.

Step 3: The title compound was obtained by essentially following Example 2 using the material obtained in Step 2 of this example in place of phenylacetic acid to afford 121 mg of the desired product as a TFA salt. ES-MS: (M+H)$^+$ 448

Example 9

1-[4-(6-ethylthiopheno[3,2-e]pyrimidin-4-yl)piperazinyl]-6-indolylhexan-1-one

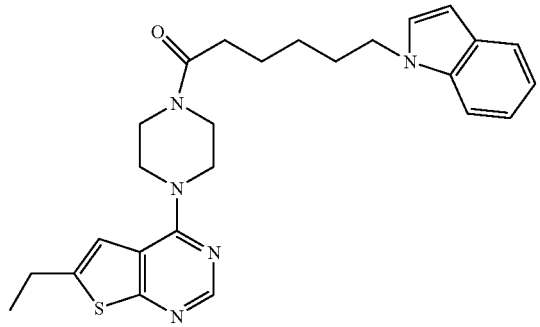

The title compound was obtained by essentially following Example 8 using Ethyl 6-Br-hexanoate for ethyl 5-bromopentanoate as a TFA salt. ES-MS: (M+H)$^+$ 462

Example 10

1-[4-(6-ethylthiopheno[3,2-e]pyrimidin-4-yl)piperazinyl]-3-phenylpropan-1-one

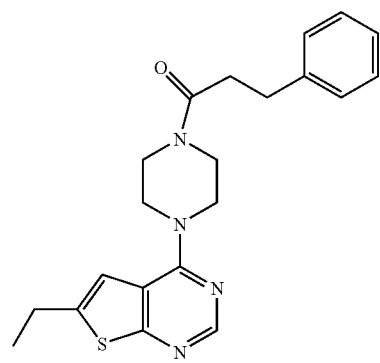

The title compound was obtained as a TFA salt by essentially following Example 3 except 3-phenylpropionyl chloride was used in place of phenyl chloroformate. ES-MS: (M+H)$^+$ 381, (M+Na)$^+$ 403

Example 11

1-[4-(6-ethylthiopheno[3,2-e]pyrimidin-4-yl)piperazinyl]-4-phenylbutan-1-one

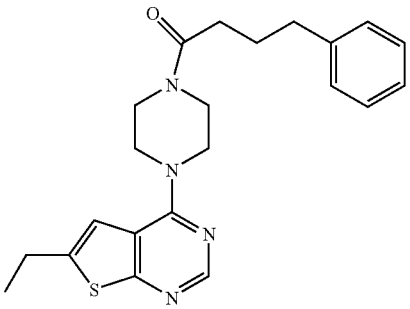

The title compound was obtained as a TFA salt by essentially following Example 2 using 4-phenylbutanoic acid in place of phenylacetic acid. ES-MS: (M+H)$^+$ 395, (M+Na)$^+$ 417

Example 12

1-acetyl-4-(6-ethylthiopheno[3,2-e]pyrimidin-4-yl)piperazine

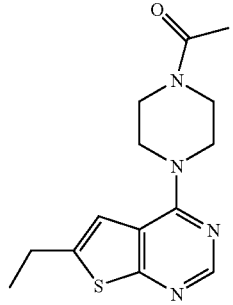

The title compound was obtained as a TFA salt by essentially following Example 3 except acetyl chloride was used in place of phenyl chloroformate. ES-MS: (M+H)$^+$ 291

Example 13

1-[4-(6-ethylthiopheno[3,2-e]pyrimidin-4-yl)piperazinyl]propan-1-one

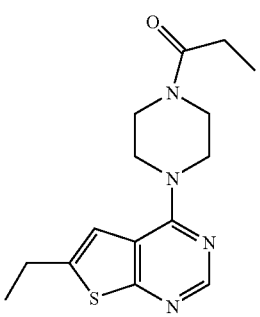

The title compound was obtained as a TFA salt by essentially following Example 3 except propionyl chloride was used in place of phenyl chloroformate. ES-MS: (M+H)+ 305

Example 14

1-[4-(6-ethylthiopheno[3,2-e]pyrimidin-4-yl)piperazinyl]butan-1-one

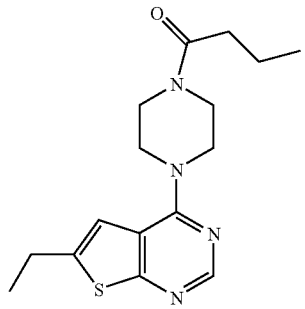

The title compound was obtained as a TFA salt by essentially following Example 3 except butyric anhydride was used in place of phenyl chloroformate. ES-MS: (M+H)+ 319

Example 15

1-[4-(6-ethylthiopheno[3,2-e]pyrimidin-4-yl)piperazinyl]pentan-1-one

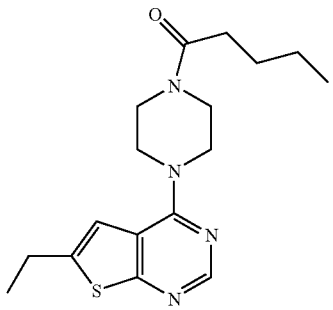

The title compound was obtained as a TFA salt by essentially following Example 3 except valeryl chloride was used in place of phenyl chloroformate. ES-MS: (M+H)+ 333

Example 16

1-[4-(6-ethylthiopheno[3,2-e]pyrimidin-4-yl)piperazinyl]hexan-1-one

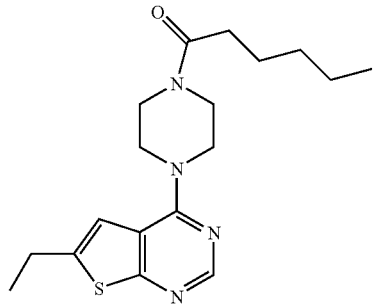

The title compound was obtained as a TFA salt by essentially following Example 2 using hexanoic acid in place of phenylacetic acid. ES-MS: (M+H)+ 347, (M+Na)+ 369

Example 17

1-[4-(6-ethylthiopheno[3,2-e]pyrimidin-4-yl)piperazinyl]-4-methylpentan-1-one

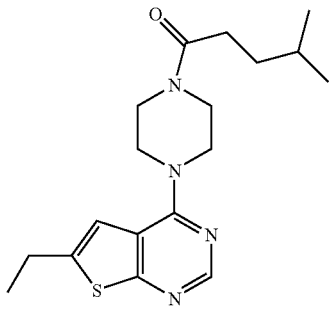

The title compound was obtained as a TFA salt by essentially following Example 2 using 4-methyl-pentanoic acid in place of phenylacetic acid. ES-MS: (M+H)+ 347, (M+Na)+ 369

Example 18

1-[4-(6-ethylthiopheno[3,2-e]pyrimidin-4-yl)piperazinyl]-2,2-dimethylpropan-1-one

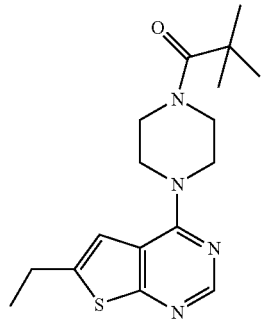

The title compound was obtained as a TFA salt by essentially following Example 3 except pivaloyl chloride was used in place of phenyl chloroformate. ES-MS: (M+H)+ 333

Example 19

1-[4-(6-ethylthiopheno[3,2-e]pyrimidin-4-yl)piperazinyl]-3,3-dimethylbutan-1-one

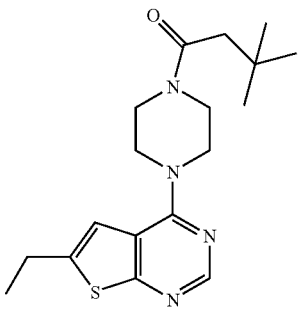

The title compound was obtained as a TFA salt by essentially following Example 3 except 3,3-dimethylpropionyl chloride was used in place of phenyl chloroformate. ES-MS: (M+H)+ 347

Example 20

Ethyl 4-(6-ethylthiopheno[3,2-e]pyrimidin-4-yl)piperazinecarboxylate

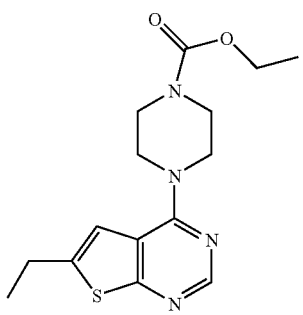

The title compound was obtained as a TFA salt by essentially following Example 3 except ethyl chloroformate was used in place of phenyl chloroformate. ES-MS: (M+H)+ 321

Example 21

Propyl 4-(6-ethylthiopheno[3,2-e]pyrimidin-4-yl)piperazinecarboxylate

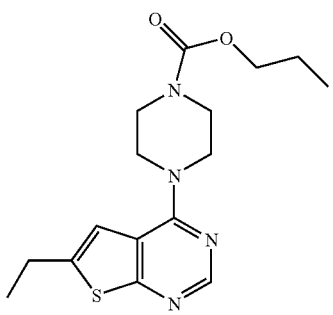

The title compound was obtained as a TFA salt by essentially following Example 3 except propyl chloroformate was used in place of phenyl chloroformate. ES-MS: (M+H)+ 335

Example 22

Butyl 4-(6-ethylthiopheno[3,2-e]pyrimidin-4-yl)piperazinecarboxylate

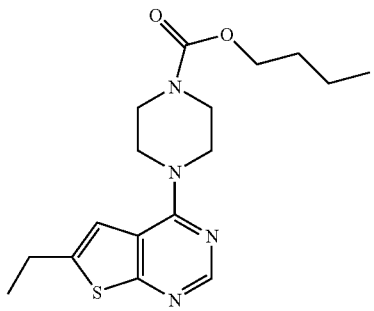

The title compound was obtained as a TFA salt by essentially following Example 3 except butyl chloroformate was used in place of phenyl chloroformate. ES-MS: (M+H)+ 349

Example 23

2-methylpropyl 4-(6-ethylthiopheno[3,2-e]pyrimidin-4-yl)piperazinecarboxylate

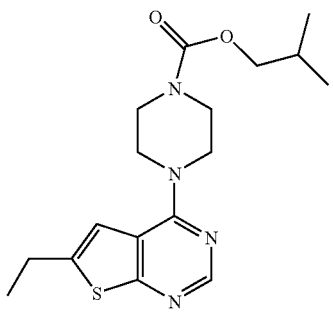

The title compound was obtained as a TFA salt by essentially following Example 3 except isobutyl chloroformate was used in place of phenyl chloroformate. ES-MS: (M+H)+ 349

Example 24

2-methylpropyl 4-(6-ethylthiopheno[3,2-e]pyrimidin-4-yl)piperazinecarboxylate

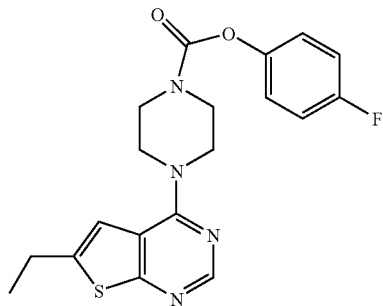

The title compound was obtained as a TFA salt by essentially following Example 3 except 4-fluorophenyl chloroformate was used in place of phenyl chloroformate. ES-MS: (M+H)+ 387, (M+Na)+ 409

Example 25

4-methoxyphenyl 4-(6-ethylthiopheno[3,2-e]pyrimidin-4-yl)piperazinecarboxylate

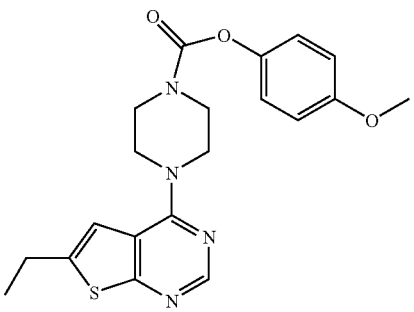

The title compound was obtained as a TFA salt by essentially following Example 3 except 4-methoxyphenyl chloroformate was used in place of phenyl chloroformate. ES-MS: (M+H)+ 399, (M+Na)+ 421

Example 26

4-bromophenyl 4-(6-ethylthiopheno[3,2-e]pyrimidin-4-yl)piperazinecarboxylate

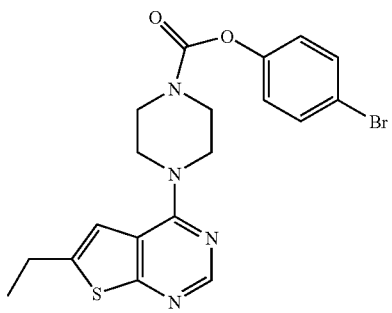

The title compound was obtained as a TFA salt by essentially following Example 3 except 4-bromophenyl chloroformate was used in place of phenyl chloroformate. ES-MS: (M+H)+ 447/449, (M+Na)+ 469/471.

Example 27

4-chlorophenyl 4-(6-ethylthiopheno[3,2-e]pyrimidin-4-yl)piperazinecarboxylate

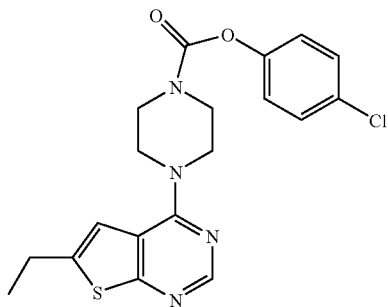

The title compound was obtained as a TFA salt by essentially following Example 3 except 4-chlorophenyl chloroformate was used in place of phenyl chloroformate. ES-MS: (M+H)+ 403/405.

Example 28

4-methylphenyl 4-(6-ethylthiopheno[3,2-e]pyrimidin-4-yl)piperazinecarboxylate

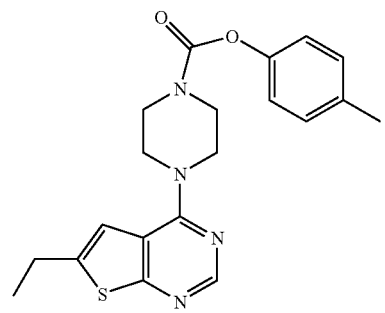

The title compound was obtained as a TFA salt by essentially following Example 3 except 4-bromophenyl chloroformate was used in place of phenyl chloroformate. ES-MS: (M+H)+ 383, (M+Na)+ 405

Example 29

2-nitrophenyl 4-(6-ethylthiopheno[3,2-e]pyrimidin-4-yl)piperazinecarboxylate

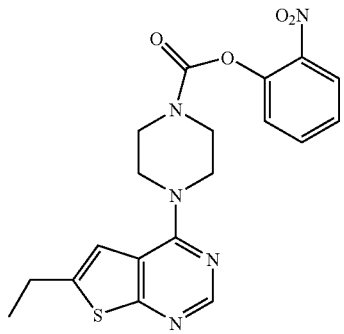

The title compound was obtained as a TFA salt by essentially following Example 3 except 4-bromophenyl chloroformate was used in place of phenyl chloroformate. ES-MS: (M+H)+ 413, (M+Na)+ 436

Example 30

3,4-dichlorophenyl 4-(6-ethylthiopheno[3,2-e]pyrimidin-4-yl)piperazinecarboxylate

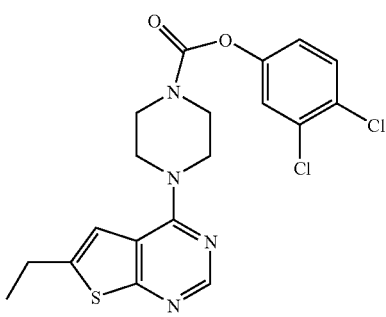

3,4-Dichlorophenol (23 mgs, 0.14 mmol) was mixed with N,N-disuccinimidyl carbonate (DSC) (40 mgs, 0.15 mmol) under argon at rt and then DCM (1 mL) was added. To this solution was then added dropwise DIEA (0.05 mL, 0.28 mmol) and stirring was maintained for 1.5 hr. To this homogeneous solution was then added the HCl salt obtained from Example 5, Step 1 (45 mgs, 0.14 mmol) followed by slow addition of DIEA (0.1 mL, 0.56 mmol). After stirring this solution overnight, the mixture was purified using prep RP-HPLC to afford 22 mgs of the title compound as a TFA salt. ES-MS: (M+H)+ 437/439.

Example 31

1-(6-ethylthiopheno[3,2-e]pyrimidin-4-yl)-4-(methylsulfonyl)piperazine

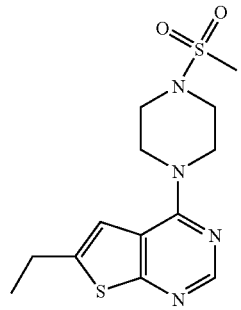

The title compound was obtained as a TFA salt by essentially following Example 3 except methanesulfonyl chloride was used in place of phenyl chloroformate. ES-MS: (M+H)$^+$327.

Example 32

4-(butylsulfonyl)-1-(6-ethylthiopheno[3,2-e]pyrimidin-4-yl)piperazine

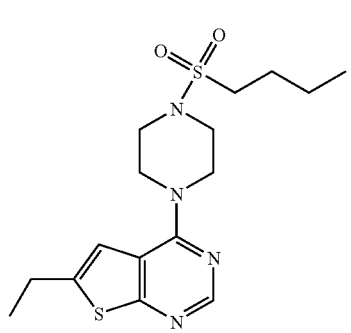

The title compound was obtained as a TFA salt by essentially following Example 3 except n-butylsulfonyl chloride was used in place of phenyl chloroformate. ES-MS: (M+H)$^+$ 369, (M+Na)$^+$ 391.

Example 33

1-(6-ethylthiopheno[3,2-e]pyrimidin-4-yl)-4-(phenylsulfonyl)piperazine

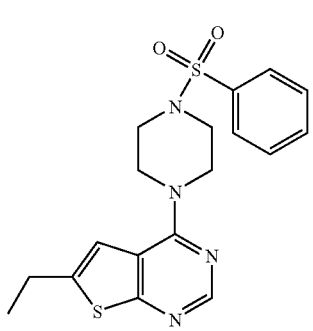

The title compound was obtained as a TFA salt by essentially following Example 3 except phenylsulfonyl chloride was used in place of phenyl chloroformate. ES-MS: (M+H)$^+$ 389

Example 34

1-(6-ethylthiopheno[3,2-e]pyrimidin-4-yl)-4-[(4-methylphenyl)sulfonyl]piperazine

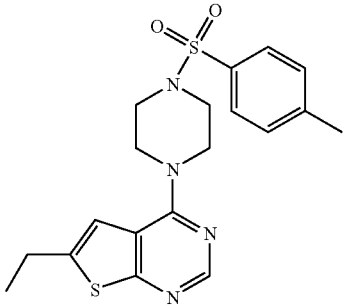

The title compound was obtained as a TFA salt by essentially following Example 3 except p-toluenesulfonyl chloride was used in place of phenyl chloroformate. ES-MS: (M+H)$^+$ 403

Example 35

1-(6-ethylthiopheno[3,2-e]pyrimidin-4-yl)-4-[benzylsulfonyl]piperazine

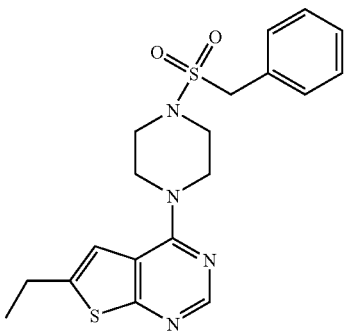

The title compound was obtained as a TFA salt by essentially following Example 3 except □-toluenesulfonyl chloride was used in place of phenyl chloroformate. ES-MS: (M+H)$^+$ 403

Example 36

N-ethyl[4-(6-ethylthiopheno[3,2-e]pyrimidin-4-yl)piperazinyl]carboxamide

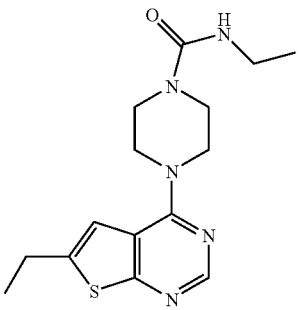

To ethylamine (2M in THF, 0.07 mL) in DCM (1 mL) at rt under argon was added DSC (54 mgs, 0.21 mmol) and then DIEA (0.1 mL). After stirring for 2.5 hrs, a mixture of compound from Example 2, Step 1 (0.14 mmol) and DIEA (0.15 mL) in DCM (1 mL) was added, and stirring was continued over night. The resulting mixture was then purified with prep RP-HPLC affording the title compound as a TFA salt. ES-MS: (M+H)+ 320, (M+Na)+ 342

Example 37

[4-(6-ethylthiopheno[3,2-e]pyrimidin-4-yl)piperazinyl]-N-propylcarboxamide

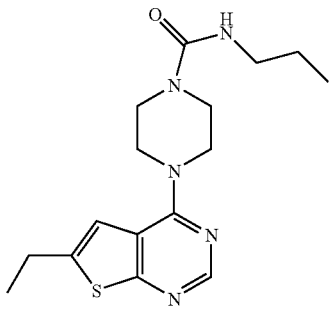

The title compound was obtained as a TFA salt by essentially following Example 3 except propyl isocyanate (0.28 mmol) was used in place of phenyl chloroformate and DMF in place of DCM in the second step. ES-MS: (M+H)+ 334

Example 38

N-butyl [4-(6-ethylthiopheno[3,2-e]pyrimidin-4-yl)piperazinyl]carboxamide

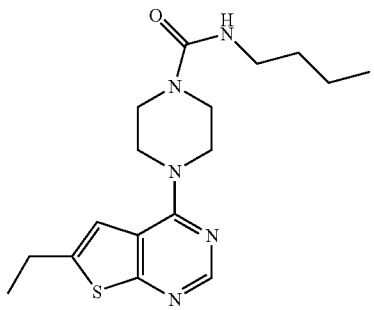

The title compound was obtained as a TFA salt by essentially following Example 3 except n-butyl isocyanate (0.28 mmol) was used in place of phenyl chloroformate and DMF in place of DCM in the second step. ES-MS: (M+H)+ 348, (M+Na)+ 370

Example 39

N-(tert-butyl)[4-(6-ethylthiopheno[3,2-e]pyrimidin-4-yl)piperazinyl]carboxamide

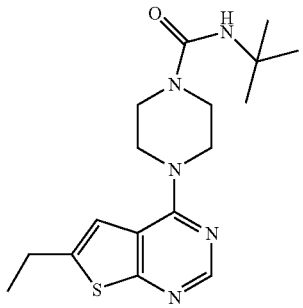

The title compound was obtained as a TFA salt by essentially following Example 3 except tert-butyl isocyanate (0.28 mmol) was used in place of phenyl chloroformate and DMF in place of DCM in the second step. ES-MS: (M+H)+ 348, (M+Na)+ 370, (M+2Na)+ 393

Example 40

[4-(6-ethylthiopheno[3,2-e]pyrimidin-4-yl)piperazinyl]-N-prop-2-ynylcarboxamide

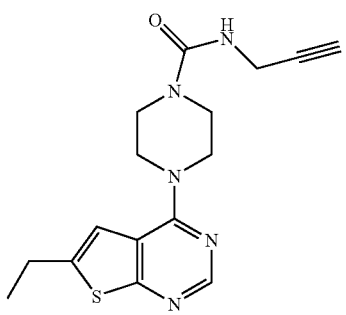

The title compound was obtained as a TFA salt by essentially following Example 36 except propargyl amine was used in place of ethylamine. ES-MS: (M+H)+ 330 (M+Na)+ 352

Example 41

Ethyl (2S)-2-{[4-(6-ethylthopheno[3,2-e]pyrimidin-4-yl)pperazinyl]carbonylamino}-3-phenylpropanoate

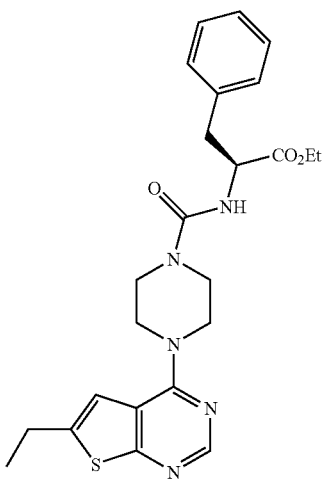

The title compound was obtained as a TFA salt by essentially following Example 36 except L-phenyl alanine ethyl ester hydrochloride was used in place of ethylamine. ES-MS: (M+H)+ 468 (M+Na)+ 490

Example 42

Methyl (2S)-2-{[4-(6-ethylthiopheno[3,2-e]pyrimidin-4-yl)piperazinyl]carbonylamino}-2-phenylacetate

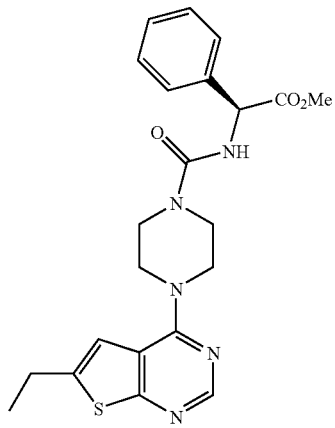

The title compound was obtained as a TFA salt by essentially following Example 36 except S-(+)-phenylglycine methyl ester hydrochloride was used in place of ethylamine. ES-MS: (M+H)⁺ 440 (M+Na)⁺ 462

Example 43 methyl (2S)-2-{[4-(6-ethylthiopheno[3,2-e]pyrimidin-4-yl)piperazinyl]carbonylamino}-2-phenylacetate

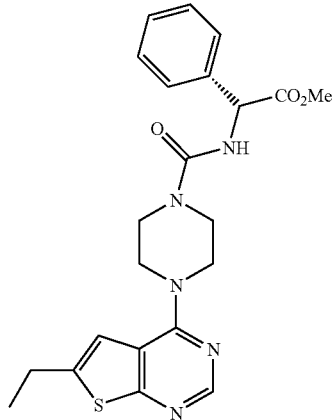

The title compound was obtained as a TFA salt by essentially following Example 36 except R-(−)-phenylglycine methyl ester hydrochloride was used in place of ethylamine. ES-MS: (M+H)⁺ 440 (M+Na)⁺ 462

Example 44

[4-(6-ethylthiopheno[3,2-e]pyrimidin-4-yl)piperazinyl]-N-benzamide

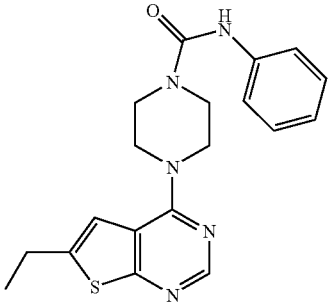

The title compound was obtained as a TFA salt by essentially following Example 3 except phenyl isocyanate (0.28 mmol) was used in place of phenyl chloroformate and DMF in place of DCM in the second step. ES-MS: (M+H)⁺ 368, (M+Na)⁺ 390

Example 45

[4-(6-ethylthiopheno[3,2-e]pyrimidin-4-yl)piperazinyl]-N-benzylcarboxamide

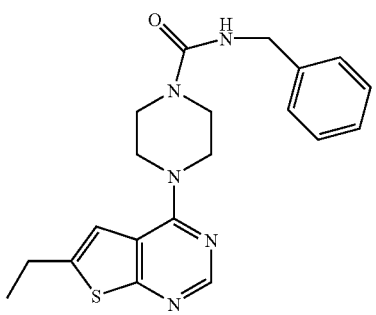

The title compound was obtained as a TFA salt by essentially following Example 3 except benzyl isocyanate (0.28 mmol) was used in place of phenyl chloroformate and DMF in place of DCM in the second step. ES-MS: (M+H)⁺ 382, (M+Na)⁺ 404

Example 46

[4-(6-ethylthiopheno[3,2-e]pyrimidin-4-yl)piperazinyl]-N-(2-phenylethyl)carboxamide

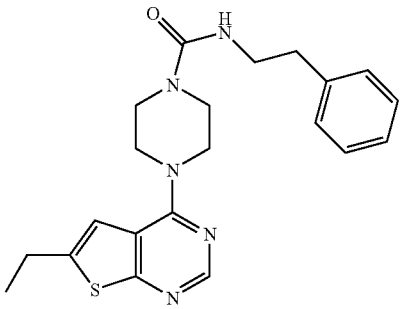

The title compound was obtained as a TFA salt by essentially following Example 36 except 2-phenethylamine was used in place of ethylamine, and 1,1'-carbonyldiimidazole (CDI) was used in place of DSC. ES-MS: (M+H)⁺ 396 (M+Na)⁺ 418

Example 47

[4-(6-ethylthiopheno[3,2-e]pyrimidin-4-yl)piperazinyl]-N-(3-phenylpropyl)carboxamide

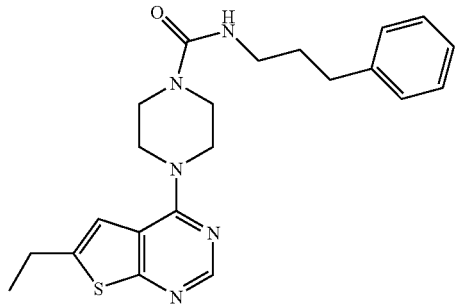

The title compound was obtained as a TFA salt by essentially following Example 36 except 3-phenyl-1-propylamine was used in place of ethylamine. ES-MS: (M+H)$^+$ 410 (M+Na)$^+$ 432

Example 48

N-(5-ethyl(1,3,4-thiadiazol-2-yl))[4-(6-ethylthiopheno[3,2-e]pyrimidin-4-yl)piperazinyl]carboxamide

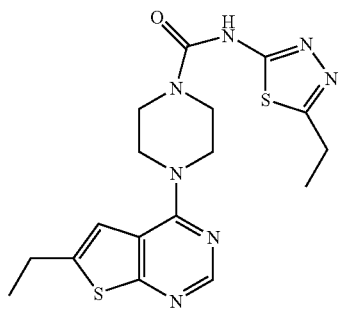

The title compound was obtained as a TFA salt by essentially following Example 36 except 2-amino-5-ethyl-1,3,4-thiadiazole was used in place of ethylamine. ES-MS: (M+H)$^+$ 404, (M+Na)$^+$ 426

Example 49

[4-(6-ethylthiopheno[3,2-e]pyrimidin-4-yl)piperazinyl]-N-(5-phenyl(1,3,4-thiadiazol-2-yl))carboxamide

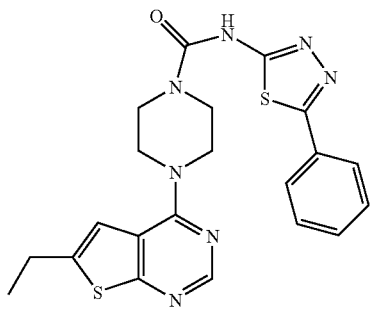

The title compound was obtained as a TFA salt by essentially following Example 36 except 2-amino-5-phenyl-1,3,4-thiadiazole was used in place of ethylamine. ES-MS: (M+H)$^+$ 452

Example 50

[4-(6-ethylthiopheno[3,2-e]pyrimidin-4-yl)piperazinyl]-N-[5-(trifluoromethyl)(1,3,4-thiadiazol-2-yl)]carboxamide

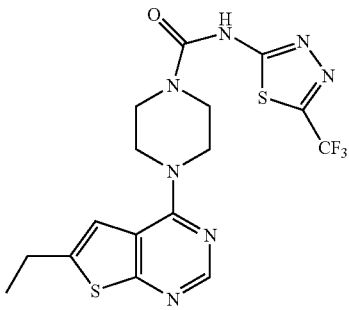

The title compound was obtained as a TFA salt by essentially following Example 36 except 2-amino-5-trifluoromethyl-1,3,4-thiadiazole was used in place of ethylamine, and the HCl salt obtained in Example 5, Step 1 was used in place of the TFA salt. ES-MS: (M+H)$^+$ 444

Example 51

N-[(5-chloro(2-thienyl))sulfonyl][4-(6-ethylthiopheno[3,2-e]pyrimidin-4-yl)piperazinyl]carboxamide

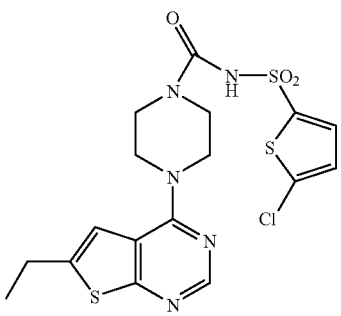

The title compound was obtained as a TFA salt by essentially following Example 36 except 5-chloro-2-sulfonamido-thiophene was used in place of ethylamine, CDI was used in place of DSC, and the HCl salt obtained in Example 5, Step 1 was used in place of the TFA salt. ES-MS: (M+H)$^+$ 472

Example 52

(butylamino)[4-(6-ethylthiopheno[3,2-e]pyrimidin-4-yl)piperazinyl]methane-1-thione

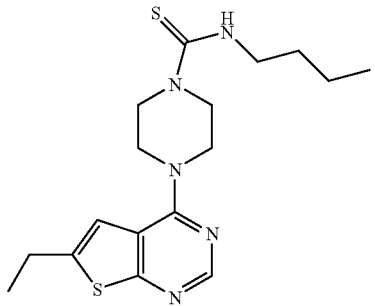

The title compound was obtained as a TFA salt by essentially following Example 3 except n-butyl isothiocyanate (0.28 mmol) was used in place of phenyl chloroformate and DMF in place of DCM in the second step. ES-MS: (M+H)+ 364

Example 53

[(tert-butyl)amino][4-(6-ethylthiopheno[3,2-e]pyrimidin-4-yl)piperazinyl]methane-1-thione

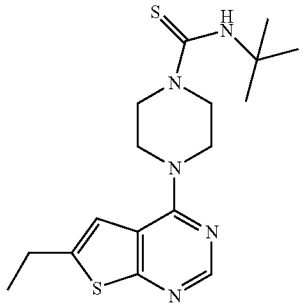

The title compound was obtained as a TFA salt by essentially following Example 3 except tert-butyl isothiocyanate (0.28 mmol) was used in place of phenyl chloroformate and DMF in place of DCM in the second step. ES-MS: (M+H)+ 364

Example 54

[4-(6-ethylthiopheno[3,2-e] pyrimidin-4-yl)piperazinyl](phenylamino)methane-1-thione

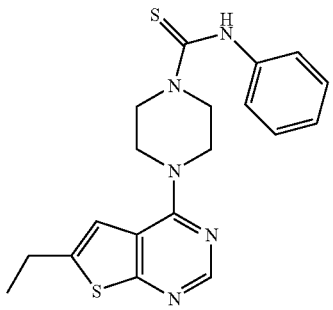

The title compound was obtained as a TFA salt by essentially following Example 3 except phenyl isothiocyanate (0.28 mmol) was used in place of phenyl chloroformate and DMF in place of DCM in the second step. ES-MS: (M+H)+ 384

Example 55

1-[4-(6-ethylthiopheno[3,2-e]pyrimidin-4-yl)piperazinyl]-2,2,2-trifluoroethan-1-one

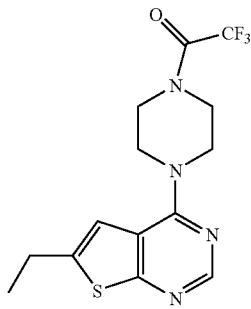

The title compound was obtained as a TFA salt by essentially following Example 3 except that trifluoromethanesulfonic anhydride (0.21 mmol) was used in place of phenyl chloroformate and the DIEA was added after the anhydride. The change in the order of addition caused the mixed anhydride to form, and then the trifluoroacetate was exclusively transferred. ES-MS: (M+H)+ 345

Example 56

1-[4-(6-ethylthiopheno[3,2-e]pyrimidin-4-yl)piperazinyl]-2,2,3,3,3-pentafluoropropan-1-one

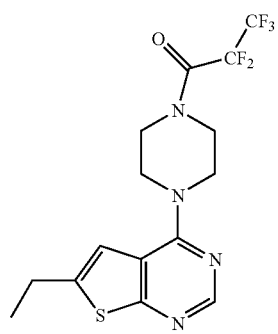

The title compound was obtained in 7% yield as a TFA salt by essentially following Example 3 except pentafluoropropionic anhydride (0.21 mmol) was used in place of phenyl chloroformate. The majority of the material isolated was compound 55. ES-MS: (M+H)+ 395

Example 57

(2Z)-1-[4-(6-ethylthiopheno[3,2-e]pyrimidin-4-yl) piperazinyl]-4,4,4-trifluoro-3-methylbut-2-en-1-one

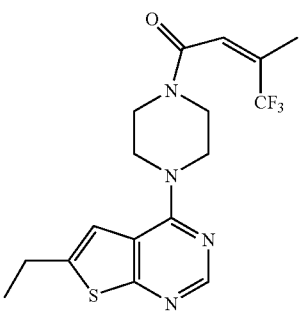

The title compound was obtained as a TFA salt by essentially following Example 3 except heptafluorobutanoyl chloride (0.21 mmol) was used in place of phenyl chloroformate. ES-MS: (M+H)+ 445

Example 58

1-[4-(6-ethylthiopheno[3,2-e]pyrimidin-4-yl)piperazinyl]-2,2,3,3,4,4,4-heptafluorobutan-1-one

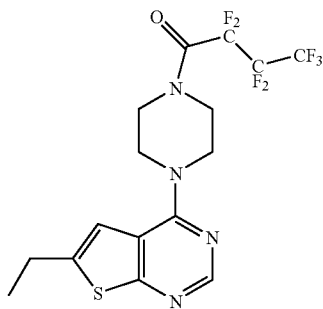

The title compound was obtained as a TFA salt by essentially following Example 2 using the material obtained in Example 5, Step 1 and β-trifluoromethylcrotonic acid in place of phenylacetic acid. ES-MS: (M+H)+ 385

Example 59

1-[4-(6-ethylthopheno[3,2-e]pyrimidin-4-yl)pperazinyl]-4,4,4-trifluoro-3-(trifluoromethyl)but-2-en-1-one

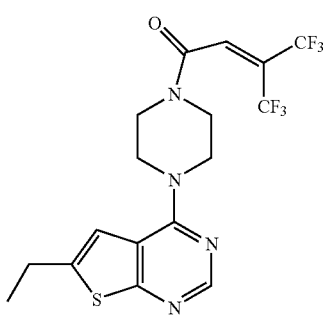

The title compound was obtained as a TFA salt by essentially following Example 2 using the material obtained in Example 5, Step 1 and 4,4,4-trifluoro-3-trifluoromethylcrotonic acid in place of phenylacetic acid. ES-MS: (M+H)+ 439

Example 60

1-[4-(6-ethylthiopheno[3,2-e]pyrimidin-4-yl)piperazinyl]-4,4,4-trifluoro-3-(trifluoromethyl)butan-1-one

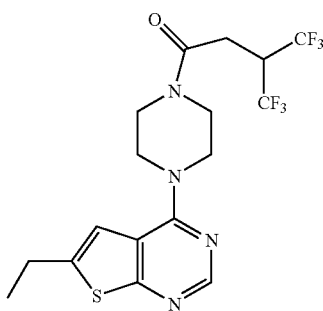

The title compound was obtained as a TFA salt by essentially following Example 2 using the material obtained in Example 5, Step 1 and 4,4,4-trifluoro-3-trifluoromethylbutyric acid in place of phenylacetic acid. ES-MS: (M+H)+ 441

Example 61

3-(difluoromethyl)-1-[4-(6-ethylthiopheno[3,2-e]pyrimidin-4-yl)piperazinyl]-4,4,4-trifluorobutan-1-one

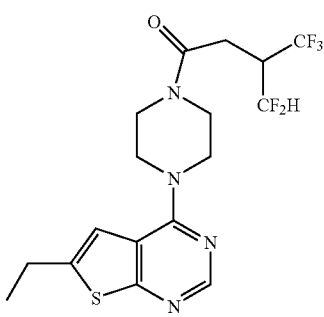

The title compound was obtained as a TFA salt as a by-product from Example 60. The source of the acid incorporated in this example is an impurity from the commercially available 4,4,4-trifluoro-3-trifluoromethylbutyric acid. ES-MS: (M+H)+ 423

Example 62

1-[4-(6-ethylthiopheno[3,2-e]pyrimidin-4-yl)piperazinyl]-4,4,4-trifluoro-3-methylbutan-1-one

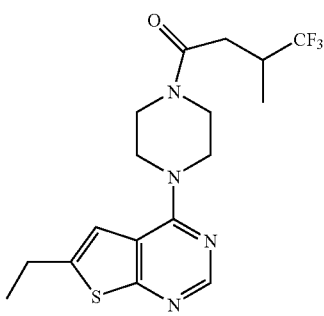

The title compound was obtained as a TFA salt by essentially following Example 2 using the material obtained in Example 5, Step 1 and 3-trifluoromethylbutyric acid in place of phenylacetic acid. ES-MS: (M+H)+ 387

Example 63

(2E)-1-[4-(6-ethylthiopheno[3,2-e]pyrimidin-4-yl)piperazinyl]-4,4,4-trifluorobut-2-en-1-one

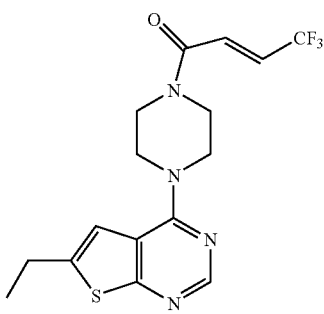

The title compound was obtained as a TFA salt by essentially following Example 2 using the material obtained in Example 5, Step 1 and 4,4,4-trifluorocrotonic acid in place of phenylacetic acid. ES-MS: (M+H)+ 371

Example 64

1-[4-(6-ethylthiopheno[3,2-e]pyrimidin-4-yl)piperazinyl]-4,4,4-trifluorobutan-1-one

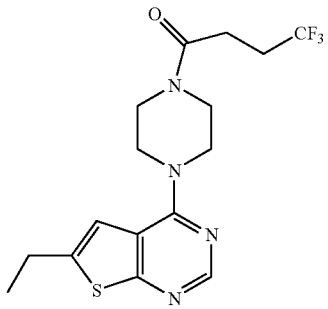

The title compound was obtained as a TFA salt by essentially following Example 2 using the material obtained in Example 5, Step 1 and 4,4,4-trifluorobutyric acid in place of phenylacetic acid. ES-MS: (M+H)$^+$ 373

Example 65

2-benzotriazolyloxy-1-[4-(6-ethylthiopheno[3,2-e]pyrimidin-4-yl)piperazinyl]ethan-1-one

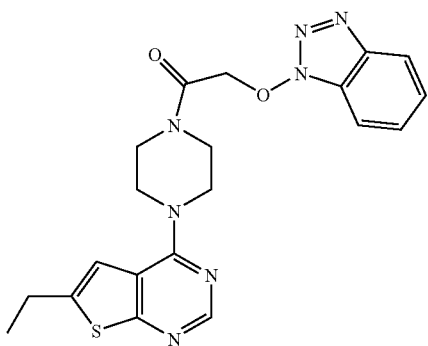

The compound from Example 1 was treated with TFA as described in Example 2. To the resulting residue at rt under argon was added DCM (1 mL), DIEA (0.15 mL, 0.84 mmol), and then bromoacetyl bromide (0.013 mL, 0.15 mmol) was added dropwise. After stirring for 20 minutes, N(1)-hydroxybenzotriazole (28 mg, 0.21 mmol) was added. Stirring was maintained for an additional 1 hr at which time additional DIEA (0.05 mL, 0.28 mmol) was added followed by stirring over night. Evaporation of the solvent followed by prep RP-HPLC gave 32 mgs of the title compound as a TFA salt. ES-MS: (M+H)$^+$ 424

Example 66

1-[4-(6-ethylthiopheno[3,2-e]pyrimidin-4-yl)piperazinyl]-2-(4-fluorophenyl)ethan-1-one

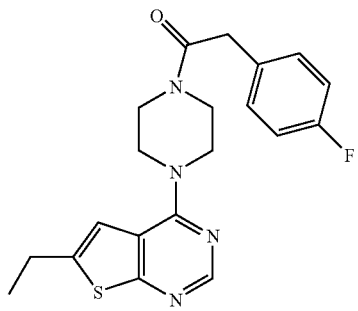

The title compound was obtained as a TFA salt by essentially following Example 2 using 4-fluorophenylacetic acid in place of phenylacetic acid. ES-MS: (M+H)$^+$ 385, (M+Na)$^+$ 407.

Example 67

1-[4-(6-ethylthiopheno[3,2-e]pyrimidin-4-yl)piperazinyl]-2-(4-pyridyl)ethan-1-one

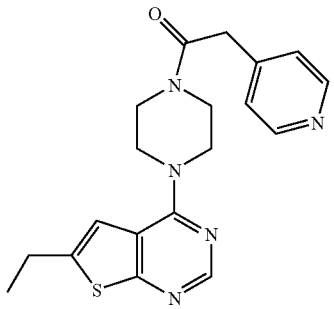

The title compound was obtained as a TFA salt by essentially following Example 2 using 4-pyridylacetic acid hydrochloride in place of phenylacetic acid. ES-MS: (M+H)$^+$ 368, (M+Na)$^+$ 390.

Example 68

1-[4-(6-ethylthiopheno[3,2-e]pyrimidin-4-yl)piperazinyl]-2-(3-pyridyl)ethan-1-one

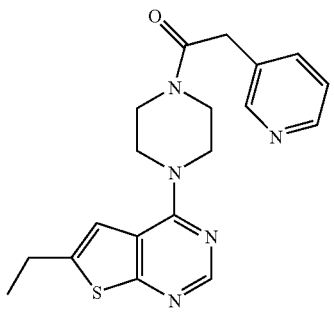

The title compound was obtained as a TFA salt by essentially following Example 2 using 3-pyridylacetic acid hydrochloride in place of phenylacetic acid. ES-MS: (M+H)$^+$ 368, (M+Na)$^+$ 390.

Example 69

1-[4-(6-ethylthiopheno[3,2-e]pyrimidin-4-yl)piperazinyl]-2-(2-pyridyl)ethan-1-one

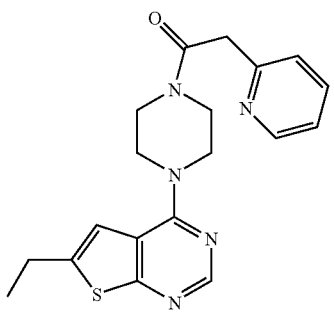

The title compound was obtained as a TFA salt by essentially following Example 2 using 2-pyridylacetic acid hydrochloride in place of phenylacetic acid. ES-MS: (M+H)$^+$ 368, (M+Na)$^+$ 390, (2M+Na)$^+$ 757.

Example 70

1-[4-(6-ethylthiopheno[3,2-e]pyrimidin-4-yl)piperazinyl]-2,2-diphenylethan-1-one

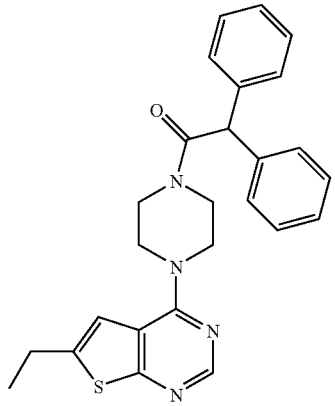

The title compound was obtained as a TFA salt by essentially following Example 3 except diphenylacetyl chloride (0.17 mmol) was used in place of phenyl chloroformate. ES-MS: (M+H)⁺ 443, (M+Na)⁺ 465.

Example 71

4-(6-ethylthiopheno[3,2-e]pyrimidin-4-yl)piperazinyl 4-phenylphenyl ketone

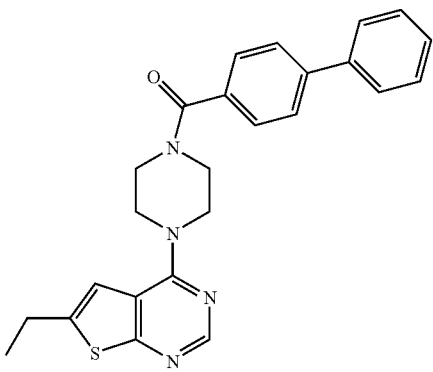

The title compound was obtained as a TFA salt by essentially following Example 3 except 4-biphenylcarbonyl chloride (0.17 mmol) was used in place of phenyl chloroformate. ES-MS: (M+H)⁺ 429.

Example 72

1-[4-(6-ethylthiopheno[3,2-e]pyrimidin-4-yl)piperazinyl]-2-(4-phenylphenyl)ethan-1-one

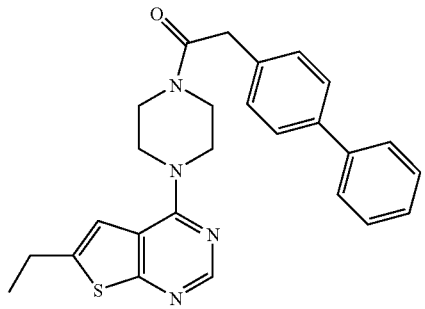

The title compound was obtained as a TFA salt by essentially following Example 2 using 4-biphenylacetic acid in place of phenylacetic acid. ES-MS: (M+H)⁺ 443, (M+Na)⁺ 465.

Example 73

4-(6-ethylthiopheno[3,2-e]pyrimidin-4-yl)piperazinyl 4-methoxyphenyl ketone

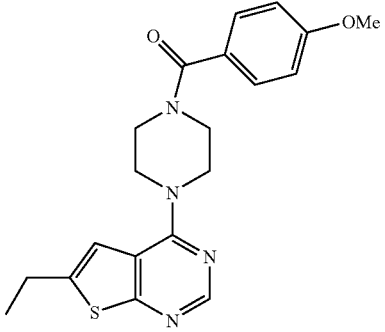

The title compound was obtained as a TFA salt by essentially following Example 3 except 4-methoxybenzoyl chloride (0.15 mmol) was used in place of phenyl chloroformate. ES-MS: (M+H)⁺ 383.

Example 74

4-chlorophenyl 4-(6-ethylthiopheno[3,2-e]pyrimidin-4-yl)piperazinyl ketone

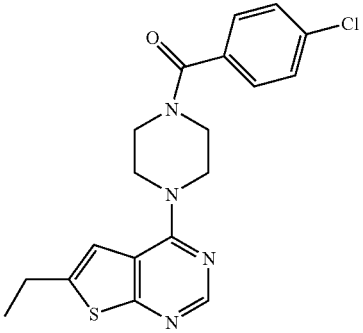

The title compound was obtained as a TFA salt by essentially following Example 3 except 4-chlorobenzoyl chloride (0.15 mmol) was used in place of phenyl chloroformate. ES-MS: (M+H)⁺ 387 and 389.

Example 75

3,4-dichlorophenyl 4-(6-ethylthiopheno[3,2-e]pyrimidin-4-yl)piperazinyl ketone

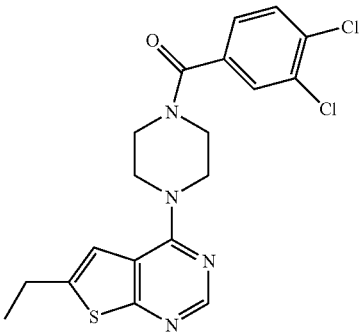

The title compound was obtained as a TFA salt by essentially following Example 2 except 3,4-dichlorobenzoic acid (0.15 mmol) was used in place of phenylacetic acid. ES-MS: (M+H)+ 421, 422, 423.

Example 76

4-(6-ethylthiopheno[3,2-e]pyrimidin-4-yl)piperazinyl 4-methylphenyl ketone

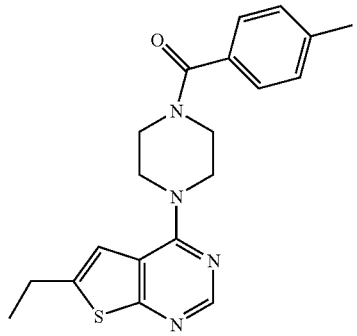

The title compound was obtained as a TFA salt by essentially following Example 2 except p-toluic acid (0.15 mmol) was used in place of phenylacetic acid. ES-MS: (M+H)+ 367.

Example 77

4-(6-ethylthiopheno[3,2-e]pyrimidin-4-yl)piperazinyl 4-nitrophenyl ketone

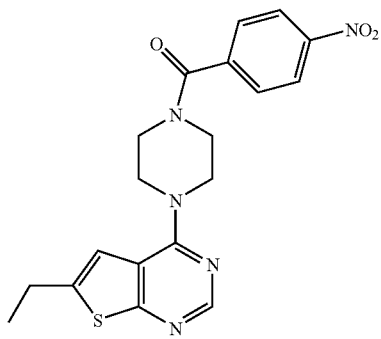

The title compound was obtained as a TFA salt by essentially following Example 3 except 4-nitrobenzoyl chloride (0.15 mmol) was used in place of phenyl chloroformate. ES-MS: (M+H)+ 398.

Example 78

4-(6-ethylthiopheno[3,2-e]pyrimidin-4-yl)piperazinyl 4-fluorophenyl ketone

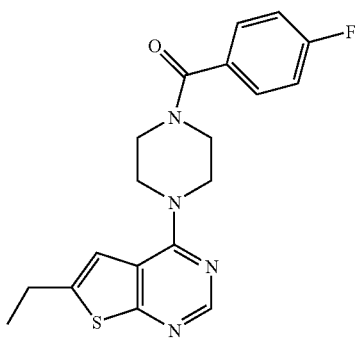

The title compound was obtained as a TFA salt by essentially following Example 2 except 4-fluorobenzoic acid (0.15 mmol) was used in place of phenylacetic acid. ES-MS: (M+H)+ 371.

Example 79

4-(6-ethylthiopheno[3,2-e]pyrimidin-4-yl)piperazinyl 4-methylthiophenyl ketone

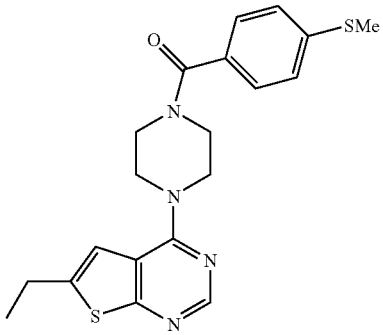

The title compound was obtained as a TFA salt by essentially following Example 2 except 4-thiomethylbenzoic acid (0.15 mmol) was used in place of phenylacetic acid. ES-MS: (M+H)+ 399.

Example 80

4-(6-ethylthiopheno[3,2-e]pyrimidin-4-yl)piperazinyl 4-(methylsulfonyl)phenyl ketone

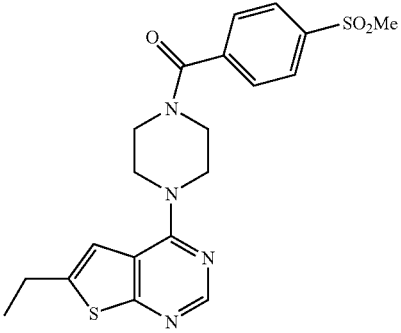

The title compound was obtained as a TFA salt by essentially following Example 2 except 4-(methylsulfonyl)benzoic acid (0.15 mmol) was used in place of phenylacetic acid. ES-MS: (M+H)+ 431.

Example 81

4-aminophenyl 4-(6-ethylthiopheno[3,2-e]pyrimidin-4-yl)piperazinyl ketone

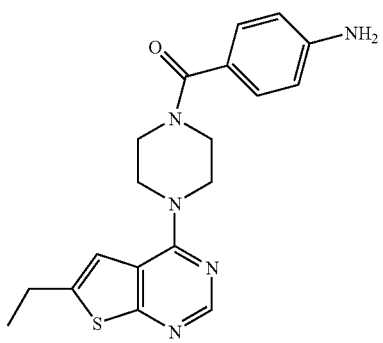

The title compound was obtained as a TFA salt by essentially following Example 2 except 4-aminobenzoic acid (0.15 mmol) was used in place of phenylacetic acid. ES-MS: (M+H)+ 368.

Example 82

4-(dimethylamino)phenyl 4-(6-ethylthiopheno[3,2-e]pyrimidin-4-yl)piperazinyl ketone

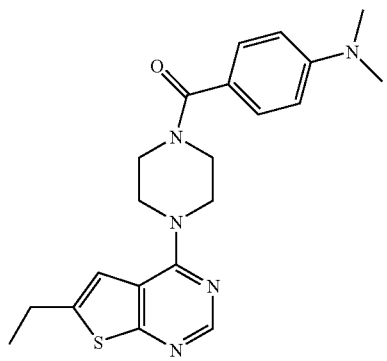

The title compound was obtained as a TFA salt by essentially following Example 3 except 4-(dimethylamino)benzoyl chloride (0.15 mmol) was used in place of phenyl chloroformate. ES-MS: (M+H)+ 396.

Example 83

1-(4-{[4-(6-ethylthiopheno[3,2-e]pyrimidin-4-yl)piperazinyl]carbonyl}phenyl)ethan-1-one

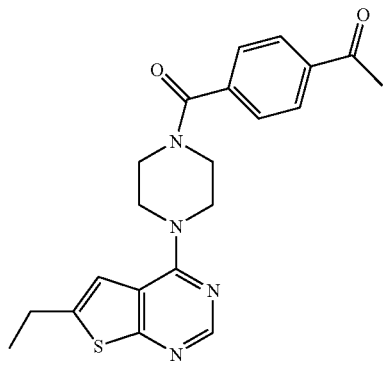

The title compound was obtained as a TFA salt by essentially following Example 2 except 4-acetylbenzoic acid (0.14 mmol) was used in place of phenylacetic acid. ES-MS: (M+H)+ 395.

Example 84

N-(4-{[4-(6-ethylthiopheno[3,2-e]pyrimidin-4-yl)piperazinyl]carbonyl}phenyl)acetamide

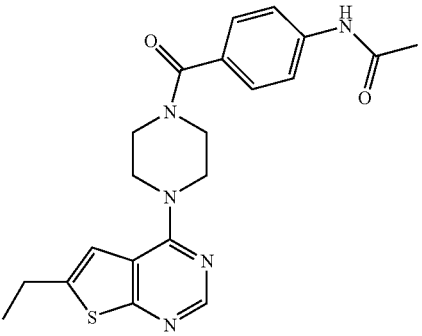

The title compound was obtained as a TFA salt by essentially following Example 2 except 4-acetamidobenzoic acid (0.14 mmol) was used in place of phenylacetic acid. ES-MS: (M+H)+ 410.

Example 85

4-{[4-(6-ethylthiopheno[3,2-e]pyrimidin-4-yl)piperazinyl]carbonyl}benzenesulfonamide

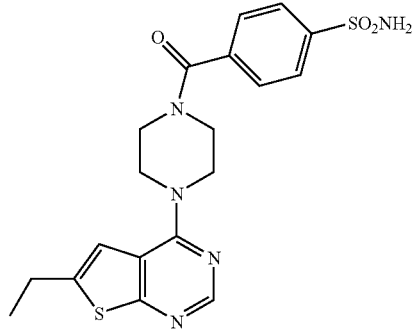

The title compound was obtained as a TFA salt by essentially following Example 2 except 4-carboxybenzenesulfonamide (0.14 mmol) was used in place of phenylacetic acid. ES-MS: (M+H)+ 432.

Example 86

4-(6-ethylthiopheno[3,2-e]pyrimidin-4-yl)piperazinyl 4-(phenylcarbonyl)phenyl ketone

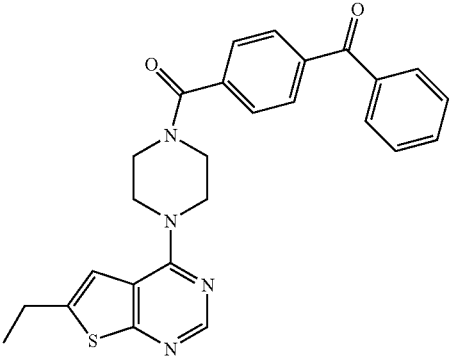

The title compound was obtained as a TFA salt by essentially following Example 2 except 4-benzoylbenzoic acid (0.14 mmol) was used in place of phenylacetic acid. ES-MS: (M+H)+ 457.

Example 87 tert-butyl 4-(6-methylthiopheno[3,2-e]pyrimidin-4-yl)piperazinecarboxylate

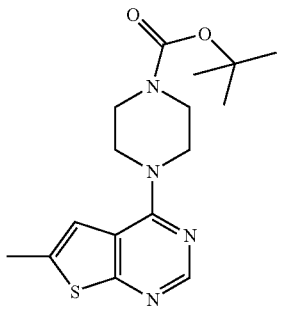

Step 1:

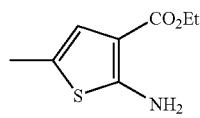

To sulfur (3.33 gm, 104 mmol) suspended in dry DMF (13 mL) at rt under argon in a 3-neck round bottom flask equipped with an internal thermometer was added ethyl cyanoacetate (11.05 mL, 104 mmol) followed by slow addition of Et₃N (7.3 mL, 52 mmol) which caused the solution to turn dark brown. Then propionaldehyde (7.5 mL, 104 mmol) was added dropwise (EXOTHERMIC) via syringe while maintaining the internal temperature below 50° C. (45–48° C.). The resulting solution was stirred over night while it slowly cooled to it, and then it was poured into brine (150 mL). The brine was washed with Et₂O (5×100 mL), and the Et₂O was dried with Na₂SO₄, filtered, and evaporated to dryness. The crude product was purified with flash chromatography (gradient elution, hexane/DCM: 2:1, 1-1, 1:5, 0:1) to afford 81% of the desired product as a reddish oil which solidified on standing. ES-MS: (M+H)+ 186.

Step 2:

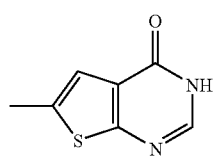

To the material from step 1 (5.0 gm, 27 mmol) was added formamide (16 mL, 405 mmol) at rt under argon followed by ammonium formate (3.41 gm, 54 mmol). The resulting solution was warmed to 150–155° C. and stirred over night. After cooling to rt, the mostly solidified reaction mixture was transferred to a cold brine solution and swirled vigorously for 15 minutes. The off-white solid was filtered, air dried for an hour, and then stored under high vacuum over night to afford a 96% yield of the desired product. ES-MS: (M+H)+ 167.

Step 3:

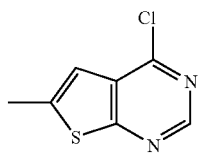

The material from step 2 was treated in the same manner as described in Example 1, Step 3, Method B to afford 91% of the desired chlorothienopyrimidine. ES-MS: (M+H)+185/187.

Step 4:

The title compound was obtained by mixing the material from step 3 (500 mg, 2.71 mmol) in MeCN (11 mL) at rt under argon with DIEA (1.9 mL, 11 mmol). To this solution was then added Boc-piperazine (553 mgs, 3.0 mmol). The mixture was then warmed to 80–85° C. for 1.5 hrs (followed by analytical RP-HPLC). The solvent was evaporated under reduced pressure and water (30 mL) was added. The water was washed with DCM (3-×15 mL), and the DCM was dried with MgSO₄, filtered, and removed in vacuuo to afford a 98% yield of the desired product. ES-MS: (M+H)+ 335.

Example 88 tert-butyl 4-(6-propylthiopheno[3,2-e]pyrimidin-4-yl)piperazinecarboxylate

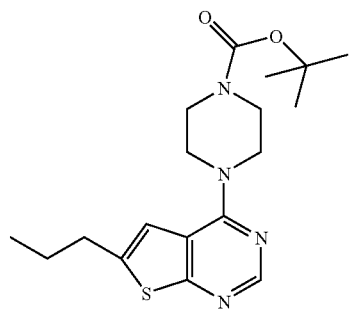

The title compound was obtained by essentially following Example 87 except using valeraldehyde instead of propionaldehyde in Step 1. ES-MS: (M+H)+ 363

Example 89 tert-butyl 4-(6-pentylthiopheno[3,2-e]pyrimidin-4-yl)piperazinecarboxylate

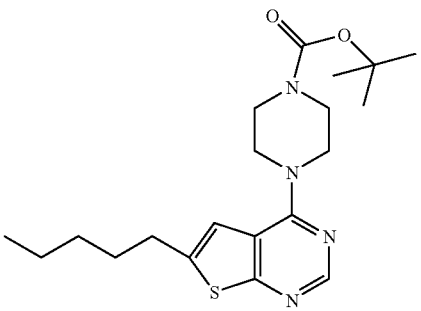

The title compound was obtained by essentially following Example 87 except using heptaldehyde instead of propionaldehyde in Step 1. ES-MS: (M+H)+ 391

Example 90 tert-butyl 4-[6-(tert-butyl)thiopheno[3,2-e]pyrimidin-4-yl]piperazinecarboxylate

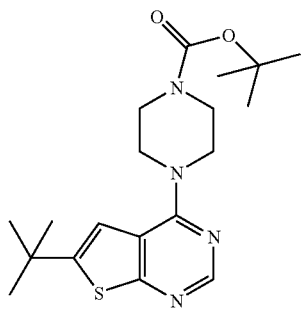

The title compound was obtained by essentially following Example 87 except using 3,3-dimethylbutyraldehyde instead of propionaldehyde in Step 1. ES-MS: (M+H)+ 377.

Example 91 tert-butyl 4-(6-phenylthiopheno[3,2-e]pyrimidin-4-yl)piperazinecarboxylate

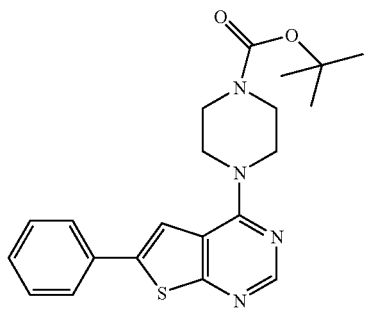

The title compound was obtained by essentially following Example 87 except using phenylacetaldehyde instead of propionaldehyde in Step 1. ES-MS: (M+H)+ 397.

Example 92 tert-butyl 4-[6-benzylthiopheno[3,2-e]pyrimidin-4-yl]piperazinecarboxylate

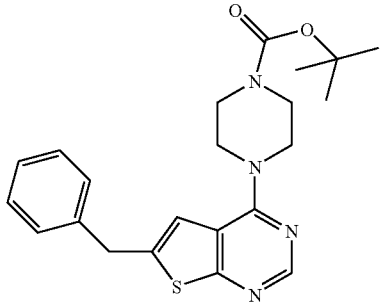

The title compound was obtained by essentially following Example 87 except using hydrocinnamaldehyde instead of propionaldehyde in Step 1. ES-MS: (M+H)+ 411.

Example 93 tert-butyl 4-(6-ethyl-5-methylthiopheno[3,2-e]pyrimidin-4-yl)piperazinecarboxylate Step 1:

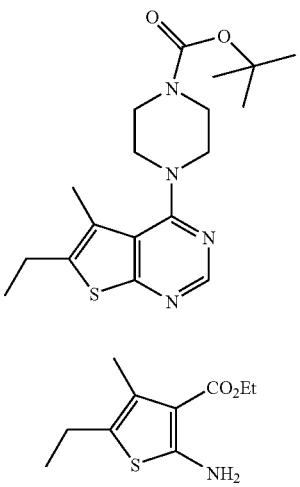

To 2-pentanone (10.7 mL, 100 mmol) in EtOH at rt under argon was added S$_8$ (3.5 gm, 110 mmol) followed by ethyl cyanoacetate (10.6 mL, 100 mmol). To this solution morpholine (10 ml, 115 mmol) was then slowly added. Upon the addition of ⅓ of the morpholine, the reaction was placed in an oil bath preheated to 40–45° C. When the morpholine was completely added, the reaction was warmed to 60–65° C. and stirring was maintained for 3.5 hrs. The mixture was cooled to rt, poured into 150 mL of ice-cold H$_2$O, and then extracted with DCM (3-×50 mL). The combined DCM washes were dried with MgSO$_4$, filtered, and evaporated under reduced pressure to afford a mixture of 2 isomers that were only partially separable with flash chromatography. The desired isomer was cleanly obtained in 6% yield. The isomer is described in Example 94. The mixture (52% yield) was carried forward and separated in the next step. ES-MS: (M+H)+ 214.

Step 2:

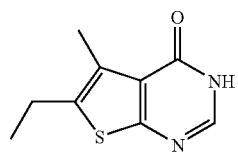

The desired compound was obtained in 43% yield after flash chromatographic purification of the mixture of isomers after treating the material from step 1 essentially the same as described in step 2 of Example 87. ES-MS: (M+H)+ 195.

Step 3.

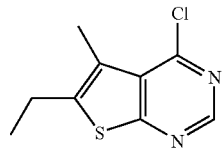

Treatment of the material from step 2 of this example with SOCl$_2$ as described in Example 87 afforded a quantitative yield of the chlorothienylpyrimidine as an HCl salt. ES-MS: (M+H)+ 213/215.

Step 4:

The title compound was obtained in 97% yield by essentially following Example 87, step 4 using the material obtained in step 3 of this example. ES-MS: (M+H)+ 363.

Example 94 tert-butyl 4-(5-propylthiopheno[3,2-e]pyrimidin-4-yl)piperazinecarboxylate

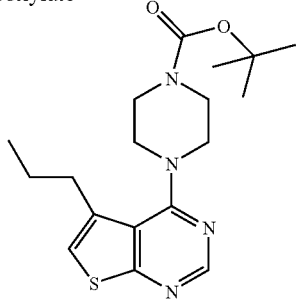

The title compound was obtained from the 2$^{nd}$ isomer from Example 93, step 2 by essentially the same procedure used in Example 87. ES-MS: (M+H)+ 363.

Example 95 tert-butyl 4-[6-(2,2,2-trifluoroethyl)thiopheno[3,2-e]pyrimidin-4-yl]piperazinecarboxylate The title compound was obtained by essentially following Example 87 except using 3,3,3-trifluorobutyraldehyde instead of propionaldehyde in Step 1. ES-MS: (M+H)+ 403.

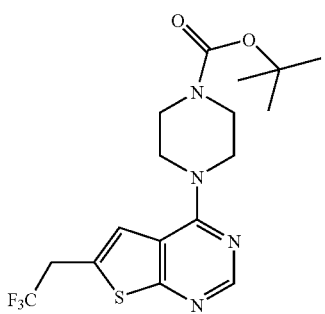

Example 96

4-benzotriazolyloxy-1-[4-(6-methylthiopheno[3,2-e]pyrimidin-4-yl)piperazinyl]butan-1-one

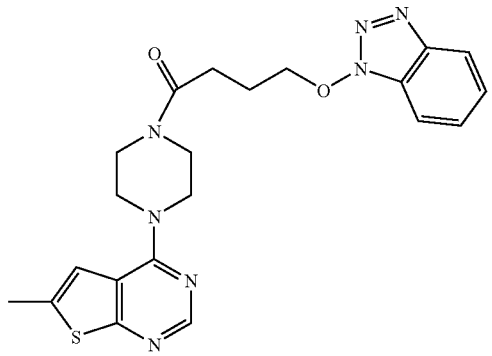

The title compound was obtained as a TFA salt by essentially the same method as for Example 2 using 87 instead of 1 and 4-benzotriazolyloxybutanoic acid from Example 4 instead of phenylacetic acid. ES-MS: (M+H)+ 438, (M+Na)+ 460.

Example 97

1-[4-(6-methylthiopheno[3,2-e]pyrimidin-4-yl)piperazinyl]-2-phenylethan-1-one

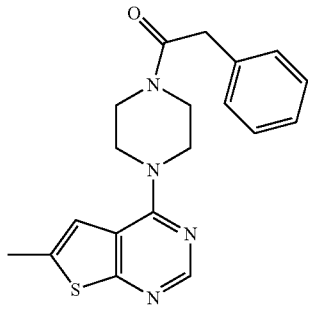

The title compound was obtained as a TFA salt by essentially the same method as for Example 2 using 87 instead of 1. ES-MS: (M+H)+ 438, (M+Na)+ 460.

Example 98 phenyl 4-(6-methylthiopheno[3,2-e]pyrimidin-4-yl)piperazinecarboxylate

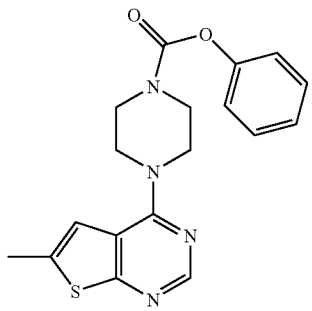

The title compound was obtained as a TFA salt by essentially the same method as for Example 3 using 87 instead of 1. ES-MS: (M+H)+ 355.

Example 99

2-phenyl-1-[4-(6-propylthiopheno[3,2-e]pyrimidin-4-yl)piperazinyl]ethan-1-one

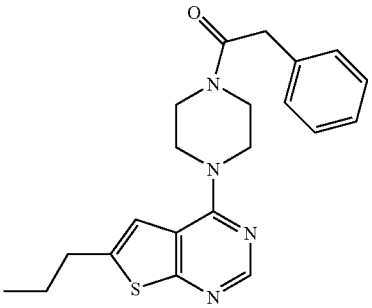

The title compound was obtained as a TFA salt by essentially following Example 3 except phenylacetyl chloride (0.15 mmol) was used in place of phenyl chloroformate and 88 instead of 1. ES-MS: (M+H)+ 381, (M+Na)+ 403.

Example 100

4-benzotriazolyloxy-1-[4-(6-propylthiopheno[3,2-e]pyrimidin-4-yl)piperazinyl]butan-1-one

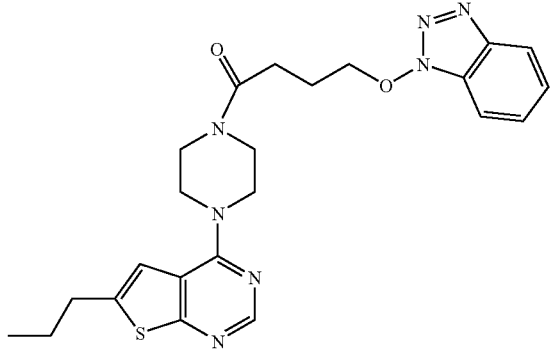

The title compound was obtained as a TFA salt by essentially the same method as for Example 2 using 88 instead of 1 and 4-benzotriazolyloxybutanoic acid from Example 4 instead of phenylacetic acid. ES-MS: (M+H)+ 466, (M+Na)+ 488.

Example 101 phenyl 4-(6-propylthiopheno[3,2-e]pyrimidin-4-yl)piperazinecarboxylate

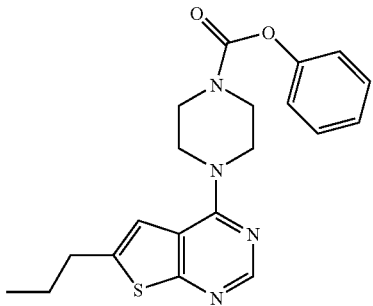

The title compound was obtained as a TFA salt by essentially following Example 3 using 88 instead of 1. ES-MS: (M+H)+ 383, (M+Na)+ 405.

Example 102

3,3,3-trifluoro-1-[4-(6-propylthiopheno[3,2-e]pyrimidin-4-yl)piperazinyl]propan-1-one

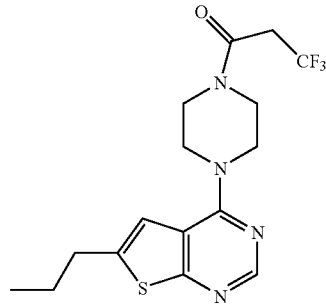

The title compound was obtained as a TFA salt by essentially following Example 5 using 88 instead of 1. ES-MS: (M+H)+ 373, (M+Na)+ 395.

Example 103

1-[4-(6-pentylthiopheno[3,2-e]pyrimidin-4-yl)piperazinyl]-2-phenylethan-1-one

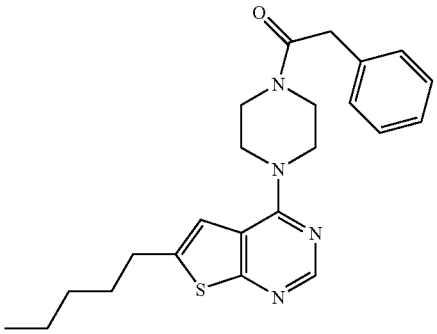

The title compound was obtained as a TFA salt by essentially following Example 3 except phenylacetyl chloride (0.15 mmol) was used in place of phenyl chloroformate and 89 instead of 1. ES-MS: (M+H)+ 409.

Example 104

4-benzotriazolyloxy-1-[4-(6-pentylthiopheno[3,2-e]pyrimidin-4-yl)piperazinyl]butan-1-one

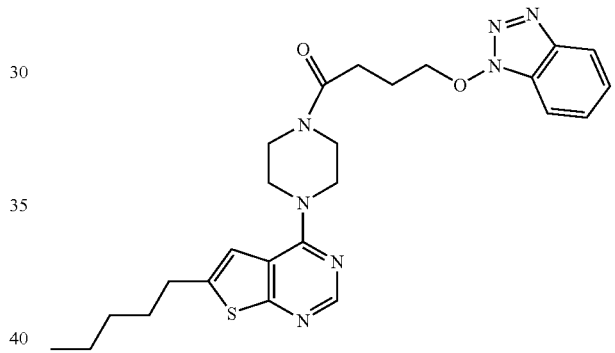

The title compound was obtained as a TFA salt by essentially the same method as for Example 2 using 89 instead of 1 and 4-benzotriazolyloxybutanoic acid from Example 4 instead of phenylacetic acid. ES-MS: (M+H)+ 494.

Example 105

3,3,3-trifluoro-1-[4-(6-pentylthiopheno[3,2-e]pyrimidin-4-yl)piperazinyl]propan-1-one

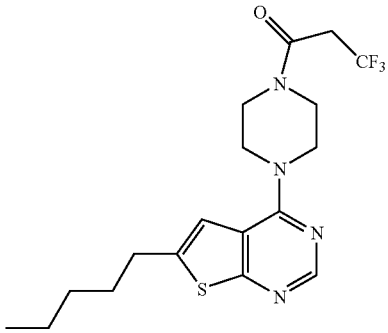

The title compound was obtained as a TFA salt by essentially following Example 5 using 89 instead of 1. ES-MS: (M+H)+ 401.

Example 106

1-{4-[6-(tert-butyl)thiopheno[3,2-e]pyrimidin-4-yl]piperazinyl}-2-phenylethan-1-one

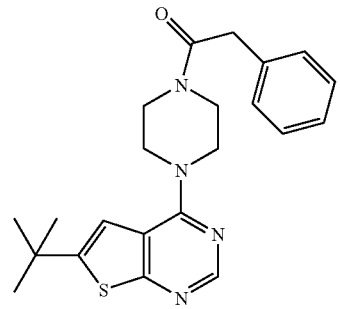

The title compound was obtained as a TFA salt by essentially following Example 3 except phenylacetyl chloride (0.21 mmol) was used in place of phenyl chloroformate and 90 instead of 1. ES-MS: $(M+H)^+$ 395.

Example 107

4-benzotriazolyloxy-1-{4-[6-(tert-butyl)thiopheno[3,2-e]pyrimidin-4-yl]piperazinyl}butan-1-one

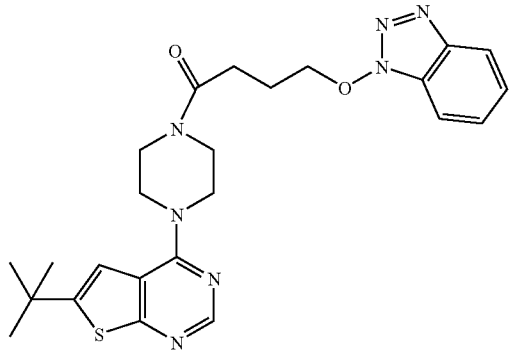

The title compound was obtained as a TFA salt by essentially the same method as for Example 2 using 90 instead of 1 and 4-benzotriazolyloxybutanoic acid from Example 4 instead of phenylacetic acid. ES-MS: $(M+H)^+$ 480.

Example 108 phenyl 4-[6-(tert-butyl)thiopheno[3,2-e]pyrimidin-4-yl]piperazinecarboxylate

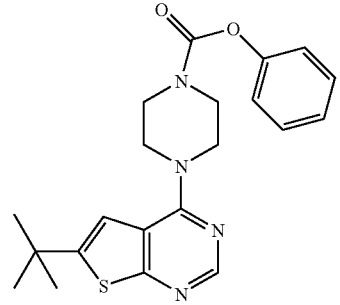

The title compound was obtained as a TFA salt by essentially following Example 3 using 90 instead of 1. ES-MS: $(M+H)^+$ 397.

Example 109

2-phenyl-1-[4-(6-phenylthiopheno[3,2-e]pyrimidin-4-yl)piperazinyl] ethan-1-one

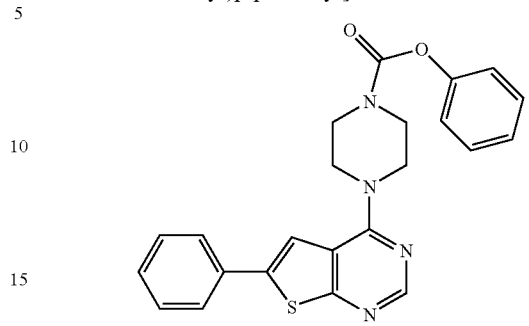

The title compound was obtained as a TFA salt by essentially following Example 3 except phenylacetyl chloride (0.21 mmol) was used in place of phenyl chloroformate and 91 instead of 1. ES-MS: $(M+H)^+$ 415, $(M+Na)^+$ 437.

Example 110

4-benzotriazolyloxy-1-[4-(6-phenylthiopheno[3,2-e]pyrimidin-4-yl)piperazinyl]butan-1-one

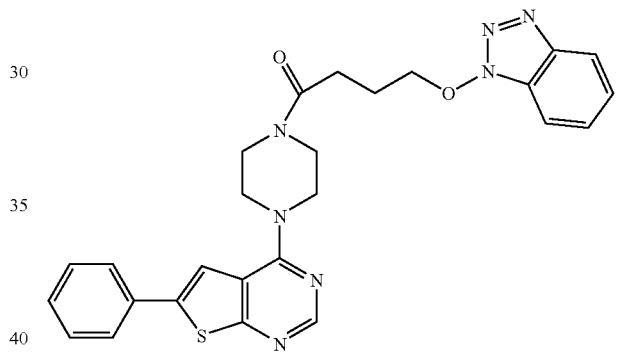

The title compound was obtained as a TFA salt by essentially the same method as for Example 2 using 91 instead of 1 and 4-benzotriazolyloxybutanoic acid from Example 4 instead of phenylacetic acid. ES-MS: $(M+H)^+$ 500.

Example 111

3,3,3-trifluoro-1-[4-(6-phenylthiopheno[3,2-e]pyrimidin-4-yl)piperazinyl]propan-1-one

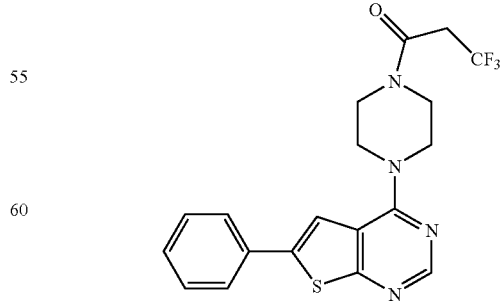

The title compound was obtained as a TFA salt by essentially following Example 5 using 91 instead of 1. ES-MS: $(M+H)^+$ 407.

Example 112

2-phenyl-1-{4-[6-benzylthiopheno[3,2-e]pyrimidin-4-yl]piperazinyl} ethan-1-one

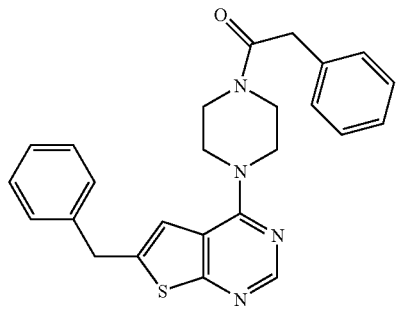

The title compound was obtained as a TFA salt by essentially following Example 3 except phenylacetyl chloride (0.21 mmol) was used in place of phenyl chloroformate and 92 instead of 1. ES-MS: (M+H)$^+$ 429, (M+Na)$^+$ 451.

Example 113

4-benzotriazolyloxy-1-{4-[6-benzylthiopheno[3,2-e]pyrimidin-4-yl]piperazinyl}butan-1-one

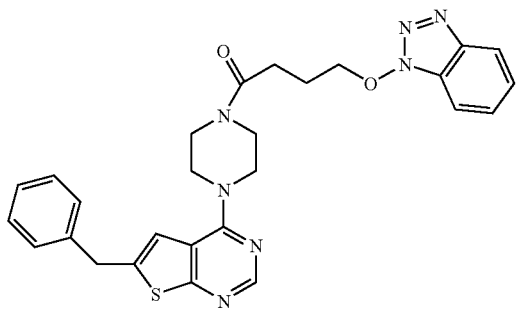

The title compound was obtained as a TFA salt by essentially the same method as for Example 2 using 92 instead of 1 and 4-benzotriazolyloxybutanoic acid from Example 4 instead of phenylacetic acid. ES-MS: (M+H)$^+$ 514, (M+Na)$^+$ 536.

Example 114

3,3,3-trifluoro-1-{4-[6-benzylthiopheno[3,2-e]pyrimidin-4-yl]piperazinyl}propan-1-one

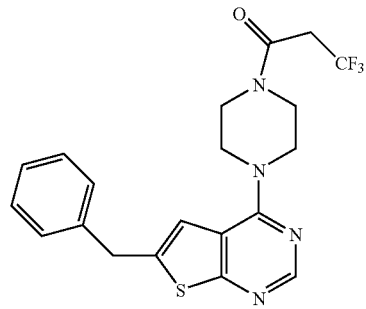

The title compound was obtained as a TFA salt by essentially following Example 5 using 92 instead of 1. ES-MS: (M+H)$^+$ 421, (M+Na)$^+$ 443.

Example 115

1-[4-(6-ethyl-5-methylthiopheno[3,2-e]pyrimidin-4-yl)piperazinyl]-2-phenylethan-1-one

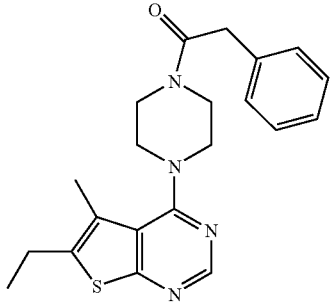

The title compound was obtained as a TFA salt by essentially following Example 3 except phenylacetyl chloride (0.21 mmol) was used in place of phenyl chloroformate and 93 instead of 1. ES-MS: (M+H)$^+$ 381, (M+Na)$^+$ 403.

Example 116

4-benzotriazolyloxy-1-[4-(6-ethyl-5-methylthiopheno[3,2-e]pyrimidin-4-yl)piperazinyl]butan-1-one

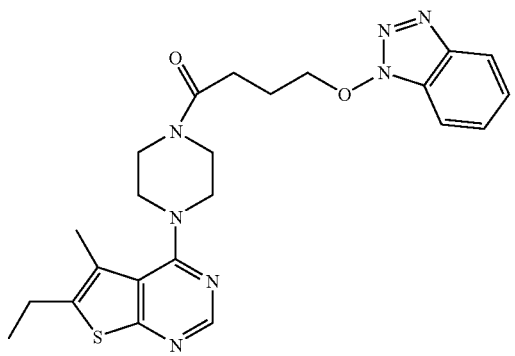

The title compound was obtained as a TFA salt by essentially the same method as for Example 2 using 93 instead of 1 and 4-benzotriazolyloxybutanoic acid from Example 4 instead of phenylacetic acid. ES-MS: (M+H)$^+$ 466, (M+Na)$^+$ 488.

Example 117

1-[4-(6-ethyl-5-methylthiopheno[3,2-e]pyrimidin-4-yl)piperazinyl]-3,3,3-trifluoropropan-1-one

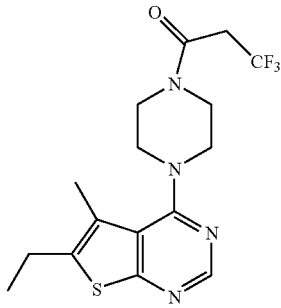

The title compound was obtained as a TFA salt by essentially following Example 5 using 93 instead of 1. ES-MS: (M+H)$^+$ 373.

Example 118

2-phenyl-1-[4-(5-propylthiopheno[3,2-e]pyrimidin-4-yl)piperazinyl]ethan-1-one

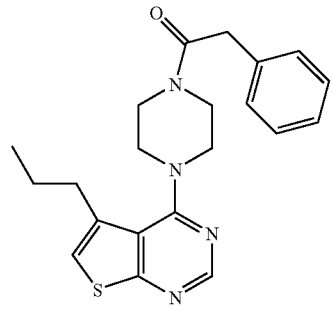

The title compound was obtained as a TFA salt by essentially following Example 3 except phenylacetyl chloride (0.21 mmol) was used in place of phenyl chloroformate and 94 instead of 1. ES-MS: (M+H)$^+$ 381, (M+Na)$^+$ 403.

Example 119

4-benzotriazolyloxy-1-[4-(5-propylthiopheno[3,2-e]pyrimidin-4-yl)piperazinyl]butan-1-one

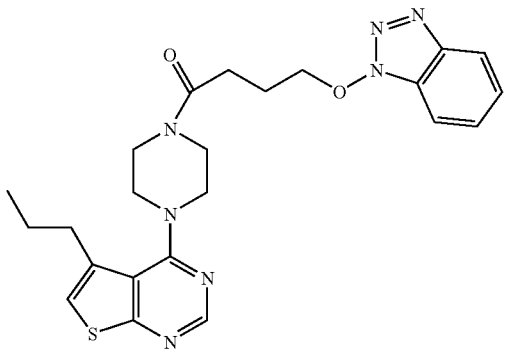

The title compound was obtained as a TFA salt by essentially the same method as for Example 2 using 94 instead of 1 and 4-benzotriazolyloxybutanoic acid from Example 4 instead of phenylacetic acid. ES-MS: (M+H)$^+$ 466, (M+Na)$^+$ 488.

Example 120

3,3,3-trifluoro-1-[4-(5-propylthiopheno[3,2-e]pyrimidin-4-yl)piperazinyl]propan-1-one

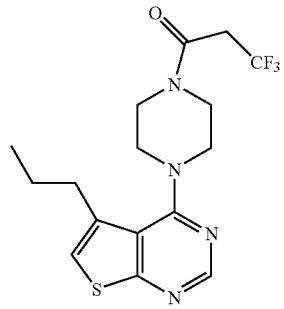

The title compound was obtained as a TFA salt by essentially following Example 5 using 94 instead of 1. ES-MS: (M+H)$^+$ 373, (M+Na)$^+$ 395.

Example 121

2-phenyl-1-{4-[6-(2,2,2-trifluoroethyl)thiopheno[3,2-e]pyrimidin-4-yl]piperazinyl}ethan-1-one

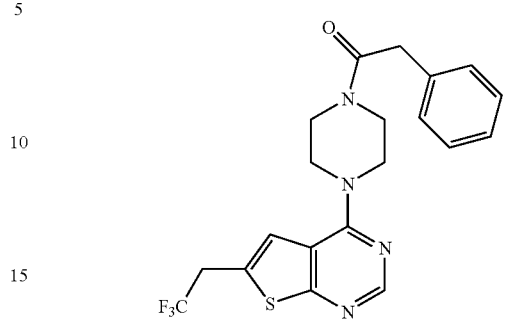

The title compound was obtained as a TFA salt by essentially following Example 3 except phenylacetyl chloride (0.21 mmol) was used in place of phenyl chloroformate and 95 instead of 1. ES-MS: (M+H)$^+$ 421, (M+Na)$^+$ 443.

Example 122

4-benzotriazolyloxy-1-{4-[6-(2,2,2-trifluoroethyl)thiopheno[3,2-e]pyrimidin-4-yl]piperazinyl}butan-1-one

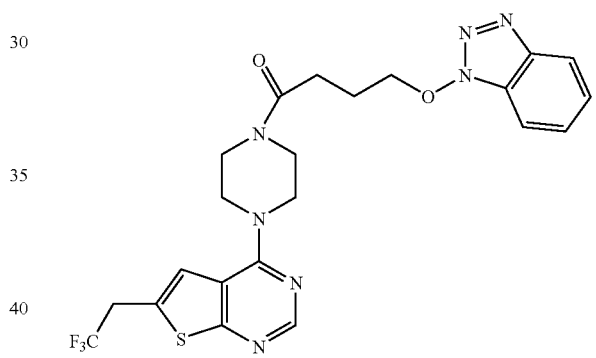

The title compound was obtained as a TFA salt by essentially the same method as for Example 2 using 95 instead of 1 and 4-benzotriazolyloxybutanoic acid from Example 4 instead of phenylacetic acid. ES-MS: (M+H)$^+$ 506, (M+Na)$^+$ 528.

Example 123

3,3,3-trifluoro-1-{4-[6-(2,2,2-trifluoroethyl)thiopheno[3,2-e]pyrimidin-4-yl]piperazinyl}propan-1-one

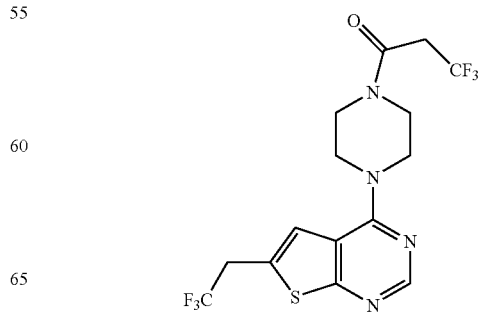

The title compound was obtained as a TFA salt by essentially following Example 5 using 95 instead of 1. ES-MS: (M+H)+ 413, (M+Na)+ 435.

Example 124 tert-butyl 4-(6-bromothiopheno[3,2-e]pyrimidin-4-yl)piperazinecarboxylate

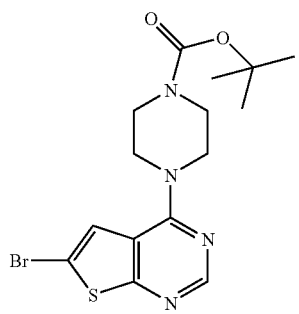

Step 1:

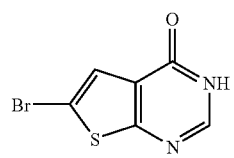

To thieno[2,3-d]pyrimidin-4-one (1.0 gm, 6.6 mmol) suspended in HOAc (13 mL) at rt under argon was added bromine (0.51 mL, 9.9 mmol) in a dropwise fashion. As the starting material slowly dissolved during the addition of bromine, the solution turned dark red. About 5 minutes later, the solution began to turn yellowish with a precipitate forming. The resulting solution was stirred over night, then poured into ice-cold brine (50 mL) with vigorous swirling for about 15 minutes. After filtering the solid, it was washed with ice-cold H₂O (50 mL), air dried on the filter paper for 30 minutes, and then further dried under high vacuum over night to afford 1.4 gms (94%) of the desired 6-bromothienopyrimidone. ES-MS: (M+H)+ 231/233.

Step 2:

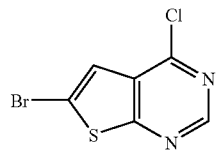

This intermediate was prepared by essentially following Example 1, Step 3, Method B using 6-bromo-thienopyrimidone from Step 1 of this example in place of 6-ethylthienopyrimidone. ES-MS: (M+H)+ 249/251.

Step 3:

The title compound was obtained in 94% yield by essentially following Example 87, step 4 using the material obtained in step 2 of this example. ES-MS: (M+H)+ 399/401.

Example 125

1-[4-(6-bromothiopheno[3,2-e]pyrimidin-4-yl)piperazinyl]-2-phenylethan-1-one

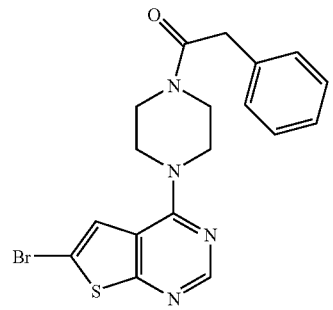

The title compound was obtained as a TFA salt by essentially following Example 3 except phenylacetyl chloride (0.14 mmol) was used in place of phenyl chloroformate and 124 instead of 1. ES-MS: (M+H)+ 417/419, (M+Na)+ 439/441.

Example 126

4-benzotriazolyloxy-1-[4-(6-bromothiopheno[3,2-e]pyrimidin-4-yl)piperazinyl]butan-1-one

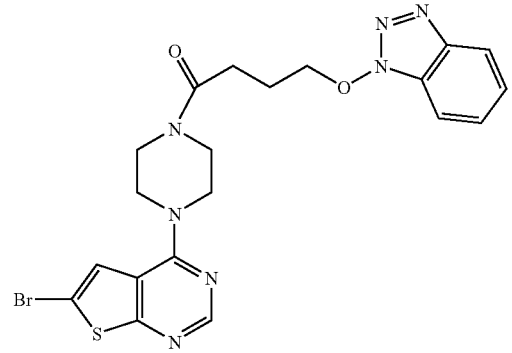

The title compound was obtained as a TFA salt by essentially the same method as for Example 2 using 124 instead of 1 and 4-benzotriazolyloxybutanoic acid from Example 4 instead of phenylacetic acid. ES-MS: (M+H)+ 502/504, (M+Na)+ 524/526.

Example 127

1-[4-(6-bromothiopheno[3,2-e]pyrimidin-4-yl)piperazinyl]-3,3,3-trifluoropropan-1-one

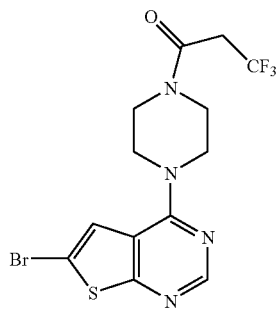

The title compound was obtained as a TFA salt by essentially following Example 5 using 124 instead of 1. ES-MS: (M+H)+ 409/411, (M+Na)+ 431/433.

Example 128 tert-butyl 4-(6-nitrothiopheno[3,2-e]pyrimidin-4-yl) piperazinecarboxylate

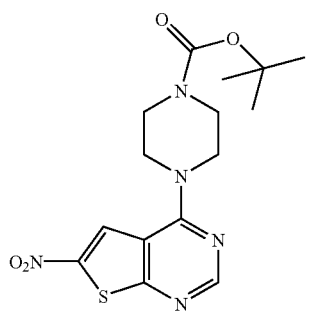

Step 1:

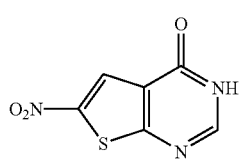

To thieno[2,3-d]pyrimidin-4-one (0.76 gm, 5.0 mmol) in conc. $H_2SO_4$ (10 mL) at 0° C. under argon was added in a dropwise fashion 1.2 ml of a mixture of fuming $HNO_3$ (0.4 mL) in conc. $H_2SO_4$ (2.0 mL). After stirring for 20 minutes, an additional 0.4 ml of the mixture of fuming $HNO_3$/conc. $H_2SO_4$ was added dropwise. After an additional 30 minutes, the mixture was carefully poured into ice-cold $H_2O$ (75 mL) with vigorous swirling for 10 minutes. The yellowish precipitate was filtered, rinsed with ice-cold $H_2O$ (100 mL), air dried on the filter paper for 3 hrs, then further dried under high vacuum over night to afford a 93% yield of the desired 6-nitrothienopyrimidone. ES-MS: (M+H)+ 198.

Step 2:

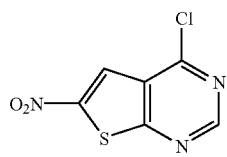

This intermediate was prepared by essentially following Example 1, Step 3, Method B using 6-nitrothienopyrimidone from Step 1 of this example in place of 6-ethylthienopyrimidone. ES-MS: (M+H)+ 216/218.

NOTE: The material isolated from Step 2 of this example also contained about 20% of the 6-chlorothienopyrimidine which was carried through to the final derivatives due to the inability to remove it from the desired 6-nitro-derivatives.

Step 3:

The title compound was obtained in 95% yield by essentially following Example 87, step 4 using the material obtained in step 2 of this example. ES-MS: (M+H)+ 366.

Example 129

1-[4-(6-nitrothiopheno[3,2-e]pyrimidin-4-yl)piperazinyl]-2-phenylethan-1-one

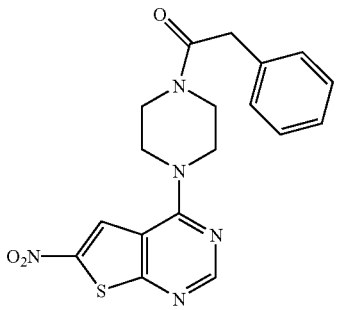

The title compound was obtained as a TFA salt by essentially following Example 3 except phenylacetyl chloride (0.14 mmol) was used in place of phenyl chloroformate and 128 instead of 1. ES-MS: (M+H)+ 384.

Example 130

4-benzotriazolyloxy-1-[4-(6-nitrothiopheno[3,2-e]pyrimidin-4-yl)piperazinyl]butan-1-one

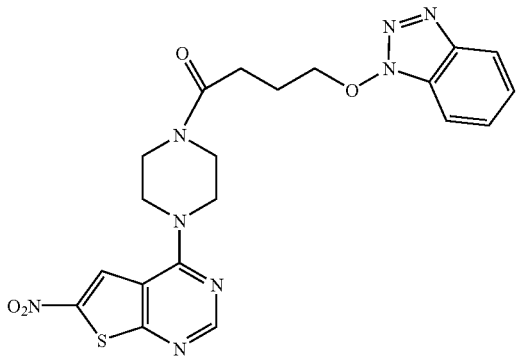

The title compound was obtained as a TFA salt by essentially the same method as for Example 2 using 128 instead of 1 and 4-benzotriazolyloxybutanoic acid from Example 4 instead of phenylacetic acid. ES-MS: (M+H)+ 469, (M+Na)+ 491.

Example 131

3,3,3-trifluoro-1-[4-(6-nitrothiopheno[3,2-e]pyrimidin-4-yl)piperazinyl]propan-1-one

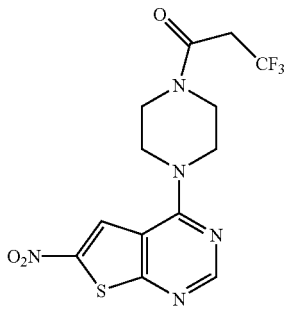

The title compound was obtained as a TFA salt by essentially following Example 5 using 128 instead of 1. ES-MS: (M+H)+ 376.

Example 132 tert-butyl 4-(6-ethynylthiopheno[3,2-e]pyrimidin-4-yl)piperazinecarboxylate

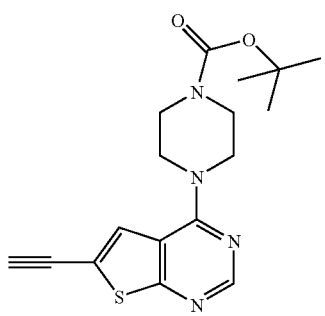

Pd(PhCN)₂Cl₂ (8.8 mg, 0.023 mmol) and CuI (4.4 mg, 0.023 mmol) were mixed at rt under argon and then THF (1 mL) was added. To this mixture was then added P(t-Bu)₃ (11 □L, 0.046 mmol) followed by TMS-acetylene (0.13 mL, 0.91 mmol), bromide 124 (150 mg, 0.38 mmol), and then diisopropylamine (0.13 mL, 0.91 mmol). The resulting solution was stirred at rt over night. The solvent was evaporated under educed pressure, an dthe residue was taken up into THF (1 mL). To this solution was added TBAF (1.1 mL of 1M in THF, 1.1 mmol). The resulting mixture was stirred for 20 minutes at which time H₂O (10 mL) was added. After stirring for 10 minutes, the mixture was washed with EtOAc (1-×20 mL). The EtOAc was then washed with brine (10 mL), dried with MgSO₄, filtered, concentrated under reduced pressure and further dried under high vaccum over night to afford 202 mg of crude product. This material was purified using automated flash chromatography (ISCO Systems, TLC-R$_f$=0.5, hexane/EtOAc 2:1) providing 53 mg (41%) of the title compound. ES-MS: (M+H)⁺ 345.

Example 133

1-[4-(6-ethynylthiopheno[3,2-e]pyrimidin-4-yl)piperazinyl]-2-phenylethan-1-one

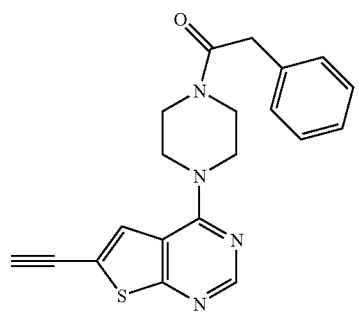

The title compound was obtained as a TFA salt by essentially following Example 3 except phenylacetyl chloride was used in place of phenyl chloroformate and 132 instead of 1. ES-MS: (M+H)⁺ 363.

Example 134

4-benzotriazolyloxy-1-[4-(6-ethylylthiopheno[3,2-e]pyrimidin-4-yl)piperazinyl]butan-1-one

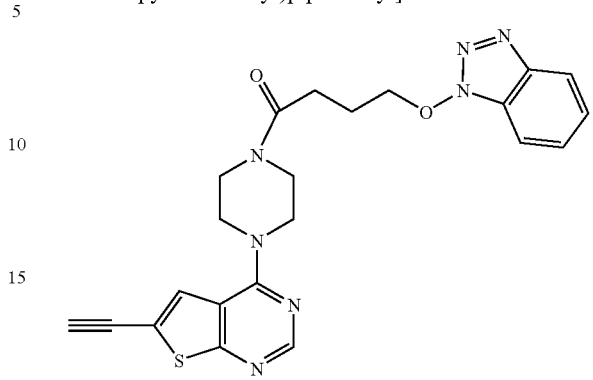

The title compound was obtained as a TFA salt by essentially the same method as for Example 2 using 132 instead of 1 and 4-benzotriazolyloxybutanoic acid from Example 4 instead of phenylacetic acid. ES-MS: (M+H)⁺ 448.

Example 135

1-[4-(6-ethlylylthiopheno[3,2-e]pyrimidin-4-yl)piperazinyl]-3,3,3-trifluoropropan-1-one

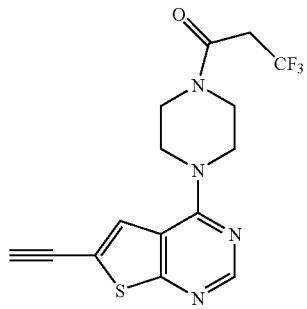

The title compound was obtained as a TFA salt by essentially following Example 5 using 132 instead of 1. ES-MS: (M+H)⁺ 355.

Example 136 tert-butyl 4-purin-6-ylpiperazinecarboxylate

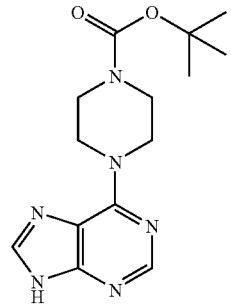

Step 1: Example 136 was prepared by reacting BOC-piperazine with 6-chloropurine according to Example 1. Yield=92%, ES-MS: (M+H)⁺ 305.

Example 137

2-phenyl-1-(4-purin-6-ylpiperazinyl)ethan-1-one

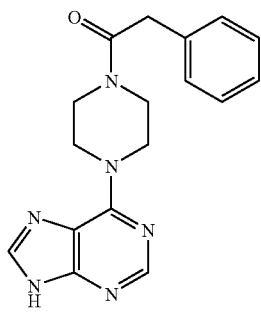

Step 1: Example 136 (1.28 g) was dissolved in methanol (25 mL) and HCl (4M in dioxane, 25 mL) was added. The reaction was allowed to stir for 24 hours and concentrated to dryness giving the bis-HCl salt (1.2 g). Yield=100%, ES-MS: (M+H)$^+$ 205. Step 2. The product from step 1 (101.4 mg) was combined with dichloromethane (2.00 mL) and diisopropylethylamine (0.26 mL). Phenylacetylchloride (49 μL) was added and the reaction was stirred at room temperature for 3 hours. The reaction was diluted with water (5 mL) and washed with ethyl acetate (3×20 mL). The combined organics were washed with aqueous saturated sodium bicarbonate (3×5 mL) and brine (5 mL). After dryine over anhydrous magnesium sulfate, the organics were filtered and concentrated. The residue was purified by reverse phase preparative HPLC and the isolated material was desalted with MP-carbonate resin in methanol giving the desired product (24.6 mg). Yield=21%, ES-MS: (M+H)$^+$ 323.

Example 138 phenyl 4-purin-6-ylpiperazinecarboxylate

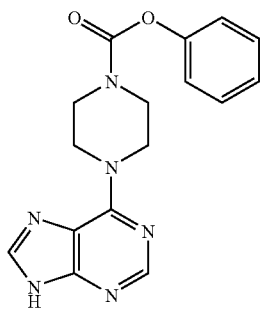

Step 1: The BOC group was removed from Example 136 according to Example 137. Step 2. The product from step 1 (103.3 mg) was combined with methanol (2.00 mL) and diisopropylethylamine (0.33 mL). Phenylchloroformate (70.4 μL) was added and the reaction was allowed to stir at room temperature for 3 hours. The reaction was diulted with ethyl acetate (20 mL) and washed with water (3×5 mL) and brine (5 mL). The organic layer was dried over anhydrous magnesium sulfate, filtered and concentrated to dryness. The residue was purified by reverse phase preparative HPLC and desalted with MP-carbonated resin in methanol giving the desired product (56.6 mg). Yield=47%, ES-MS: (M+H)$^+$ 325.

Example 139

4-benzotriazolyloxy-1-(4-purin-6-ylpiperazinyl)butan-1-one

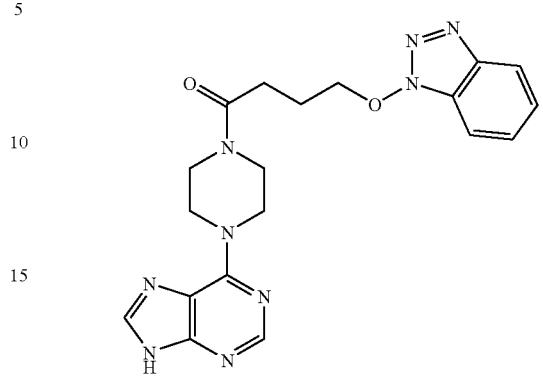

Step 1: The BOC group was removed from Example 136 according to Example 137. Step 2. The product from step 1 was reacted with 4-benzotriazolyloxybutanoic acid according Example 4. The isolated material was desalted with MP-carbonate resin in methanol giving the desired product. Yield=36%, ES-MS: (M+H)$^+$ 408.

Example 140 tert-butyl 4-(8-ethylpurin-6-yl)piperazinecarboxylate

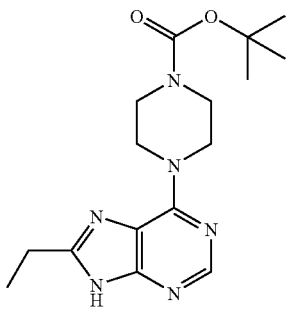

Step 1: 8-Ethyl-6-chloropurine was prepared utilizing propionic acid and 4,5-diamino-6-hydroxypyrimidine according to J. Chem. Soc. Perkin Trans. I (1984) 879–885. Step 2: BOC-piperazine was reacted with 8-ethyl-6-chloropurine according to Example 87. Yield=100%, ES-MS: (M+H)$^+$ 333.

Example 141

1-[4-(8-ethylpurin-6-yl)piperazinyl]-2-phenylethan-1-one

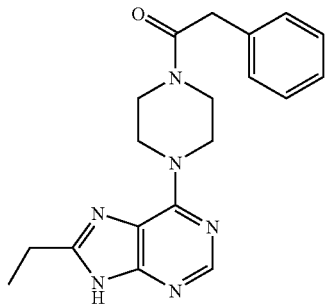

Step 1: BOC-Piperazine (1.06 g) was combined with dichloromethane (20.0 mL) and diisopropylethylamine (1.49 mL). Phenylacetylchloride (0.90 mL) was added dropwise and the reaction was allowed to stir at room temperature for 24 hours. The reaction was then washed with HCl (1N in water, 3×5 mL), saturated aqueous sodium bicarbonate (3×5 mL) and brine (5 mL). The organic layer was dried over anhydrous magnesium sulfate, filtered and concentrated giving 1-BOC-4-phenylacetamidopiperazine (1.73 g). Yield=100% Step 2: The BOC group was removed from 1-BOC-4-phenylacetamidopiperazine according to example 137 giving phenylacetamidopiperazine hydrochloride. Yield=93%. Step 3: Phenylacetamidopiperazine hydrochloride was reacted with 8-ethyl-6-chloropurine (Example 140) according to Example 87. Yield=27%, ES-MS: (M+H)$^+$ 351.

Example 142

4-benzotriazolyloxy-1-[4-(8-ethylpurin-6-yl)piperazinyl]butan-1-one

Step 1: 2-Amino-dimethylmalonate-monohydrochloride (3.16 g) was combined with diisopropylethylamine (8.99 mL) and dichloromethane (50 mL). Propionylchloride was added dropwise and the reaction was stirred at room temperature for 2 hours. The resulting mixture was washed with HCl (1N in water, 3×10 mL), saturated aqueous sodium bicarbonate (3×10 mL) and brine (10 mL). The organics were dried over anhydrous magnesium sulfate, filtered and concentrated to dryness giving 2-propionamido-dimethylmalonate (3.21 g). Yield=92%

Step 2: Sodium (1.09 g) was dissolved in anhydrous methanol (17.0 mL) and formamidine acetate (1.65 g) was added. The resulting mixture was stirred at room temperature for 5 minutes and cooled to 0° C. 2-Propionamido-dimethylmalonate (3.21 g) was added and the reaction was stirred at room temperature for 5 hours. Water (10 mL) was then added and the reaction was neutralized with DOWEX H$^+$ ion exchange resin. The resin was removed by filtration and the filtrate was concentrated to dryness. Crystallization of the residue in methanol followed by filtration and drying of the solids under vacuum gave 4,6-dihydroxy-5-propionamidopyrimidine (2.86 g). Yield=99%

Step 3: 4,6-Dihydroxy-5-propionamidopyrimidine (2.86 g) was combined with phosphorus oxychloride (42 mL) and dimethylaniline (4.20 mL). The mixture was heated to reflux for 3 hours and then concentrated to dryness. The residue was poured onto crushed ice (50 mL) and neutralized with saturated aqueous sodium bicarbonate. The reulting mixture was washed with ethyl acetate (3×30 mL). The combined organic washes were dried over anhydrous magnesium sulfate, filtered and concentrated to dryness. The residue was purified on silica gel (10% ethyl acetate/hexane) giving 6-ethyl-4-chlorooxazolopyrimidine (1.70 g). Yield=59%, Rf=0.29 (10% ethyl acetate/hexane)

Step 4: BOC-piperazine was reacted with 6-ethyl-4-chlorooxazolopyrimidine according to Example 87. Yield=100%, ES-MS: (M+H)$^+$ 334.

Example 150

1-[4-(2-ethyl(1,3-oxazolo[4,5-e]pyrimidin-7-yl))piperazinyl]-2-phenylethan-1-one

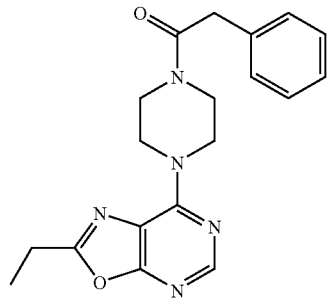

Step 1: Phenylacetamidopiperazine hydrochloride (Example 141) was reacted with 6-ethyl-4-chlorooxazolopyrimidine (Example 149) according to Example 87. Yield=44%, ES-MS: (M+H)$^+$ 352.

Example 151

4-benzotriazolyloxy-1-[4-(2-ethyl(1,3-oxazolo[4,5-e]pyrimidin-7-yl))piperazinyl]butan-1-one

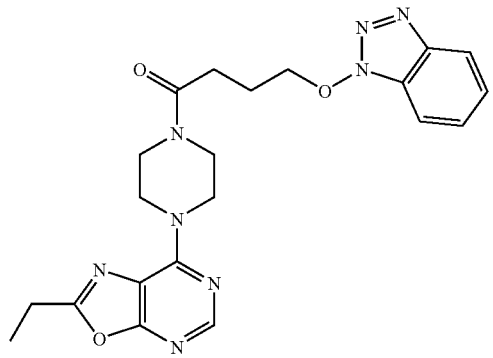

Step 1: Example 149 (224.1 mg) was dissolved in dichloromethane (10 mL) and trifluoroacetic acid (0.50 mL) was added. The reaction was stirred at room temperature for 24 hours after which the reaction was concentrated to dryness giving the desired product as the mono-trifluoroacetate (241.1 mg). Yield=100%

Step 2: The product from step 1 was reacted with 4-benzotriazolyloxybutanoic acid according Example 4. The isolated material was desalted with MP-carbonate resin in methanol giving the desired product. Yield=52%, ES-MS: (M+H)$^+$ 437.

Example 152

Tert-Butyl 4-(6-ethyl-2-methylthiopheno[3,2-e]pyrimidin-4-yl)piperazinecarboxylate

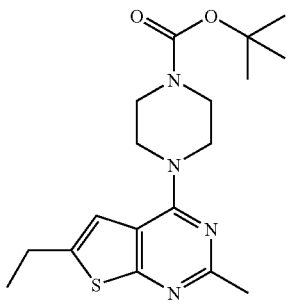

Step 1: Ethyl 2-amino-5-ethylthiophene-3-carboxylate (0.97 g) was dissolved in acetonitrile (35 mL) and HCl gas was bubbled in for 1.5 hours. The reaction was capped and allowed to stir at room temperature for 20 hours after which, it was concentrated to dryness. The residue was dissolved in ethanol (20 mL) and NaOH (6% in water, 6.70 mL) was added. After refluxing for 1 hour, the reaction was cooled to room temperature and concentrated to ¼ its original volume. The resulting solids were filtered, washed with water and purified on silica gel (ethyl acetate) giving 2-methyl-4-hydroxy-6-ethylthienopyrimidine (0.82 g). Yield=86%

Step 2: 2-Methyl-4-hydroxy-6-ethylthienopyrimidine (0.71 g) was dissolved in phosphorus oxychloride (10 mL) and heated to reflux for 19 hours. After concentrating to dryness, the residue was diluted with water (20 mL) and the product was extracted with methylene chloride (3×5 mL). The combined extracts were dried over anhydrous sodium sulfate, filtered and concentrated. The residue was purified on silica gel (50% ethyl acetate/hexane) giving 2-methyl-4-chloro-6-ethylthienopyrimidine (0.58 g). Yield=74%, Rf=0.73 (25% ethyl acetate/hexane).

Step 3: BOC-piperazine was reacted with 2-methyl-4-chloro-6-ethylthienopyrimidine according to Example 87. Yield=100%, ES-MS: (M+H)⁺ 363

Example 153

1-[4-(6-ethyl-2-methylthiopheno[3,2-e]pyrimidin-4-yl)piperazinyl]-2-phenylethan-1-one

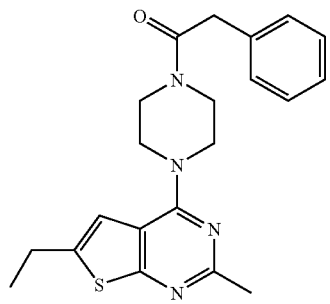

Step 1: Phenylacetamidopiperazine hydrochloride (Example 141) was reacted 2-methyl-4-chloro-6-ethylthienopyrimidine (Example 152) according to Example 87. Yield=47%, ES-MS: (M+H)⁺ 381.

Example 154

4-benzotriazolyloxy-1-[4-(6-ethyl-2-methylthiopheno[3,2-e]pyrimidin-4-yl)piperazinyl]butan-1-one

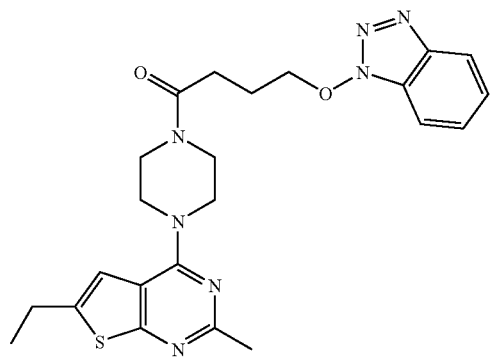

Step 1: The BOC group was removed from Example 152 according to Example 137.

Step 2: The product from step 1 was reacted with 4-benzotriazolyloxybutanoic acid according to Example 4. The isolated material was desalted with MP-carbonate resin in methanol giving the desired product. Yield=65%, ES-MS: (M+H)⁺ 466.

Example 155

1-[4-(6-ethyl-2-methylthiopheno[3,2-e]pyrimidin-4-yl)piperazinyl]-3,3,3-trifluoropropan-1-one

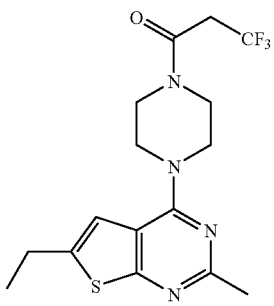

Step 1: The BOC group was removed from Example 152 according to Example 137.

Step 2: The product from step 1 was reacted with 3,3,3-trifluoropropionic acid according to Example 5. The isolated material was desalted with MP-carbonate resin in methanol giving the desired product. Yield=63%, ES-MS: (M+H)⁺ 373.

Example 156 tert-butyl 4-(2,6-diethylthiopheno[3,2-e]pyrimidin-4-yl)piperazinecarboxylate

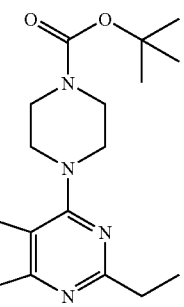

Step 1: Ethyl 2-amino-5-ethylthiophene-3-carboxylate was reacted with propionitrile according to Example 152 giving 2-ethyl-4-hydroxy-6-ethylthienopyrimidine. Yield=88%.

Step 2. 2-Ethyl-4-hydroxy-6-ethylthienopyrimidine was treated with phosphorus oxychloride according to Example 152 giving 2-methyl-4-chloro-6-ethylthieno-pyrimidine. Yield=29%, Rf=0.48 (10% ethyl acetate/hexane).

Step 3: BOC-piperazine was reacted with 2-ethyl-4-chloro-6-ethylthienopyrimidine according to Example 87. Yield=100%, ES-MS: (M+H)⁺ 377.

Example 157

1-[4-(2,6-diethylthiopheno[3,2-e]pyrimidin-4-yl)piperazinyl]-2-phenylethan-1-one

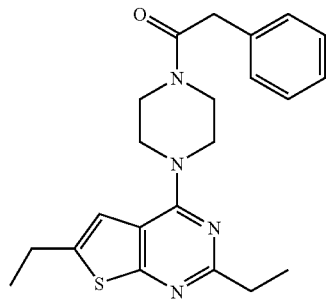

Step 1: Phenylacetamidopiperazine hydrochloride (Example 141) was reacted 2-ethyl-4-chloro-6-ethylthienopyrimidine (Example 156) according to Example 87. Yield=27%, ES-MS: (M+H)+ 395.

Example 158

4-benzotriazolyloxy-1-[4-(2,6-diethylthiopheno[3,2-e]pyrimidin-4-yl)piperazinyl]butan-1-one

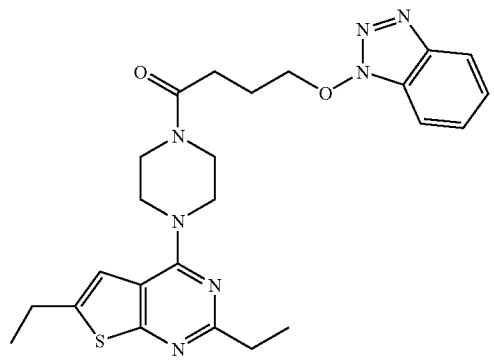

Step 1. The BOC group was removed from Example 156 according to Example 137.

Step 2: The product from step 1 was reacted with 4-benzotriazolyloxybutanoic acid according to Example 4. The isolated material was desalted with MP-carbonate resin in methanol giving the desired product. Yield=58%, ES-MS: (M+H)+ 480.

Example 159 tert-butyl 4-(6-ethyl-2-propylthiopheno[3,2-e]pyrimidin-4-yl)piperazinecarboxylate

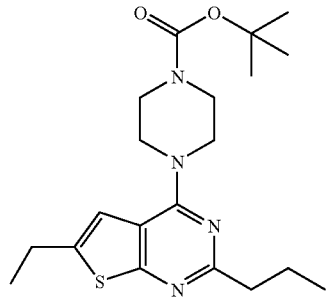

Step 1: Ethyl 2-amino-5-ethylthiophene-3-carboxylate was reacted with butyronitrile according to Example 152 giving 2-propyl-4-hydroxy-6-ethylthienopyrimidine. Yield=92%

Step 2: 2-Propyl-4-hydroxy-6-ethylthienopyrimidine was treated with phosphorus oxychloride according to Example 152 giving 2-propyl-4-chloro-6-ethylthieno-pyrimidine. Yield=39%, Rf=0.57 (10% ethyl acetate/hexane).

Step 3: BOC-piperazine was reacted with 2-propyl-4-chloro-6-ethylthienopyrimidine according to Example 87. Yield=100%, ES-MS: (M+H)+ 391.

Example 160

1-[4-(6-ethyl-2-propylthiopheno[3,2-e]pyrimidin-4-yl)piperazinyl]-2-phenylethan-1-one

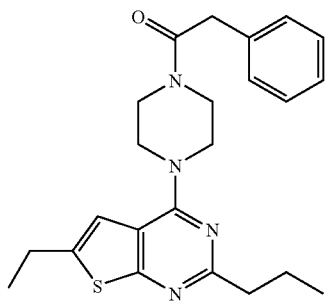

Step 1: Phenylacetamidopiperazine hydrochloride (Example 141) was reacted 2-propyl-4-chloro-6-ethylthienopyrimidine (Example 159) according to Example 87. Yield 36%, ES-MS: (M+H)+ 409.

Example 161

4-benzotriazolyloxy-1-[4-(6-ethyl-2-propylthiopheno[3,2-e]pyrimidin-4-yl)piperazinyl]butan-1-one

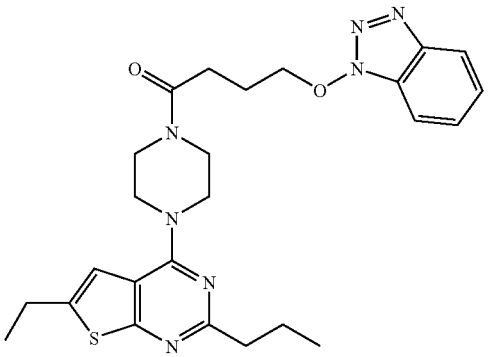

Step 1: The BOC group was removed from Example 159 according to Example 137.

Step 2: The product from step 1 was reacted with 4-benzotriazolyloxybutanoic acid according to Example 4. The isolated material was desalted with MP-carbonate resin in methanol giving the desired product. Yield=44%, ES-MS: (M+H)⁺ 494.

Example 162 tert-butyl 4-[6-ethyl-2-(methylethyl)thiopheno[3,2-e]pyrimidin-4-yl]piperazinecarboxylate

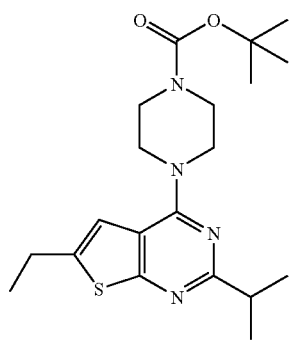

Step 1: Ehyl 2-amino-5-ethylthiophene-3-carboxylate was reacted with isobutyronitrile according to Example 152 giving 2-isopropyl-4-hydroxy-6-ethylthienopyrimidine. Yield=100%.

Step 2: 2-Isopropyl-4-hydroxy-6-ethylthienopyrimidine was treated with phosphorus oxychloride according to Example 152 giving 2-isopropyl-4-chloro-6-ethylthieno-pyrimidine. Yield=78%, Rf=0.52 (10% ethyl acetate/hexane).

Step 3: BOC-piperazine was reacted with 2-isopropyl-4-chloro-6-ethylthienopyrimidine according to Example 87. Yield=99%, ES-MS: (M+H)⁺ 391.

Example 163

1-{4-[6-ethyl-2-(methylethyl)thiopheno[3,2-e]pyrimidin-4-yl]piperazinyl}-2-phenylethan-1-one

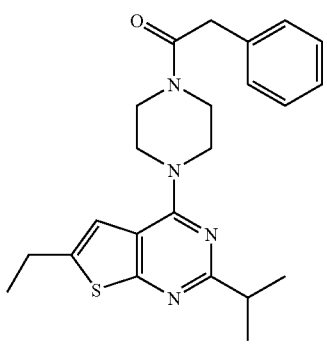

Step 1: Phenylacetamidopiperazine hydrochloride (Example 141) was reacted 2-isopropyl-4-chloro-6-ethylthienopyrimidine (Example 162) according to Example 87. Yield=21%, ES-MS: (M+H)⁺ 409.

Example 164

4-benzotriazolyloxy-1-{4-[6-ethyl-2-(methylethyl)thiopheno[3,2-e]pyrimidin-4-yl]piperazinyl}butan-1-one

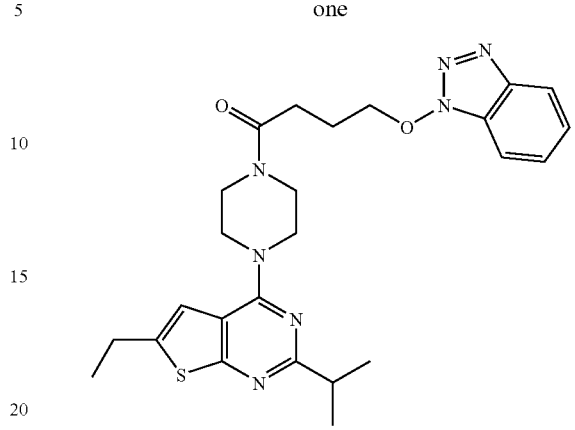

Step 1: The BOC group was removed from Example 162 according to Example 137.

Step 2: The product from step 1 was reacted with 4-benzotriazolyloxybutanoic acid according to Example 4. The isolated material was desalted with MP-carbonate resin in methanol giving the desired product. Yield=18%, ES-MS: (M+H)⁺ 494.

Example 165 tert-butyl 4-(2-chloro-6-ethylthiopheno[3,2-e]pyrimidin-4-yl)piperazinecarboxylate

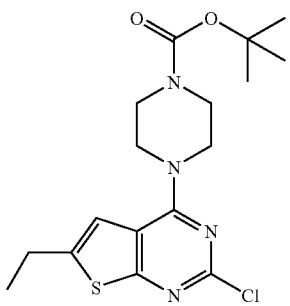

Step 1: Ethyl 2-amino-5-ethylthiophene-3-carboxylate (1.01 g) was dissolved in acetic acid (25 mL) and water (2.5 mL). Potassium cyanate (1.24 g) was dissolved in water (4.1 mL) and added, dropwise, to the acetic acid solution. The reaction was stirred at room temperature for 15 hours after which, it was diluted with water (50 mL) and cooled to 0° C. The solids were filtered, washed with water and combined with sodium hydroxide (6% in water, 25 mL). After heating at reflux for 2 hours, the reaction was cooled to room temperature and the pH was adjusted to 6 with concentrated HCl. The resulting solids were filtered, washed with water and air dried giving 6-ethyl-2,4-dihydroxythieonpyrimidine (0.40 g). Yield=41%.

Step 2: 6-Ethyl-2,4-dihydroxythieonpyrimidine (0.36 g) was combined with phosphorus oxychloride (5.00 mL) and heated to reflux for 19.5 hours. After adding additional phosphorus oxychloride (10 mL), heating at reflux was continued for an additional 4 days. After cooling to room temperature, the reaction was concentrated to dryness and diluted with ice water (10 mL). The pH of the resulting mixture was adjusted to 6 with concentrated ammonium hydroxide. The product was extracted with dichloromethane (3×10 mL) and the organic extracts were dried over anhydrous sodium sulfate, filtered and concentrated to dryness. Additional drying under vacuum gave 6-ethyl-2,4-dichlorothienopyrimidine (0.40 g). Yield=92%.

Step 3: 6-Ethyl-2,4-dichlorothienopyrimidine (51 mg) was combined with BOC-piperazine (45 mg), tetrahydrofuran (2.20 mL) and diisopropylethylamine (0.77 µL). The reaction was stirred at room temperature for 2 hours and diluted with ethyl acetate (20 mL). The resulting mixture was washed with water (3×5 mL) and brine (5 mL). The organic layer was dried over anhydrous sodium sulfate, filtered and concentrated to dryness giving the desired product (76 mg). Yield=90%, ES-MS: (M+H)$^+$ 383.

Example 166

1-[4-(2-chloro-6-ethylthiopheno[3,2-e]pyrimidin-4-yl)piperazinyl]-2-phenylethan-1-one

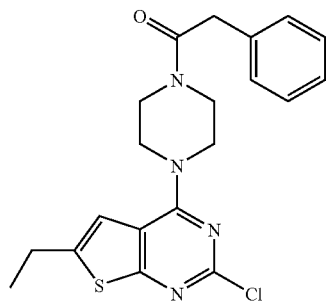

Step 1: The BOC group was removed from Example 165 according to Example 137. Yield=94%.

Step 2: The product from step 1 was reacted with phenylacetylchloride according to Example 137. Yield=46%, ES-MS: (M+H)$^+$ 401.

Example 167

4-benzotriazolyloxy-1-[4-(2-chloro-6-ethylthiopheno[3,2-e]pyrimidin-4-yl)piperazinyl]butan-1-one

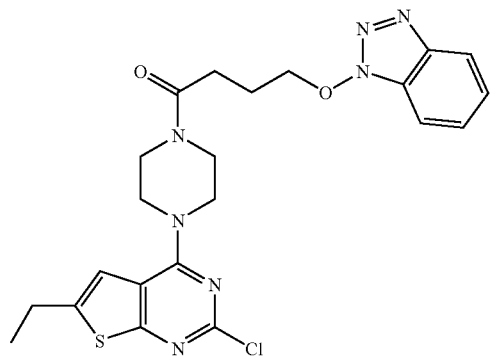

Step 1: The BOC group was removed from Example 165 according to Example 137. Yield=94%.

Step 2: The product from step 1 was reacted with 4-benzotriazolyloxybutanoic acid according Example 4. The isolated material was desalted with MP-carbonate resin in methanol giving the desired product. Yield=58%, ES-MS: (M+H)$^+$ 486.

Example 168 tert-butyl 4-(6-ethyl-2-methylthiothiopheno[3,2-e]pyrimidin-4-yl)piperazinecarboxylate

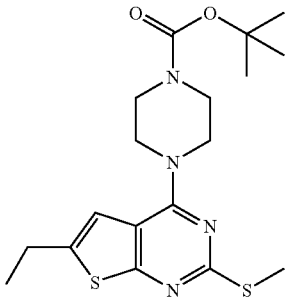

Step 1: Example 165 (50.4 mg) was combined with sodium thiomethoxide (46.2 mg) and dimethylsulfoxide (0.53 mL). The mixture was heated to 100° C. to dissolve all solids. After stirring at room temperature for 45 minutes, the reaction was diluted with water (20 mL) and washed with dichloromethane (3×5 mL). The combined organic extracts were dried over anhydrous sodium sulfate, filtered and concentrated to dryness giving the desired product (53 mg). Yield=100%, ES-MS: (M+H)$^+$ 395.

Example 169

1-[4-(6-ethyl-2-methylthiothiopheno[3,2-e]pyrimidin-4-yl)piperazinyl]-2-phenylethan-1-one

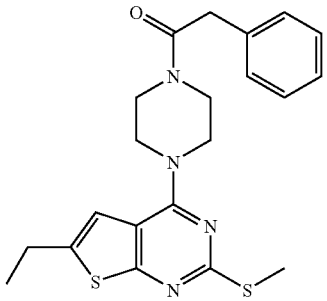

Step 1: The BOC group was removed from Example 168 according to Example 137. Yield=99%.

Step 2: The product from step 1 was reacted with phenylacetylchloride according to Example 137. Yield=73%, ES-MS: (M+H)$^+$ 413.

Example 170

4-benzotriazolyloxy-1-[4-(6-ethyl-2-methylthiothiopheno[3,2-e]pyrimidin-4-yl)piperazinyl]butan-1-one

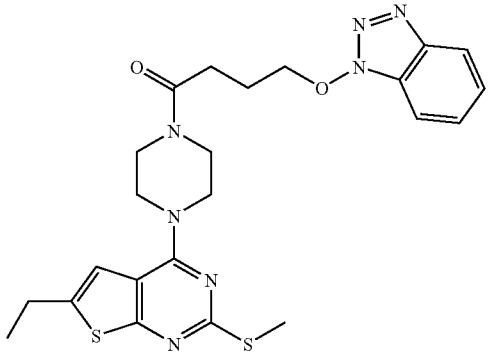

Step 1: The BOC group was removed from Example 168 according to Example 137. Yield=99%.

Step 2: The product from step 1 was reacted with 4-benzotriazolyloxybutanoic acid according Example 4. The isolated material was desalted with MP-carbonate resin in methanol giving the desired product. Yield=71%, ES-MS: (M+H)⁺ 498.

Example 171 tert-butyl 4-[6-ethyl-2-(methylamino)thiopheno[3,2-e]pyrimidin-4-yl]piperazinecarboxylate

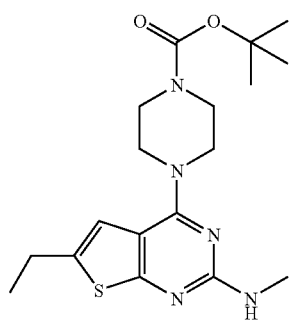

Step 1: Example 165 (254 mg) was combined with 1-butanol (3.35 mL) and methylamine (40% in water, 1.04 mL). The mixture was heated to 100° C. in a sealed tube for 24 hours. After cooling to room temperature, the mixture was concentrated to dryness giving the desired product. ES-MS: (M+H)⁺ 378.

Example 172

1-{4-[6-ethyl-2-(methylamino)thiopheno[3,2-e]pyrimidin-4-yl]piperazinyl}-2-phenylethan-1-one

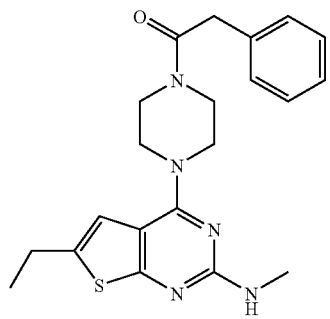

Step 1: The BOC group was removed from Example 171 according to Example 137. Yield=97%.

Step) 2. The product from step 1 was reacted with phenlylacetylchloride according to Example 137. Yield=47%, ES-MS: (M+H)⁺ 396.

Example 173

4-benzotriazolyloxy-1-{4-[6-ethyl-2-(methylamino)thiopheno[3,2-e]pyrimidin-4-yl]piperazinyl}butan-1-one

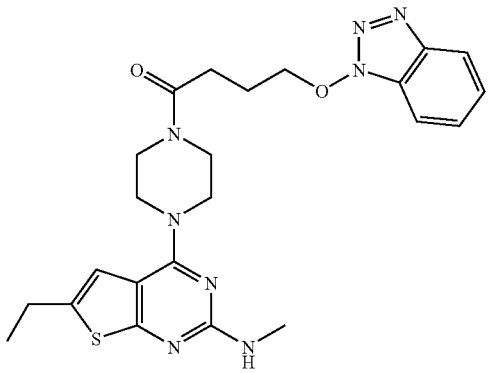

Step 1: The BOC group was removed from Example 171 according to Example 137. Yield=97%.

Step 2: The product from step 1 was reacted with 4-benzotriazolyloxybutanoic acid according Example 4. The isolated material was desalted with MP-carbonate resin in methanol giving the desired product. Yield=30%, ES-MS: (M+H)⁺ 481.

Example 174 tert-butyl 4-[2-(dimethylamino)-6-ethylthiopheno[3,2-e]pyrimidin-4-yl]piperazinecarboxylate

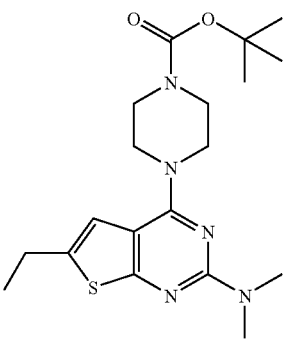

Step 1. Example 165 (252 mg) was combined with 1-butanol (3.30 mL) and dimethylamine (40% in water, 1.0 mL). The mixture was heated to 100° C. in a sealed tube for 3 hours. After cooling to room temperature, the mixture was concentrated to dryness giving the desired product. ES-MS: (M+H)⁺ 392.

Example 175

1-{4-[2-(dimethylamino)-6-ethylthiopheno[3,2-e]pyrimidin-4-yl]piperazinyl}-2-phenylethan-1-one

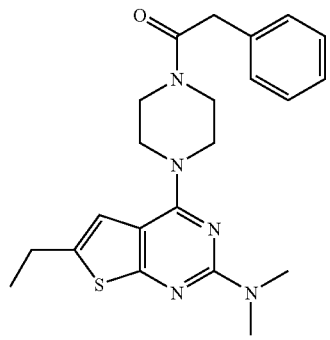

Step 1: The BOC group was removed from Example 174 according to Example 137. Yield=100%

Step 2. The product from step 1 was reacted with phenylacetylchloride according to Example 137. Yield=38%, ES-MS: (M+H)+ 410.

Example 176

4-benzotriazolyloxy-1-{4-[2-(dimethylamino)-6-ethylthiopheno[3,2-e]pyrimidin-4-yl]piperazinyl}butan-1-one

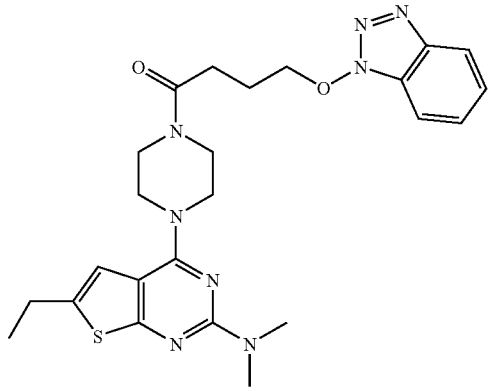

Step 1 The BOC group was removed from Example 174 according to Example 137. Yield=100%.

Step 2: The product from step 1 was reacted with 4-benzotriazolyloxybutanoic acid according Example 4. The isolated material was desalted with MP-carbonate resin in methanol giving the desired product. Yield=30%, ES-MS: (M+H)+ 495.

Example 177 tert-butyl 4-(6-ethyl-2-methoxythiopheno[3,2-e]pyrimidin-4-yl)piperazinecarboxylate

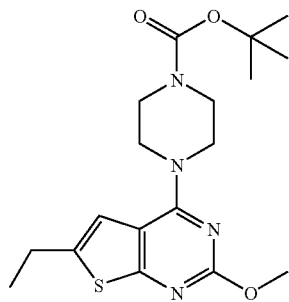

Step 1: Sodium (79 mg) was dissolved in methanol (2.00 mL) and Example 165 (262 mg) was added. The reaction was heated to 60° C. for 18 hours and cooled to room temperature. After diluting with water (20 mL), the reaction was washed with dichloromethane (3×5 mL). The combined organic extracts were dried over anhydrous sodium sulfate, filtered and concentrated giving the desired product (254 mg). Yield=98%, ES-MS: (M+H)+ 379.

Example 178

1-[4-(6-ethyl-2-methoxythiopheno[3,2-e]pyrimidin-4-yl)piperazinyl]-2-phenylethan-1-one

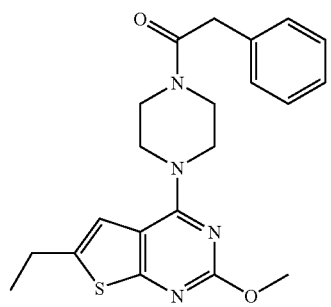

Step 1: The BOC group was removed from Example 177 according to Example 137. Yield=100%.

Step 2. The product from step 1 was reacted with phenylacetylchloride according to Example 137. Yield=43%, ES-MS: (M+H)+ 397.

Example 179

4-benzotriazolyloxy-1-[4-(6-ethyl-2-methoxythiopheno[3,2-e]pyrimidin-4-yl)piperazinyl]butan-1-one

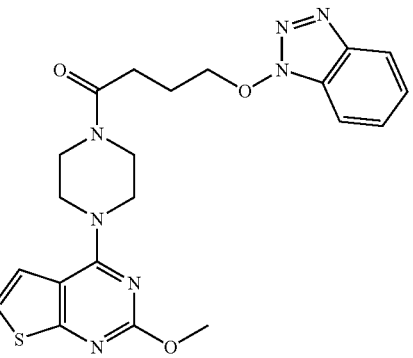

Step 1: The BOC group was removed from Example 177 according to Example 137. Yield=100%.

Step 2. The product from step 1 was reacted with 4-benzotriazolyloxybutanoic acid according Example 4. The isolated material was desalted with MP-carbonate resin in methanol giving the desired product. Yield=65%, ES-MS: (M+H)+ 482.

Example 180 tert-butyl 4-(2-amino-6-ethylthiopheno[3,2-e]pyrimidin-4-yl)piperazinecarboxylate

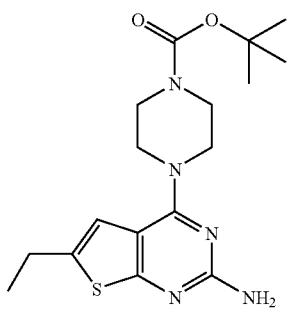

Step 1. Example 165 (0.50 g) was combined with sodium azide (0.43 g) and dimethyl sulfoxide (5.00 mL). The reaction was heated to 60° C. for 18 hours, 80° C. for 4.5 hours and 100° C. for 46 hours. After cooling to room temperature, the reaction was diluted with water (30 mL) and allowed to stir at room temperature for 1 hour. The solids were filtered, washed with water and purified on silica gel (10% ethyl acetate/hexane to 100% ethyl acetate over 30 minutes) giving the desired product (60 mg). Yield=13%, ES-MS: $(M+H)^+$ 364.

Example 181

1-[4-(2-amino-6-ethylthiopheno[3,2-e]pyrimidin-4-yl)piperazinyl]-4-benzotriazolyloxybutan-1-one

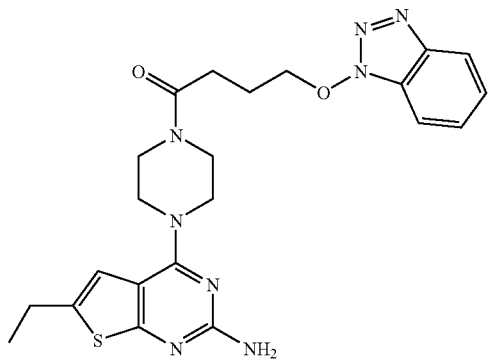

Step 1: The BOC group was removed from Example 180 according to Example 137. Yield=93%

Step 2: The product from step 1 was reacted with 4-benzotriazolyloxybutanoic acid according Example 4. The isolated material was desalted with MP-carbonate resin in methanol giving the desired product. Yield=48%, ES-MS: $(M+H)^+$ 467.

Example 182 tert-butyl 4-(6-ethyl-2-hydroxythiopheno[3,2-e]pyrimidin-4-yl)piperazinecarboxylate

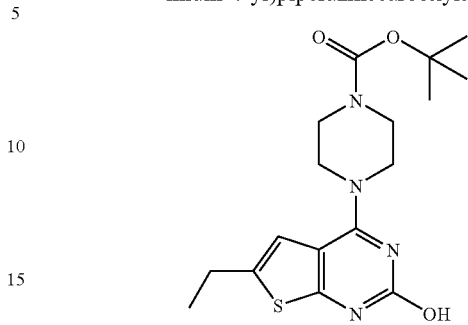

Step 1: 6-Ethyl-2,4-dihydroxythienopyrimidine (Example 165, 0.66 g) was combined with acetonitrile (35 mL) and diisopropylethylamine (2.35 mL). Methanesulfonyl-chloride (0.55 mL) was added dropwise and the reaction was allowed to stir at room temperature for 2.5 hours. BOC-Piperazine (0.69 g) was then added and the reaction was stirred for an additional 2 hours. After diluting with water (350 mL), the reaction was washed with dichloromethane (3×50 mL) and ethyl acetate (3×100 mL). The combined organic extracts were dried over anhydrous sodium sulfate, filtered and concentrated. The residue was passed through silica gel (50% ethyl acetate/hexane), concentrated and dried under vacuum giving the desired intermediate (0.85 g). Yield=57%.

Step 2: The product from Step 1 was combined with methanol (10 mL) and potassium hydroxide (3.8 M in methanol). After stirring at room temperature for 30 minutes, the reaction was diluted with water (200 mL) and washed with ethyl acetate (3×100 mL). The combined organic extracts were dried over anhydrous sodium sulfate, filtered and concentrated. The residue was purified by preparative reverse phase HPLC and the isolated material was desalted with MP-carbonate resin in methanol giving the desired product (130 mg). Yield=19%, ES-MS: $(M+H)^+$ 365.

Example 183

1-[4-(6-ethyl-2-hydroxythiopheno[3,2-e]pyrimidin-4-yl)piperazinyl]-2-phenylethan-1-one

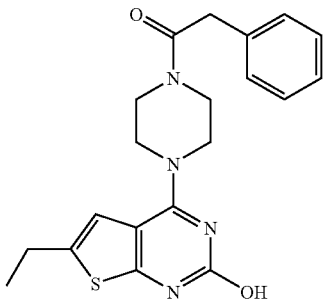

Step 1: The BOC group was removed from Example 182 according to Example 137. Yield=99%.

Step 2: The product from step 1 was reacted with phenylacetylchloride according to Example 137. Yield=65%, ES-MS: $(M+H)^+$ 383.

Example 184

4-benzotriazolyloxy-1-[4-(6-ethyl-2-hydroxythiopheno[3,2-e]pyrimidin-4-yl)piperazinyl]butan-1-one

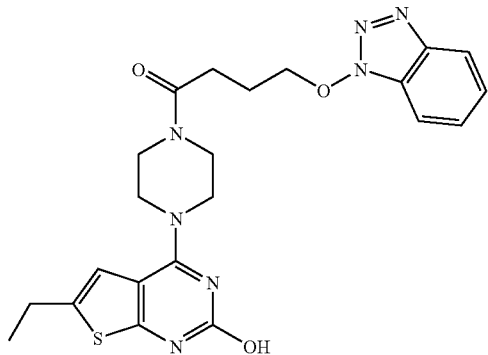

Step 1: The BOC group was removed from Example 182 according to Example 137. Yield=99%.

Step 2. The product from step 1 was reacted with 4-benzotriazolyloxybutanoic acid according Example 4. The isolated material was desalted with MP-carbonate resin in methanol giving the desired product. Yield=53%, ES-MS: (M+H)$^+$ 468.

Example 185 tert-butyl 4-(6-ethylthiopheno[3,2-e]pyrimidin-4-yl)-1,4-diazaperhydroepinecarboxylate

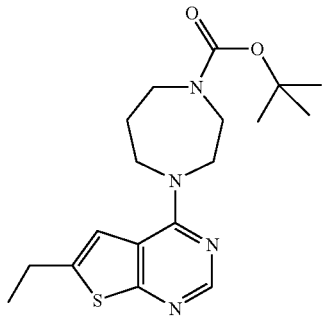

Step 1: Homopiperazine (24 g) was dissolved in dichloromethane (250 mL) and a solution of di-tert-butyl-dicarbonate (40 g) in dichloromethane (100 mL) was added dropwise. The reaction was stirred at room temperature for 20 hours after which, it was concentrated to dryness. The residue was partitioned between water (50 mL) and 50% ethyl acetate/hexane (100 mL). The layers were separated and the aqueous phase was washed with 50% ethyl acetate/hexane (4×50 mL). The combined organic extracts were washed with HCl (0.1 N in water, 6×50 mL) and the combined aqueous phases were neutralized with saturated aqueous sodium bicarbonate. The resulting aqueous solution was saturated with sodium chloride and made basic with the addition of 2 pellets of sodium hydroxide. After washing with 50% ethyl acetate/hexane (100 mL), the organic phase was dried over anhydrous magnesium sulfate, filtered and concentrated giving 1-BOC-homopiperazine (3.32 g). Yield=7%

Step 2: 1-BOC-Homopiperazine was coupled with 4-chloro-6-ethylthiopheno[2,3-d]pyrimidine according to Example 1. Yield=100%, ES-MS: (M+H)$^+$ 363.

Example 186

1-[4-(6-ethylthiopheno[3,2-e]pyrimidin-4-yl)(1,4-diazaperhydroepinyl)]-2-phenylethan-1-one

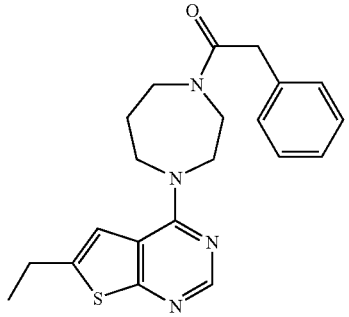

Step 1: The BOC group was removed from Example 185 according to Example 137. Yield=100%.

Step 2: The product from step 1 was reacted with phenylacetylchloride according to Example 137. Yield=31%, ES-MS: (M+H)$^+$ 381.

Example 187 phenyl 4-(6-ethylthiopheno[3,2-e]pyrimidin-4-yl)-1,4-diazaperhydroepinecarboxylate

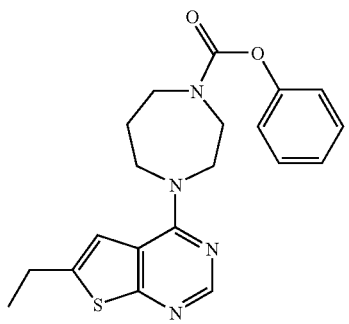

Step 1: The BOC group was removed from Example 185 according to Example 137. Yield=100%.

Step 2. The product from step 1 was reacted with phenylchloroformate according to Example 3. The isolated material was desalted with MP-carbonate resin in methanol giving the desired product. Yield=35%, ES-MS: (M+H)$^+$ 383.

Example 188

4-benzotriazolyloxy-1-[4-(6-ethylthiopheno[3,2-e]pyrimidin-4-yl)(1,4-diazaperhydroepinyl)]butan-1-one

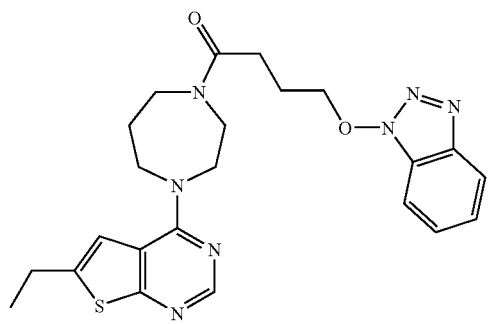

Step 1: The BOC group was removed from Example 185 according to Example 137. Yield=100%.

Step 2. The product from step 1 was reacted with 4-benzotriazolyloxybutanoic acid according Example 4. The isolated material was desalted with MP-carbonate resin in methanol giving the desired product. Yield=44%, ES-MS: (M+H)$^+$ 466.

Example 189 phenylmethyl (2S,5R)-4-(6-ethylthiopheno[3,2-e]pyrimidin-4-yl)-2,5-dimethylpiperazinecarboxylate

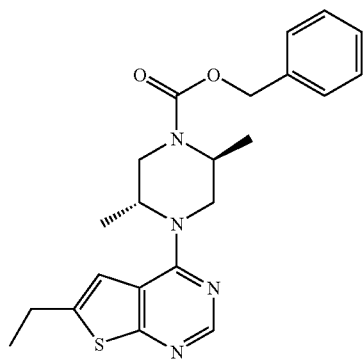

Step 1: trans-2,5-Dimethylpiperazine was protected as its mono-CBZ analog according to Example 231. Yield=15%.

Step 2. The product from step 1 was coupled with 4-chloro-6-ethylthiopheno[2,3-d]pyrimidine according to Example 87. Yield=88%, ES-MS: (M+H)$^+$ 411.

Example 190

1-[(2S,5R)-4-(6-ethylthiopheno[3,2-e]pyrimidin-4-yl)-2,5-dimethylpiperazinyl]-2-phenylethan-1-one

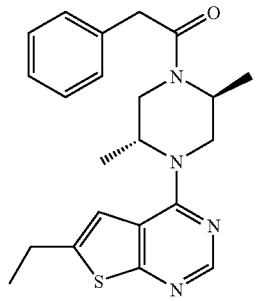

Step 1: The product from Example 189 was dissolved in trifluoroacetic acid (3.2 mL) and allowed to stand at room temperature for 5 days. The reaction was then diluted with water (40 mL) and washed with dichloromethane (3×10 mL). The aqueous layer was made basic with sodium hydroxide (6 M in water) and then saturated with solid sodium chloride. The resulting mixture was washed with ethyl acetate (3×10 mL). The combined organic extracts were dried over anhydrous magnesium sulfate, filtered and concentrated giving the desired amine. Yield=53%

Step 2: The product from step 1 was reacted with phenylacetylchloride according to Example 137. Yield 30%, ES-MS: (M+H)$^+$ 395.

Example 191

1-[(2S,5R)-4-(6-ethylthiopheno[3,2-e]pyrimidin-4-yl)-2,5-dimethylpiperazinyl]-4-benzotriazolyloxybutan-1-one

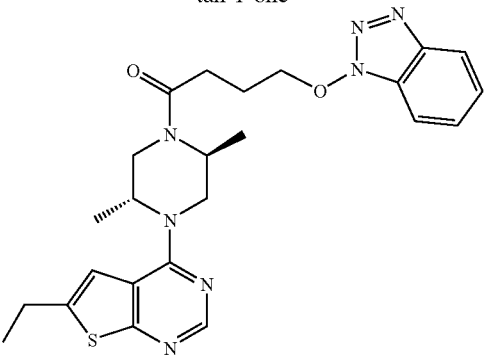

Step 1: The CBZ group was removed from Example 189 according to Example 190. Yield=53%.

Step 2: The product from step 1 was reacted with 4-benzotriazolyloxybutanoic acid according to Example 4. The isolated material was desalted with MP-carbonate resin in methanol giving the desired product. Yield=43%, ES-MS: (M+H)$^+$ 480.

Example 192 tert-butyl 4-(6-ethylthiopheno[3,2-e]pyrimidin-4-yl)-3-methylpiperazinecarboxylate

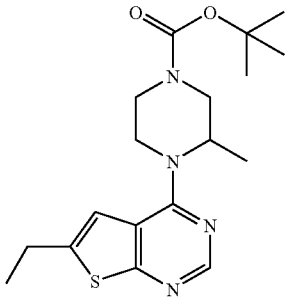

Step 1: 2-Methylpiperazine (5.03 g) was dissolved in dichloromethane (200 mL) and a solution of di-tert-butyldicarbonate (10.96 g) in dichloromethane (100 mL) was added over 2.5 hours. The reaction was stirred at room temperature for 24 hours and concentrated to dryness giving 1-BOC-3-methylpiperazine. Yield=100%

Step 2: 1-BOC-3-Methylpiperazine was coupled with 4-chloro-6-ethylthiopheno[2,3-d]pyrimidine according to Example 87. Yield=96%, ES-MS: (M+H)$^+$ 363.

Example 193

1-[4-(6-ethylthiopheno[3,2-e]pyrimidin-4-yl)-3-methylpiperazinyl]-2-phenylethan-1-one

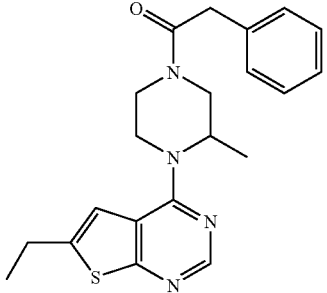

Step 1: The BOC group was removed from Example 192 according to Example 137. Yield=100%.

Step 2: The product from step 1 was reacted with phenylacetylchloride according to Example 137. Yield=22%, ES-MS: (M+H)+ 381.

Example 194

4-benzotriazolyloxy-1-[4-(6-ethylthiopheno[3,2-e]pyrimidin-4-yl)-3-methylpiperazinyl]butan-1-one

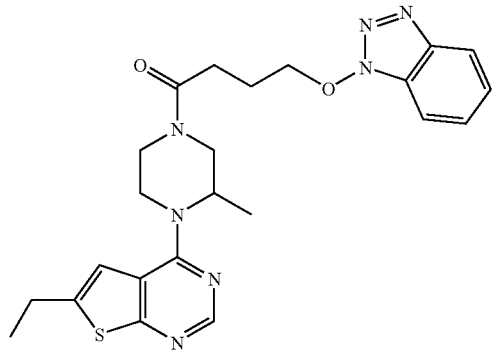

Step 1 The BOC group was removed from Example 192 according to Example 137. Yield=100%

Step 2. The product from step 1 was reacted with 4-benzotriazolyloxybutanoic acid according to Example 4. The isolated material was desalted with MP-carbonate resin in methanol giving the desired product. Yield=39%, ES-MS: (M+H)+ 466.

Example 195

1-[4-(6-ethylthiopheno[3,2-e]pyrimidin-4-yl)-3-methylpiperazinyl]-3,3,3-trifluoropropan-1-one

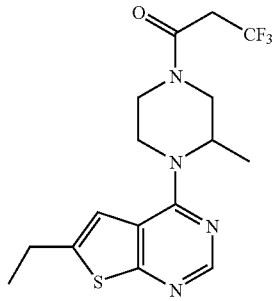

Step 1: The BOC group was removed from Example 192 according to Example 137. Yield=100%.

Step 2: The product from step 1 was reacted with 3,3,3-trifluoropropionic acid according to Example 5. The isolated material was desalted with MP-carbonate resin in methanol giving the desired product. Yield=44%, ES-MS: (M+H)+ 373.

Example 196 phenylmethyl 4-(6-ethylthiopheno[3,2-e]pyrimidin-4-yl)-2-methylpiperazinecarboxylate

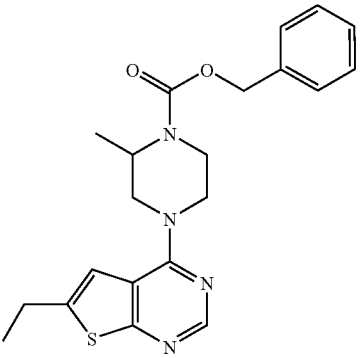

Step 1: 1-BOC-3-Methylpiperazine (1.00 g) was combined with dichloromethane (10 mL), diisopropylethylamine (0.94 mL) and N-(benzyloxy-carbonyloxy)succinimide. The reaction was stirred at room temperature for 3 days and concentrated to dryness. The residue was diluted with ethyl acetate (20 mL) and washed with HCl (1 N in water, 3×5 mL), saturated aqueous sodium bicarbonate (3×5 mL) and brine (5 mL). The organic layer was dried over anhydrous magnesium sulfate, filtered and concentrated giving the desired benzyl carbamate. Yield=100%

Step 2. The BOC group was removed from the product from Step 1 according to Example 137. Yield=100%.

Step 3: The product from Step 2 was coupled with 4-chloro-6-ethylthiopheno[2,3-d]pyrimidine according to Example 87. Yield=100%, ES-MS: (M+H)+ 397.

Example 197

1-[4-(6-ethylthiopheno[3,2-e]pyrimidin-4-yl)-2-methylpiperazinyl]-2-phenylethan-1-one

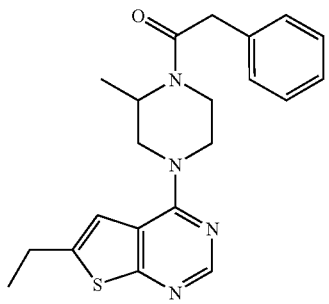

Step 1: The CBZ group was removed from the product from Example 196 according to Example 190. Yield=98%

Step 2. The product from step 1 was reacted with phenylacetylchloride according to Example 137. Yield=48%, ES-MS: (M+H)+ 381.

Example 198

4-benzotriazolyloxy-1-[4-(6-ethylthiopheno[3,2-e]pyrimidin-4-yl)-2-methylpiperazinyl]butan-1-one

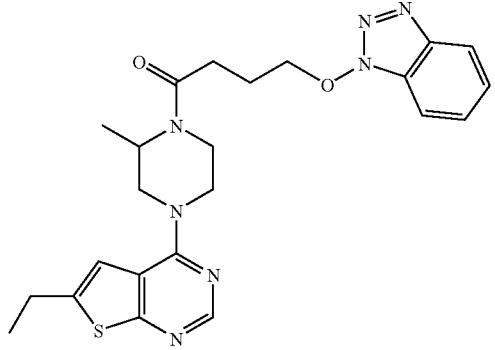

Step 1: The CBZ group was removed from Example 196 according to Example 190. Yield=98%.

Step 2: The product from step 1 was reacted with 4-benzotriazolyloxybutanoic acid according to Example 4. The isolated material was desalted with MP-carbonate resin in methanol giving the desired product. Yield=55%, ES-MS: (M+H)⁺ 466.

Example 199 tert-butyl (3R)-4-(6-ethylthiopheno[3,2-e]pyrimidin-4-yl)-3-methylpiperazinecarboxylate

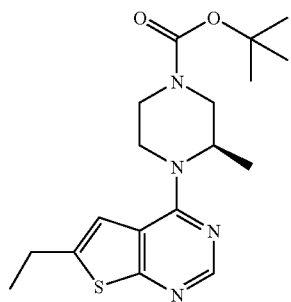

Step 1: (R)-2-Methylpiperazine was converted to 1-BOC-3-(R)-methylpiperazine according to Example 192. Yield=96%.

Step 2: 1-BOC-3-(R)-methylpiperazine was coupled with 4-chloro-6-ethylthiopheno[2,3-d]pyrimidine according to Example 87. Yield=92%, ES-MS: (M+H)⁺ 363.

Example 200

1-[(3R)-4-(6-ethylthiopheno[3,2-e]pyrimidin-4-yl)-3-methylpiperazinyl]-2-phenylethan-1-one

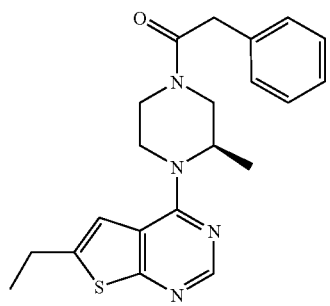

Step 1: The BOC group was removed from Example 199 according to Example 137. Yield 100%.

Step 2: The product from step 1 was reacted with phenylacetylchloride according to Example 137. Yield=31%, ES-MS: (M+H)⁺ 381.

Example 201

1-[(3R)-4-(6-ethylthopheno[3,2-e]pyrimidin-4-yl)-3-methylpiperazinyl]-4-benzotriazolyloxybutan-1-one

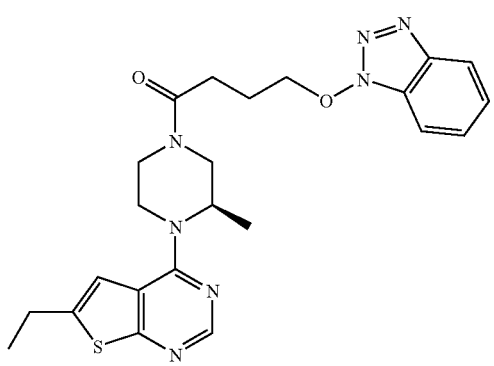

Step 1: The BOC group was removed from Example 199 according to Example 137. Yield=100%.

Step 2: The product from step 1 was reacted with 4-benzotriazolyloxybutanoic acid according to Example 4. The isolated material was desalted with MP-carbonate resin in methanol giving the desired product. Yield=48%, ES-MS: (M+H)⁺ 466.

Example 202 tert-butyl (3S)-4-(6-ethylthiopheno[3,2-e]pyrimidin-4-yl)-3-methylpiperazinecarboxylate

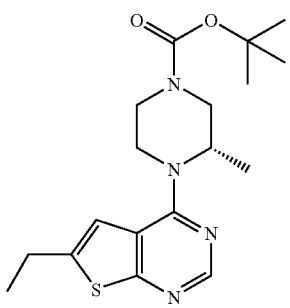

Step 1. (S)-2-Methylpiperazine was converted to 1-BOC-3-(S)-methylpiperazine according to Example 192. Yield=94%.

Step 2: 1-BOC-3-(S)-methylpiperazine was coupled with 4-chloro-6-ethylthiopheno[2,3-d]pyrimidine according to Example 87. Yield=98%, ES-MS: (M+H)⁺ 363.

Example 203

1-[(3S)-4-(6-ethylthiopheno[3,2-e]pyrimidin-4-yl)-3-methylpiperazinyl]-2-phenylethan-1-one

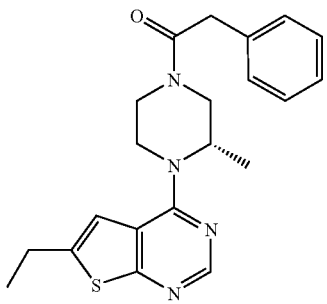

Step 1: The BOC group was removed from Example 202 according to Example 137. Yield=100%.

Step 2: The product from step 1 was reacted with phenylacetylchloride according to Example 137. Yield=39%, ES-MS: (M+H)$^+$ 381.

Example 204

1-[(3S)-4-(6-ethylthiopheno[3,2-e]pyrimidin-4-yl)-3-methylpiperazinyl]-4-benzotriazolyloxybutan-1-one

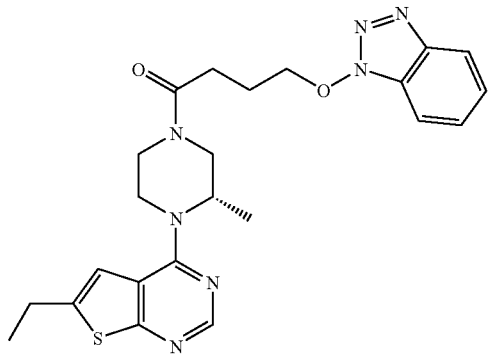

Step 1: The BOC group was removed from Example 202 according to Example 137. Yield=100%.

Step 2. The product from step 1 was reacted with 4-benzotriazolyloxybutanoic acid according to Example 4. The isolated material was desalted with MP-carbonate resin in methanol giving the desired product. Yield=50%, ES-MS: (M+H)$^+$ 466.

Example 205 tert-butyl 4-(6-ethylthiopheno[3,2-e]pyrimidin-4-yl)-3-phenylpiperazinecarboxylate

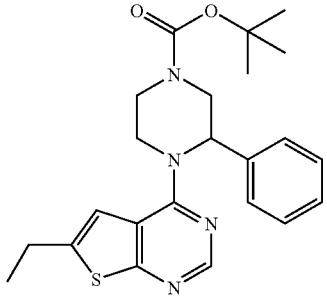

Step 1 (d,1)-Phenylglycine (5.04 g) was combined with dichloromethane (50 mL) and triethylamine (4.65 mL). Di-tert-butyldicarbonate (7.27 g) was added and the reaction was stirred at room temperature for 6 days. After concentrating to dryness, the residue was diluted with ethyl acetate (50 mL) and washed with HCl (1N in water, 3×10 mL), water (10 mL) and brine (10 mL). The organic phase was then dried over anhydrous magnesium sulfate, filtered and concentrated giving N-BOC-(d,1)-phenylglycine (8.54 g). Yield=100%.

Step 2: N-BOC-(d,1)-Phenylglycine (8.31 g) was dissolved in tetrahydrofuran (100 mL) and carbonyldiimidazole (5.37 g) was added. After stirring at room temperature for 1.5 hours, glycine methylester hydrochloride (4.16 g) was added. The reaction was stirred at room temperature for 5 days after which, it was concentrated to dryness. The residue was dissolved in ethyl acetate (50 mL) and washed with HCl (1 N in water, 3×10 mL), saturated aqueous sodium bicarbonate (3×10 mL) and brine (10 mL). The organic layer was dried over anhydrous magnesium sulfate, filtered and concentrated giving N-(N-BOC-phenylglycinyl) glycine methyl ester (9.01 g). Yield=85%.

Step 3: N-(N-BOC-Phenylglycinyl)glycine methyl ester (8.93 g) was dissolved in formic acid (100 mL) and allowed to stir at room temperature for 4 hours. After concentrating to dryness, the residue was combined with n-butanol (40 mL) and toluene (20 mL). The resulting mixture was heated to reflux for 23 hours after which, it was concentrated to dryness. Toluene (100 mL) was added and the mixture was concentrated to a volume of 20 mL. The resulting mixture was cooled to 0° C. and the solids were filtered, washed with toluene and dried under vacuum giving 3-phenyl-2,5-diketopiperazine (2.20 g). Yield=42%.

Step 4: Lithium aluminum hydride (1.77 g) was placed in a 500 mL round bottom flask and evacuated three times with argon purging. After the third evacuation, tetrahydrofuran (150 mL) was added via cannula. Solid 3-phenyl-2,5-diketopiperazine (1.11 g) was slowly added after which, the resulting mixture was heated to reflux under argon for 20 hours. After cooling to room temperature, the reaction was quenched by careful addition of solid sodium sulfate decahydrate until gas evolution ceased. The mixture was then vigorously stirred for 3 hours at room temperature. The solids were removed by filtration and the filtrate was concentrated to dryness givine d,1-2-phenylpiperazine (0.76 g). Yield=80%.

Step 5: (d,1)-2-Phenylpiperazine was converted to 1-BOC-d,1-3-phenylpiperazine according to Example 192. Yield=22%.

Step 6: 1-BOC(-d,1)-3-Phenylpiperazine was coupled with 4-chloro-6-ethylthiopheno[2,3-d]pyrimidine according to Example 87. Purification on silica gel (10% to 35% ethyl acetate/hexane over 40 minutes) gave the desired product. Rf=0.25 (25% ethyl acetate/hexane), Yield=35%, ES-MS: (M+H)$^+$ 425.

Example 206

1-[4-(6-ethylthiopheno[3,2-e]pyrimidin-4-yl)-3-phenylpiperazinyl]-2-phenylethan-1-one

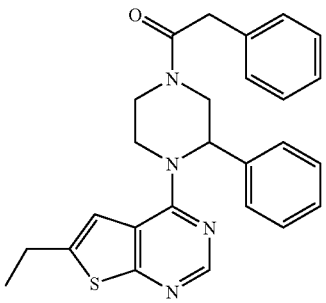

Step 1: The BOC group was removed from Example 205 according to Example 137. Yield=100%.
Step 2: The product from step 1 was reacted with phenylacetylchloride according to Example 137. Yield=69%, ES-MS: (M+H)+ 443.

Example 207

4-benzotriazolyloxy-1-[4-(6-ethylthiopheno[3,2-e]pyrimidin-4-yl)-3-phenylpiperazinyl]butan-1-one

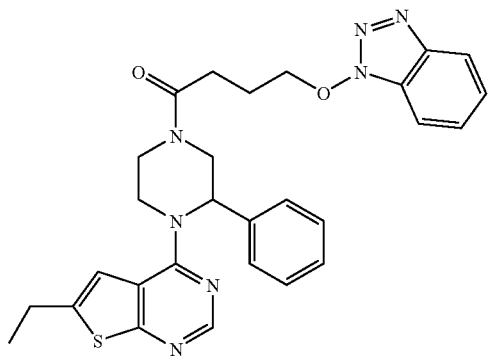

Step 1: The BOC group was removed from Example 205 according to Example 137. Yield=100%
Step 2: The product from step 1 was reacted with 4-benzotriazolyloxybutanoic acid according to Example 4. The isolated material was desalted with MP-carbonate resin in methanol giving the desired product. Yield=86%, ES-MS: (M+H)+ 528.

Example 208 tert-butyl 4-(6-ethylthiopheno[3,2-e]pyrimidin-4-yl)-3-propylpiperazinecarboxylate

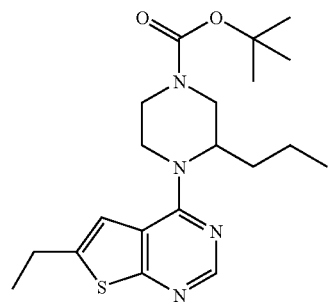

Step 1: 1-BOC-(d,1)-3-Propylpiperazine was prepared from (d,1)-norvaline according to Example 205.
Step 2: 1-BOC-(d,1)-3-Propylpiperazine was coupled with 4-chloro-6-ethylthiopheno[2,3-d]pyrimidine according to Example 87. Purification on silica gel (15% acetate/hexane) gave the desired product. Rf=0.35 (25% ethyl acetate/hexane), Yield=33%, ES-MS: (M+H)+ 391.

Example 209

1-[4-(6-ethylthiopheno[3,2-e]pyrimidin-4-yl)-3-propylpiperazinyl]-2-phenylethan-1-one

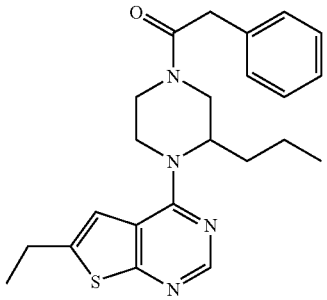

Step 1: The BOC group was removed from Example 208 according to Example 137. Yield=98%.
Step 2: The product from step 1 was reacted with phenylacetylchloride according to Example 137. Yield=66%, ES-MS: (M+H)+ 409.

Example 210

4-benzotriazolyloxy-1-[4-(6-ethylthiopheno[3,2-e]pyrimidin-4-yl)-3-propylpiperazinyl]butan-1-one

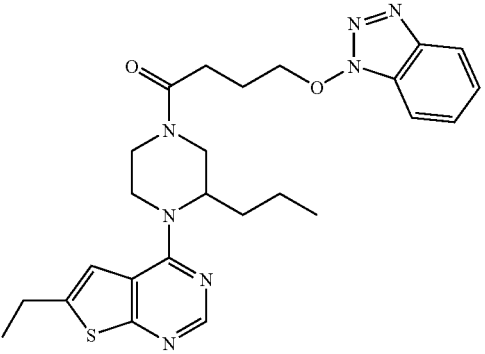

Step 1: The BOC group was removed from Example 208 according to Example 137. Yield=98%.
Step 2: The product from step 1 was reacted with 4-benzotriazolyloxybutanoic acid according to Example 4. The isolated material was desalted with MP-carbonate resin in methanol giving the desired product. Yield=76%, ES-MS: (M+H)+ 494.

Example 211 tert-butyl 4-(6-ethylthiopheno[3,2-e]pyrimidin-4-yl)-3-benzylpiperazinecarboxylate

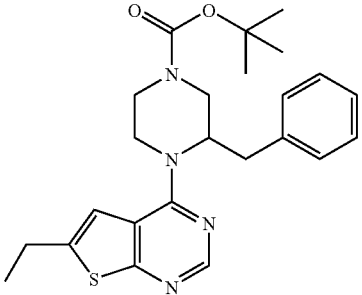

Step 1: 1-BOC-(d,1)-3-Benzylpiperazine was prepared from (d,1)-phenylalanine according to Example 205.

Step 2: 1-BOC-(d,1)-3-Benzylpiperazine was coupled with 4-chloro-6-ethylthiopheno[2,3-d]pyrimidine according to Example 87. Purification on silica gel (15% ethyl acetate/hexane) gave the desired product. Rf=0.30 (25% ethyl acetate/hexane), Yield=48%, ES-MS: (M+H)+ 439.

Example 212

1-[4-(6-ethylthiopheno[3,2-e]pyrimidin-4-yl)-3-benzylpiperazinyl]-2-phenylethan-1-one

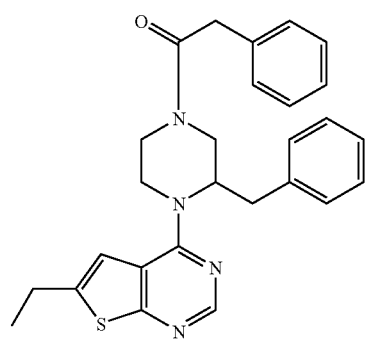

Step 1: The BOC group was removed from Example 211 according to Example 137. Yield=100%.

Step 2: The product from step 1 was reacted with phenylacetylchloride according to Example 137. Yield=65%, ES-MS: (M+H)+ 457.

Example 213

4-benzotriazolyloxy-1-[4-(6-ethylthiopheno[3,2-e]pyrimidin-4-yl)-3-benzylpiperazinyl]butan-1-one

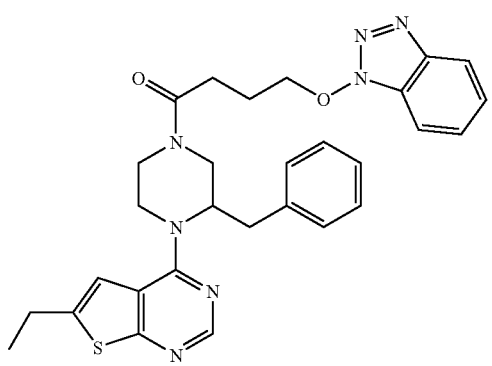

Step 1: The BOC group was removed from Example 211 according to Example 137. Yield=100%

Step 2: The product from step 1 was reacted with 4-benzotriazolyloxybutanoic acid according to Example 4. The isolated material was desalted with MP-carbonate resin in methanol giving the desired product. Yield=79%, ES-MS: (M+H)+ 542.

Example 214 tert-butyl 3-ethyl-4-(6-ethylthiopheno[3,2-e]pyrimidin-4-yl)piperazinecarboxylate

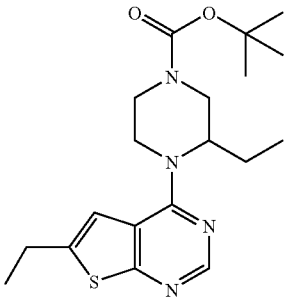

Step 1: 1-BOC-(d,1)-3-Ethylpiperazine was prepared from (d,1)-α-amino-n-butyric acid according to Example 205.

Step 2: 1-BOC-(d,1)-3-Ethylpiperazine was coupled with 4-chloro-6-ethylthiopheno[2,3-d]pyrimidine according to Example 87. Purification on silica gel (25% ethyl acetate/hexane) gave the desired product. Rf=0.29 (25% ethyl acetate/hexane), Yield=45%, ES-MS: (M+H)+ 377.

Example 215

1-[3-ethyl-4-(6-ethylthiopheno[3,2-e]pyrimidin-4-yl)piperazinyl]-2-phenylethan-1-one

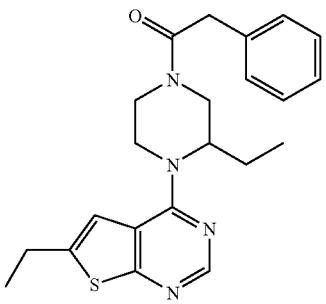

Step 1: The BOC group was removed from Example 214 according to Example 137. Yield=95%.

Step 2: The product from step 1 was reacted with phenylacetylchloride according to Example 137. Yield=63%, ES-MS: (M+H)+ 395.

Example 216

4-benzotriazolyloxy-1-[3-ethyl-4-(6-ethylthiopheno[3,2-e]pyrimidin-4-yl)piperazinyl]butan-1-one

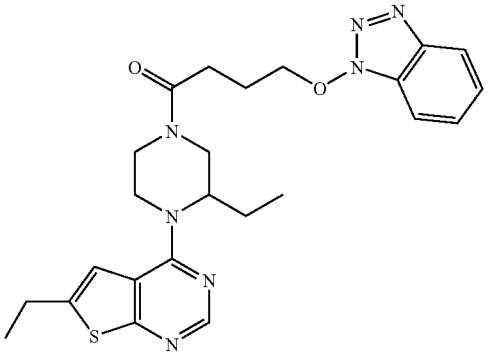

Step 1. The BOC group was removed from Example 214 according to Example 137. Yield=95%.

Step 2: The product from step 1 was reacted with 4-benzotriazolyloxybutanoic acid according to Example 4. The isolated material was desalted with MP-carbonate resin in methanol giving the desired product. Yield=69%, ES-MS: (M+H)$^+$ 480.

Example 217 tert-butyl 4-(6-ethylthiopheno[3,2-e]pyrimidin-4-yl)-3-(methylethyl)piperazinecarboxylate

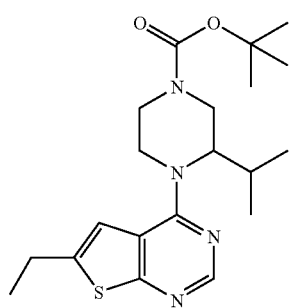

Step 1: 1-BOC-(d,1)-3-Isopropylpiperazine was prepared from N-BOC-(d,1)-valine according to Example 205.

Step 2: 1-BOC-(d,1)-3-Isopropylpiperazine was coupled with 4-chloro-6-ethylthiopheno[2,3-d]pyrimidine according to Example 87. Purification on silica gel (25% ethyl acetate/hexane) gave the desired product. Rf=0.30 (25% ethyl acetate/hexane), Yield=37%, ES-MS: (M+H)$^+$ 391.

Example 218

1-[4-(6-ethylthiopheno[3,2-e]pyrimidin-4-yl)-3-(methylethyl)piperazinyl]-2-phenylethan-1-one

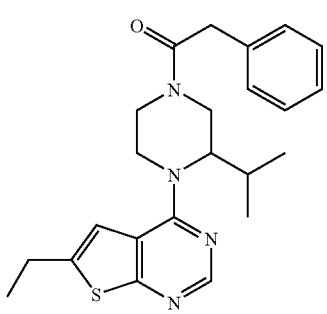

Step 1: The BOC group was removed from Example 217 according to Example 137. Yield=100%

Step 2. The product from step 1 was reacted with phenylacetylchloride according to Example 137. Yield=73%, ES-MS: (M+H)$^+$ 409.

Example 219

4-benzotriazolyloxy-1-[4-(6-ethylthiopheno[3,2-e]pyrimidin-4-yl)-3-(methylethyl)piperazinyl]butan-1-one

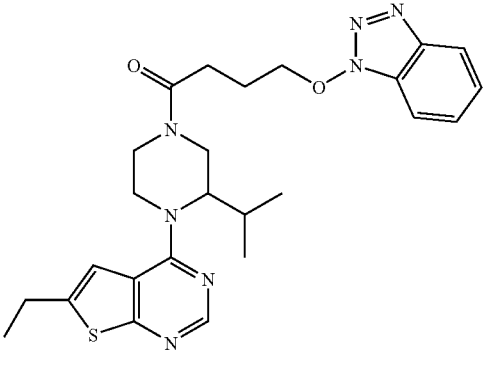

Step 1: The BOC group was removed from Example 217 according to Example 137. Yield=100%

Step 2: The product from step 1 was reacted with 4-benzotriazolyloxybutanoic acid according to Example 4. The isolated material was desalted with MP-carbonate resin in methanol giving the desired product. Yield=91%, ES-MS: (M+H)$^+$ 494.

Example 220

4-(3,4-dichlorophenyl)phenyl 4-(6-ethylthiopheno[3,2-e]pyrimidin-4-yl)piperazinyl ketone

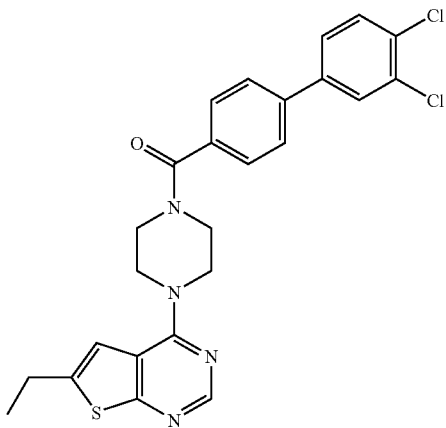

Step 1: The product from step 1 of Example 5 was reacted with 3',4'-dichloro-4-biphenylcarboxylic acid according to Example 4. The isolated material was desalted with MP-carbonate resin in methanol giving the desired product. Yield=38%, ES-MS: (M+H)$^+$ 497.

Example 221

4-(6-ethylthiopheno[3,2-e]pyrimidin-4-yl)piperazinyl 4-(4-methylphenyl)phenyl ketone

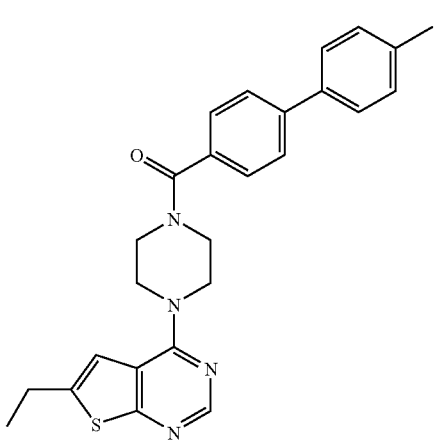

Step 1: The product from step 1 of Example 5 was reacted with 4'-methyl-4-biphenylcarboxylic acid according to Example 4. The isolated material was desalted with MP-carbonate resin in methanol giving the desired product. Yield=72%, ES-MS: (M+H)+ 443.

Example 222

4-(6-ethylthiopheno[3,2-e]pyrimidin-4-yl)piperazinyl 4-(4-methoxyphenyl)phenyl ketone

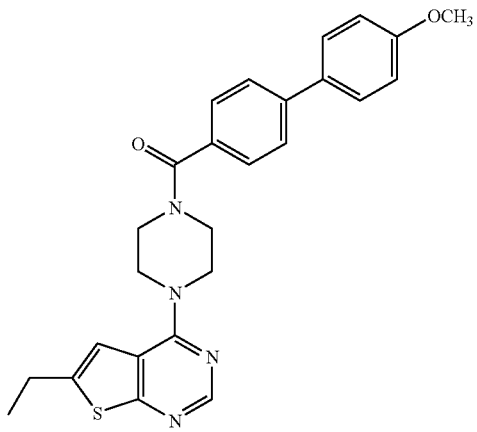

Step 1: Ethyl-4'-methoxy-4-biphenylcarboxylate (1.29 g) was dissolved in methanol (7.5 mL) and sodium hydroxide (2 N in water, 7.5 mL) was added. The reaction was stirred at room temperature for 9 days and concentrated to dryness. Water (50 mL) was added and the mixture was made acidic with HCl (6 N in water). The precipitate was removed by filtration and dried under vacuum giving 4'-methoxy-4-biphenylcarboxylic acid (1.08 g). Yield=94%.

Step 2. The product from step 1 of Example 5 was reacted with 4'-methoxy-4-biphenylcarboxylic acid according to Example 4. The isolated material was desalted with MP-carbonate resin in methanol giving the desired product. Yield=82%, ES-MS: (M+H)+ 459.

Example 223

4-(4-chlorophenyl)phenyl 4-(6-ethylthiopheno[3,2-e]pyrimidin-4-yl)piperazinyl ketone

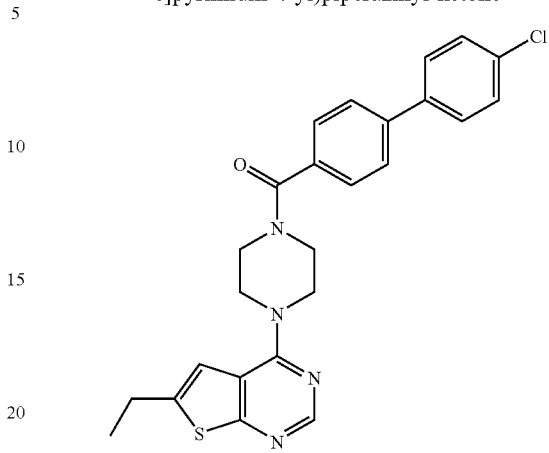

Step 1: 4-Chlorophenylboronic acid (501 mg) was combined with 4-iodobenzoic acid (795 mg), cesium carbonate (5.22 g), toluene (16 mL), water (8 mL) and n-butanol (4 mL). The mixture was degassed under vacuum with argon purging after which, tetrakis-triphenylphosphine palladium (40 mg) was added. The reaction was heated to 80° C. for 20 hours after which, it was cooled to room temperature and diluted with ethyl acetate (16 mL). The solids were collected on a Celite pad and washed with hot methanol. The methanol filtrate was concentrated to dryness giving 4'-chloro-4-biphenylcarboxylic acid (305 mg). Yield=41%

Step 2: The product from step 1 of Example 5 was reacted with 4'-chloro-4-biphenylcarboxylic acid according to Example 4. The isolated material was desalted with MP-carbonate resin in methanol giving the desired product. Yield=72%, ES-MS: (M+H)+ 463.

Example 224

4-(6-ethylthiopheno[3,2-e]pyrimidin-4-yl)piperazinyl 4-(4-hydroxyphenyl)phenyl Ketone

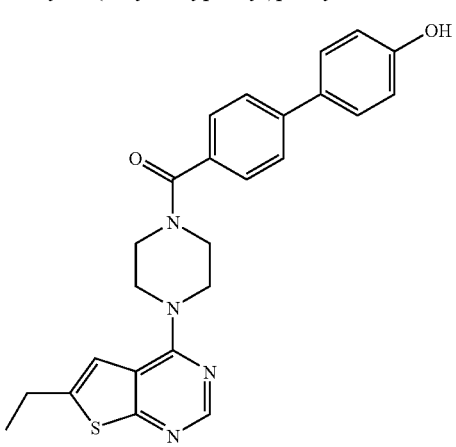

Step 1: The product from step 1 of Example 5 was reacted with 4'-hydroxy-4-biphenylcarboxylic acid according to Example 4. The isolated material was desalted with MP-carbonate resin in methanol giving the desired product. Yield=50%, ES-MS: (M+H)+ 445.

Example 225

4-(6-ethylthiopheno[3,2-e]pyrimidin-4-yl)piperazinyl 4-(4-methoxy-3-methylphenyl)phenyl ketone

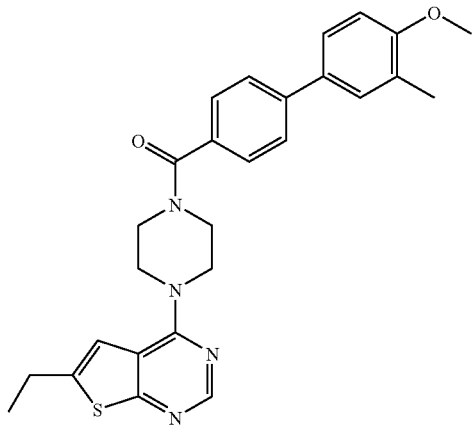

Step 1: 3-Methyl-4-methoxyphenylboronic acid (542 mg) was combined with 4-iodobenzoic acid (810 mg), cesium carbonate (5.32 g), toluene (16 mL), water (8 mL) and n-butanol (4 mL). The mixture was degassed under vacuum with argon purging after which, tetrakis-triphenylphosphine palladium (38 mg) was added. The reaction was heated to 80° C. for 20 hours after which, it was cooled to room temperature and diluted with ethyl acetate (16 mL). The layers were separated and the organics were concentrated to dryness. The residue was purified on silica gel (50% to 100% ethyl acetate/hexane over 40 minutes) giving 3'-methyl-4'-methoxy-4-biphenylcarboxylic acid (240 mg). Yield=30%

Step 2: The product from step 1 of Example 5 was reacted with 3'-methyl-4'-methoxy-4-biphenylcarboxylic acid according to Example 4. The isolated material was desalted with MP-carbonate resin in methanol giving the desired product. Yield=60%, ES-MS: (M+H)$^+$ 473.

Example 226

2-(4-{[4-(6-ethylthiopheno[3,2-e]pyrimidin-4-yl)piperazinyl]carbonyl}phenyl)benzenecarbonitrile

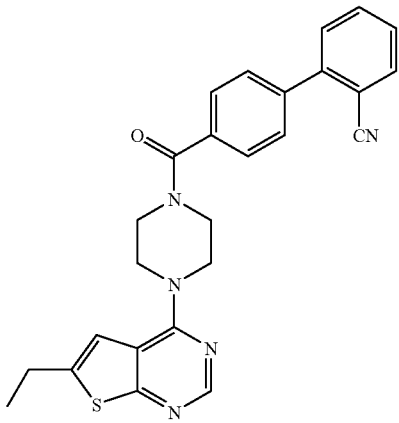

Step 1: 2-Bromobenzonitrile was reacted with 4-carboxyphenyl boronic acid according to Example 225 giving 2'-cyano-4-biphenylcarboxylic acid.

Step 2: The product from step 1 of Example 5 was reacted with 2'-cyano-4-biphenylcarboxylic acid according to Example 4. The isolated material was desalted with MP-carbonate resin in methanol giving the desired product. Yield=67%, ES-MS: (M+H)$^+$ 454.

Example 227

4-(4-aminophenyl)phenyl 4-(6-ethylthiopheno[3,2-e]pyrimidin-4-yl)piperazinyl ketone

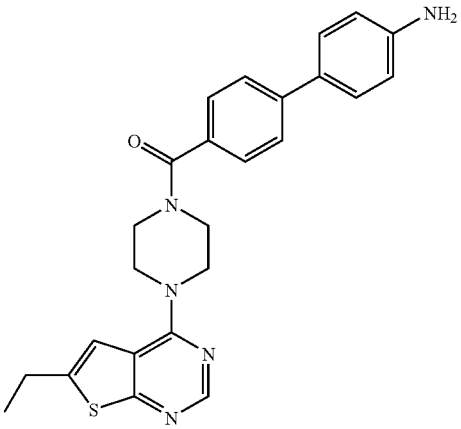

Step 1: 4-Iodobenzoic acid was reacted with 4-(4,4,5,5-tetramethyl-1,3,2-dioxaborolan-2-yl)aniline according to Example 225 giving 4'-amino-4-biphenylcarboxylic acid.

Step 2. The product from step 1 of Example 5 was reacted with 4'-amino-4-biphenylcarboxylic acid according to Example 4. The isolated material was desalted with MP-carbonate resin in methanol giving the desired product. Yield=73%, ES-MS: (M+H)$^+$ 444.

Example 228

4-(6-ethylthiopheno[3,2-e]pyrimidin-4-yl)piperazinyl 4-[4-(methylethoxy)phenyl]phenyl ketone

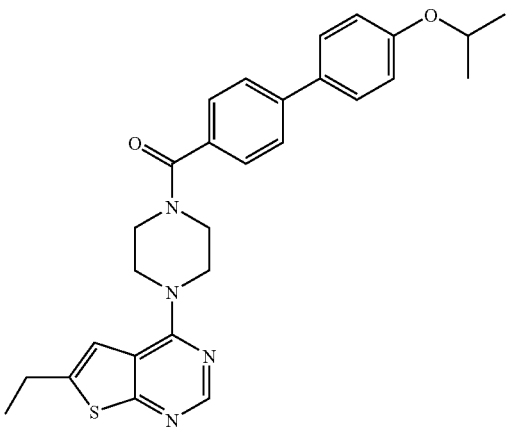

Step 1: 1-Bromo-4-isopropoxybenzene was combined with dioxane (10.5 mL) and dichloropalladium(dppf) dichloromethane complex (36 mg) under argon. 4,4,5,5-Tetramethyl-1,3,2-dioxaborolane (0.96 mL) was added followed by triethylamine (1.29 mL). The reaction was heated to 90° C. for 23 hours after which, dichloropalladium(dppf) dichloromethane complex (36 mg), 4,4,5,5-tetramethyl-1,3,2-dioxaborolane (0.96 mL) and triethylamine (1.29 mL) was added. Heating was continued for an additional 19 hours after which, it was cooled to room temperature and diluted with ethyl acetate (25 mL). The mixture was washed with water (2×20 mL) and brine (20 mL). The organic phase was dried over anhydrous sodium sulfate, filtered and concentrated. Purification of the residue on silica gel (0% to 50% ethyl acetate/hexane over 40 minutes) gave 4-(4,4,5,5-tetramethyl-1,3,2-dioxaborolan-2-yl)isopropoxybenzene (544 mg). Yield=47%.

Step 2: 4-Iodobenzoic acid was reacted with 4-(4,4,5,5-tetramethyl-1,3,2-dioxaborolan-2-yl)isopropoxybenzene according to Example 225 giving 4'-isopropoxy-4-biphenylcarboxylic acid. Yield=48%.

Step 3: The product from step 1 of Example 5 was reacted with 4'-isopropoxy-4-biphenylcarboxylic acid according to Example 4. The isolated material was desalted with MP-carbonate resin in methanol giving the desired product. Yield=50%, ES-MS: (M+H)$^+$ 487.

Example 229

4-[4-(dimethylamino)phenyl]phenyl 4-(6-ethylthiopheno[3,2-e]pyrimidin-4-yl)piperazinyl ketone

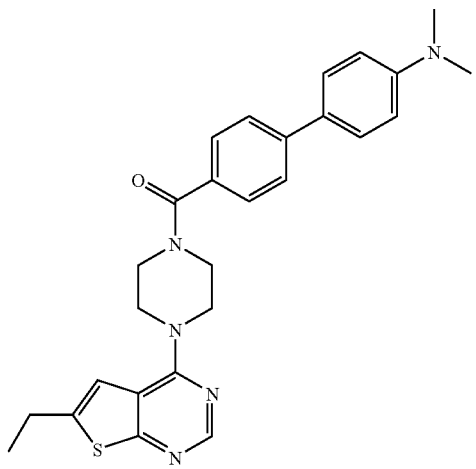

Step 1: 4-Iodobenzoic acid was reacted with 4-(dimethylamino)phenylboronic acid according to Example 225 giving 4'-dimethylamino-4-biphenylcarboxylic acid. Yield=29%.

Step 2: The product from step 1 of Example 5 was reacted with 4'-dimethylamino-4-biphenylcarboxylic acid according to Example 4. The isolated material was desalted with MP-carbonate resin in methanol giving the desired product. Yield=23%, ES-MS: (M+H)$^+$ 472.

Example 230

4-(2-{[(tert-butyl)amino]sulfonyl}phenyl)phenyl 4-(6-ethylthiopheno[3,2-e]pyrimidin-4-yl)piperazinyl ketone

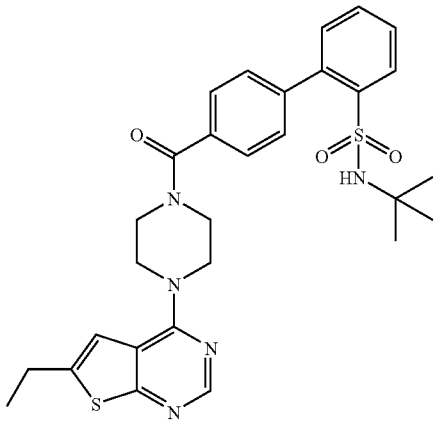

Step 1: 2-Bromobenzenesulfonyl chloride (20 g) was dissolved in dichloromethane (100 mL) and cooled to 0° C. tert-Butylamine (8.2 mL) was added followed by triethylamine (16 mL). The reaction was stirred at room temperature until determined complete by analytical HPLC analysis. Water (100 mL) was added and the layers were separated. The aqueous layer was washed with dichloromethane (50 mL) and the combined organic layers were washed with brine (100 mL). Concentration of the organic phase gave 2-bromobenzene-tert-butylsulfonamide (20 g).

Step 2: 2-Bromobenzene-tert-butylsulfonamide was reacted with 4-carboxyphenyl boronic acid according to Example 225 giving 2'-tert-butylsulfonoamido-4-biphenylcarboxylic acid.

Step 3: The product from step 1 of Example 5 was reacted with 2'-tert-butylsulfonoamido-4-biphenylcarboxylic acid according to Example 4. The isolated material was desalted with MP-carbonate resin in methanol giving the desired product. Yield=17%, ES-MS: (M+H)$^+$ 564.

Example 231

1-[4-(2-ethylthiopheno[3,2-c]pyridin-4-yl)piperazinyl]-2-phenylethan-1-one

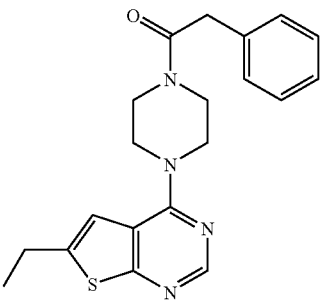

Step 1: To a solution of malonic acid (5.9 g) and 5-ethyl-2-thiophenecarboxaldehyde (4.0 g) in dry pyridine (12 mL) was added piperidine (0.42 mL). The reaction mixture was stirred at 80° C. for 17 hours, chilled and diluted with water (70 mL). This mixture was acidified with concentrated HCl (14 mL) and the white precipitate was collected by filtration, washed with water (5×10 mL) and dried under vacuum giving (2E)-3-(5-ethyl(2-thienyl))prop-2-enoic acid (5.0 g). Yield=96%

Step 2. To a chilled suspension of (2E)-3-(5-ethyl(2-thienyl))prop-2-enoic acid (3.0 g) in benzene (20 mL) and dimethylformamide (2 drops) was added thionyl chloride (1.7 mL). The reaction mixture was stirred at 60° C. for 2 hours, cooled to room temperature and concentrated to dryness giving the crude acid chloride. The crude acid chloride was dissolved in 1,2-dichlorobenzene (17 mL) and sodium azide (1.6 g) was added. After heating at 140° C. for 6 hours, catalytic iodine was added. After heating to 180° C. for 17 hours, the reaction was cooled to room temperature and the product was precipitated with the addition of acetonitrile (10 mL). The precipitate was collected by filtration and washed with hot dichloromethane. The solid was then dried under vacuum giving 2-ethyl-5-hydrothiopheno[3,2-c]pyridin-4-one (0.70 g). Yield=24%.

Step 3: 2-Ethyl-5-hydrothiopheno[3,2-c]pyridin-4-one was treated with phosphorus oxychloride according to Example 152 giving 4-chloro-6-ethylthienopyridine. Yield=68%.

Step 4: Phenylacetamidopiperazine hydrochloride (Example 141) was reacted 4-chloro-6-ethylthienopyridine according to Example 87. Yield=16%, ES-MS: (M+H)+ 366.

Example 232 tert-butyl (3S)-3-methyl-4-(2-methyl-6-propylthiopheno[3,2-e]pyrimidin-4-yl)piperazinecarboxylate

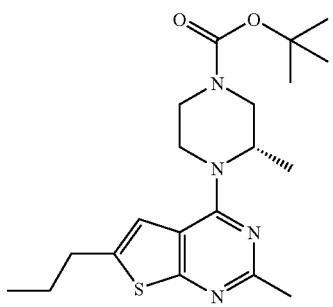

Step 1: Ethyl 2-amino-5-propylthiophene-3-carboxylate was reacted with acetonitrile according to Example 152 giving 2-ethyl-4-hydroxy-6-propylthienopyrimidine. Yield=95%.

Step 2: 2-Ethyl-4-hydroxy-6-propylthienopyrimidine was treated with phosphorus oxychloride according to Example 152 giving 2-methyl-4-chloro-6-propylthieno-pyrimidine. Yield=89%.

Step 3: 1-BOC-3-(S)-methylpiperazine was coupled with 2-methyl-4-chloro-6-propylthieno-pyrimidine according to Example 87. Yield=81%, ES-MS: (M+H)+ 391.

Example 233

1-[(3S)-3-methyl-4-(2-methyl-6-propylthiopheno[3,2-e]pyrimidin-4-y)piperazinyl]-2-phenylethan-1-one

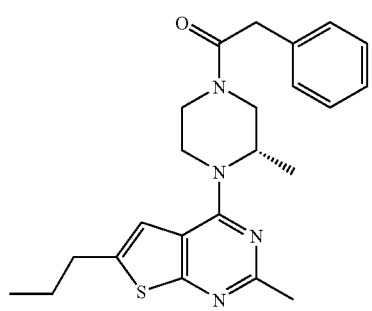

Step 1: The BOC group was removed from Example 232 according to Example 137. Yield=99%.

Step 2: The product from step 1 was reacted with phenylacetylchloride according to Example 137. Yield=31%, ES-MS: (M+H)+ 409.

Example 234

1-[(3S)-3-methyl-4-(2-methyl-6-propylthiopheno[3,2-e]pyrimidin-4-yl)pperazinyl]-4-benzotriazolyloxybutan-1-one

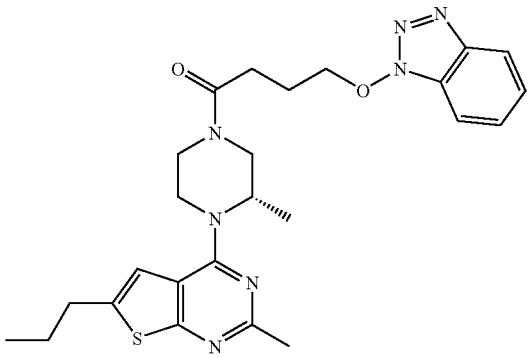

Step 1: The BOC group was removed from Example 232 according to Example 137. Yield=99%.

Step 2: The product from step 1 was reacted with 4-benzotriazolyloxybutanoic acid according Example 4. The isolated material was desalted with MP-carbonate resin in methanol giving the desired product. Yield=40%, ES-MS: (M+H)+ 494.

Example 235

4-(4-tert-Butoxycarbonyl-piperazin-1-yl)-6-ethyl-thieno[2,3-d]pyrimidine-2-carboxylic acid ethyl ester

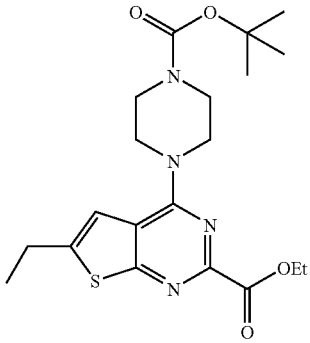

Step 1: Ethyl 2-amino-5-ethylthiophene-3-carboxylate (4.03 g) and ethylcyanoformate (2.40 mL) were dissolved in dioxane (40 mL) and HCl gas was bubbled in for 1.5 hours. The reaction was capped and allowed to stir at room temperature for 3 days, after which, it was concentrated to dryness. The residue was diluted with water (20 mL) and made basic with saturated aqueous sodium bicarbonate. The resulting solids were filtered and the residue was purified on silica get (30% to 70% ethyl acetate/hexane over 45 minutes) giving 2-ethoxycarbonyl-4-hydroxy-6-ethylthienopyrimidine (3.55 g). Yield=70%

Step 2: 2-Ethoxycarbonyl-4-hydroxy-6-ethylthienopyrimidine was treated with phosphorus oxychloride according to Example 152 giving 2-ethoxycarbonyl-4-chloro-6-ethylthienopyrimidine. Yield=96%, Rf=0.38 (25% ethyl acetate/hexane)

Step 3: BOC-piperazine was reacted with 2-methyl-4-chloro-6-ethylthienopyrimidine according to Example 87. Yield=92%, ES-MS: (M+H)+ 421.

Example 236

6-Ethyl-4-(4-phenylacetyl-piperazin-1-yl)-thieno[2,3-d]pyrimidine-2-carboxylic acid ethyl ester

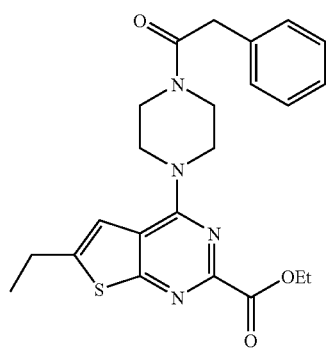

Step 1: 4-(4-tert-Butoxycarbonyl-piperazin-1-yl)-6-ethyl-thieno[2,3-d]pyrimidine-2-carboxylic acid ethyl ester (2.28 g) was dissolved in ethanol (10 mL) and HCl (4 M in dioxane, 10 mL) was added. The reaction was stirred at room temperature for 30 minutes and concentrated to dryness giving the desired amine as its bis HCl salt. Yield=97%

Step 2: The product from step 1 was reacted with phenylacetyl chloride according to Example 137. Yield=72%, ES-MS: (M+H)⁺ 439.

Example 237

4-{4-[4-(Benzotriazol-1-yloxy)-butyryl]-piperazin-1-yl}-6-ethyl-thieno[2,3-d]pyrimidine-2-carboxylic acid ethyl ester

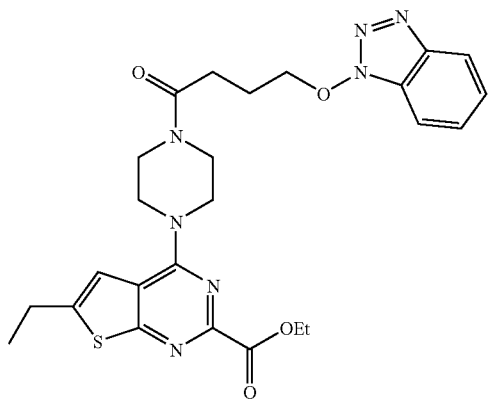

Step 1: The BOC group was removed from Example 235 according to Example 137. Yield=97%

Step 2: The product from step 1 (310.4 mg) was combined with 4-benzotriazolyl-oxybutanoic acid (210.0 mg), HBTU (450.5 mg) and acetonitrile (5 mL). Diisopropyl-ethylamine (0.83 mL) was added and the reaction was stirred at room temperature for 18 hours. The product was isolated from the reaction via silica gel chromatography (80% to 100% ethyl acetate/hexane over 30 minutes. Yield=91%, ES-MS: (M+H)⁺ 524.

Example 238

4-(4-tert-Butoxycarbonyl-piperazin-1-yl)-6-ethyl-thieno[2,3-d]pyrimidine-2-carboxylic acid

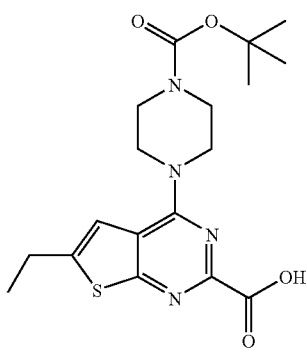

4-(4-tert-Butoxycarbonyl-piperazin-1-yl)-6-ethyl-thieno[2,3-d]pyrimidine-2-carboxylic acid ethyl ester (118.9 mg) was dissolved in methanol (0.42 mL) and NaOH (2 M in water, 0.42 mL) was added. The reaction was stirred at room temperature for 3 hours after which, it was neutralized with DOWEX acid ion exchange resin. The mixture was filtered and the filtrate was concentrated to dryness giving the desired product. Yield=100%, ES-MS: (M+H)⁺ 393.

Example 239

6-Ethyl-4-(4-phenylacetyl-piperazin-1-yl)-thieno[2,3-d]pyrimidine-2-carboxylic acid

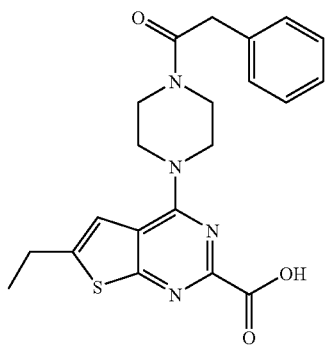

6-Ethyl-4-(4-phenylacetyl-piperazin-1-yl)-thieno[2,3-d]pyrimidine-2-carboxylic acid ethyl ester (199.2 mg) was converted to the desired product according to Example 238. Yield=100%, ES-MS: (M+H)⁺ 411.

Example 240

4-{4-[4-(Benzotriazol-1-yloxy)-butyryl]-piperazin-1-yl}-6-ethyl-thieno[2,3-d]pyrimidine-2-carboxylic acid

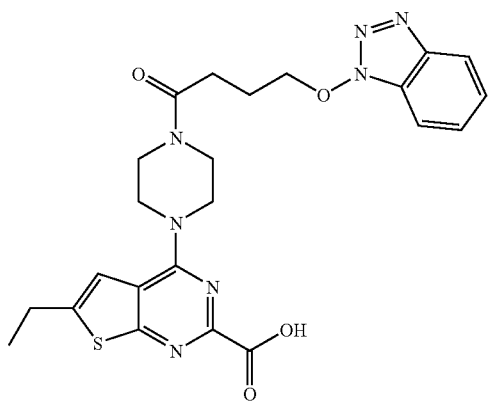

4-{4-[4-(Benzotriazol-1-yloxy)-butyryl]-piperazin-1-yl}-6-ethyl-thieno[2,3-d]pyrimidine-2-carboxylic acid ethyl ester (302.4 mg) was converted to the desired product according to Example 238. Yield=94%, ES-MS: (M+H)$^+$ 496.

Example 241

4-(2-Carbamoyl-6-ethyl-thieno[2,3-d]pyrimidin-4-yl)-piperazine-1-carboxylic acid tert-butyl ester

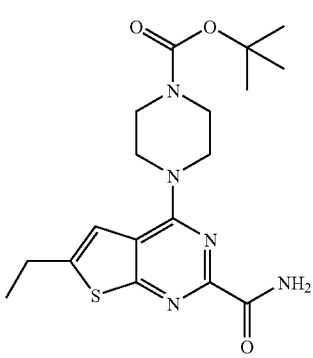

4-(4-tert-Butoxycarbonyl-piperazin-1-yl)-6-ethyl-thieno[2,3-d]pyrimidine-2-carboxylic acid (102.3 mg) was dissolved in tetrahydrofuran (0.50 mL) and 1,1'-carbonyl-diimidazole (42.3 mg) was added. The reaction was stirred at room temperature for 30 minutes and ammonia (0.5 M in dioxane, 1.57 mL) was added. The reaction was stirred at room temperature for 8 days and concentrated to dryness. The residue was purified on silica gel (0% to 10% ethyl acetate/hexane over 30 minutes) giving the desired product. Yield=47%, ES-MS: (M+H)$^+$ 392.

Example 242

6-Ethyl-4-(4-phenylacetyl-piperazin-1-yl)-thieno[2,3-d]pyrimidine-2-carboxylic acid amide

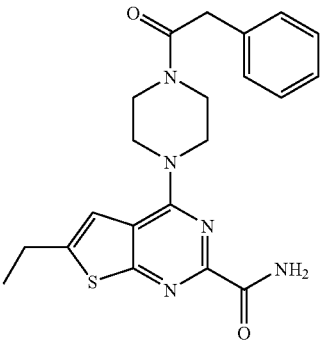

6-Ethyl-4-(4-phenylacetyl-piperazin-1-yl)-thieno[2,3-d]pyrimidine-2-carboxylic acid was converted to the desired product according to Example 241. Yield=48%, ES-MS: (M+H)$^+$ 410.

Example 243

4-{4-[4-(Benzotriazol-1-yloxy)-butyryl]-piperazin-1-yl}-6-ethyl-thieno[2,3-d]pyrimidine-2-carboxylic acid amide

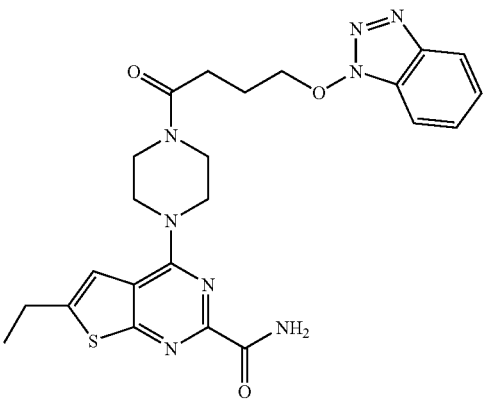

4-{4-[4-(Benzotriazol-1-yloxy)-butyryl]-piperazin-1-yl}-6-ethyl-thieno[2,3-d]pyrimidine-2-carboxylic acid was converted to the desired product according to Example 241. Yield=48%, ES-MS: (M+H)$^+$ 495.

Example 244

4-(2-Cyano-6-ethyl-thieno[2,3-d]pyrimidin-4-yl)-piperazine-1-carboxylic acid tert-butyl ester

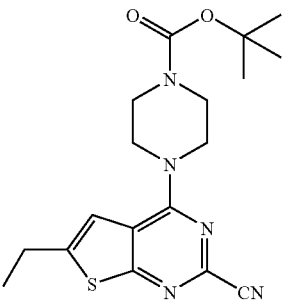

4-(2-Carbamoyl-6-ethyl-thieno[2,3-d]pyrimidin-4-yl)-piperazine-1-carboxylic acid tert-butyl ester (28.2 mg) was dissolved in methylene chloride (1.00 mL) and diisopropylethylamine (0.13 mL) and trifluroacetic anhydride (40.7 μL) was added. After stirring at room temperature for 2.5 hours, the product was isolated from silica gel chromatography (15% to 35% ethyl acetate/hexane over 40 minutes). Yield=46%, ES-MS: (M+H)$^+$ 374.

Example 245

6-Ethyl-4-(4-phenylacetyl-piperazin-1-yl)-thieno[2,3-d]pyrimidine-2-carbonitrile

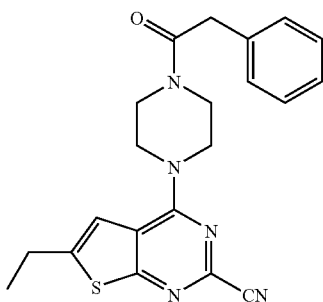

6-Ethyl-4-(4-phenylacetyl-piperazin-1-yl)-thieno[2,3-d]pyrimidine-2-carboxylic acid amide was converted to the desired product according to Example 244. Yield=91%, ES-MS: (M+H)$^+$ 392.

Example 246

4-{4-[4-(Benzotriazol-1-yloxy)-butyryl]-piperazin-1-yl}-6-ethyl-thieno[2,3-d]pyrimidine-2-carbonitrile

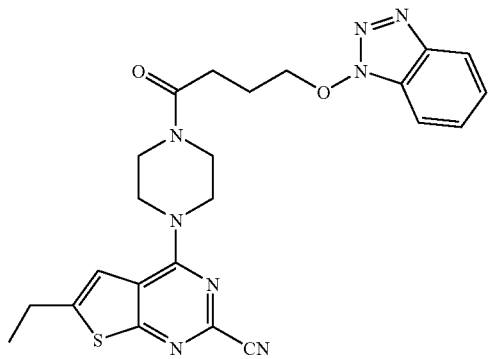

4-{4-[4-(Benzotriazol-1-yloxy)-butyryl]-piperazin-1-yl}-6-ethyl-thieno[2,3-d]pyrimidine-2-carboxylic acid amide was converted to the desired product according to Example 244. Yield=88%, ES-MS: (M+H)$^+$ 477.

Example 247

4-(6-Methoxymethyl-thieno[2,3-d]pyrimidin-4-yl)-piperazine-1-carboxylic acid tert-butyl ester

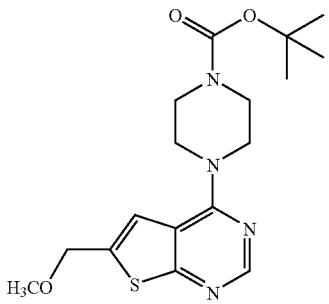

Step 1: Thieno[2,3-d]pyrimidin-4-ol (1.01 g) was placed into a dry round bottomed flask under argon at rt, and then POCl$_3$ (10.0 mL) was carefully added and a reflux condenser was attached. The resulting suspension was warmed to 120° C. and stirred 24 hr. After cooling to rt, the mixture was diluted with ethyl acetate (20 mL) and washed with saturated aqueous sodium bicarbonate (3×10 mL) and brine (10 mL). The EtOAc was then dried with sodium sulfate, filtered, and concentrated giving the desired chloropyrimidine. Yield=92%.

Step 2. The product from Step 1 was coupled with BOC-piperazine according to Example 87. Yield=91%, ES-MS: (M+H)$^+$ 321.

Step 3: The product from Step 2 (217.6 mg) was dissolved in tetrahydrofuran (3.0 mL) and cooled to −78 deg C. under argon. n-Butyllithium (1.6 M in hexanes, 0.47 mL) was added and the reaction was stirred at −78 deg C. for 30 minutes. Chloromethyl methyl ether (62 μL) was added and the reaction was stirred from −78 deg C. to −30 deg C. over 1.5 hours. After quenching with methanol and diisopropyl ethylamine, the product was isolated from the reaction mixture via silica gel chromatography (15% to 45% ethyl acetate/hexane over 40 minutes). Yield=34%, ES-MS: (M+H)$^+$ 365.

Example 248

1-[4-(6-Methoxymethyl-thieno[2,3-d]pyrimidin-4-yl)-piperazin-1-yl]-2-phenyl-ethanone

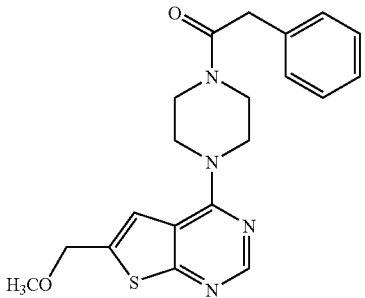

Step 1: The BOC group was removed from Example 247 according to Example 236. Yield=99%

Step 2. The product from step 1 was reacted with phenylacetyl chloride according to Example 137. Yield=52%, ES-MS: (M+H)$^+$ 383.

Example 249

4-(Benzotriazol-1-yloxy)-1-[4-(6-methoxymethyl-thieno[2,3-d]pyrimidin-4-yl)-piperazin-1-yl]-butan-1-one

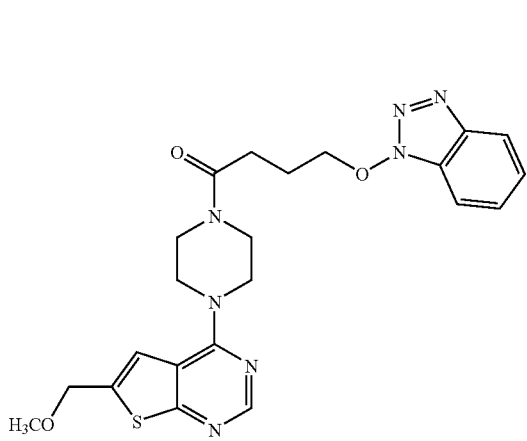

Step 1: The BOC group was removed from Example 247 according to Example 236. Yield=99%

Step 2: The product from step 1 was coupled with 4-benzotriazolyl-oxybutanoic acid according to Example 237. Yield=85%, ES-MS: (M+H)$^+$ 468.

Example 250

[3-(Benzotriazol-1-yloxymethyl)-phenyl]-[4-(6-ethyl-thieno[2,3-d]pyrimidin-4-yl)-piperazin-1-yl]-methanone

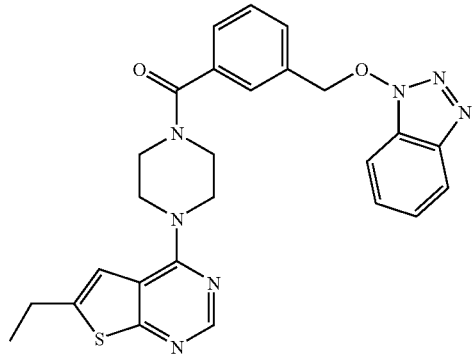

Step 1: 3-Chloromethylbenzoic acid (932.3 mg) was combined with cesium carbonate (4.45 g), hydroxybenzotriazole (738.5 mg) and acetonitrile (20 mL). The reaction was stirred at room temperature for 24 hours and diluted with water (100 mL). The mixture was acidified with 6 N HCl and the solids were collected by filtration. Recrystallization of the solids gave the desired carboxylic acid. Yield=37%

Step 2. The HCl salt from Example 5 was coupled with the product from step 1 according to Example 237. Yield=57%, ES-MS: (M+H)$^+$ 500

Example 251

(3-Benzotriazol-1-ylmethyl-phenyl)-[4-(6-ethyl-thieno[2,3-d]pyrimidin-4-yl)-piperazin-1-yl]-methanone

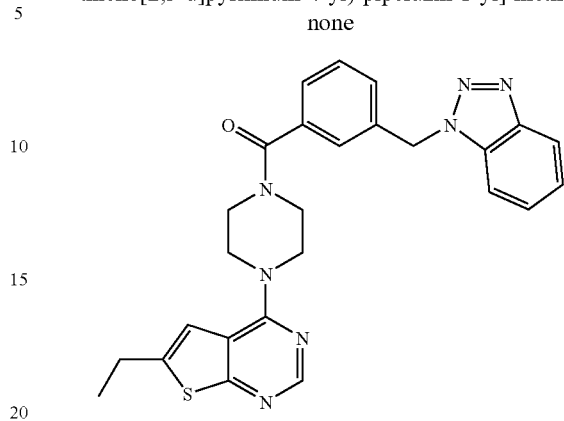

Step 1: 3-Chloromethylbenzoic acid was coupled with benzotriazole according to Example 250 giving an inseparable mixture of 1- and 2-substituted benzotriazoles. Yield=56%

Step 2: The HCl salt from Example 5 was coupled with the product from step 1 according to Example 237 giving only the 1-substituted benzotriazole. Yield=38%, ES-MS: (M+H)$^+$ 484.

Example 252

[4-(Benzotriazol-1-yloxymethyl)-phenyl]-[4-(6-ethyl-thieno[2,3-d]pyrimidin-4-yl)-piperazin-1-yl]-methanone

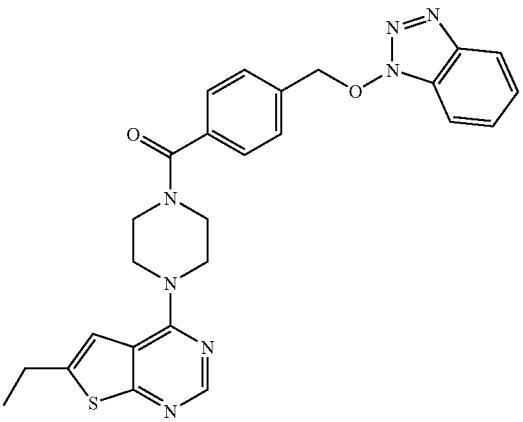

Step 1: 4-Bromomethylbenzoic acid methyl ester was coupled with hydroxybenzotriazole according to Example 250. Yield=95%

Step 2: The product from step 1 (1.12 g) was dissolved in methanol (6.00 mL) and 2 M NaOH (6 mL) was added. After stirring at room temperature for 3 days, the reaction was concentrated to dryness. The residue was dissolved in water (20 mL) and acidified with 6 N HCl. The solids were filtered and dried under vacuum giving the desired carboxylic acid. Yield=97%.

Step 3: The HCl salt from Example 5 was coupled with the product from step 2 according to Example 237. Yield=78%, ES-MS: (M+H)$^+$ 500

Example 253

(4-Benzotriazol-2-ylmethyl-phenyl)-[4-(6-ethyl-thieno[2,3-d]pyrimidin-4-yl)-piperazin-1-yl]-methanone

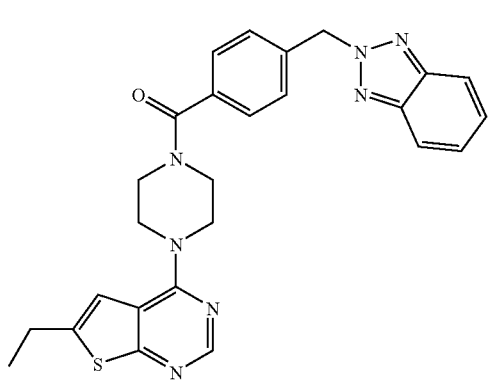

Step 1: 4-Bromomethylbenzoic acid methyl ester was coupled with benzotriazole according to Example 250 giving a mixture of 1- and 2-substituted benzotriazoles. 1-substituted Yield=60%, 2-substituted Yield=22%

Step 2: The 2-substituted benzotriazole from step 1 was converted to its carboxylic acid according to Example 252. Yield=100%

Step 3. The HCl salt from Example 5 was coupled with the product from step 2 according to Example 237 giving the desired product. Yield=81%, ES-MS: (M+H)$^+$ 484

Example 254

(4-Benzotriazol-1-ylmethyl-phenyl)-[4-(6-ethyl-thieno[2,3-d]pyrimidin-4-yl)-piperazin-1-yl]-methanone

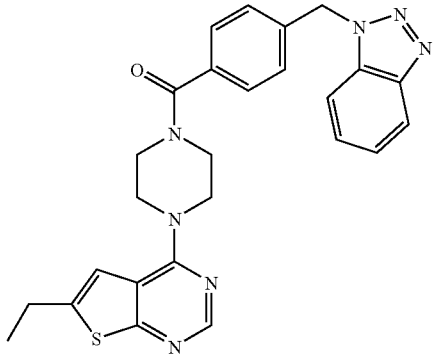

Step 1: 4-Bromomethylbenzoic acid methyl ester was coupled with benzotriazole according to Example 250 giving a mixture of 1- and 2-substituted benzotriazoles. 1-substituted Yield=60%, 2-substituted Yield=22%

Step 2: The 1-substituted benzotriazole from step 1 was converted to its carboxylic acid according to Example 252. Yield=100%

Step 3: The HCl salt from Example 5 was coupled with the product from step 2 according to Example 237 giving the desired product. Yield=99%, ES-MS: (M+H)$^+$ 484.

Example 255

2-(Benzotriazol-1-ylmethoxy)-1-[4-(6-ethyl-thieno[2,3-d]pyrimidin-4-yl)-piperazin-1-yl]-ethanone

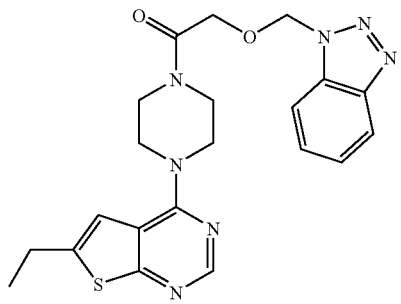

Step 1: Sodium hydride (60%, 145.0 mg) was suspended in anhydrous tetrahydrofuran (5.00 mL) and 1-chloromethylbenzotriazole (506.4 mg) was added. Methyl glycolate (0.35 mL) was added dropwise and the reaction was stirred at room temperature for 1.5 hours and heated to 50 deg C. for 21.5 hours. After removing the solvent, the residue was purified on silica gel (25% to 50% ethyl acetate/hexane over 30 minutes) giving the desired ether. Yield=65%

Step 2: The product from step 1 was converted to its carboxylic acid according to Example 252. Yield=86%

Step 3: The HCl salt from Example 5 was coupled with the product from step 2 according to Example 237 giving the desired product. Yield=62%, ES-MS: (M+H)$^+$ 438.

Example 256

2-[4-(6-Ethyl-thieno[2,3-d]pyrimidin-4-yl)-piperazine-1-carbonyl]-piperidine-1-carboxylic acid tert-butyl ester

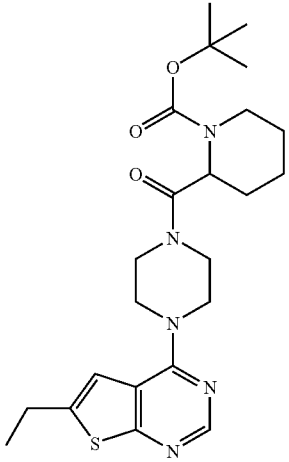

The HCl salt from Example 5 was coupled with the N-BOC-pipecolinic acid according to Example 237 giving the desired product. Yield=80%, ES-MS: (M+H)$^+$ 460.

Example 257

4-[4-(6-Ethyl-thieno[2,3-d]pyrimidin-4-yl)-piperazine-1-carbonyl]-piperidine-1-carboxylic acid tert-butyl ester

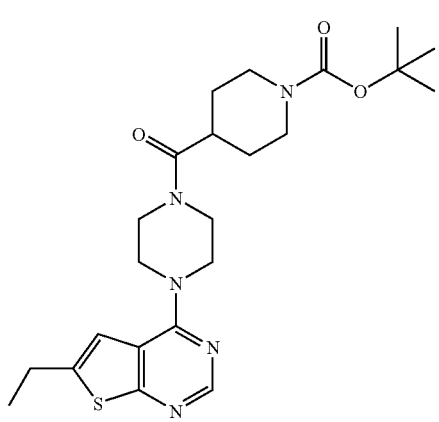

The HCl salt from Example 5 was coupled with the N-BOC-isonipecotic acid according to Example 237 giving the desired product. Yield=25%, ES-MS: (M+H)$^+$ 460

Example 258

2-[4-(6-Ethyl-thieno[2,3-d]pyrimidin-4-yl)-piperazine-1-carbonyl]-pyrrolidine-1-carboxylic acid tert-butyl ester

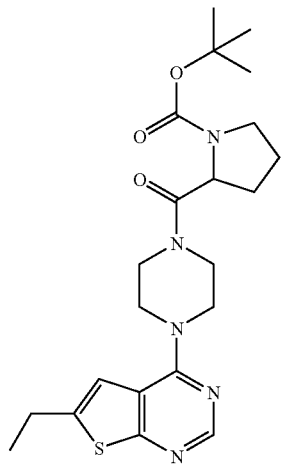

The HCl salt from Example 5 was coupled with the N-BOC-proline according to Example 237 giving the desired product. Yield=82%, ES-MS: (M+H)$^+$ 446

Example 259

[4-(6-Ethyl-thieno[2,3-d]pyrimidin-4-yl)-piperazin-1-yl]-piperidin-2-yl-methanone

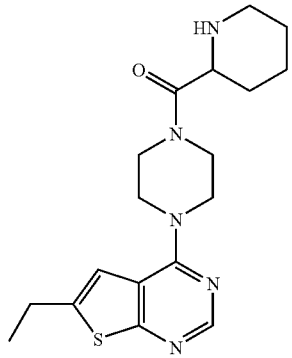

2-[4-(6-Ethyl-thieno[2,3-d]pyrimidin-4-yl)-piperazine-1-carbonyl]-piperidine-1-carboxylic acid tert-butyl ester (276.1 mg) was dissolved in methanol (1.00 mL) and HCl (4 M in dioxane, 1.00 mL) was added. After stirring at room temperature for 1.5 hours, the solvents were removed and the residue was desalted with MP-carbonate resin in methanol giving the desired free amine. Yield=100%, ES-MS: (M+H)$^+$ 360

Example 260

[4-(6-Ethyl-thieno[2,3-d]pyrimidin-4-yl)-piperazin-1-yl]-piperidin-4-yl-methanone

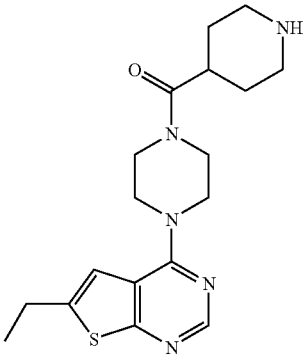

4-[4-(6-Ethyl-thieno[2,3-d]pyrimidin-4-yl)-piperazine-1-carbonyl]-piperidine-1-carboxylic acid tert-butyl ester was converted to its free amine according to Example 259. Yield=100%, ES-MS: (M+H)$^+$ 360

Example 261

(4-Benzotriazol-1-yl-phenyl)-[4-(6-ethyl-thieno[2,3-d]pyrimidin-4-yl)-piperazin-1-yl]-methanone

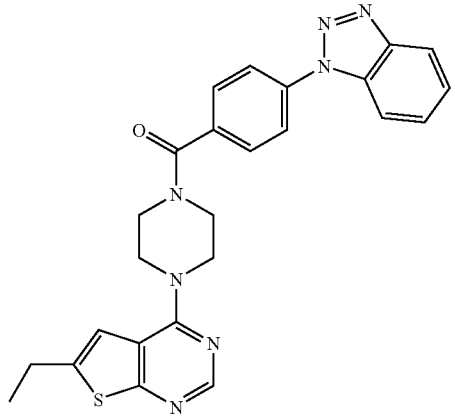

Step 1: 4-Fluorobenzoic acid ethyl ester (0.87 mL) was combined with benzotriazole (0.78 g), cesium carbonate (2.91 g) and dimethylformamide (5.0 mL). The mixture was heated to 150 deg C. for 24 hours. Following dilution with water (100 mL), the solids were filtered, washed with water, air dried and purified on silica gel (10% to 25% ethyl acetate/hexane over 40 minutes) giving the desired 1-substituted benzotriazole carboxylic acid. Yield=32%

Step 2: The HCl salt from Example 5 was coupled with the carboxylic acid from step 1 according to Example 237 giving the desired product. Yield=50%, ES-MS: (M+H)+ 470

Example 262

(3-Benzotriazol-1-yl-phenyl)-[4-(6-ethyl-thieno[2,3-d]pyrimidin-4-yl)-piperazin-1-yl]-methanone

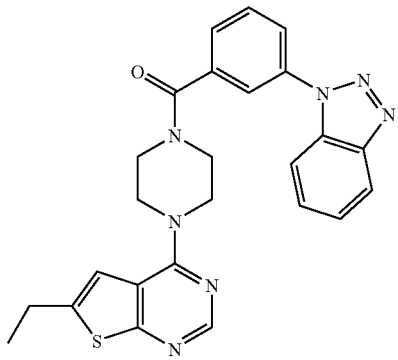

Step 1: 3-Iodobenzoic acid methl ester (527.4 mg) was combined with benzotriazole (287.8 mg), cesium carbonate (688.7 mg), copper (I) iodide (57.5 mg), 8-hydroxyquinoline (43.8 mg) and anhydrous dimethylsulfoxide (2.00 mL). The mixture was degassed under vacuum with argon purge and then heated to 120 deg C. for 18 hours. After diluting the reaction with water (50 mL), the mixture was washed with methylene chloride (3×20 mL). The aqueous phase was acidified with 6 N HCl and the solids were collected by filtration and air dried giving the crude 1-substituted benzotriazole carboxylic acid. Yield=28%

Step 2: The HCl salt from Example 5 was coupled with the carboxylic acid from step 1 according to Example 237 giving the desired product. Yield=58%, ES-MS: (M+H)+ 470

Example 263

(2-Benzotriazol-1-yl-phenyl)-[4-(6-ethyl-thieno[2,3-d]pyrimidin-4-yl)-piperazin-1-yl]-methanone

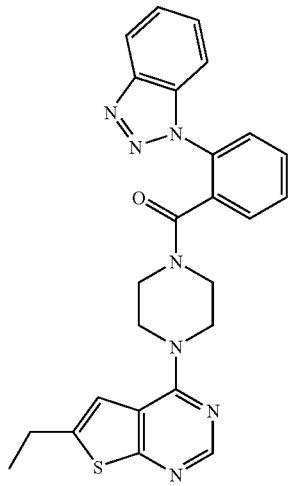

Step 1: 2-Fluorobenzoic acid ethyl ester was coupled with benzotriazole according to Example 261 giving a 1:1 mixture of the 1-substituted benzotriazole carboxylic acid and the 1-substituted benzotriazole carboxylic acid ethyl ester. Carboxylic acid Yield 17%, ethyl ester Yield=17%

Step 2: The HCl salt from Example 5 was coupled with the carboxylic acid from step 1 according to Example 237 giving the desired product. Yield=27%, ES-MS: (M+H)+ 470.

Example 264

2-(2-Benzotriazol-1-yl-phenyl)-1-[4-(6-ethyl-thieno[2,3-d]pyrimidin-4-yl)-piperazin-1-yl]-ethanone

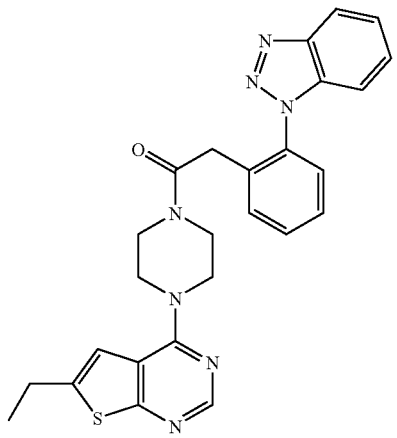

Step 1: 2-Iodophenylacetic acid (1.45 g) was added to a mixture of methanol (100 mL) and acetyl chloride (5 mL). After stirring at room temperature for 3 hours, the solvent was removed and the residue was dried under vacuum giving the desired 2-iodophenylacetic acid methyl ester. Yield=100%

Step 2. 2-Iodophenylacetic acid methyl ester (509.8 mg) was combined with benzotriazole (264.1 mg), cesium carbonate (631.9 mg), copper (I) iodide (52.8 mg), 8-hydroxyquinoline (40.2 mg) and anhydrous dimethylsulfoxide (1.8 mL). The mixture was degassed under vacuum with argon purge and then heated to 120 deg C. for 22 hours. After diluting the reaction with water (100 mL), 6 N aqueous sodium hydroxide (0.92 mL) was added. Stirring was continued for 2 hours at room temperature after which, the mixture was washed with methylene chloride (3×30 mL). The aqueous phase was acidified with 6 N HCl and washed with methylene chloride (3×30 mL). The combined extracts were dried over anhydrous sodium sulfate, filtered and concentrated and the residue was added to a mixture of methanol (20 mL) and acetyl chloride (1 mL). After stirring at room temperature for 3 days, the solvent was removed and the residue was partitioned between methylene chloride (20 mL) and saturated aqueous sodium bicarbonate (50 mL). After washing with methylene chloride (3×20 mL), the combined organics were dried over anhydrous sodium sulfate, filtered and concentrated giving the desired methyl ester. Yield=26%

Step 3. The product from step 2 (126 mg) was dissolved in methanol (2.12 mL) and sodium hydroxide (2 M in water, 0.71 mL) was added. The reaction was stirred at room temperature for 18 hours and diluted with water (100 mL). After acidifying with 1N HCl, the product was extracted with methylene chloride (3×20 mL). The combined organics were dried over anhydrous sodium sulfate, filtered and concentrated giving the desired carboxylic acid. Yield=91%

Step 4: The HCl salt from Example 5 was coupled with the carboxylic acid from step 3 according to Example 237 giving the desired product. Yield=48%, ES-MS: (M+H)+ 484

Example 265

2-(3-Benzotriazol-1-yl-phenyl)-1-[4-(6-ethyl-thieno[2,3-d]pyrimidin-4-yl)-piperazin-1-yl]-ethanone

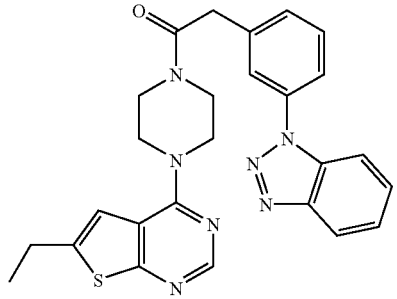

Step 1: 3-Iodophenylacetic acid was converted to its methyl ester according to Example 264. Yield=100%

Step 2: The product from step 1 was coupled with benzotriazole according to Example 264. Yield=53%

Step 3: The methyl ester from step 2 was converted to its corresponding carboxylic acid according to Example 264. Yield=94%

Step 4: The HCl salt from Example 5 was coupled with the carboxylic acid from step 3 according to Example 237 giving the desired product. Yield=46%, ES-MS: (M+H)+ 484

Example 266

2-(4-Benzotriazol-1-yl-phenyl)-1-[4-(6-ethyl-thieno[2,3-d]pyrimidin-4-yl)-piperazin-1-yl]-ethanone

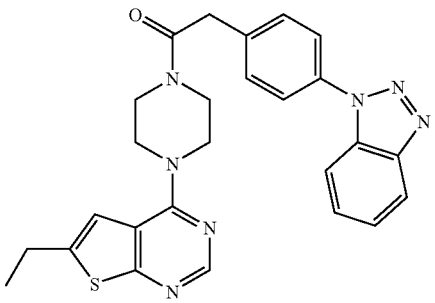

Step 1: 4-Iodophenylacetic acid was converted to its methyl ester according to Example 264. Yield=100%

Step 2: The product from step 1 was coupled with benzotriazole according to Example 264. Yield=58%

Step 3: The methyl ester from step 2 was converted to its corresponding carboxylic acid according to Example 264. Yield=88%

Step 4. The HCl salt from Example 5 was coupled with the carboxylic acid from step 3 according to Example 237 giving the desired product. Yield=75%, ES-MS: (M+H)+ 484

Example 267

2-(3-Benzotriazol-1-ylmethyl-piperidin-1-yl)-1-[4-(6-ethyl-thieno[2,3-d]pyrimidin-4-yl)-piperazin-1-yl]-ethanone

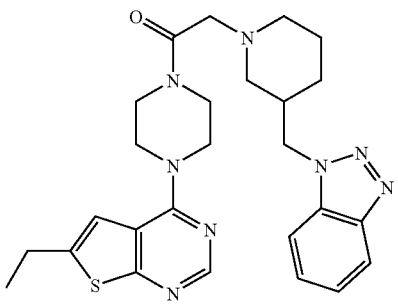

Step 1: 3-Piperidine methanol (0.98 g) was combined with benzyl bromoacetate (1.42 mL), methylene chloride (10 mL) and diisopropylethylamine (1.63 mL). The reaction was stirred at room temperature for 3 days and applied to silica gel. Chromatorgraphic purification (60% to 100% ethyl acetate/hexane over 30 minutes gave the desired N-substituted piperidine. Yield=37%

Step 2. The alcohol from step 1 (488.9 mg) was combined with methylene chloride (10 mL) and diisopropylethylamine (0.39 mL). Methanesulfonyl chloride (0.16 mL) was added and the reaction was stirred at room temperature for 1 hour. The reaction was diluted with ethyl acetate (100 mL) and washed with saturated aqueous sodium bicarbonate (3×20 mL) and brine (20 mL). The organics were dried over anhydrous sodium sulfate, filtered and concentrated to dryness giving the desired mesylate. Yield=100%

Step 3: The mesylate from step 2 (650.5 mg) was combined with benzotriazole (227.3 mg), cesium carbonate (932.3 mg) and acetonitrile (10 mL). After heating to 50 deg C. for 24 hours, the reaction was diluted with ethyl acetate (100 mL) and washed with saturated aqueous sodium bicarbonate (3×20 mL) and brine (20 mL). The organic phase was dried over anhydrous sodium sulfate, filtered and concentrated. The residue was purified on silica gel (35% to 65% ethyl acetate/hexane over 30 minutes) giving the desired 1-substituted benzotriazole. Yield=40%

Step 4: The benzyl ester from step 3 (267.6 mg) was dissolved in methanol (5 mL) and added to a degassed suspension of 10% palladium on carbon (267.6 mg) in methanol (5 mL). The mixture was stirred for 24 hours at room temperature under a hydrogen atmosphere. The solids were removed by filtration and concentration of the filtrate gave the desired carboxylic acid. Yield=74%

Step 5: The HCl salt from Example 5 was coupled with the carboxylic acid from step 4 according to Example 237 giving the desired product. Yield=86%, ES-MS: (M+H)+ 505

Example 268

2-(3-Benzotriazol-1-yl-pyrrolidin-1-yl)-1-[4-(6-ethyl-thieno[2,3-d]pyrimidin-4-yl)-piperazin-1-yl]-ethanone

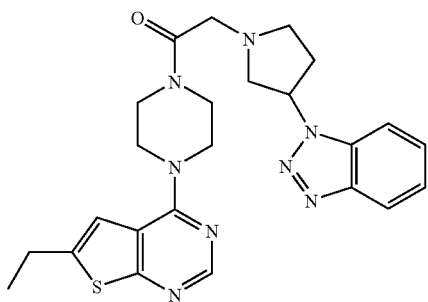

Step 1: 3-hydroxypyrrolidine was coupled with benzyl bromoacetate according to Example 267. Yield=61%

Step 2. The alcohol from step 1 was converted to its corresponding mesylate according to Example 267. Yield=91%

Step 3: The mesylate from step 2 coupled with benzotriazole according to Example 267 giving a mixture of 1- and 2-substituted benzotriazoles. The individual isomers were separated on silica gel (35% to 65% ethyl acetate/hexane over 30 minutes). 1-substituted Yield=22%, 2-substituted Yield=47%

Step 4: The benzyl ester of the 1-substituted benzotriazole from step 3 was converted to its corresponding carboxylic acid according to Example 267. Yield=74%

Step 5: The HCl salt from Example 5 was coupled with the carboxylic acid from step 4 according to Example 237 giving the desired product. Yield=79%, ES-MS: (M+H)+ 477

Example 269

1-[4-(6-Ethyl-thieno[2,3-d]pyrimidin-4-yl)-piperazin-1-yl]-2-[3-(4,5,6,7-tetrahydro-benzotriazol-2-yl)-pyrrolidin-1-yl]-ethanone

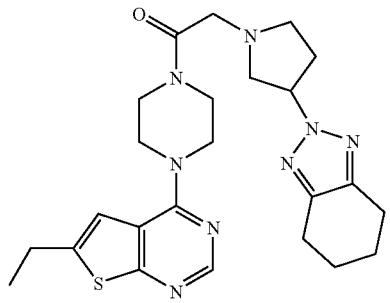

Step 1: 3-hydroxypyrrolidine was coupled with benzyl bromoacetate according to Example 267. Yield=61%

Step 2: The alcohol from step 1 was converted to its corresponding mesylate according to Example 267. Yield=91%

Step 3: The mesylate from step 2 coupled with benzotriazole according to Example 267 giving a mixture of 1- and 2-substituted benzotriazoles. The individual isomers were separated on silica gel (35% to 65% ethyl acetate/hexane over 30 minutes). 1-substituted Yield=22%, 2-substituted Yield=47%

Step 4: The benzyl ester of the 2-substituted benzotriazole from step 3 was converted to its corresponding carboxylic acid/tetrahydrobenzotriazole according to Example 267. Yield=87%

Step 5: The HCl salt from Example 5 was coupled with the carboxylic acid from step 4 according to Example 237 giving the desired product. Yield=84%, ES-MS: (M+H)+ 481

Example 270

1-[4-(6-Ethyl-thieno[2,3-d]pyrimidin-4-yl)-piperazin-1-yl]-2-[4-(4,5,6,7-tetrahydro-benzotriazol-2-yl)-piperidin-1-yl]-ethanone

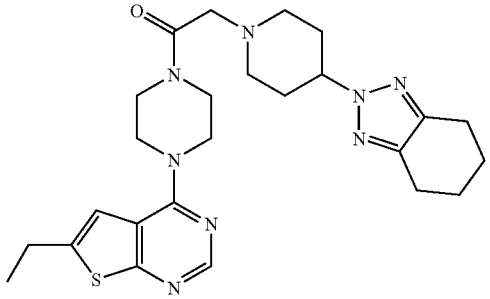

Step 1: 4-Hydroxypiperidine was coupled with benzyl bromoacetate according to Example 267. Yield=96%

Step 2: The alcohol from step 1 was converted to its corresponding mesylate according to Example 267.

Step 3: The mesylate from step 2 coupled with benzotriazole according to Example 267 giving a mixture of 1- and 2-substituted benzotriazoles. The individual isomers were separated on silica gel (35% to 65% ethyl acetate/hexane over 30 minutes). 1-substituted Yield=9%, 2-substituted Yield=17%

Step 4: The benzyl ester of the 2-substituted benzotriazole from step 3 was converted to its corresponding carboxylic acid/tetrahydrobenzotriazole according to Example 267. Yield=84%

Step 5: The HCl salt from Example 5 was coupled with the carboxylic acid from step 4 according to Example 237 giving the desired product. Yield=84%, ES-MS: (M+H)+ 495

Example 271

2-(3-Benzotriazol-1-yl-piperidin-1-yl)-1-[4-(6-ethyl-thieno[2,3-d]pyrimidin-4-yl)-piperazin-1-yl]-ethanone

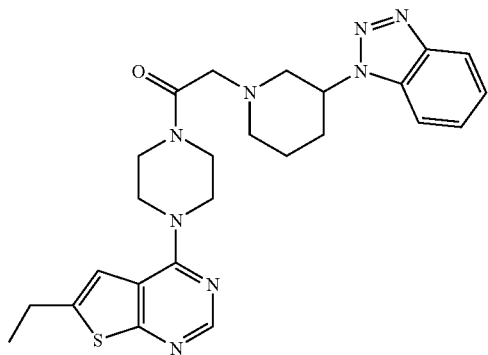

Step 1: 3-Hydroxypiperidine was coupled with benzyl bromoacetate according to Example 267. Yield=95%

Step 2: The alcohol from step 1 was converted to its corresponding mesylate according to Example 267.

Step 3: The mesylate from step 2 coupled with benzotriazole according to Example 267 giving a mixture of 1- and 2-substituted benzotriazoles. The individual isomers were separated on silica gel (20% to 50% ethyl acetate/hexane over 30 minutes). 1-substituted Yield=11%, 2-substituted Yield=3%

Step 4: The benzyl ester of the 1-substituted benzotriazole from step 3 was converted to its corresponding carboxylic acid according to Example 267. Yield=81%

Step 5: The HCl salt from Example 5 was coupled with the carboxylic acid from step 4 according to Example 237 giving the desired product. Yield=71%, ES-MS: (M+H)+ 491

Example 272

1-[4-(6-Ethyl-thieno[2,3-d]pyrimidin-4-yl)-piperazin-1-yl]-2-[3-(4,5,6,7-tetrahydro-benzotriazol-2-yl)-piperidin-1-yl]-ethanone

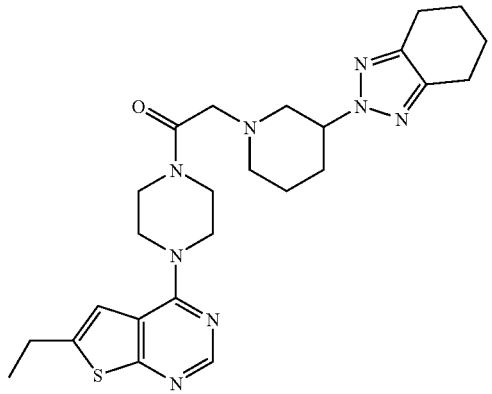

Step 1: 3-hydroxypiperidine was coupled with benzyl bromoacetate according to Example 267. Yield=61%

Step 2: The alcohol from step 1 was converted to its corresponding mesylate according to Example 267. Yield=91%

Step 3: The mesylate from step 2 coupled with benzotriazole according to Example 267 giving a mixture of 1- and 2-substituted benzotriazoles. The individual isomers were separated on silica gel (20% to 50% ethyl acetate/hexane over 30 minutes). 1-substituted Yield=22%, 2-substituted Yield=47%

Step 4: The benzyl ester of the 2-substituted benzotriazole from step 3 was converted to its corresponding carboxylic acid/tetrahydrobenzotriazole according to Example 267. Yield=77%

Step 5: The HCl salt from Example 5 was coupled with the carboxylic acid from step 4 according to Example 237 giving the desired product. Yield=35%, ES-MS: (M+H)+ 495

Example 273

2-(2-Benzotriazol-1-ylmethyl-pyrrolidin-1-yl)-1-[4-(6-ethyl-thieno[2,3-d]pyrimidin-4-yl)-piperazin-1-yl]-ethanone

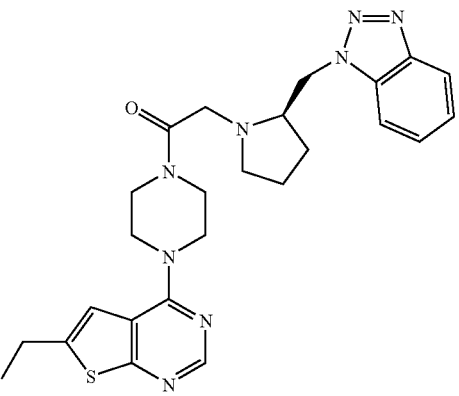

Step 1: 2-(R)-Pyrrolidinemethanol (0.92 g) was combined with methylene chloride (10 mL) and diisopropylethylamine (1.90 mL). N-(Benzyloxycarbonyloxy)succinimide (2.49 g) was added and the reaction was stirred at room temperature for 24 hours. The reaction was diluted with ethyl acetate (100 mL) and washed with 1 N HCl (3×10 mL), saturated aqueous sodium bicarbonate (3×10 mL) and brine (10 mL). The organic phase was dried over anhydrous sodium sulfate, filtered and concentrated giving the desired N-CBZ-pyrrolidinemethanol. Yield=100%

Step 2. The alcohol from step 1 was converted to its corresponding mesylate according to Example 267.

Step 3: The mesylate from step 2 coupled with benzotriazole according to Example 267 giving a mixture of 1- and 2-substituted benzotriazoles. The individual isomers were separated on silica gel (20% to 50% ethyl acetate/hexane over 30 minutes). 1-substituted Yield=22%, 2-substituted Yield=20%

Step 4: The 1-substituted benzotriazole from step 3 (170.9 mg) was dissolved in methanol (5 mL) and added to a degassed suspension of 10% palladium on carbon (170.9 mg) in methanol (5 mL). The mixture was stirred for 24 hours at room temperature under a hydrogen atmosphere. The solids were removed by filtration and concentration of the filtrate gave the desired unprotected pyrrolidine. Yield=76%

Step 5. The pyrrolidine from step 4 was coupled with benzyl bromoacetate according to Example 267. Yield=76%

Step 6. The benzyl ester of the 2-substituted benzotriazole from step 5 was converted to its corresponding carboxylic acid according to Example 267. Yield=77%

Step 7: The HCl salt from Example 5 was coupled with the carboxylic acid from step 6 according to Example 237 giving the desired product. Yield=51%, ES-MS: (M+H)+ 491

Example 274

1-[4-(6-Ethyl-thieno[2,3-d]pyrimidin-4-yl)-piper-azin-1-yl]-2-[2-(4,5,6,7-tetrahydro-benzotriazol-2-ylmethyl)-pyrrolidin-1-yl]-ethanone

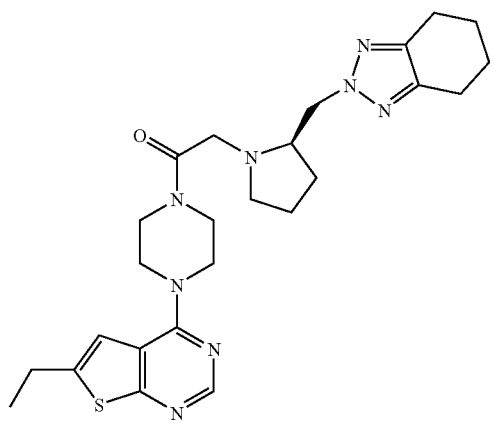

Step 1: 2-(R)-Pyrrolidinemethanol was treated with N-(Benzyloxycarbonyloxy)-succinimide according to Example 273. Yield=100%

Step 2: The alcohol from step 1 was converted to its corresponding mesylate according to Example 267.

Step 3: The mesylate from step 2 coupled with benzotriazole according to Example 267 giving a mixture of 1- and 2-substituted benzotriazoles. The individual isomers were separated on silica gel (20% to 50% ethyl acetate/hexane over 30 minutes). 1-substituted Yield=22%, 2-substituted Yield=20%

Step 4: The 2-substituted benzotriazole from step 3 was converted to its corresponding unprotected pyrrolidine/tetrahydrobenzotriazole according to Example 273. Yield=74%

Step 5. The pyrrolidine from step 4 was coupled with benzyl bromoacetate according to Example 267. Yield=80%

Step 6. The benzyl ester of the 2-substituted benzotriazole from step 5 was converted to its corresponding carboxylic acid according to Example 267. Yield=82%

Step 7: The HCl salt from Example 5 was coupled with the carboxylic acid from step 6 according to Example 237 giving the desired product. Yield=46%, ES-MS: (M+H)+ 495

Example 275

2-(2-Benzotriazol-1-ylmethyl-pyrrolidin-1-yl)-1-[4-(6-ethyl-thieno[2,3-d]pyrimidin-4-yl)-piperazin-1-yl]-ethanone

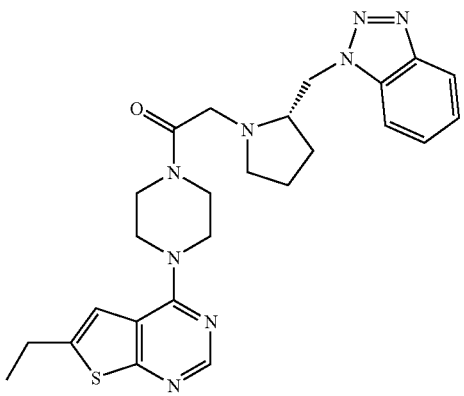

Step 1: 2-(S)-Pyrrolidinemethanol was treated with N-(Benzyloxycarbonyloxy)-succinimide according to Example 273. Yield=100%

Step 2: The alcohol from step 1 was converted to its corresponding mesylate according to Example 267.

Step 3: The mesylate from step 2 coupled with benzotriazole according to Example 267 giving a mixture of 1- and 2-substituted benzotriazoles. The individual isomers were separated on silica gel (20% to 50% ethyl acetate/hexane over 30 minutes). 1-substituted Yield=20%, 2-substituted Yield=16%

Step 4: The 1-substituted benzotriazole from step 3 was converted to its corresponding unprotected pyrrolidine according to Example 273. Yield=75%

Step 5. The pyrrolidine from step 4 was coupled with benzyl bromoacetate according to Example 267. Yield=55%

Step 6: The benzyl ester of the 1-substituted benzotriazole from step 5 was converted to its corresponding carboxylic acid according to Example 267. Yield=86%

Step 7: The HCl salt from Example 5 was coupled with the carboxylic acid from step 6 according to Example 237 giving the desired product. Yield=61%, ES-MS: (M+H)+ 491

Example 276

1-[4-(6-Ethyl-thieno[2,3-d]pyrimidin-4-yl)-piper-azin-1-yl]-2-[2-(4,5,6,7-tetrahydro-benzotriazol-2-ylmethyl)-pyrrolidin-1-yl]-ethanone

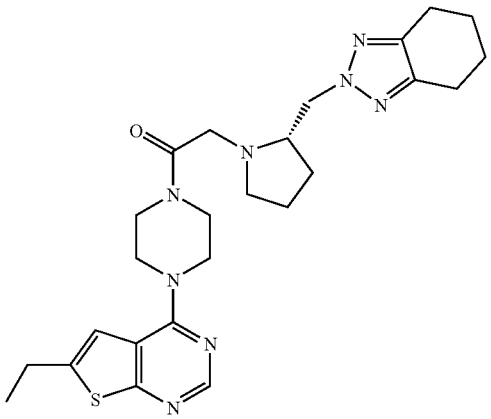

Step 1: 2-(S)-Pyrrolidinemethanol was treated with N-(Benzyloxycarbonyloxy)-succinimide according to Example 273. Yield=100%

Step 2: The alcohol from step 1 was converted to its corresponding mesylate according to Example 267.

Step 3. The mesylate from step 2 coupled with benzotriazole according to Example 267 giving a mixture of 1- and 2-substituted benzotriazoles. The individual isomers were separated on silica gel (20% to 50% ethyl acetate/hexane over 30 minutes). 1-substituted Yield=22%, 2-substituted Yield=20%

Step 4: The 2-substituted benzotriazole from step 3 was converted to its corresponding unprotected pyrrolidine/tetrahydrobenzotriazole according to Example 273. Yield=83%

Step 5: The pyrrolidine from step 4 was coupled with benzyl bromoacetate according to Example 267. Yield=81%

Step 6: The benzyl ester of the 2-substituted benzotriazole from step 5 was converted to its corresponding carboxylic acid according to Example 267. Yield=93%

Step 7: The HCl salt from Example 5 was coupled with the carboxylic acid from step 6 according to Example 235 giving the desired product. Yield=65%, ES-MS: (M+H)$^+$ 495

Example 277

(4-Benzotriazol-1-ylmethyl-cyclohexyl)-[4-(6-ethyl-thieno[2,3-d]pyrimidin-4-yl)-piperazin-1-yl]-methanone

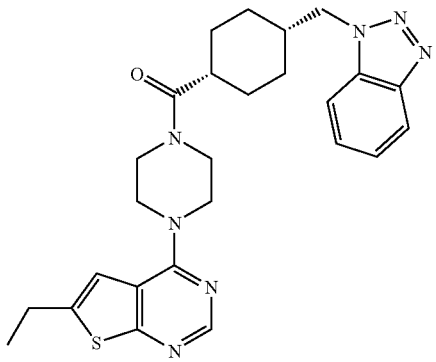

Step 1: cis-4-Hydroxymethyl-cyclohexanecarboxylic acid methyl ester (1.00 g) was combined with methylene chloride (50 mL) and diisopropylethylamine (1.52 mL). Methanesulfonyl chloride (0.54 mL) was added and the reaction was stirred at room temperature for 1 hour. The reaction was washed with 1 N HCl (3×10 mL), saturated aqueous sodium bicarbonate (3×10 mL) and brine (10 mL). The organic phase was dried over anhydrous sodium sulfate, filtered and concentrated giving the desired mesylate. Yield=100%

Step 2: The mesylate from step 1 was coupled with benzotriazole according to Example 267 giving a mixture of 1- and 2-substituted benzotriazoles. The individual isomers were separated on silica gel (15% to 35% ethyl acetate/hexane over 30 minutes). 1-substituted Yield=37%, 2-substituted Yield=30%

Step 3: The 1-substituted benzotriazole from step 2 (0.58 g) was dissolved in methanol (9.56 mL) and sodium hydroxide (2 M in water, 3.19 mL) was added. The reaction was stirred at room temperature for 24 hours and concentrated to dryness. The residue was dissolved in water (10 mL) and acidified with 1 N HCl. The resulting solids were collected by filtration and dried under vacuum giving the desired carboxylic acid. Yield=84%

Step 4: The HCl salt from Example 5 was coupled with the carboxylic acid from step 3 according to Example 237 giving the desired product. Yield=47%, ES-MS: (M+H)$^+$ 490

Example 278

(4-Benzotriazol-2-ylmethyl-cyclohexyl)-[4-(6-ethyl-thieno[2,3-d]pyrimidin-4-yl)-piperazin-1-yl]-methanone

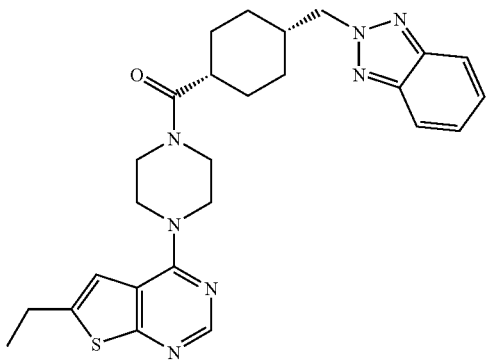

Step 1: cis-4-Hydroxymethyl-cyclohexanecarboxylic acid methyl ester was converted to its corresponding mesylate according to Example 277. Yield=100%

Step 2. The mesylate from step 1 was coupled with benzotriazole according to Example 267 giving a mixture of 1- and 2-substituted benzotriazoles. The individual isomers were separated on silica gel (15% to 35% ethyl acetate/hexane over 30 minutes). 1-substituted Yield=37%, 2-substituted Yield=30%

Step 3: The 2-substituted benzotriazole from step 2 was converted to its corresponding carboxylic acid according to Example 277. Yield=85%

Step 4: The HCl salt from Example 5 was coupled with the carboxylic acid from step 3 according to Example 237 giving the desired product. Yield=57%, ES-MS: (M+H)$^+$ 490

Example 279

(3-Benzotriazol-1-ylmethyl-cyclohexyl)-[4-(6-ethyl-thieno[2,3-d]pyrimidin-4-yl)-piperazin-1-yl]-methanone

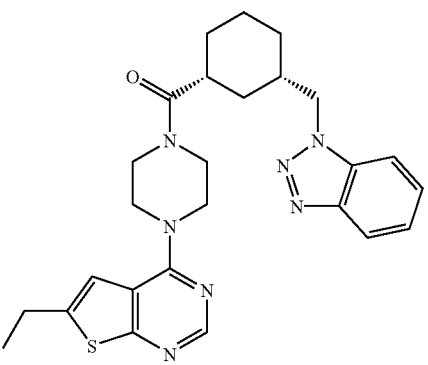

Step 1: cis-3-Hydroxymethyl-cyclohexanecarboxylic acid methyl ester was converted to its corresponding mesylate according to Example 277. Yield=99%

Step 2: The mesylate from step 1 was coupled with benzotriazole according to Example 267 giving a mixture of 1- and 2-substituted benzotriazoles. The individual isomers were separated on silica gel (15% to 35% ethyl acetate/hexane over 30 minutes). 1-substituted Yield=42%, 2-substituted Yield=38%

Step 3. The 1-substituted benzotriazole from step 2 was converted to its corresponding carboxylic acid according to Example 277. Yield=87%

Step 4: The HCl salt from Example 5 was coupled with the carboxylic acid from step 3 according to Example 237 giving the desired product. Yield=69%, ES-MS: (M+H)+ 490

Example 280

(3-Benzotriazol-2-ylmethyl-cyclohexyl)-[4-(6-ethyl-thieno[2,3-d]pyrimidin-4-yl)-piperazin-1-yl]-methanone

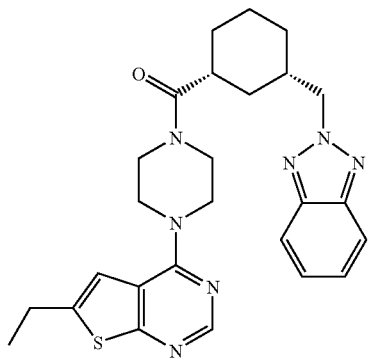

Step 1: cis-3-Hydroxymethyl-cyclohexanecarboxylic acid methyl ester was converted to its corresponding mesylate according to Example 277. Yield=99%

Step 2: The mesylate from step 1 was coupled with benzotriazole according to Example 267 giving a mixture of 1- and 2-substituted benzotriazoles. The individual isomers were separated on silica gel (15% to 35% ethyl acetate/hexane over 30 minutes). 1-substituted Yield=42%, 2-substituted Yield=38%

Step 3: The 2-substituted benzotriazole from step 2 was converted to its corresponding carboxylic acid according to Example 277. Yield=86%

Step 4: The HCl salt from Example 5 was coupled with the carboxylic acid from step 3 according to Example 237 giving the desired product. Yield=77%, ES-MS: (M+H)+ 490

Example 281

(2-Benzotriazol-1-ylmethyl-cyclopentyl)-[4-(6-ethyl-thieno[2,3-d]pyrimidin-4-yl)-piperazin-1-yl]-methanone

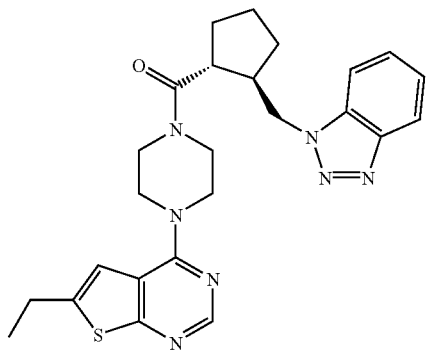

Step 1: trans-2-Hydroxymethyl-cyclopentanecarboxylic acid methyl ester was converted to its corresponding mesylate according to Example 277. Yield=97%

Step 2: The mesylate from step 1 was coupled with benzotriazole according to Example 267 giving a mixture of 1- and 2-substituted benzotriazoles. The individual isomers were separated on silica gel (15% to 35% ethyl acetate/hexane over 30 minutes). 1-substituted Yield=44%, 2-substituted Yield=41%

Step 3: The 1-substituted benzotriazole from step 2 was converted to its corresponding carboxylic acid according to Example 277. Yield=100%

Step 4: The HCl salt from Example 5 was coupled with the carboxylic acid from step 3 according to Example 237 giving the desired product. Yield=54%, ES-MS: (M+H)+ 476

Example 282

(2-Benzotriazol-2-ylmethyl-cyclopentyl)-[4-(6-ethyl-thieno[2,3-d]pyrimidin-4-yl)-piperazin-1-yl]-methanone

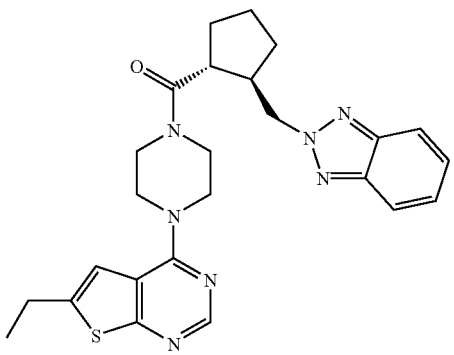

Step 1: trans-2-Hydroxymethyl-cyclopentanecarboxylic acid methyl ester was converted to its corresponding mesylate according to Example 277. Yield=97%

Step 2: The mesylate from step 1 was coupled with benzotriazole according to Example 267 giving a mixture of 1- and 2-substituted benzotriazoles. The individual isomers were separated on silica gel (15% to 35% ethyl acetate/hexane over 30 minutes). 1-substituted Yield=44%, 2-substituted Yield=41%

Step 3: The 2-substituted benzotriazole from step 2 was converted to its corresponding carboxylic acid according to Example 277. Yield=94%

Step 4: The HCl salt from Example 5 was coupled with the carboxylic acid from step 3 according to Example 237 giving the desired product. Yield=18%, ES-MS: (M+H)+ 476

Example 283

1-[4-(2-Azido-6-ethyl-thieno[2,3-d]pyrimidin-4-yl)-piperazin-1-yl]-4-(benzotriazol-1-yloxy)-butan-1-one

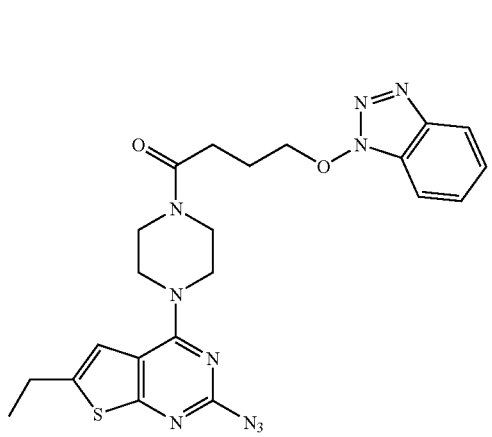

Step 1: tert-Butyl 4-(2-chloro-6-ethylthiopheno[3,2-e]pyrimidin-4-yl)piperazine-carboxylate (Example 165, 122.0 mg) was combined with sodium azide (207.6 mg) and dimethylsulfoxide (0.60 mL). The mixture was heated to 100 deg C. for 2.5 days, cooled to room temperature and diluted with water (5 mL). The solids were filtered, washed with water and purified on silica gel (15% to 40% ethyl acetate/hexane over 40 minutes) giving the desired azide. Yield=77%

Step 2: The BOC group was removed from the product of step 1 according to Example 236 giving the desired amine as its bis-HCl salt.

Step 3: The HCl salt from step 2 was coupled with 4-benzotriazolyl-oxybutanoic acid according to Example 237. Yield=36%, ES-MS: (M+H)+ 493

Example 284

Cyclohexyl-[4-(6-ethyl-thieno[2,3-d]pyrimidin-4-yl)-piperazin-1-yl]-methanone

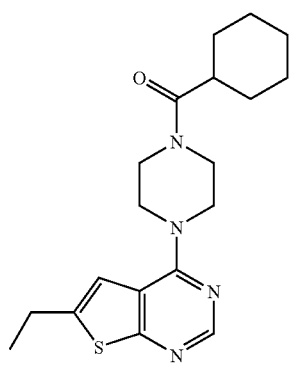

The HCl salt from Example 5 was coupled with cyclohexanecarboxylic acid according to Example 237. Yield=94%, ES-MS: (M+H)+ 359

Example 285

3-[4-(6-Ethyl-thieno[2,3-d]pyrimidin-4-yl)-piperazine-1-carbonyl]-piperidine-1-carboxylic acid tert-butyl ester

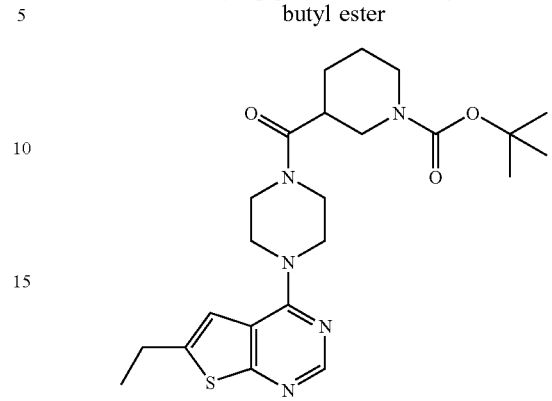

The HCl salt from Example 5 was coupled with the N-BOC-nipecotic acid according to Example 237. Yield=92%, ES-MS: (M+H)+ 460

Example 286

[4-(6-Ethyl-thieno[2,3-d]pyrimidin-4-yl)-piperazin-1-yl]-piperidin-3-yl-methanone

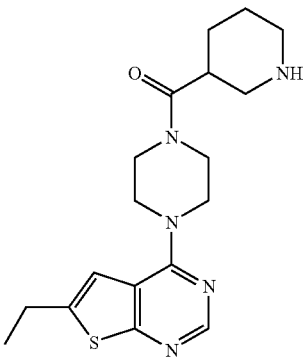

3-[4-(6-Ethyl-thieno[2,3-d]pyrimidin-4-yl)-piperazine-1-carbonyl]-piperidine-1-carboxylic acid tert-butyl ester (Example 367) was converted to its free amine according to Example 259. Yield=100%, ES-MS: (M+H)+ 360

Example 287

[4-(2-Amino-6-ethyl-thieno[2,3-d]pyrimidin-4-yl)-piperazin-1-yl]-(3-benzotriazol-1-ylmethyl-cyclohexyl)-methanone

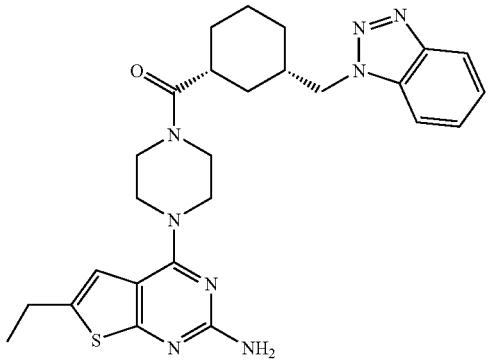

Step 1: tert-Butyl 4-(2-chloro-6-ethylthiopheno[3,2-e]pyrimidin-4-yl)piperazine-carboxylate (Example 165, 122.0 mg) was combined with sodium azide (207.6 mg) and dimethylsulfoxide (0.60 mL). The mixture was heated to 100 deg C. for 2.5 days, cooled to room temperature and diluted with water (5 mL). The solids were filtered, washed with water and purified on silica gel (15% to 40% ethyl acetate/hexane over 40 minutes) giving the desired azide. Yield=77%

Step 2: The azide from step 1 (57.8 mg) was dissolved in methanol (1.0 mL) and added to a degassed suspension of 10% palladium on carbon (57.8 mg) in methanol (1.0 mL). The mixture was stirred for 2.5 hours at room temperature under hydrogen. The solids were removed by filtration. Concentration of the filtrate gave the desired amine. Yield=84%

Step 3: The BOC group was removed from the product of step 2 according to Example 236 giving the desired amine as its tris-HCl salt. Yield=99%

Step 4. The HCl salt from step 3 was coupled with the carboxylic acid from step 3 of Example 279 according to Example 237. Yield=64%, ES-MS: (M+H)$^+$ 505

Example 288

[4-(2-Amino-6-ethyl-thieno[2,3-d]pyrimidin-4-yl)-3-methyl-piperazin-1-yl]-(3-benzotriazol-1-ylmethyl-cyclohexyl)-methanone

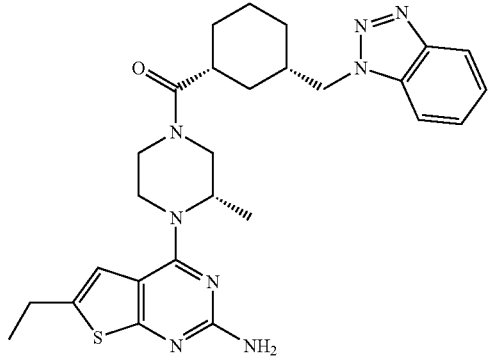

Step 1: 6-Ethyl-2,4-dichlorothienopyrimidine (Example 165) was coupled with 1-BOC-3-(S)-methylpiperazine (Example 202) according to Example 87. Yield=37%

Step 2: The product from step 1 was converted to its corresponding azide on treatment with sodium azide according to Example 287. Yield=71%

Step 3: The azide from step 2 was converted to its corresponding amine according to Example 287. Yield=84%

Step 4: The BOC group was removed from the product of step 3 according to Example 236 giving the desired amine as its tris-HCl salt. Yield=99%

Step 5: The HCl salt from step 4 was coupled with the carboxylic acid from step 3 of Example 279 according to Example 237. Yield=84%, ES-MS: (M+H)$^+$ 519

Example 289

(3-Benzotriazol-1-ylmethyl-cyclohexyl)-[4-(6-ethyl-thieno[2,3-d]pyrimidin-4-yl)-3-methyl-piperazin-1-yl]-methanone

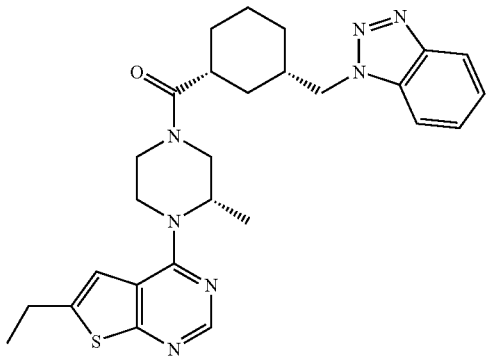

Step 1: The BOC group was removed from Example 202 according to Example 137. Yield=100%

Step 2: The product from step 1 was coupled with the carboxylic acid from step 3 of Example 279 according to Example 237. Yield=68%, ES-MS: (M+H)$^+$ 504

Example 290

1-{3-[4-(6-Ethyl-thieno[2,3-d]pyrimidin-4-yl)-piperazine-1-carbonyl]-piperidin-1-yl}-ethanone

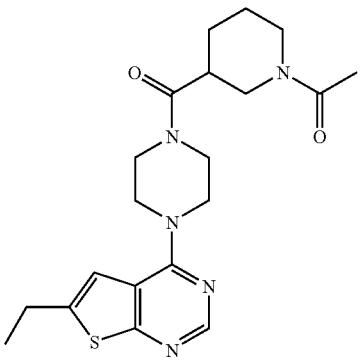

[4-(6-Ethyl-thieno[2,3-d]pyrimidin-4-yl)-piperazin-1-yl]-piperidin-3-yl-methanone (Example 294, 17.0 mg) was dissolved in methylene chloride (1.00 mL) and diisopropylethylamine (12.4 μL). Acetylchloride (3.7 μL) was added and the reaction was stirred at room temperature for 30 minutes. The reaction was applied to silica gel and the product was isolated by eluting from 0% to 4% methanol/methylene chloride over 45 minutes then 10% methanol/methylene chloride for 15 minutes. Yield=53%, ES-MS: (M+H)$^+$ 402

Example 291

1-[4-(6-Ethyl-thieno[2,3-d]pyrimidin-4-yl)-piperazin-1-yl]-4-phenoxy-butan-1-one

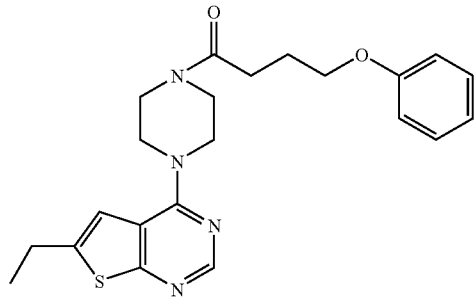

The HCl salt from Example 5 was coupled with 4-phenoxy-butyric acid according to Example 237. Yield=68%, ES-MS: (M+H)+ 411.

Example 292

4-(4-Chloro-2-methyl-phenoxy)-1-[4-(6-ethyl-thieno[2,3-d]pyrimidin-4-yl)-piperazin-1-yl]-butan-1-one

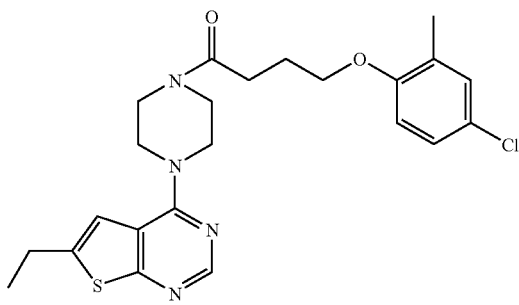

The HCl salt from Example 5 was coupled with 4-(4-chloro-2-methyl-phenoxy)-butyric acid according to Example 237. Yield=47%, ES-MS: (M+H)+ 459/461.

Example 293

4-(2,4-Dichloro-phenoxy)-1-[4-(6-ethyl-thieno[2,3-d]pyrimidin-4-yl)-piperazin-1-yl]-butan-1-one

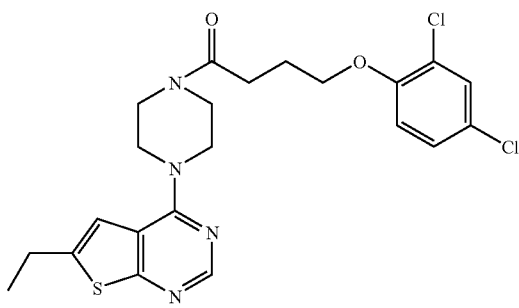

The HCl salt from Example 5 was coupled with 4-(2,4-Dichloro-phenoxy)-butyric acid according to Example 237. Yield=20%, ES-MS: (M+H)+ 479/481

Example 294

1-[4-(6-Ethyl-thieno[2,3-d]pyrimidin-4-yl)-piperazin-1-yl]-5-(4-fluoro-phenyl)-pentane-1,5-dione

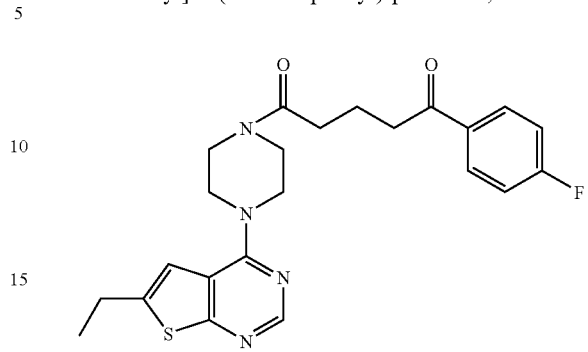

The HCl salt from Example 5 was coupled with 5-(4-Fluoro-phenyl)-5-oxo-pentanoic acid according to Example 237. Yield=62%, ES-MS: (M+H)+ 441

Example 295

1-[4-(6-Ethyl-thieno[2,3-d]pyrimidin-4-yl)-piperazin-1-yl]-5-(3-trifluoromethyl-phenyl)-pentane-1,5-dione

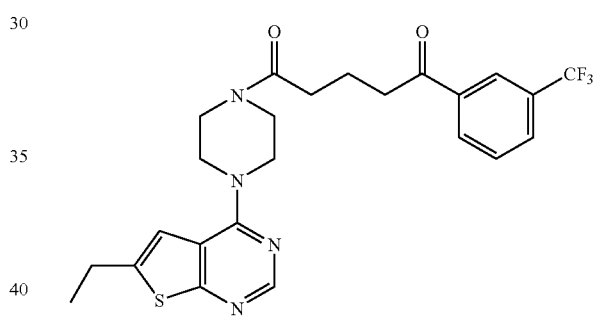

The HCl salt from Example 5 was coupled with 5-Oxo-5-(3-trifluoromethyl-phenyl)-pentanoic acid according to Example 237. Yield=66%, ES-MS: (M+H)+ 491

Example 296

1-(4-Chloro-phenyl)-5-[4-(6-ethyl-thieno[2,3-d]pyrimidin-4-yl)-piperazin-1-yl]-pentane-1,5-dione

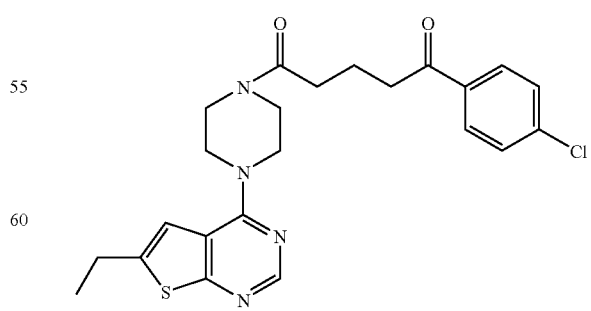

The HCl salt from Example 5 was coupled with 5-(4-Chloro-phenyl)-5-oxo-pentanoic acid according to Example 237. Yield=65%, ES-MS: (M+H)+ 457

Example 297

1-[4-(6-Ethyl-thieno[2,3-d]pyrimidin-4-yl)-piperazin-1-yl]-5-(4-methoxy-phenyl)-pentane-1,5-dione

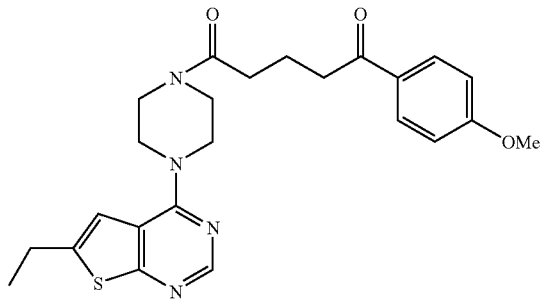

The HCl salt from Example 5 was coupled with 5-(4-Methoxy-phenyl)-5-oxo-pentanoic acid according to Example 237. Yield=100%, ES-MS: (M+H)$^+$ 453

Example 298

1-(3,4-Dimethoxy-phenyl)-5-[4-(6-ethyl-thieno[2,3-d]pyrimidin-4-yl)-piperazin-1-yl]-pentane-1,5-dione

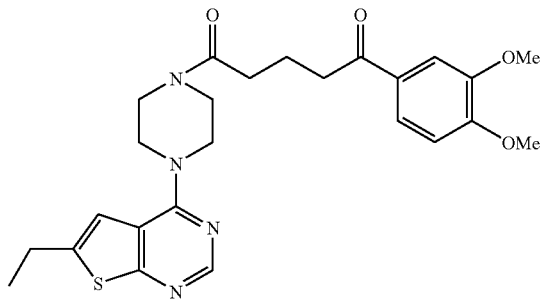

The HCl salt from Example 5 was coupled with 5-(3,4-Dimethoxy-phenyl)-5-oxo-pentanoic acid according to Example 237. Yield=80%, ES-MS: (M+H)$^+$ 483

Example 299

1-(3,4-Dichloro-phenyl)-5-[4-(6-ethyl-thieno[2,3-d]pyrimidin-4-yl)-piperazin—yl]-pentane-1,5-dione

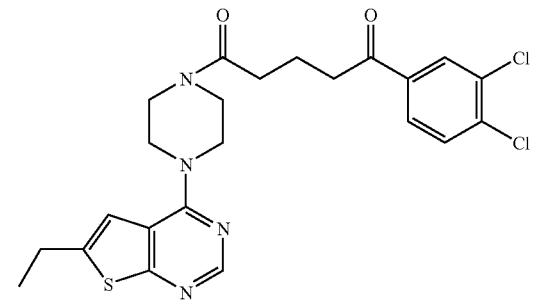

The HCl salt from Example 5 was coupled with 5-(3,4-Dichloro-phenyl)-5-oxo-pentanoic acid according to Example 237. Yield=72%, ES-MS: (M+H)$^+$ 491/493

Example 300

1-[4-(6-Ethyl-thieno[2,3-d]pyrimidin-4-yl)-piperazin-1-yl]-5-phenyl-pentane-1,5-dione

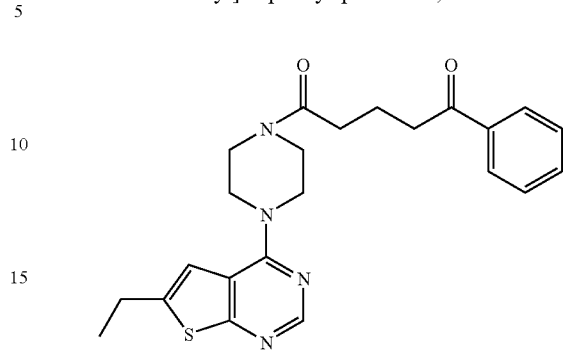

The HCl salt from Example 5 was coupled with 5-Oxo-5-phenyl-pentanoic acid according to Example 237. Yield=89%, ES-MS: (M+H)$^+$ 423

Example 301

1-[4-(6-Ethyl-thieno[2,3-d]pyrimidin-4-yl)-piperazin-1-yl]-5-p-tolyl-pentane-1,5-dione

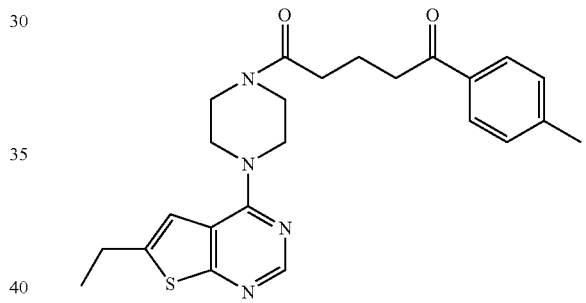

The HCl salt from Example 5 was coupled with 5-Oxo-5-p-tolyl-pentanoic acid according to Example 237. Yield=77%, ES-MS: (M+H)$^+$ 437

Example 302

1-(4-Ethyl-phenyl)-5-[4-(6-ethyl-thieno[2,3-d]pyrimidin-4-yl)-piperazin-1-yl]-pentane-1,5-dione

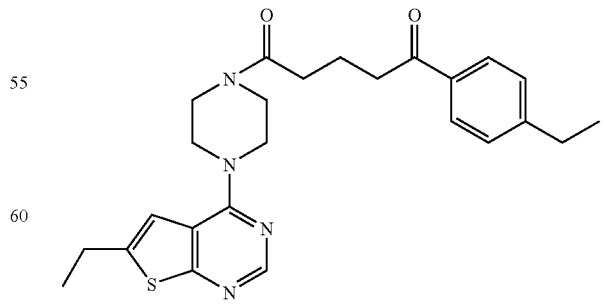

The HCl salt from Example 5 was coupled with 5-(4-Ethyl-phenyl)-5-oxo-pentanoic acid according to Example 237. Yield=57%, ES-MS: (M+H)$^+$ 451

Example 303

1-[4-(6-Ethyl-thieno [2,3-d]pyrimidin-4-yl)-piper-azin-1-yl]-6-(3-trifluoromethyl-phenyl)-hexane-1,6-dione

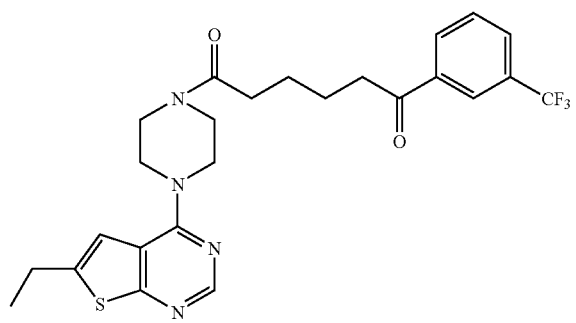

The HCl salt from Example 5 was coupled with 6-Oxo-6-(3-trifluoromethyl-phenyl)-hexanoic acid according to Example 237. Yield=26%, ES-MS: (M+H)+ 505

Example 304

1-[4-(6-Ethyl-thieno[2,3-d]pyrimidin-4-yl)-piper-azin-1-yl]-6-(4-fluoro-phenyl)-hexane-1,6-dione

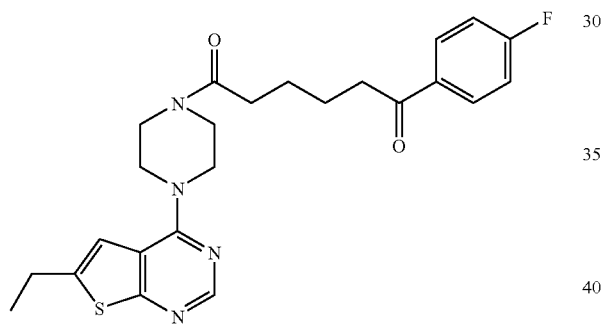

The HCl salt from Example 5 was coupled with 6-(4-Fluoro-phenyl)-6-oxo-hexanoic acid according to Example 237. Yield=52%, ES-MS: (M+H)+ 455

Example 305

1-[4-(6-Ethyl-thieno[2,3-d]pyrimidin-4-yl)-piper-azin-1-yl]-5-phenoxy-pentan-1-one

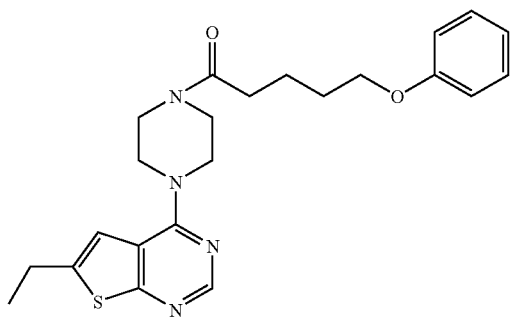

The HCl salt from Example 5 was coupled with 5-Phe-noxy-pentanoic acid according to Example 237. Yield=55%, ES-MS: (M+H)+ 425

Example 306

1-[4-(6-Ethyl-thieno[2,3-d]pyrimidin-4-yl)-piper-azin-1-yl]-6-phenoxy-hexan-1-one

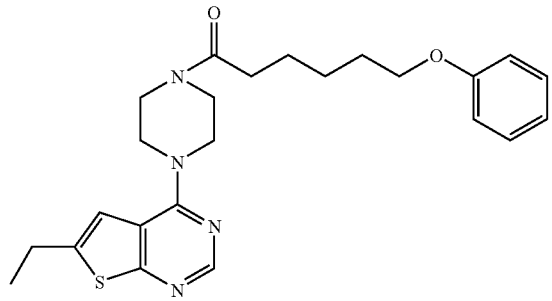

The HCl salt from Example 5 was coupled with 6-Phe-noxy-hexanoic acid according to Example 237. Yield=63%, ES-MS: (M+H)+ 439

Example 307

4-(4-Chloro-phenoxy)-1-[4-(6-ethyl-thieno[2,3-d]pyrimidin-4-yl)-piperazin-1-yl]-butan-1-one

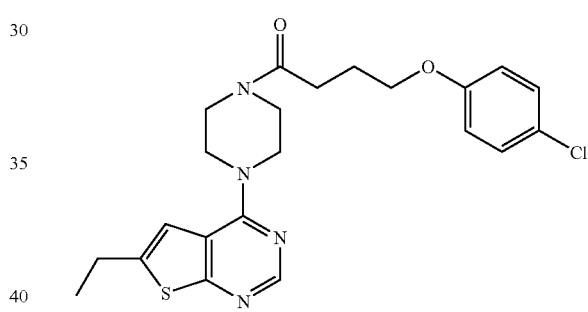

The HCl salt from Example 5 was coupled with 4-(4-Chloro-phenoxy)-butyric acid according to Example 237. Yield=79%, ES-MS: (M+H)+ 445

Example 308

1-[4-(6-Ethyl-thieno[2,3-d]pyrimidin-4-yl)-piper-azin-1-yl]-4-phenylsulfanyl-butan-1-one

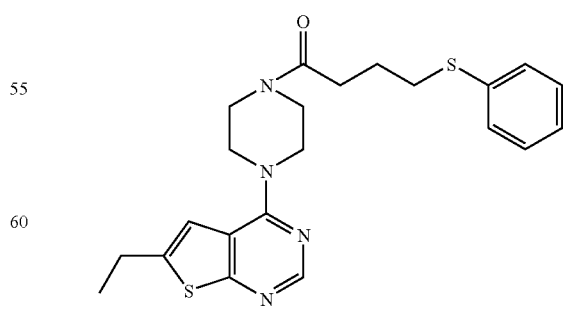

The HCl salt from Example 5 was coupled with 4-Phe-nylsulfanyl-butyric acid according to Example 237. Yield=46%, ES-MS: (M+H)+ 427

Example 309

4-Benzyloxy-1-[4-(6-ethyl-thieno[2,3-d]pyrimidin-4-yl)-piperazin-1-yl]-butan-1-one

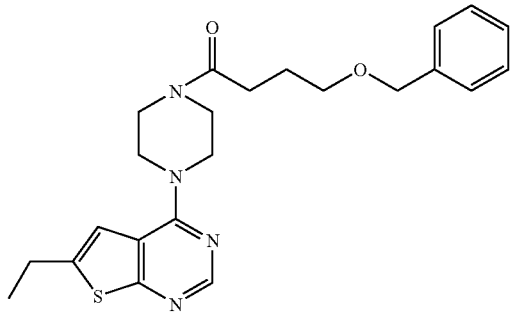

The HCl salt from Example 5 was coupled with 4-Benzyloxy-butyric acid according to Example 237. Yield=86%, ES-MS: (M+H)+ 425

Example 310

1-[4-(6-Ethyl-thieno[2,3-d]pyrimidin-4-yl)-piperazin-1-yl]-4-(5,6,7,8-tetrahydro-naphthalen-2-yl)-butan-1-one

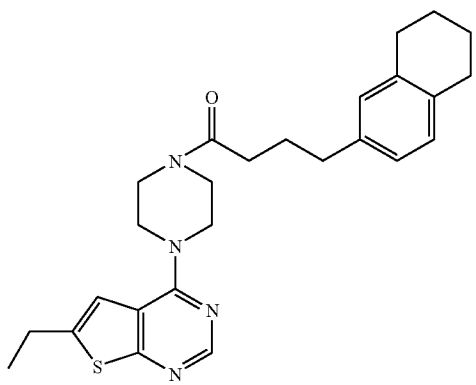

The HCl salt from Example 5 was coupled with 4-(1,2,3,4-Tetrahydro-naphthalen-2-yl)-butyric acid according to Example 237. Yield=87%, ES-MS: (M+H)+ 449

Example 311

5-Cyclohexyl-1-[4-(6-ethyl-thieno[2,3-d]pyrimidin-4-yl)-piperazin-1-yl]-pentan-1-one

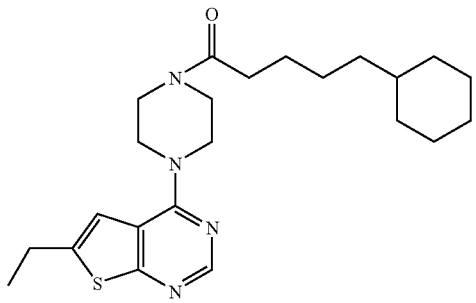

The HCl salt from Example 5 was coupled with 5-Cyclohexyl-pentanoic acid according to Example 237. Yield=90%, ES-MS: (M+H)+ 415

Example 312

5-[4-(6-Ethyl-thieno[2,3-d]pyrimidin-4-yl)-piperazin-1-yl]-5-oxo-pentanoic acid phenylamide

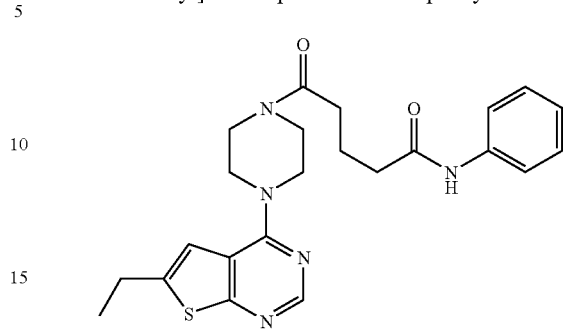

The HCl salt from Example 5 was coupled with 4-Phenylcarbamoyl-butyric acid according to Example 237. Yield=84%, ES-MS: (M+H)+ 438

Example 313

N-{5-[4-(6-Ethyl-thieno[2,3-d]pyrimidin-4-yl)-piperazin-1-yl]-5-oxo-pentyl}-benzamide

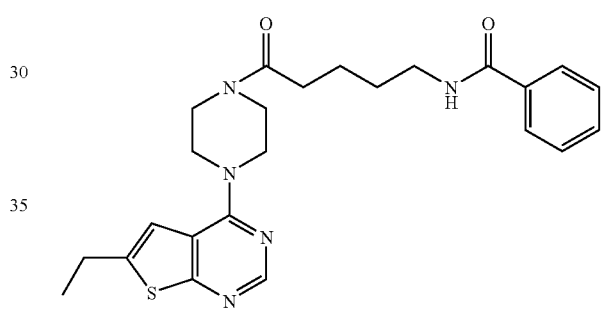

The HCl salt-from Example 5 was coupled with 5-Benzoylamino-pentanoic acid according to Example 237. Yield=83%, ES-MS: (M+H)+ 452

Example 314

1-[4-(6-Ethyl-thieno[2,3-d]pyrimidin-4-yl)-piperazin-1-yl]-6-(4-phenyl-piperazin-1-yl)-hexan-1-one

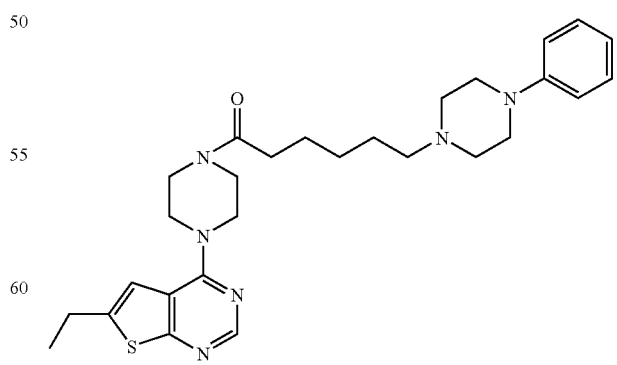

The HCl salt from Example 5 was coupled with 6-(4-Phenyl-piperazin-1-yl)-hexanoic acid according to Example 237. Yield=69%, ES-MS: (M+H)+ 507

Example 315

1-[4-(6-Ethyl-thieno[2,3-d]pyrimidin-4-yl)-piperazin-1-yl]-6-phenyl-hexane-1,6-dione

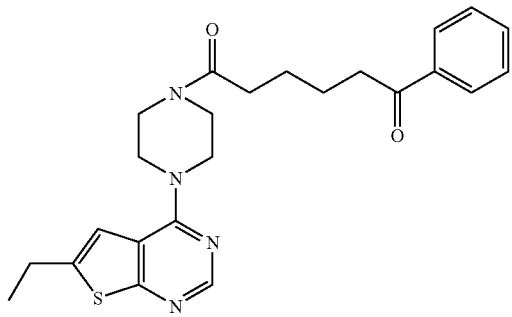

The HCl salt from Example 5 was coupled with 6-Oxo-6-phenyl-hexanoic acid according to Example 237. Yield=76%, ES-MS: (M+H)$^+$ 437

Example 316

1-[4-(6-Ethyl-thieno[2,3-d]pyrimidin-4-yl)-piperazin-1-yl]-6-p-tolyl-hexane-1,6-dione

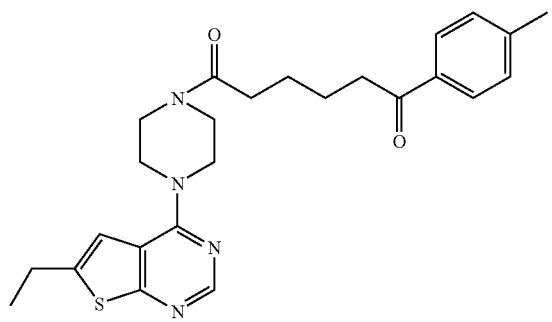

The HCl salt from Example 5 was coupled with 6-Oxo-6-p-tolyl-hexanoic acid according to Example 237. Yield=16%, ES-MS: (M+H)$^+$ 451

Example 317

1-(3,4-Dichloro-phenyl)-7-[4-(6-ethyl-thieno[2,3-d]pyrimidin-4-yl)-piperazin-1-yl]-heptane-1,7-dione

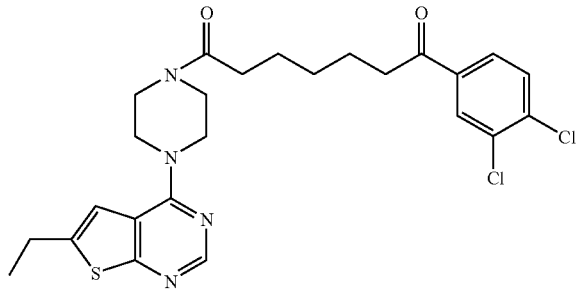

The HCl salt from Example 5 was coupled with 7-(3,4-Dichloro-phenyl)-7-oxo-heptanoic acid according to Example 237. Yield=87%, ES-MS: (M+H)$^+$ 519/521

Example 318

1-[4-(6-Ethyl-thieno[2,3-d]pyrimidin-4-yl)-piperazin-1-yl]-7-(3-trifluoromethyl-phenyl)-heptane-1,7-dione

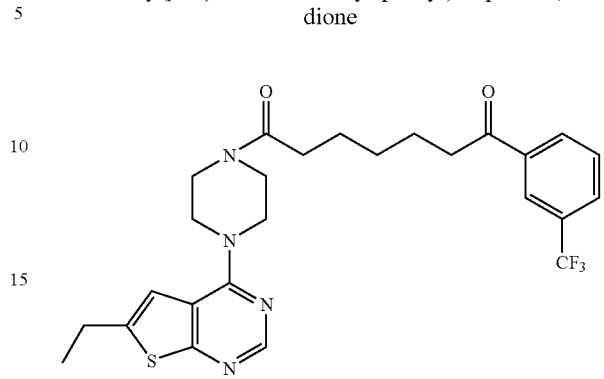

The HCl salt from Example 5 was coupled with 7-Oxo-7-(3-trifluoromethyl-phenyl)-heptanoic acid according to Example 237. Yield=79%, ES-MS: (M+H)$^+$ 519

Example 319

1-[4-(6-Ethyl-thieno[2,3-d]pyrimidin-4-yl)-piperazin-1-yl]-3-phenylsulfanyl-propenone

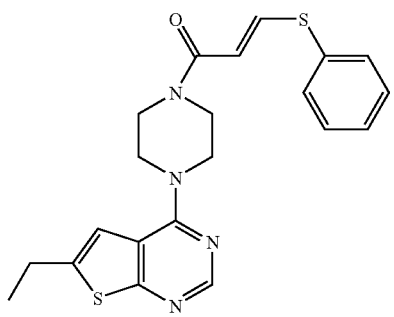

The HCl salt from Example 5 was coupled with 3-Phenylsulfanyl-acrylic acid according to Example 237. Yield=90%, ES-MS: (M+H)$^+$ 411

Example 320

1-[4-(6-Ethyl-thieno[2,3-d]pyrimidin-4-yl)-piperazin-1-yl]-3-thiophen-3-yl-propenone

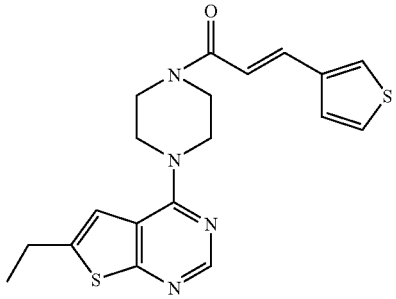

The HCl salt from Example 5 was coupled with 3-Thiophen-3-yl-acrylic acid according to Example 237. Yield=100%, ES-MS: (M+H)$^+$ 385

Example 321

1-[4-(6-Ethyl-thieno[2,3-d]pyrimidin-4-yl)-piper-azin-1-yl]-3-pyridin-3-yl-propenone

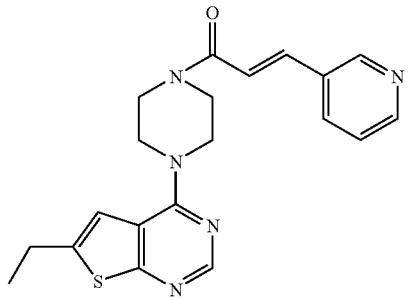

The HCl salt from Example 5 was coupled with 3-Pyridin-3-yl-acrylic acid according to Example 237. Yield=36%, ES-MS: (M+H)$^+$ 380

Example 322

1-[4-(6-Ethyl-thieno [2,3-d]pyrimidin-4-yl)-piper-azin-1-yl]-3-furan-3-yl-propenone

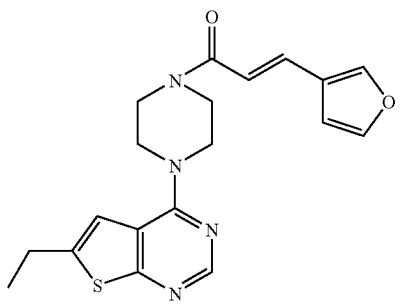

The HCl salt from Example 5 was coupled with 3-Furan-3-acrylic acid according to Example 237. Yield=55%, ES-MS: (M+H)$^+$ 369

Example 323

1-[4-(6-Ethyl-thieno[2,3-d]pyrimidin-4-yl)-piper-azin-1-yl]-3-furan-2-yl-propenone

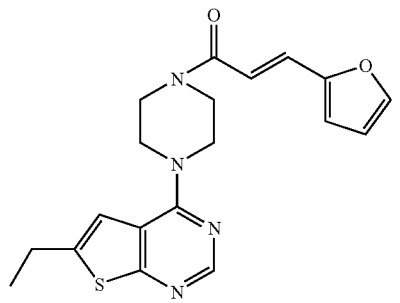

The HCl salt from Example 5 was coupled with 3-Furan-2-yl-acrylic acid according to Example 237. Yield=75%, ES-MS: (M+H)$^+$ 369

Example 324

1-[4-(6-Ethyl-thieno[2,3-d]pyrimidin-4-yl)-piper-azin-1-yl]-3-(1H-indol-3-yl)-propenone

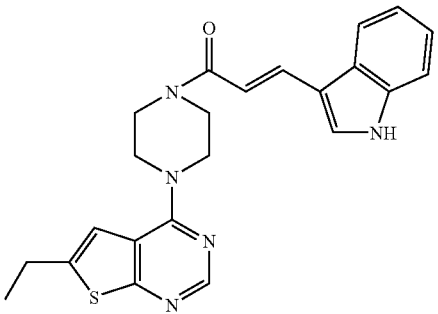

The HCl salt from Example 5 was coupled with 3-(1H-Indol-3-yl)-acrylic acid according to Example 237. Yield=40%, ES-MS: (M+H)$^+$ 418

Example 325

1-[4-(6-Ethyl-thieno[2,3-d]pyrimidin-4-yl)-piper-azin-1-yl]-3-thiophen-2-yl-propenone

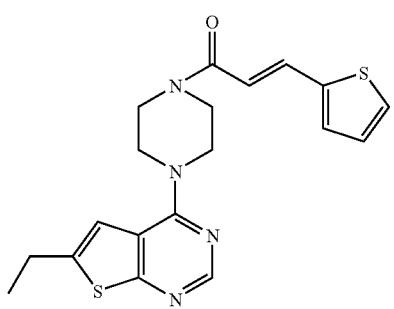

The HCl salt from Example 5 was coupled with 3-Thiophen-2-yl-acrylic acid according to Example 237. Yield=81%, ES-MS: (M+H)$^+$ 385

Example 326

[4-(6-Ethyl-thieno[2,3-d]pyrimidin-4-yl)-piperazin-1-yl]-(tetrahydro-furan-2-yl)-methanone

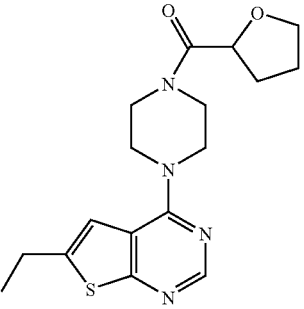

The HCl salt from Example 5 was coupled with Tetrahydro-furan-2-carboxylic acid according to Example 237. Yield=59%, ES-MS: (M+H)$^+$ 347

Example 327

1-[4-(6-Ethyl-thieno[2,3-d]pyrimidin-4-yl)-piperazin-1-yl]-6-(4-trifluoromethyl-phenyl)-hexane-1,6-dione

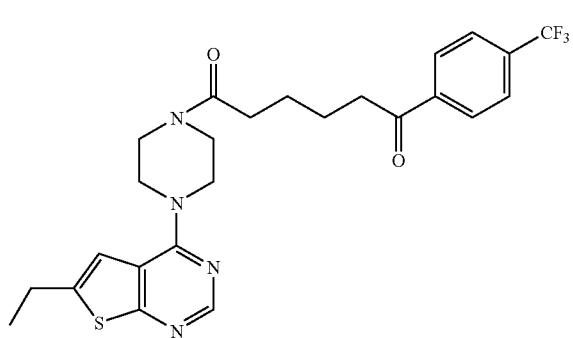

The HCl salt from Example 5 was coupled with 6-Oxo-6-(4-trifluoromethyl-phenyl)-hexanoic acid according to Example 237. Yield=47%, ES-MS: (M+H)$^+$ 505

Example 328

1-(4-Ethyl-phenyl)-6-[4-(6-ethyl-thieno[2,3-d]pyrimidin-4-yl)-piperazin-1-yl]-hexane-1,6-dione

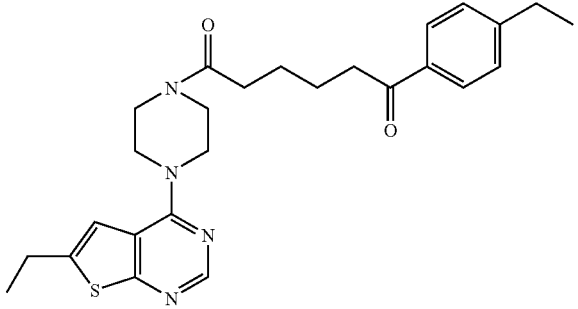

The HCl salt from Example 5 was coupled with 6-(4-Ethyl-phenyl)-6-oxo-hexanoic acid according to Example 237. Yield=44%, ES-MS: (M+H)$^+$ 465

Example 329

1-(4-Ethyl-phenyl)-7-[4-(6-ethyl-thieno[2,3-d]pyrimidin-4-yl)-piperazin-1-yl]-heptane-1,7-dione

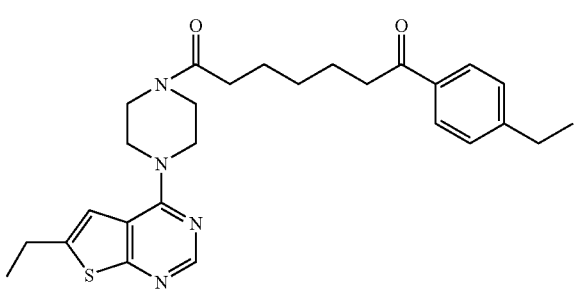

The HCl salt from Example 5 was coupled with 7-(4-Ethyl-phenyl)-7-oxo-heptanoic acid according to Example 237. Yield=40%, ES-MS: (M+H)$^+$ 479

Example 330

[4-(6-Ethyl-thieno[2,3-d]pyrimidin-4-yl)-piperazin-1-yl]-[1,2,3]thiadiazol-5-yl-methanone

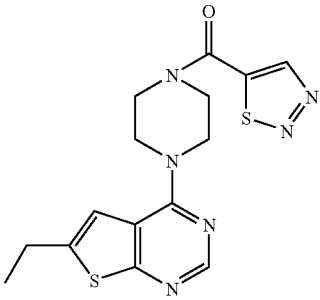

The HCl salt from Example 5 was coupled with [1,2,3] Thiadiazole-5-carboxylic acid according to Example 237. Yield=83%, ES-MS: (M+H)$^+$ 361

Example 331

1-[4-(6-Ethyl-thieno[2,3-d]pyrimidin-4-yl)-piperazin-1-yl]-3-(1H-imidazol-4-yl)-propenone

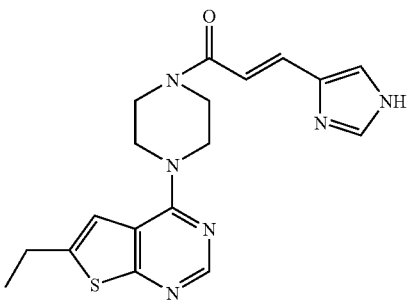

The HCl salt from Example 5 was coupled with 3-(1H-Imidazol-4-yl)-acrylic acid according to Example 237. Yield=52%, ES-MS: (M+H)$^+$ 369

Example 332

1-[4-(6-Ethyl-thieno[2,3-d]pyrimidin-4-yl)-piperazin-1-yl]-3-phenyl-propynone

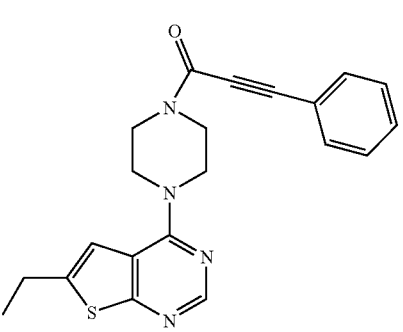

The HCl salt from Example 5 was coupled with 3 Phenyl-propynoic acid according to Example 237. Yield=90%, ES-MS: (M+H)$^+$ 377

Example 333

[4-(6-Ethyl-thieno[2,3-d]pyrimidin-4-yl)-piperazin-1-yl]-furan-2-yl-methanone

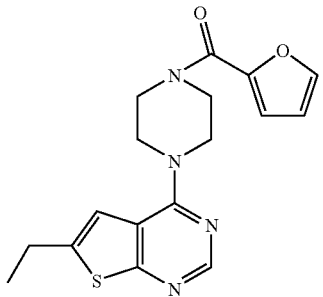

The HCl salt from Example 5 was coupled with Furan-2-carboxylic acid according to Example 237. Yield=67%, ES-MS: (M+H)+ 343

Example 334

1-[4-(6-Ethyl-thieno[2,3-d]pyrimidin-4-yl)-piperazin-1-yl]-7-(4-trifluoromethyl-phenyl)-heptane-1,7-dione

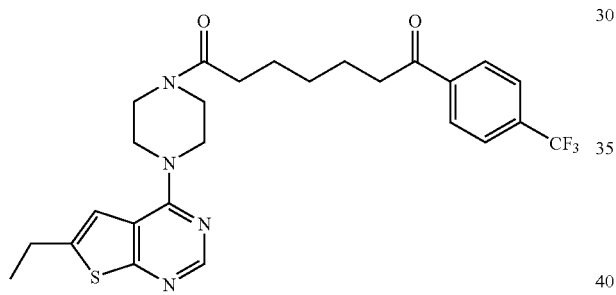

The HCl salt from Example 5 was coupled with 7-Oxo-7-(4-trifluoromethyl-phenyl)-heptanoic acid according to Example 237. Yield=81%, ES-MS: (M+H)+ 519

Example 335

1-(4-Chloro-phenyl)-6-[4-(6-ethyl-thieno[2,3-d]pyrimidin-4-yl)-piperazin-1-yl]-hexane-1,6-dione

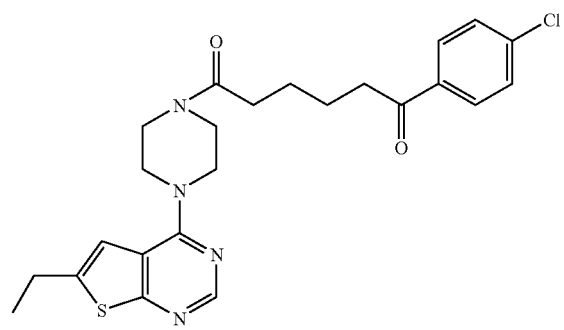

The HCl salt from Example 5 was coupled with 6-(4-Chloro-phenyl)-6-oxo-hexanoic acid according to Example 237. Yield=96%, ES-MS: (M+H)+ 471

Example 336

1-[4-(6-Ethyl-thieno[2,3-d]pyrimidin-4-yl)-piperazin-1-yl]-6-(4-methoxy-phenyl)-hexane-1,6-dione

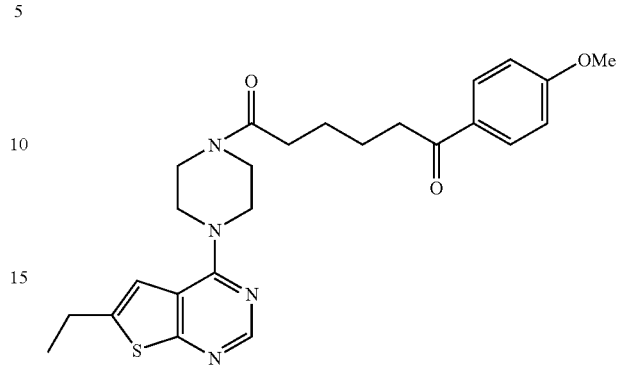

The HCl salt from Example 5 was coupled with 6-(4-Methoxy-phenyl)-6-oxo-hexanoic acid according to Example 237. Yield=73%, ES-MS: (M+H)+ 467

Example 337

1-[4-(6-Ethyl-thieno[2,3-d]pyrimidin-4-yl)-piperazin-1-yl]-5-(2-trifluoromethyl-phenyl)-pentane-1,5-dione

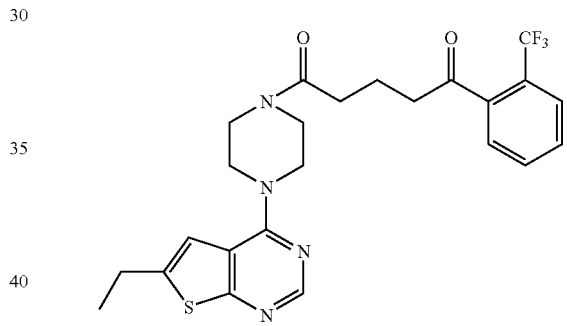

The HCl salt from Example 5 was coupled with 5-Oxo-5-(2-trifluoromethyl-phenyl)-pentanoic acid according to Example 237. Yield=90%, ES-MS: (M+H)+ 491

Example 338

[4-(6-Ethyl-thieno[2,3-d]pyrimidin-4-yl)-piperazin-1-yl]-furan-3-yl-methanone

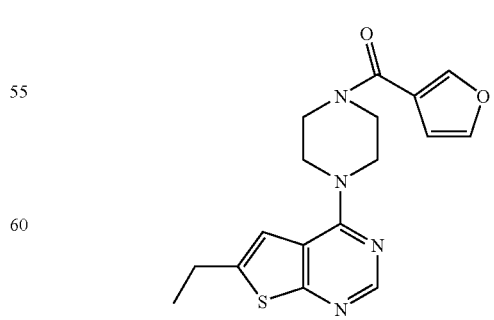

The HCl salt from Example 5 was coupled with Furan-3-carboxylic acid according to Example 237. Yield=38%, ES-MS: (M+H)+ 343

Example 339

3-(3-Chloro-phenyl)-1-[4-(6-ethyl-thieno[2,3-d]pyrimidin-4-yl)-piperazin-1-yl]-propenone

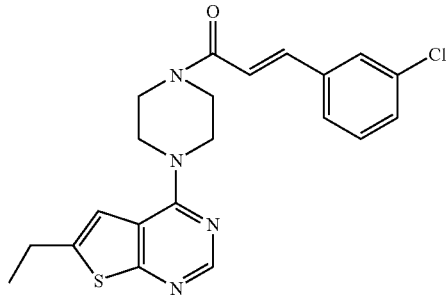

The HCl salt from Example 5 was coupled with 3-(3-Chloro-phenyl)-acrylic acid according to Example 237. Yield=78%, ES-MS: (M+H)+ 413/415

Example 340

1-[4-(6-Ethyl-thieno[2,3-d]pyrimidin-4-yl)-piperazin-1-yl]-3-(3-nitro-phenyl)-propenone

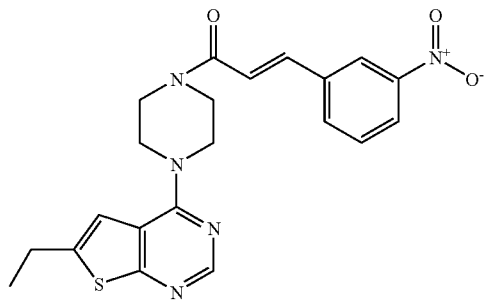

The HCl salt from Example 5 was coupled with 3-(3-Nitro-phenyl)-acrylic acid according to Example 237. Yield=89%, ES-MS: (M+H)+ 424

Example 341

1-[4-(6-Ethyl-thieno[2,3-d]pyrimidin-4-yl)-piperazin-1-yl]-3-m-tolyl-propenone

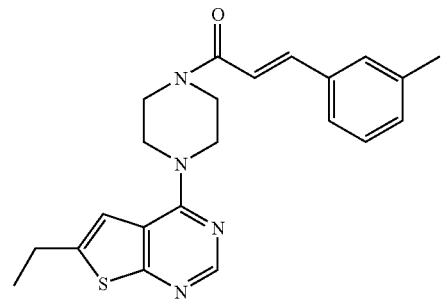

The HCl salt from Example 5 was coupled with 3-m-Tolyl-acrylic acid according to Example 237. Yield=91%, ES-MS: (M+H)+ 393

Example 342

1-[4-(6-Ethyl-thieno[2,3-d]pyrimidin-4-yl)-piperazin-1-yl]-3-(4-methoxy-phenyl)-propenone

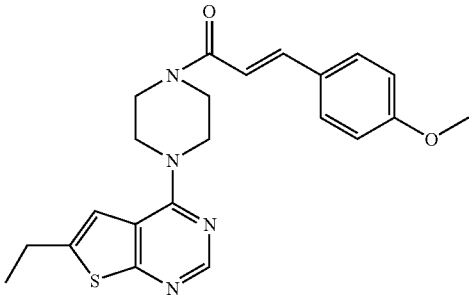

The HCl salt from Example 5 was coupled with 3-(4-Methoxy-phenyl)-acrylic acid according to Example 237. Yield=86%, ES-MS: (M+H)+ 409

Example 343

1-[4-(6-Ethyl-thieno[2,3-d]pyrimidin-4-yl)-piperazin-1-yl]-3-(4-fluoro-phenyl)-propenone

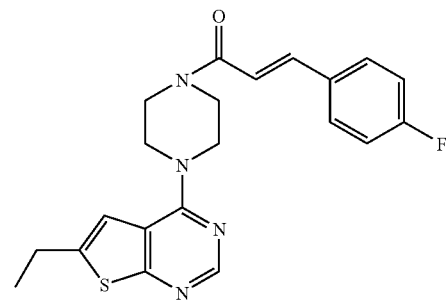

The HCl salt from Example 5 was coupled with 3-(4-Fluoro-phenyl)-acrylic acid according to Example 237. Yield=79%, ES-MS: (M+H)+ 397

Example 344

3-(4-Chloro-phenyl)-1-[4-(6-ethyl-thieno[2,3-d]pyrimidin-4-yl)-piperazin-1-yl]-propenone

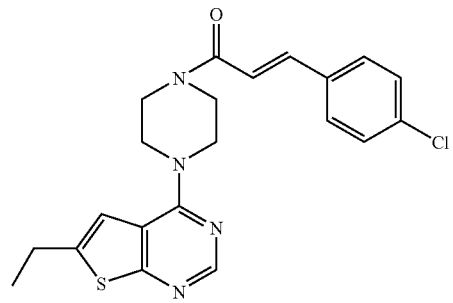

The HCl salt from Example 5 was coupled with 3-(4-Chloro-phenyl)-acrylic acid according to Example 237. Yield=47%, ES-MS: (M+H)+ 413/415

Example 345

3-(2,3-Dihydro-benzofuran-5-yl)-1-[4-(6-ethyl-thieno[2,3-d]pyrimidin-4-yl)-piperazin-1-yl]-propenone

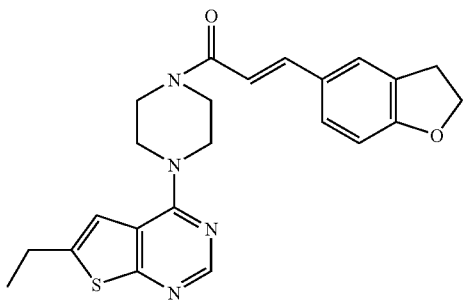

The HCl salt from Example 5 was coupled with 3-(2,3-Dihydro-benzofuran-5-yl)-acrylic acid according to Example 237. Yield=54%, ES-MS: (M+H)+ 421

Example 346

1-[4-(6-Ethyl-thieno[2,3-d]pyrimidin-4-yl)-piperazin-1-yl]-3-indan-5-yl-propenone

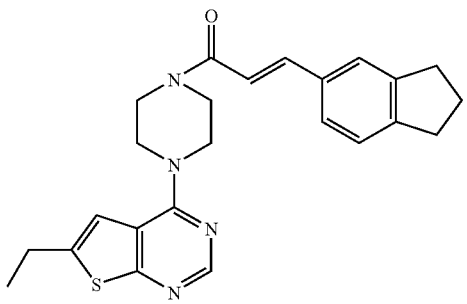

The HCl salt from Example 5 was coupled with 3-Indan-5-yl-acrylic acid according to Example 237. Yield=85%, ES-MS: (M+H)+ 419

Example 347

1-[4-(6-Ethyl-thieno[2,3-d]pyrimidin-4-yl)-piperazin-1-yl]-3-(3-methoxy-phenyl)-propenone

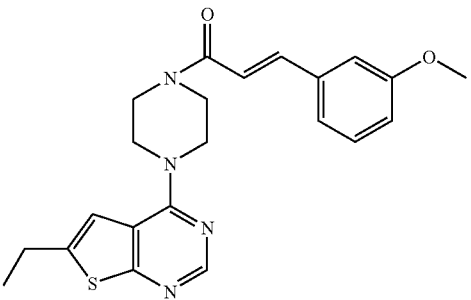

The HCl salt from Example 5 was coupled with 3-(3-Methoxy-phenyl)-acrylic acid according to Example 237. Yield=100%, ES-MS: (M+H)+ 409

Example 348

[4-(6-Ethyl-thieno[2,3-d]pyrimidin-4-yl)-piperazin-1-yl]-(4-phenyl-[1,2,3]-thiadiazol-5-yl)-methanone

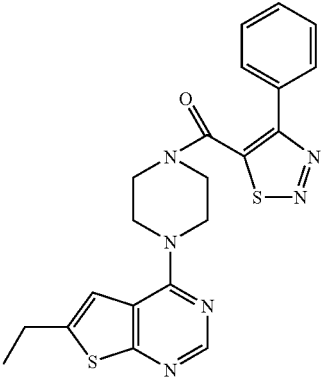

The HCl salt from Example 5 was coupled with 4-Phenyl-[1,2,3]thiadiazole-5-carboxylic acid according to Example 237. Yield=56%, ES-MS: (M+H)+ 437

Example 349

1-[4-(6-Ethyl-thieno[2,3-d]pyrimidin-4-yl)-piperazin-1-yl]-2-phenyl-propan-1-one

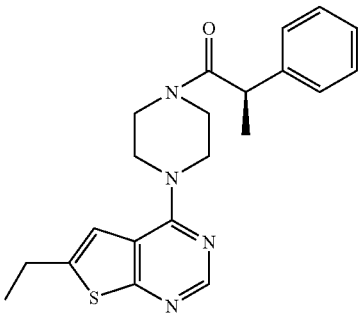

The HCl salt from Example 5 was coupled with 2-Phenyl-propionic acid according to Example 237. Yield=79%, ES-MS: (M+H)+ 381

Example 350

(2,7-Dimethyl-pyrazolo[1,5-a]pyrimidin-6-yl)-[4-(6-ethyl-thieno[2,3-d]pyrimidin-4-yl)-piperazin-1-yl]-methanone

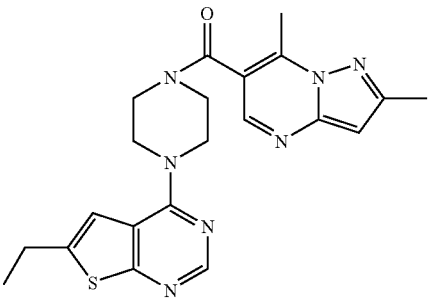

The HCl salt from Example 5 was coupled with 2,7-Dimethyl-pyrazolo[1,5-a]pyrimidine-6-carboxylic acid according to Example 237. Yield=21%, ES-MS: (M+H)+ 422

Example 351

Benzo[b]thiophen-3-yl-[4-(6-ethyl-thieno[2,3-d]pyrimidin-4-yl)-piperazin-1-yl]-methanone

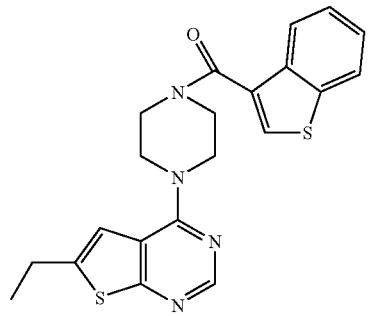

The HCl salt from Example 5 was coupled with Benzo[b]thiophene-3-carboxylic acid according to Example 237. Yield=100%, ES-MS: (M+H)+ 409

Example 352

[4-(6-Ethyl-thieno[2,3-d]pyrimidin-4-yl)-piperazin-1-yl]-(6-phenoxy-pyridin-3-yl)-methanone

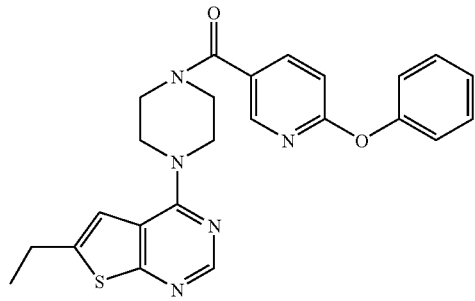

The HCl salt from Example 5 was coupled with 6-Phenoxy-nicotinic acid according to Example 237. Yield=76%, ES-MS: (M+H)+ 446

Example 353

4-(6-Isopropyl-thieno[2,3-c]pyrimidin-4-yl)-piperazine-1-carboxylic acid tert-butyl ester

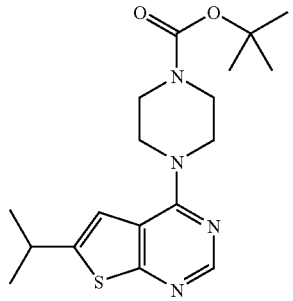

Step 1:

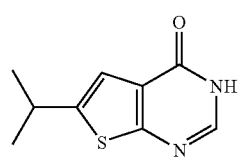

This intermediate was prepared by essentially following the method described in Example 1, Step 2 substituting ethyl 2-amino-5-isopropylthiophene-3-carboxylate for ethyl 2-amino-5-ethylthiophene-3-carboxylate. ES-MS: (M+H)+ 195

Step 2:

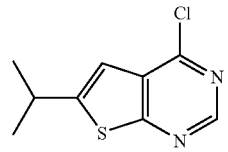

This intermediate was prepared utilizing the method described in Example 1, Step 3, Method B using 6-isopropyl-thienopyrimidone from Step 1 of this example in place of 6-ethylthienopyrimidone. ES-MS: (M+H)+ 213/215

Step 3:

The title compound was obtained utilizing the method described in Example 87, step 4 using the material obtained in step 2 of this example. ES-MS: (M+H)+ 363

Example 354

1-[4-(6-Isopropyl-thieno[2,3-d]pyrimidin-4-yl)-piperazin-1-yl]-2-phenyl-ethanone

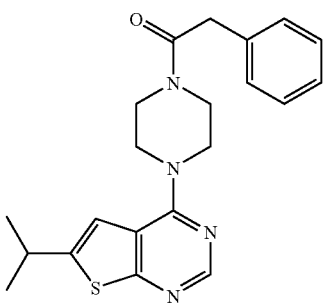

The title compound was obtained as a TFA salt utilizing the method described in Example 3 except phenylacetyl chloride (0.14 mmol) was used in place of phenyl chloroformate and 353 instead of 1. ES-MS: (M+H)+ 381, (M+Na)+ 403

Example 355

4-(Benzotriazol-1-yloxy)-1-[4-(6-isopropyl-thieno[2,3-d]pyrimidin-4-yl)-piperazin-1-yl]-butan-1-one

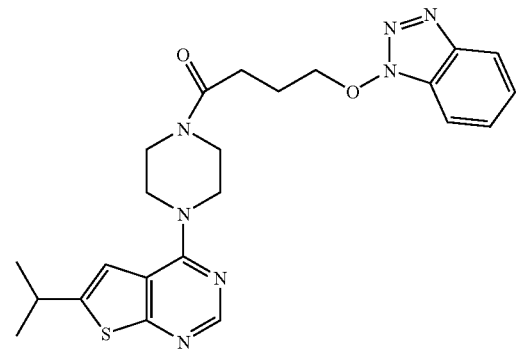

The title compound was obtained as a TFA salt utilizing the method described in Example 2 using 353 instead of 1 and 4-benzotriazolyloxybutanoic acid from Example 4 instead of phenylacetic acid. ES-MS: (M+H)+ 466, (M+Na)+ 488

Example 356

3,3,3-Trifluoro-1-[4-(6-isopropyl-thieno[2,3-d]pyrimidin-4-yl)-piperazin-1-yl]-propan-1-one

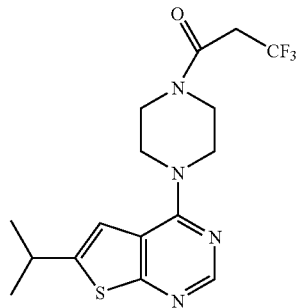

The title compound was obtained as a TFA salt utilizing the method described in Example 5 using 353 instead of 1. ES-MS: (M+H)+ 373

Example 357

(3-Chloro-phenyl)-[4-(6-ethyl-thieno[2,3-d]pyrimidin-4-yl]-methanone

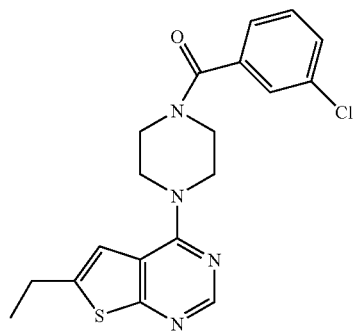

The title compound was obtained as a TFA salt utilizing the procedure outlined in Example 3 except 3-chlorobenzoyl chloride was used in place of phenyl chloroformate. ES-MS: (M+H)+ 387/389

Example 358

Benzo[1,3]dioxol-5-yl-[4-(6-ethyl-thieno[2,3-d]pyrimidin-4-yl)-piperazin-1-yl]-methanone

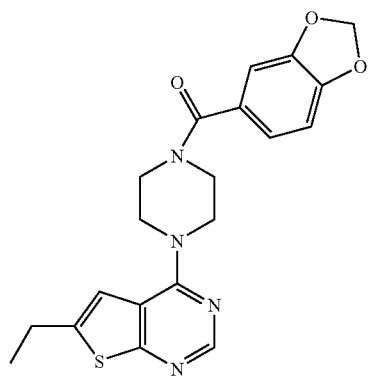

The title compound was obtained as a TFA salt utilizing the procedure outlined in Example 3 except piperonyl chloride was used in place of phenyl chloroformate. ES-MS: (M+H)+ 397

Example 359

2-Benzo[1,3]dioxol-5-yl 1-[4-(6-ethyl-thieno[2,3-d]pyrimidin-4-yl)-piperazin-1-yl]-ethanone

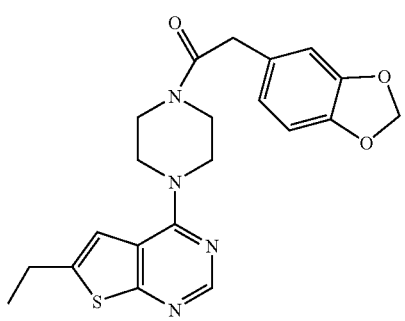

The title compound was obtained as a TFA salt utilizing the procedure outlined in Example 2 except 3,4-methylenedioxyphenylacetic acid was used in place of phenylacetic acid. ES-MS: (M+H)+ 411

Example 360

[4-(6-Ethyl-thieno[2,3-d]pyrimidin-4-yl)-piperazin-1-yl]-pyridin-2-yl-methanone

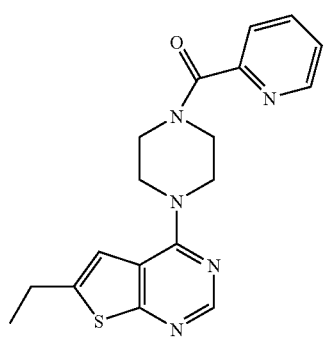

The title compound was obtained as a TFA salt utilizing the procedure outlined in Example 2 except picolinic acid was used in place of phenylacetic acid. ES-MS: (M+H)+ 354

Example 361

[4-(6-Ethyl-thieno[2,3-d]pyrimidin-4-yl)-piperazin-1-yl]-pyridin-3-yl-methanone

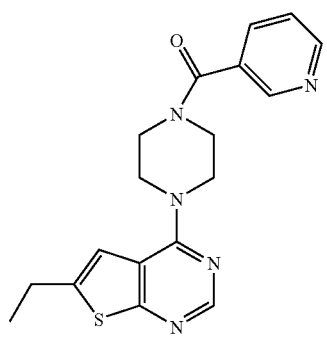

The title compound was obtained as a TFA salt utilizing the procedure outlined in Example 2 except nicotinic acid was used in place of phenylacetic acid. ES-MS: (M+H)+ 354

Example 362

[4-(6-Ethyl-thieno[2,3-d]pyrimidin-4-yl)-piperazin-1-yl]-pyridin-4-yl-methanone

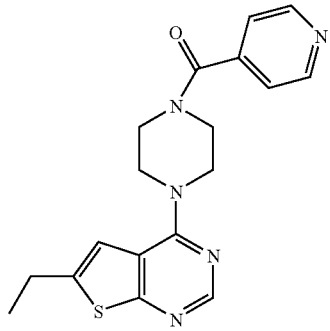

The title compound was obtained as a TFA salt utilizing the procedure outlined in Example 3 except isonicotinoyl chloride hydrochloride was used in place of phenyl chloroformate. ES-MS: (M+H)$^+$ 354

Example 363

Cyclopropyl-[4-(6-Ethyl-thieno[2,3-d]pyrimidin-4-yl)-piperazin-1-yl]-methanone

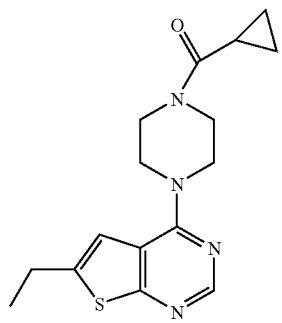

The title compound was obtained as a TFA salt utilizing the procedure outlined in Example 3 except cyclopropanecarbonyl chloride was used in place of phenyl chloroformate. ES-MS: (M+H)$^+$ 317

Example 364

4-Benzoimidazol-1-yl-1-[4-(6-ethyl-thieno[2,3-d]pyrimidin-4-yl)-piperazin-1-yl]-butan-1-one Step 1:

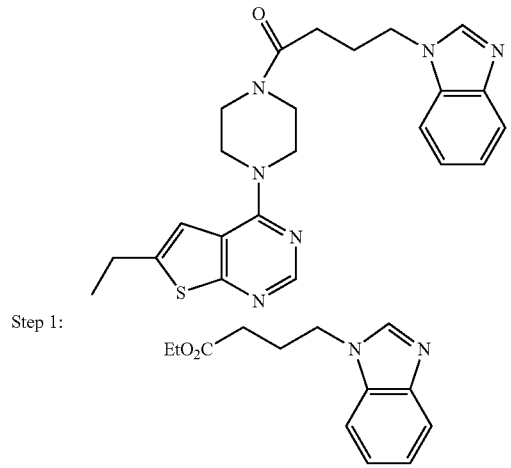

The ester was obtained utilizing the procedure outlined in Example 4 Step 1 where Cs$_2$CO$_3$ was used instead of DIEA and benzimidazole was used in place of N(1)-hydroxybenzotriazole. ES-MS: (M+H)$^+$ 219 (exchange of methyl group for ethyl group Step 2:

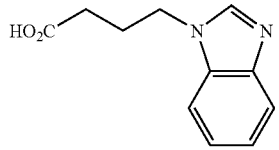

The desired intermediate acid was obtained by essentially following Step 2 of Example 4 utilizing the ester obtained in Step 1 of this example and using THF in place of MeOH. The desired product was isolated from the aqueous layer via lyopholization. ES-MS: (M+H)$^+$ 205

Step 3 The title compound was obtained by essentially following Example 2 using the acid obtained in Step 2 of this example in place of phenylacetic acid to afford the desired product as a TFA salt. ES-MS: (M+H)$^+$ 435

Example 365

5-Benzoimidazol-1-yl-1-[4-(6-ethyl-thieno[2,3-d]pyrimidin-4-yl)-piperazin-1-yl]-pentan-1-one

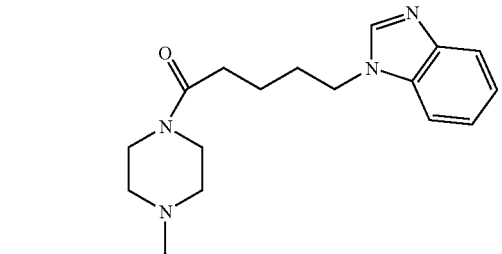

Step 1:

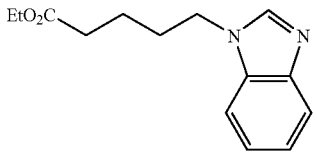

The ester was obtained utilizing the procedure outlined in Example 4 Step 1 where ethyl-5-bromovalerate was used for ethyl-4-bromobutyrate and Cs$_2$CO$_3$ was used instead of DIEA and benzimidazole was used in place of N(1)-hydroxybenzotriazole. ES-MS: (M+H)$^+$ 247

Step 2:

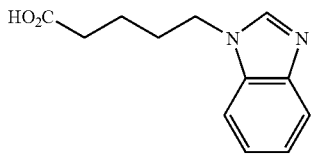

The desired intermediate acid was obtained by essentially following Step 2 of Example 4 utilizing in Step 1 of this example and using THF in place of MeOH. The desired product was isolated from the aqueous layer via lyopholization. ES-MS: (M+H)+ 219

Step 3: The title compound was obtained by essentially following Example 2 using the acid obtained in Step 2 of this example in place of phenylacetic acid to afford the desired product as a TFA salt. ES-MS: (M+H)+ 449

Example 366

1-[4-(6-Ethyl-thieno[2,3-d]pyrimidin-4-yl)-piperazin-1-yl]-5-indazol-1-yl-pentan-1-one

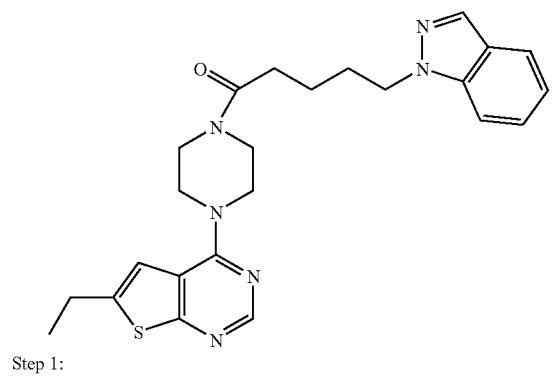

Step 1:

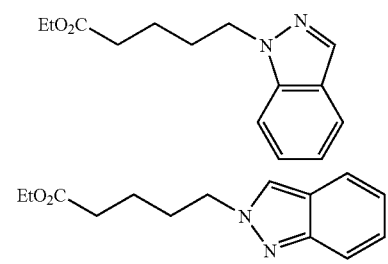

The ester was obtained initially as a mixture of N(1)- and N(2)-isomers utilizing the procedure outlined in Example 4 Step 1 where ethyl-5-bromovalerate was used for ethyl-4-bromobutyrate and $Cs_2CO_3$ was used instead of DIEA and indazole was used in place of N(1)-hydroxybenzotriazole. The isomers were readily separated using silica gel chromatography to provide 57% yield of the N(1)-isomer and 38% of the N(2)-isomer. Both isomers afforded the same result for mass spectral analysis. ES-MS: (M+H)+ 247

Step 2:

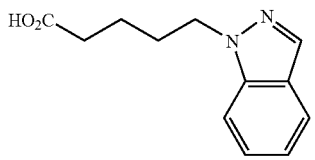

The desired intermediate acid was obtained by essentially following Step 2 of Example 4 utilizing the N(1)-ester obtained in Step 1 of this example and using THF in place of MeOH. ES-MS: (M+H)+ 219

Step 3: The title compound was obtained by essentially following Example 2 using the acid obtained in Step 2 of this example in place of phenylacetic acid to afford the desired product as a TFA salt. ES-MS: (M+H)+ 449

Example 367

1-[4-(6-Ethyl-thieno[2,3-d]pyrimidin-4-yl)-piperazin-1-yl]-5-indazol-2-yl-pentan-1-one

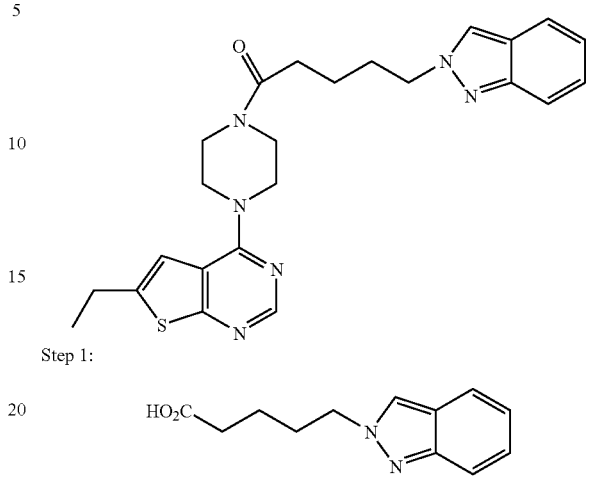

Step 1:

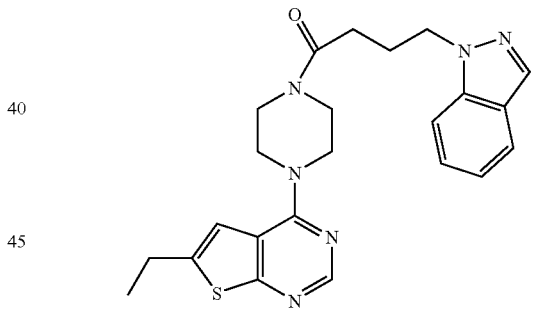

The desired intermediate acid was obtained by essentially following Step 2 of Example 366 utilizing the N(2)-ester obtained in Step 1 of Example 366. ES-MS: (M+H)+219

Step 2: The title compound was obtained by essentially following Example 2 using the acid obtained in Step 1 of this example in place of phenylacetic acid to afford the desired product as a TFA salt. ES-MS: (M+H)+ 449

Example 368

1-[4-(6-Ethyl-thieno[2,3-d]pyrimidin-4-yl)-piperazin-1-yl]-4-indazol-1-yl-butan-1-one Step 1:

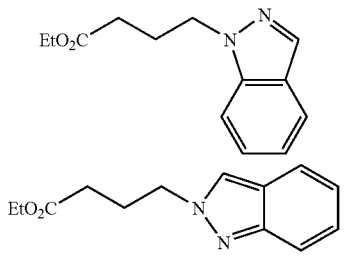

The ester was obtained initially as a mixture of N(1)- and N(2)-isomers utilizing the procedure outlined in Example 4 Step 1 where $Cs_2CO_3$ was used instead of DIEA and indazole was used in place of N(1)-hydroxybenzotriazole. The isomers were readily separated using silica gel chromatography to provide 52% yield of the N(1)-isomer and 33% of the N(2)-isomer. Both isomers afforded the same result for mass spectral analysis. ES-MS: (M+H)+ 233

Step 1:

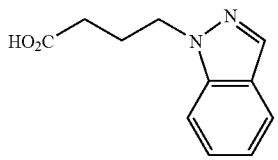

The desired intermediate acid was obtained by essentially following Step 2 of Example 4 utilizing the N(1)-ester obtained in Step 1 of this example and using THF in place of MeOH. ES-MS: (M+H)+ 205

Step 3: The title compound was obtained by essentially following Example 2 using the acid obtained in Step 2 of this example in place of phenylacetic acid to afford the desired product as a TFA salt. ES-MS: (M+H)+ 435

Example 369

1-[4-(6-Ethyl-thieno[2,3-d]pyrimidin-4-yl)-piperazin-1-yl]-4-indazol-2-yl-butan-1-one

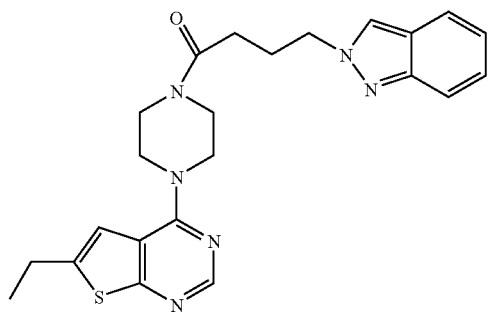

Step 1:

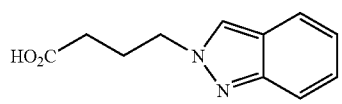

The desired intermediate acid was obtained by essentially following Step 2 of Example 366 utilizing the N(2)-ester obtained in Step 1 Example 368. ES-MS: (M+H)+ 219

Step 2: The title compound was obtained by essentially following Example 2 using the acid obtained in Step 1 of this example in place of phenylacetic acid to afford the desired product as a TFA salt. ES-MS: (M+H)+ 435

Example 370

5-Benzotriazol-1-yl-1-[4-(6-Ethyl-thieno[2,3-d]pyrimidin-4-yl)-piperazin-1-yl]-pentan-1-one

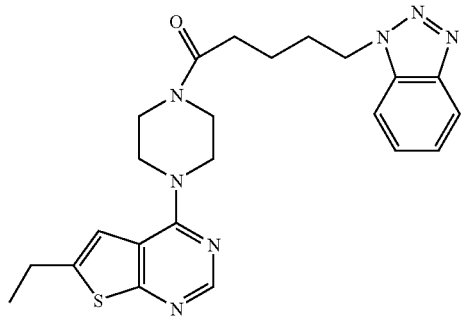

Step 1:

-continued

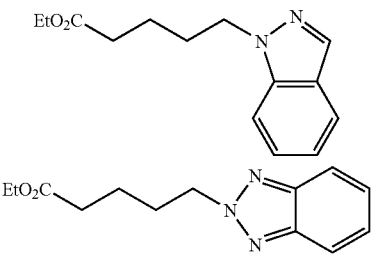

The ester was obtained initially as a mixture of N(1)- and N(2)-isomers utilizing the procedure outlined in Example 4 Step 1 where ethyl-5-bromovalerate was used in place of ethyl-4-bromobutyrate and Cs$_2$CO$_3$ was used instead of DIEA and benzotriazole was used in place of N(1)-hydroxybenzotriazole. The isomers were readily separated using silica gel chromatography to provide 44% yield of the N(1)-isomer and 47% of the N(2)-isomer. Both isomers afforded the same result for mass spectral analysis. ES-MS: (M+H)+ 248

Step 2:

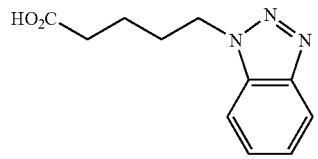

The desired intermediate acid was obtained by essentially following Step 2 of Example 4 utilizing the N(1)-ester obtained in Step 1 of this example and using THF in place of MeOH. ES-MS: (M+H)+ 220

Step 3. The title compound was obtained by essentially following Example 2 using the acid obtained in Step 2 of this example in place of phenylacetic acid to afford the desired product as a TFA salt. ES-MS: (M+H)+ 450

Example 371

5-Benzotriazol-2-yl-1-[4-(6-Ethyl-thieno[2,3-d]pyrimidin-4-yl)-piperazin-1-yl]-pentan-1-one

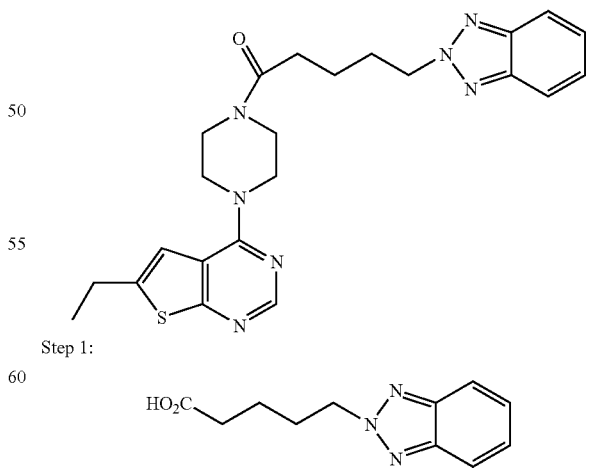

Step 1:

The desired intermediate acid was obtained by essentially following Step 2 of Example 366 utilizing the N(2)-ester obtained in Step 1 of Example 370. ES-MS: (M+H)+220

Step 2: The title compound was obtained by essentially following Example 2 using the acid obtained in Step 1 of this example in place of phenylacetic acid to afford the desired product as a TFA salt. ES-MS: (M+H)+ 450

Example 372

4-Benzotriazol-1-yl-1-[4-(6-Ethyl-thieno[2,3-d]pyrimidin-4-yl)-piperazin-1-yl]-butan-1-one

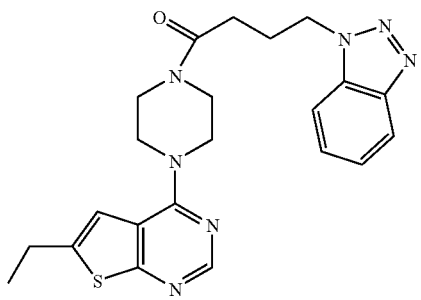

Step 1:

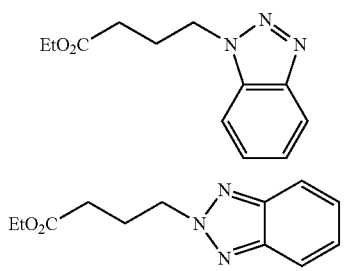

The ester was obtained initially as a mixture of N(1)- and N(2)-isomers utilizing the procedure outlined in Example 4 Step 1 where benzotriazole was used in place of N(1)-hydroxybenzotriazole. The isomers were readily separated using silica gel chromatography to provide 35% yield of the N(1)-isomer and 32% of the N(2)-isomer. Both isomers afforded the same result for mass spectral analysis. ES-MS: (M+H)+ 234

Step 2:

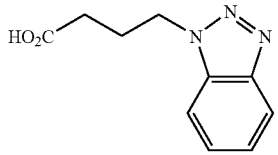

The desired intermediate acid was obtained by essentially following Step 2 of Example 4 utilizing the N(1)-ester obtained in Step 1 of this example and using THF in place of MeOH. ES-MS: (M+H)+ 206

Step 3. The title compound was obtained by essentially following Example 2 using the acid obtained in Step 2 of this example in place of phenylacetic acid to afford the desired product as a TFA salt. ES-MS: (M+H)+ 436

Example 373

4-Benzotriazol-2-yl-1-[4-(6-Ethyl-thieno[2,3-d]pyrimidin-4-yl)-piperazin-1-yl]-butan-1-one

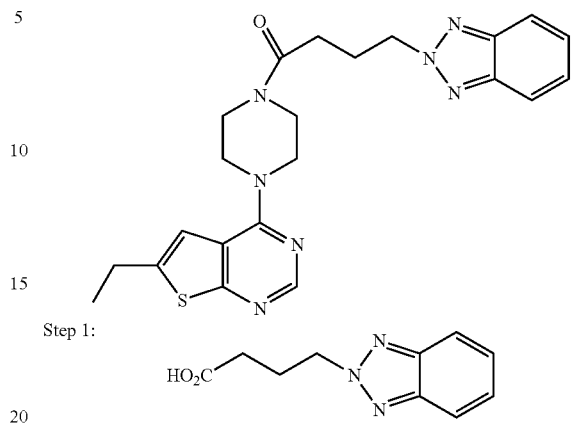

Step 1:

The desired intermediate acid was obtained by essentially following Step 2 of Example 366 utilizing the N(2)-ester obtained in Step 1 of Example 372. The desired acid was somewhat soluble in both the organic and aqueous layers. Thus, the aqueous washes were lyophilized, then triturated repeatedly with EtOAc. The combined EtOAc washes were then dried with MgSO4, filtered, and the solvent was removed in vacuo. This material was then combined with that initially obtained from the EtOAc extraction of the reaction to afford 96% yield of the desired acid. ES-MS: (M+H)+ 206

Step 2. The title compound was obtained by essentially following Example 2 using the acid obtained in Step 1 of this example in place of phenylacetic acid to afford the desired product as a TFA salt. ES-MS: (M+H)+ 436

Example 374

4-(6-Cyano-thieno[2,3-d]pyrimidin-4-yl)-piperazine-1-carboxylic acid tert-butyl ester

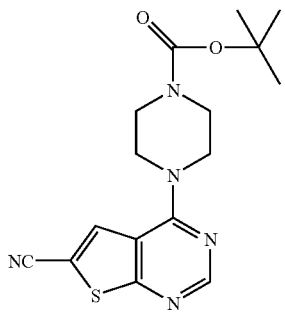

Argon was gently bubbled through dry acetone for ½ hr. Bromide 124 (50 mg, 0.125 mmol), Pd2(dba)3 (7.3 mg, 0.0075 mmol), DPPF (14 mg, 0.025 mmol), CuI (3 mg, 0.016 mmol), and KCN (16 mg, 0.25 mmol) were combined under argon at rt and then the degassed acetone (1.0 mL) was added. The resulting mixture was stirred at it for ½ hr under argon, and then warmed to reflux overnight. At this time, all of the acetone had evaporated. A fresh mixture of the Pd2(dba)3 (8 mg), DPPF (14 mg), and CuI (3 mg) was prepared in degassed acetone (1 mL) and stirred at rt for 30 minutes. This mixture was then added to the initial reaction mixture at rt and then warmed to reflux for 4.5 hrs. The reaction was then evaporated to dryness, CH2Cl2 was added and the residue was purified using silica gel chromatography to afford 20 mg (45%) of the desired product. ES-MS: (M+H)+ 346

Example 375

4-{4-[4-(Benzotriazol-1-yloxy)-butyryl]-piperazin-1-yl}-thieno[2,3-d]pyrimidine-6-carbonitrile

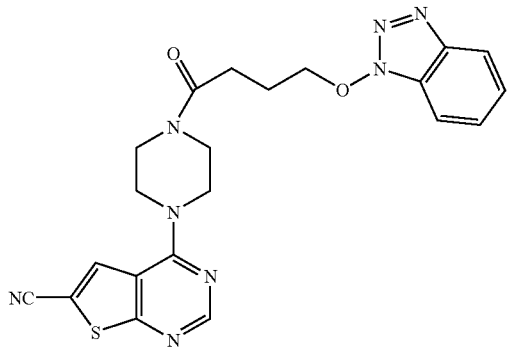

The title compound was obtained as a TFA salt by essentially following Example 2 except 374 was used instead of 1 and the acid from Step 2 of Example 4 was used in place of phenyl acetic acid. ES-MS: (M+H)+ 449

Example 376

4-(6-Acetyl-thieno[2,3-d]pyrimidin-4-yl)-piperazine-1-carboxylic acid tert-butyl ester

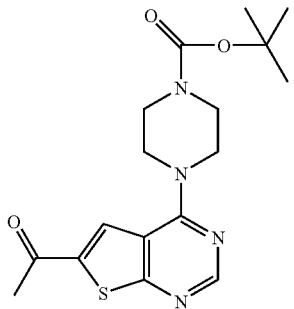

To Bromide 124 (100 mg, 0.25 mmol) in fresh anhydrous THF (2 mL) under argon at 0° C. was added dropwise isopropylmagnesium chloride (Aldrich, 2M in THF, 0.2 mL) via syringe. After stirring at 0° C. for 45 minutes, Ac$_2$O (0.06 mL, 0.6 mmol) was added dropwise via syringe, and stirring was maintained for ½ hr. The reaction was quenched via the careful addition of saturated brine (2 mL). The resulting solution was washed with EtOAc (3×2 mL), and the combined organic washes were dried with MgSO$_4$, filtered, and stripped in vacuo. The resulting residue was purified using silica gel chromatography to afford a 43% yield of the desired compound. ES-MS: (M+H)+ 363

Example 377

1-(4-Piperazin-1-yl-thieno[2,3-d]pyrimidin-6-yl)-ethanone

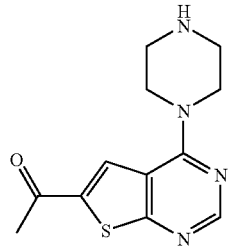

A mixture of bromide 124 (40 mg, 0.1 mmol), Pd(PPh$_3$)$_4$ (2 mg, 0.002 mmol), and tributyl(1-ethoxyvinyl)tin (0.034 mL, 0.1 mmol) in anhydrous dioxane (1 mL) was warmed to 100–110° C. and stirred overnight. An additional amount of Pd(PPh$_3$)$_4$ (4 mg) was added and stirring at reflux was maintained for another 4 hrs. The reaction was then cooled to rt and 1M HCl (1 mL) was added. Stirring was continued for 1.5 hrs, and then the solution was washed with EtOAc (3×3 mL). The acidic aqueous layer contained the desired product which was isolated via filtration through celite and then lyopholization. ES-MS: (M+H)+ 263

Example 378

1-[4-(6-Acetyl-thieno[2,3-d]pyrimidin-4-yl)-piperazin-1-yl]-4-(benzotriazol-1-yloxy)-butan-1-one

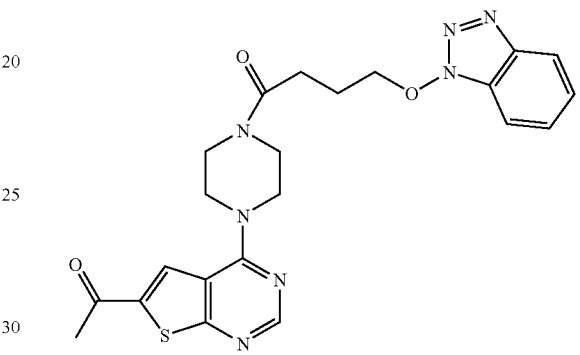

The title compound was obtained as a TFA salt by essentially following Example 2 except 376 was used instead of 1 and the acid from Step 2 of Example 4 was used in place of phenyl acetic acid. ES-MS: (M+H)+ 466

Example 379

4-(4-tert-Butoxycarbonyl-piperazin-1-yl)-thieno[2,3-d]pyrimidine-6-carboxylic acid ethyl ester

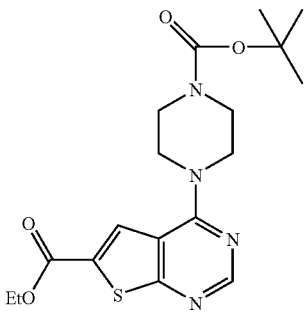

To Bromide 124 (100 mg, 0.25 mmol) in fresh anhydrous THF (2 mL) under argon at 0° C. was added dropwise isopropylmagnesium chloride (Aldrich, 2M in THF, 0.2 mL) via syringe. After stirring at 0° C. for 30 minutes, EtO$_2$C—CN (0.04 mL, 0.4 mmol) was added dropwise via syringe and stirring was maintained overnight as it warmed to rt. The reaction was cooled to −5° C. and quenched via the careful addition of acidic saturated brine (2 mL) affording a pH=5–6. The resulting solution was washed with EtOAc (3×2 mL), and the combined organic washes were dried with MgSO$_4$, filtered, and stripped in vacuo. The resulting residue was purified using silica gel chromatography to afford a 16% yield of the desired compound. ES-MS: (M+H)+ 393

Example 380

4-{4-[4-(Benzotriazol-1-yloxy)-butyryl]-piperazin-1-yl}-thieno[2,3-d]pyrimidine-6-carboxylic acid ethyl ester

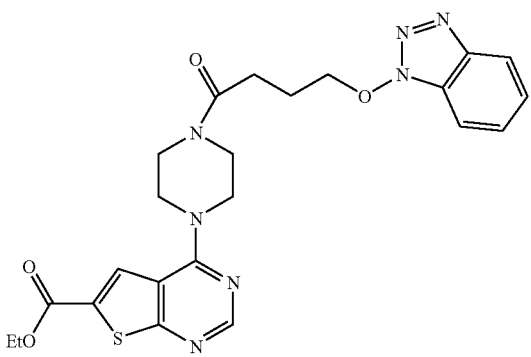

The title compound was obtained as a TFA salt by essentially following Example 2 except 379 was used instead of 1 and the acid from Step 2 of Example 4 was used in place of phenyl acetic acid. ES-MS: (M+H)+ 496

Example 381

1-[4-(6-Amino-thieno[2,3-d]pyrimidin-4-yl)-piperazin-1-yl]-4-(benzotriazol-1-yloxy)-butan-1-one

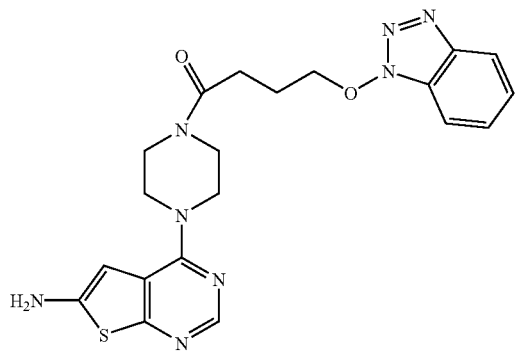

Step 1: Preparation of 4-(6-Amino-thieno[2,3-d]pyrimidin-4-yl)-piperazine-1-carboxylic acid tert-butyl ester

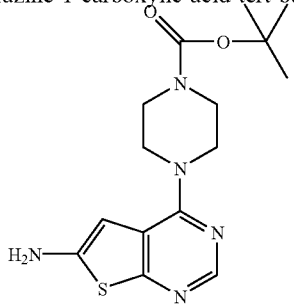

Compound 128 (36 mg, 0.1 mol) was mixed with SnCl$_2$—H$_2$O (90 mg, 0.4 mmol) in EtOH (1.5 mL) at rt and then warmed to gentle reflux. After 1 hr, the reaction was cooled to rt, and the solvent removed in vacuo. The residue was mixed with brine (3 mL), and then washed with EtOAc (6×3 mL). The combined organic washes were dried with MgSO$_4$, filtered, and stripped to afford 23 mg of crude amino compound. ES-MS: (M+H)+ 336 Step 2. The title compound was obtained as a TFA salt by essentially following Example 2 except the material from Step 1 of this example was used instead of 1 and the acid from Step 2 of Example 4 was used in place of phenyl acetic acid. ES-MS: (M+H)+ 439

Example 382

[4-(6-Ethyl-thieno[2,3-c]pyrimidin-4-yl)-piperazin-1-yl]-oxo-acetic acid ethly ester

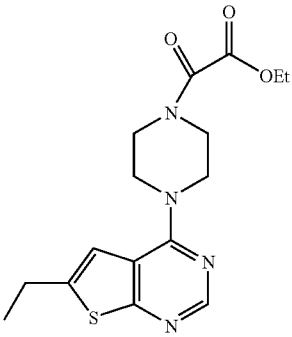

The title compound was obtained as a TFA salt utilizing the procedure outlined in Example 3 except ethyl chlorooxoacetate was used in place of phenyl chloroformate. ES-MS: (M+H)+ 349

Example 383

3-[4-(6-Ethyl-thieno[2,3-d]pyrimidin-4-yl)-piperazin-1-yl]-3-oxo-propionic acid ethyl ester

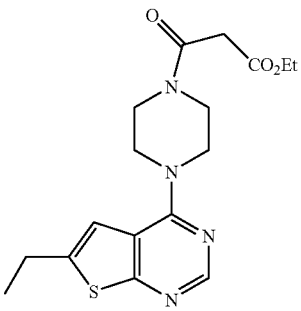

alt utilizing the procedure outlined in Example 3 except ethyl malonyl chloride was used in place of phenyl chloroformate. ES-MS: (M+H)+ 363

Example 384

4-[4-(6-Ethyl-thieno[2,3-d]pyrimidin-4-yl)-piperazin-1-yl]-4-oxo-butyric acid methyl ester

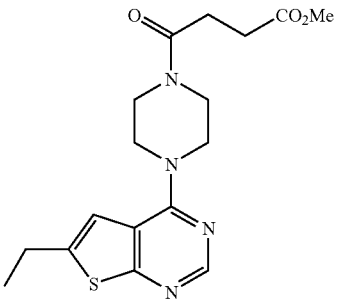

The title compound was obtained as a TFA salt utilizing the procedure outlined in Example 3 except methyl 4-chloro-4-oxobutyrate was used in place of phenyl chloroformate. ES-MS: (M+H)+ 363

Example 385

5-[4-(6-Ethyl-thieno[2,3-d]pyrimidin-4-yl)-piperazin-1-yl]-5-oxo-pentanoic acid methyl ester

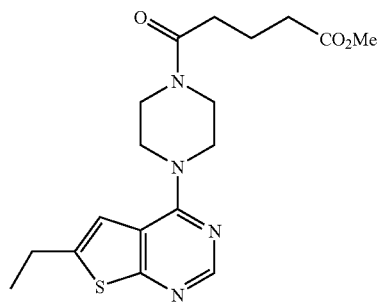

The title compound was obtained as a TFA salt utilizing the procedure outlined in Example 3 except methyl 5-chloro-5-oxovalerate was used in place of phenyl chloroformate. ES-MS: (M+H)+ 377

Example 386

6-[4-(6-Ethyl-thieno[2,3-d]pyrimidin-4-yl)-piperazin-1-yl]-6-oxo-hexanoic acid methyl ester

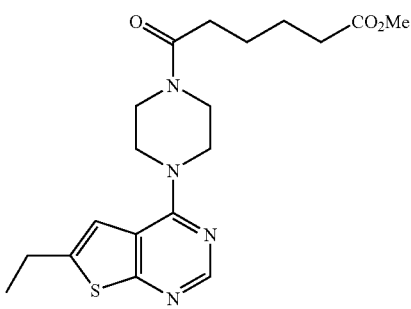

The title compound was obtained as a TFA salt utilizing the procedure outlined in Example 3 except 5-chlorocarbonyl-pentanoic acid methyl ester was used in place of phenyl chloroformate. ES-MS: (M+H)+ 391

Example 387

[4-(6-Ethyl-thieno[2,3-d]pyrimidin-4-yl)-piperazin-1-yl]-oxo-acetic acid

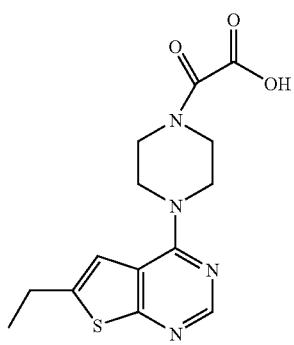

The desired acid was obtained by essentially following Step 2 of Example 4 utilizing ester 382 and using EtOH in place of MeOH. ES-MS: (M+H)+ 321

Example 388

3-[4-(6-Ethyl-thieno[2,3-d]pyrimidin-4-yl)-piperazin-1-yl]-3-oxo-propionic acid

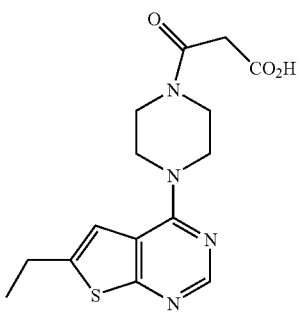

The target acid was obtained by essentially following Step 2 of Example 4 utilizing ester 383 and using EtOH in place of MeOH. ES-MS: (M+H)+ 335

Example 389

4-[4-(6-Ethyl-thieno[2,3-d]pyrimidin-4-yl)-piperazin-1-yl]-4-oxo-butyric acid

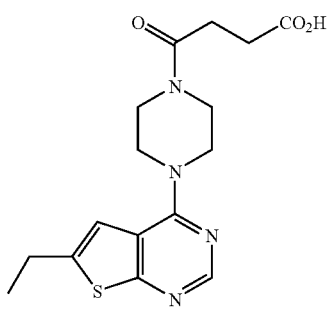

The target acid was obtained by essentially following Step 2 of Example 4 utilizing ester 384. ES-MS: (M+H)+ 349

Example 390

5-[4-(6-Ethyl-thieno[2,3-d]pyrimidin-4-yl)-piperazin-1-yl]-5-oxo-pentanoic acid

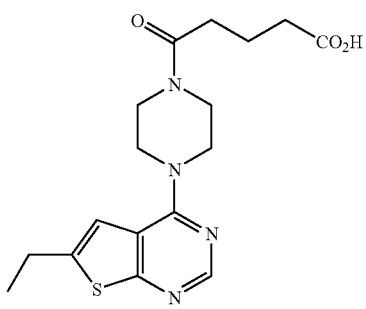

The target acid was obtained by essentially following Step 2 of Example 4 utilizing ester 385. ES-MS: (M+H)+ 363

Example 391

6-[4-(6-Ethyl-thieno[2,3-d]pyrimidin-4-yl)-piperazin-1-yl]-6-oxo-hexanoic acid

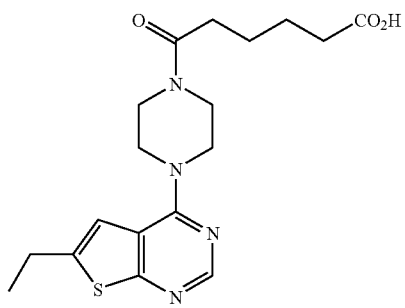

The target acid was obtained by essentially following Step 2 of Example 4 utilizing ester 386. ES-MS: (M+H)+ 377

Example 392

3-[4-(6-Ethyl-thieno[2,3-d]pyrimidin-4-yl)-piperazin-1-yl]-3-oxo-propionamide

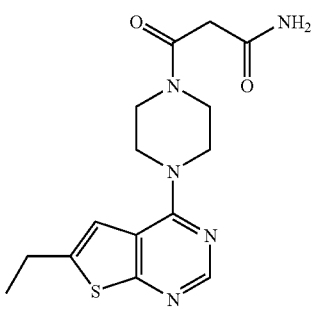

The title compound was obtained as a TFA salt by essentially following Example 5 except that malonamic acid was used in place of 3,3,3-trifluoropropionic acid in Step 2. ES-MS: (M+H)+ 334

Example 393

4-[4-(6-Ethyl-thieno[2,3-d]pyrimidin-4-yl)-piperazin-1-yl]-4-oxo-butyramide

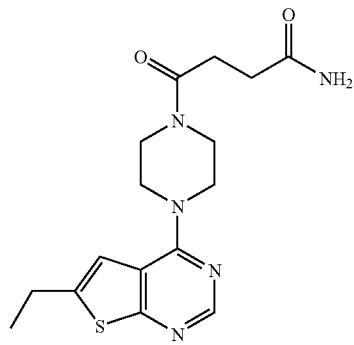

The title compound was obtained as a TFA salt by essentially following Example 5 except that succinamic acid was used in place of 3,3,3-trifluoropropionic acid in Step 2. ES-MS: (M+H)+ 348

Example 394

3-[4-(6-Ethyl-thieno[2,3-d]pyrimidin-4-yl)-piperazin-1-yl]-3-oxo-propionitrile

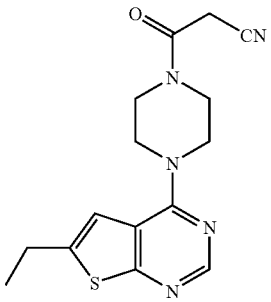

The title compound was obtained as a TFA salt by essentially following Example 5 except that cyanoacetic acid was used in place of 3,3,3-trifluoropropionic acid in Step 2. ES-MS: (M+H)+ 316

Example 395

6-[4-(6-Ethyl-thieno[2,3-d]pyrimidin-4-yl)-piperazin-1-yl]-6-oxo-hexanenitrile

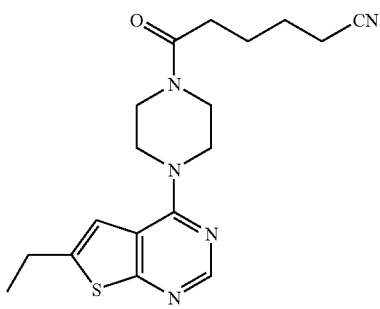

The title compound was obtained as a TFA salt by essentially following Example 5 except that 5-cyanopentanoic acid was used in place of 3,3,3-trifluoropropionic acid in Step 2. ES-MS: (M+H)+ 358

Example 396

{2-[4-(6-Ethyl-thieno[2,3-d]pyrimidin-4-yl)-piperazin-1-yl]-2-oxo-ethyl}-carbamic acid tert-butyl ester

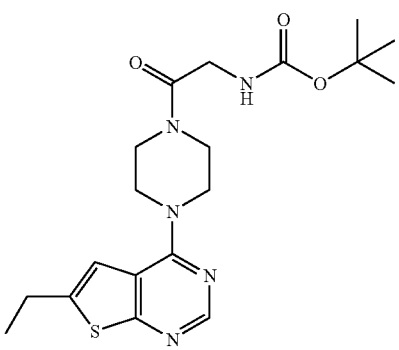

The title compound was obtained as a TFA salt by essentially following Example 5 except that N-Boc-glycine was used in place of 3,3,3-trifluoropropionic acid in Step 2. ES-MS (M+H)+ 406

Example 397

{3-[4-(6-Ethyl-thieno[2,3-d]pyrimidin-4-yl)-piper-azin-1-yl]-3-oxo-propyl}-carbamic acid tert-butyl ester

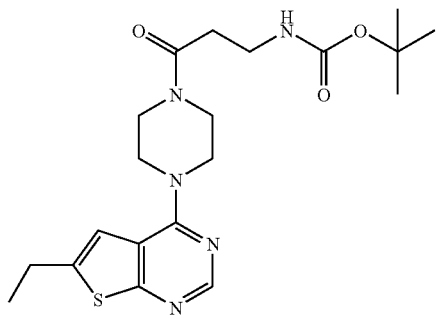

The title compound was obtained as a TFA salt by essentially following Example 5 except that 3-tert-butoxy-carbonylamino-propionic acid was used in place of 3,3,3-trifluoropropionic acid in Step 2. ES-MS: (M+H)$^+$ 420

Example 398

{4-[4-(6-Ethyl-thieno[2,3-d]pyrimidin-4-yl)-piper-azin-1-yl]-4-oxo-butyl}-carbamic acid tert-butyl ester

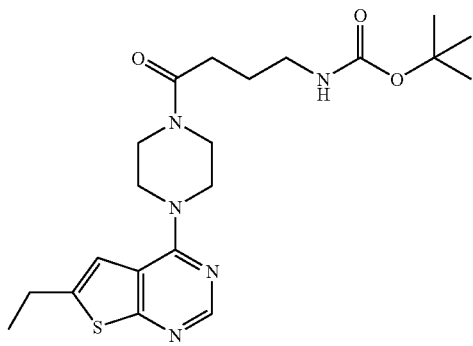

The title compound was obtained as a TFA salt by essentially following Example 5 except that 4-tert-butoxy-carbonylamino-butanoic acid was used in place of 3,3,3-trifluoropropionic acid in Step 2. ES-MS: (M+H)$^+$ 434

Example 399

{5-[4-(6-Ethyl-thieno[2,3-d]pyrimidin-4-yl)-piper-azin-1-yl]-5-oxo-pentyl}-carbamic acid tert-butyl ester

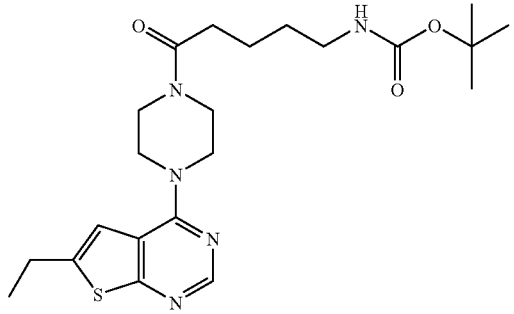

The title compound was obtained as a TFA salt by essentially following Example 5 except that 5-tert-butoxy-carbonylamino-pentanoic acid was used in place of 3,3,3-trifluoropropionic acid in Step 2. ES-MS: (M+H)$^+$ 448

Example 400

{6-[4-(6-Ethyl-thieno[2,3-d]pyrimidin-4-yl)-piper-azin-1-yl]-6-oxo-hexyl}-carbamic acid tert-butyl ester

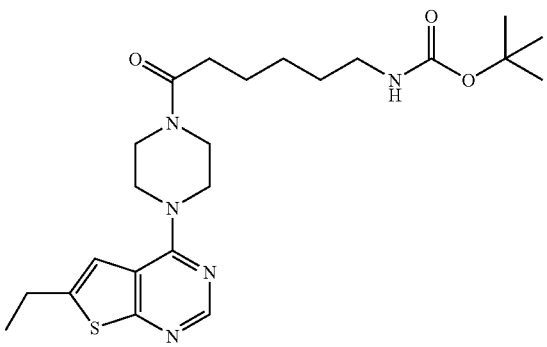

The title compound was obtained as a TFA salt by essentially following Example 5 except that 6-tert-butoxy-carbonylamino-hexanoic acid was used in place of 3,3,3-trifluoropropionic acid in Step 2. ES-MS: (M+H)$^+$ 462

Example 401

2-Amino-1-[4-(6-ethyl-thieno[2,3-d]pyrimidin-4-yl)-piperazin-1-yl]-ethanone

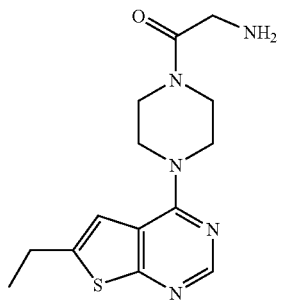

The title compound was obtained from 396 as a TFA salt by essentially following Step 1 of Example 2 and then purification using preparative RP-HPLC. ES-MS: (M+H)$^+$ 306

Example 402

3-Amino-1-[4-(6-ethyl-thieno[2,3-d]pyrimidin-4-yl)-piperazin-1-yl]-propan-1-one

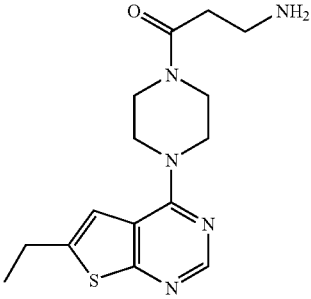

The title compound was obtained from 397 as a TFA salt by essentially following Step 1 of Example 2 and then purification using preparative RP-HPLC. ES-MS: (M+H)+ 320

Example 403

4-Amino-1-[4-(6-ethyl-thieno[2,3-d]pyrimidin-4-yl)-piperazin-1-yl]-butan-1-one

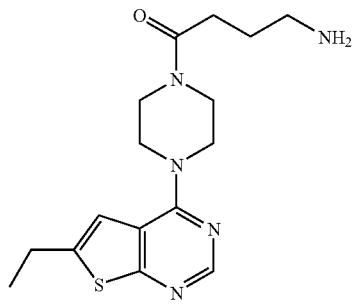

The title compound was obtained from 398 as a TFA salt by essentially following Step 1 of Example 2 and then purification using preparative RP-HPLC. ES-MS: (M+H)+ 334

Example 404

5-Amino-1-[4-(6-ethyl-thieno[2,3-d]pyrimidin-4-yl)-piperazin-1-yl]-pentan-1-one

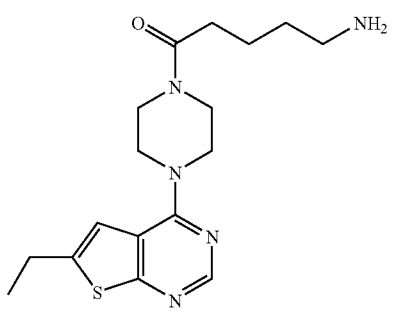

The title compound was obtained from 399 as a TFA salt by essentially following Step 1 of Example 2 and then purification using preparative RP-HPLC. ES-MS: (M+H)+ 348

Example 405

6-Amino-1-[4-(6-ethyl-thieno[2,3-d]pyrimidin-4-yl)-piperazin-1-yl]-hexan-1-one

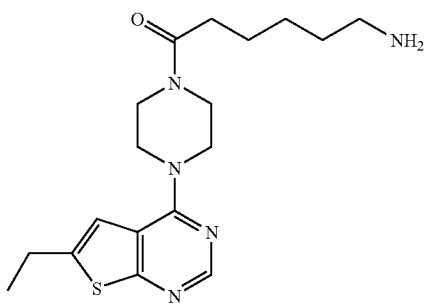

The title compound was obtained from 400 as a TFA salt by essentially following Step 1 of Example 2 and then purification using preparative RP-HPLC. ES-MS: (M+H)+ 362

Example 406

4-[4-(6-Ethyl-thieno[2,3-d]pyrimidin-4-yl)-piperazin-1-yl]-4-oxo-butyronitrile

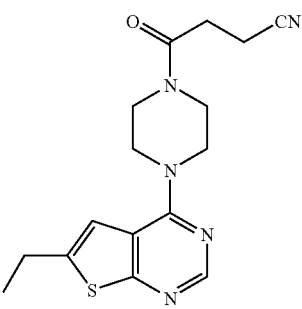

The title compound was obtained as a TFA salt by essentially following Example 5 except that MeCN was used instead of DMF and 3-cyanopropionic acid was used in place of 3,3,3-trifluoropropionic acid in Step 2. ES-MS: (M+H)+ 330

Example 407

[4-(6-Ethyl-thieno[2,3-cd]pyrimidin-4-yl)-piperazin-1-yl]-thiophen-2-yl-methanone

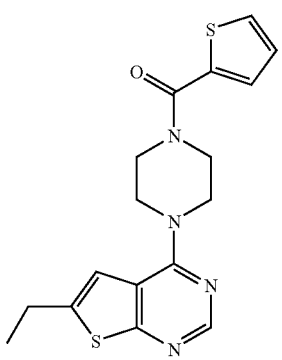

The title compound was obtained as a TFA salt by essentially following Example 5 except that thiophene-2-carboxylic acid was used in place of 3,3,3-trifluoropropionic acid in Step 2. ES-MS: (M+H)+ 359

Example 408

[4-(6-Ethyl-thieno[2,3-d]pyrimidin-4-yl)-piperazin-1-yl]-(5-phenyl-thiophen-2-yl)-methanone

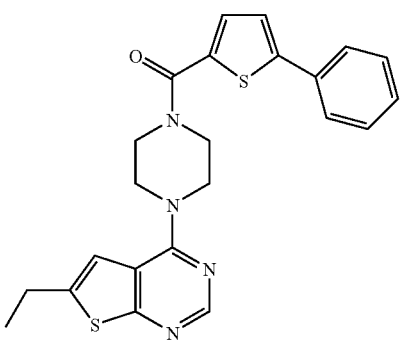

The title compound was obtained as a TFA salt by essentially following Example 3 beginning with the material from Example 5, Step 1 and 5-phenyl-thiophene-2-carbonyl chloride was used in place of phenylacetyl chloride. ES-MS: (M+H)+ 435

Example 409

[2,2']Bithiophenyl-5-yl-[4-(6-ethyl-thieno[2,3-d]pyrimidin-4-yl)-piperazin-1-yl]-methanone

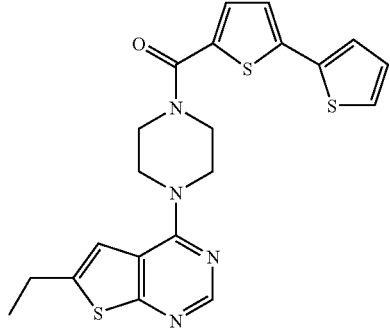

The title compound was obtained as a TFA salt by essentially following Example 3 beginning with the material from Example 5, Step 1 and [2,2']bithiophenyl-5-carbonyl chloride was used in place of phenylacetyl chloride. ES-MS: (M+H)+ 441

Example 410

[4-(6-Ethyl-thieno[2,3-d]pyrimidin-4-yl)-piperazin-1-yl]-(5-pyridin-2-yl-thiophen-2-yl)-methanone

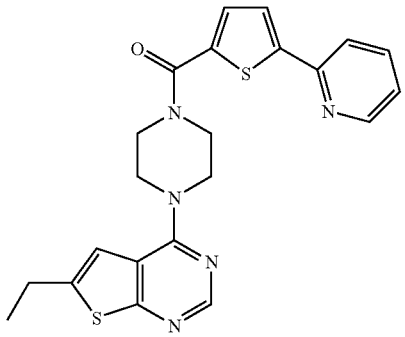

The title compound was obtained as a TFA salt by essentially following Example 3 beginning with the material from Example 5, Step 1 and 5-pyridin-2-yl-thiophene-2-carbonyl chloride was used in place of phenylacetyl chloride. ES-MS: (M+H)+ 436

Example 411

[4-(6-Ethyl-thieno[2,3-d]pyrimidin-4-yl)-piperazin-1-yl]-(4-thiophen-2-yl-phenyl)-methanone

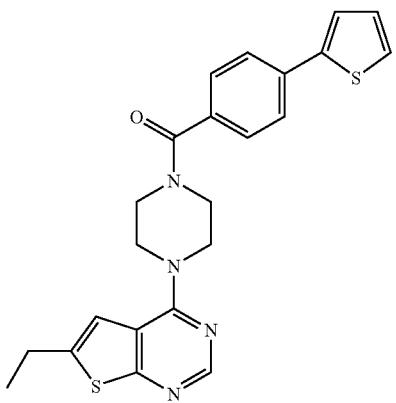

The title compound was obtained as a TFA salt by essentially following Example 3 beginning with the material from Example 5, Step 1 and 4-thiophen-2-yl-benzoyl chloride was used in place of phenylacetyl chloride. ES-MS: (M+H)+ 435

Example 412

[4-(6-Ethyl-thieno[2,3-d]pyrimidin-4-yl)-piperazin-1-yl]-(4-pyrazol-1-yl-phenyl)-methanon

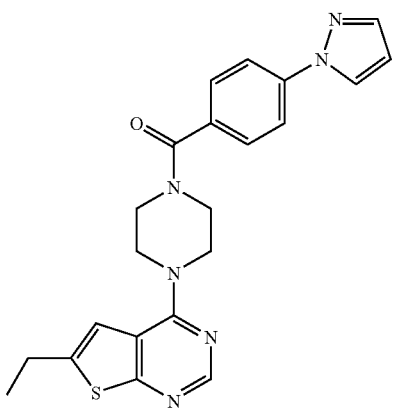

The title compound was obtained as a TFA salt by essentially following Example 3 beginning with the material from Example 5, Step 1 and 4-pyrazol-1-yl-benzoyl chloride was used in place of phenylacetyl chloride. ES-MS: (M+H)+ 419

Example 413

[4-(6-Ethyl-thieno[2,3-d]pyrimidin-4-yl)-piperazin-1-yl]-(4-[1,2,4]triazol-1-yl-phenyl)-methanone

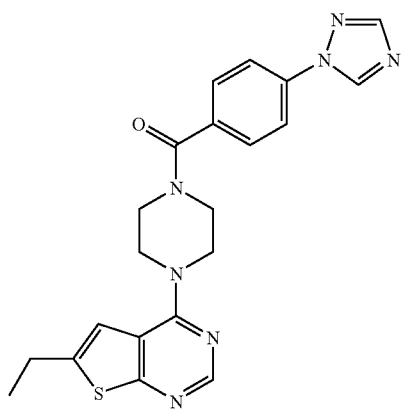

The title compound was obtained as a TFA salt by essentially following Example 5 except that 4-[1,2,4]triazol-1-yl-benzoic acid was used in place of 3,3,3-trifluoropropionic acid and MeCN in place of DMF in Step 2. ES-MS: (M+H)$^+$ 420

Example 414

[4-(6-Ethyl-thieno[2,3-d]pyrimidin-4-yl)-piperazin-1-yl]-(4-oxazol-5-yl-phenyl)-methanone

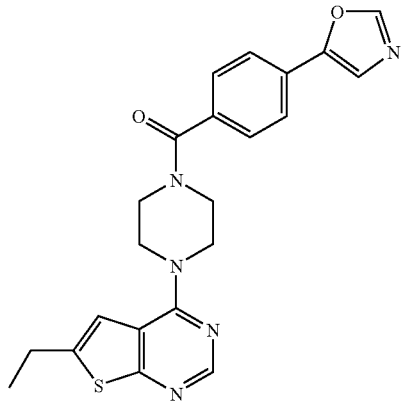

The title compound was obtained as a TFA salt by essentially following Example 5 except that 4-oxazol-5-yl-benzoic acid was used in place of 3,3,3-trifluoropropionic acid and MeCN in place of DMF in Step 2. ES-MS: (M+H)$^+$ 420

Example 415

[4-(6-Ethyl-thieno[2,3-d]pyrimidin-4-yl)-piperazin-1-yl]-(4-morpholin-4-yl-phenyl)-methanone

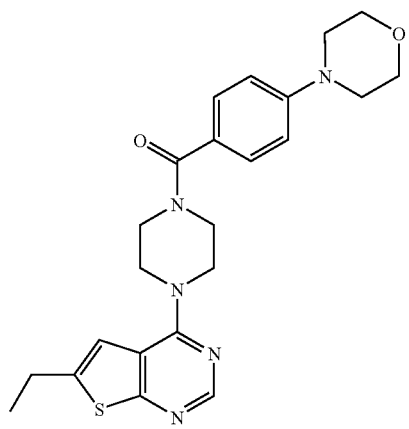

The title compound was obtained as a TFA salt by essentially following Example 5 except that 4-morpholin-4-yl-benzoic acid was used in place of 3,3,3-trifluoropropionic acid and MeCN in place of DMF in Step 2. ES-MS: (M+H)$^+$ 438

Example 416

[4-(6-Ethyl-thieno[2,3-d]pyrimidin-4-yl)-piperazin-1-yl]-quinoxalin-6-yl-methanone

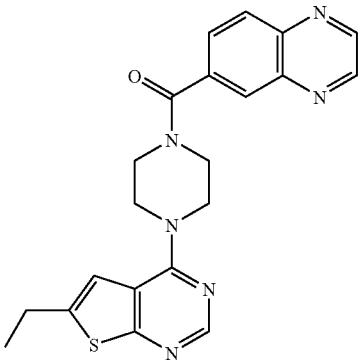

The title compound was obtained as a TFA salt by essentially following Example 3 beginning with the material from Example 5, Step 1 and quinoxaline-6-carbonyl chloride was used in place of phenylacetyl chloride. ES-MS: (M+H)$^+$ 405

Example 417

1-[4-(6-Ethyl-thieno[2,3-d]pyrimidin-4-yl)-piperazin-1-yl]-5-thiophen-2-yl-pentane-1,5-dione

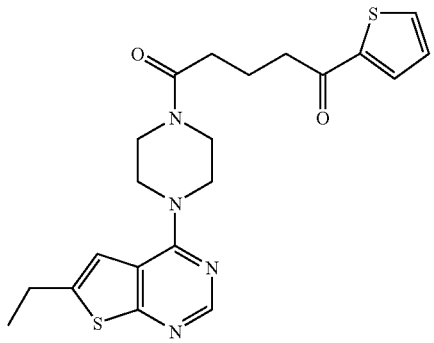

The title compound was obtained as a TFA salt by essentially following Example 5 except that 5-oxo-5-thiophen-2-yl-pentanoic acid was used in place of 3,3,3-trifluoropropionic acid and DCM in place of DMF in Step 2. ES-MS: (M+H)$^+$ 429

Example 418

4-(3-Chloro-5-trifluoromethyl-pyridin-2-ylamino)-1-[4-(6-ethyl-thieno[2,3-d]pyrimidin-4-yl)-piperazin-1-yl]-butan-1-one

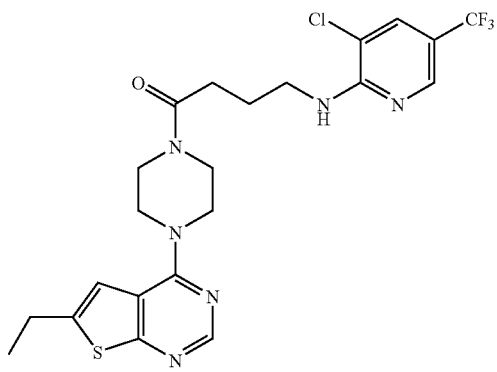

The title compound was obtained as a TFA salt by essentially following Example 5 except that 4-(3-chloro-5-trifluoromethyl-pyridin-2-ylamino)-butyric acid was used in place of 3,3,3-trifluoropropionic acid and DCM in place of DMF in Step 2. ES-MS: (M+H)$^+$ 513

Example 419

1-[4-(6-Ethyl-thieno[2,3-d]pyrimidin-4-yl)-piperazin-1-yl]-5-(imidazol-1-yloxy)-pentan-1-one

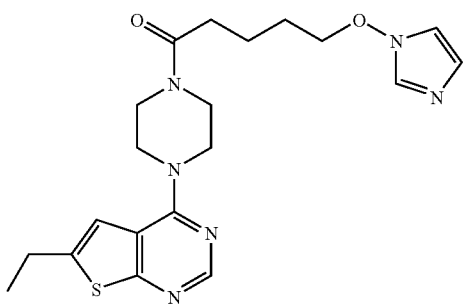

The title compound was obtained as a TFA salt by essentially following Example 5 except that 5-(imidazol-1-yloxy)-pentanoic acid was used in place of 3,3,3-trifluoropropionic acid and DCM in place of DMF in Step 2. ES-MS: (M+H)$^+$ 415

Example 420

1-[4-(6-Ethyl-thieno[2,3-d]pyrimidin-4-yl)-piperazin-1-yl]-8-imidazol-1-yl-octan-1-one

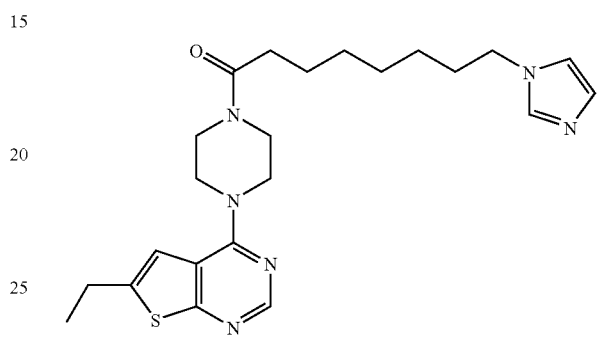

The title compound was obtained as a TFA salt by essentially following Example 5 except that 8-imidazol-1-yl-octanoic acid was used in place of 3,3,3-trifluoropropionic acid and DCM in place of DMF in Step 2. ES-MS: (M+H)$^+$ 441

Example 421

5-[4-(6-Ethyl-thieno[2,3-d]pyrimidin-4-yl)-piperazin-1-yl]-5-oxo-pentanoic acid (4-phenyl-thiazol-2-yl)-amide

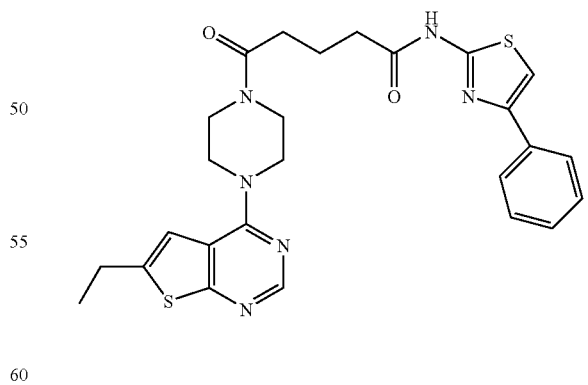

The title compound was obtained as a TFA salt by essentially following Example 5 except that 4-(4-phenyl-thiazol-2-ylcarbamoyl)-butyric acid was used in place of 3,3,3-trifluoropropionic acid and MeCN in place of DMF in Step 2. ES-MS: (M+H)$^+$ 521

Example 422

5-[4-(6-Ethyl-thieno[2,3-d]pyrimidin-4-yl)-piper-azin-1-yl]-5-oxo-pentanoic acid thiazol-2-ylamide

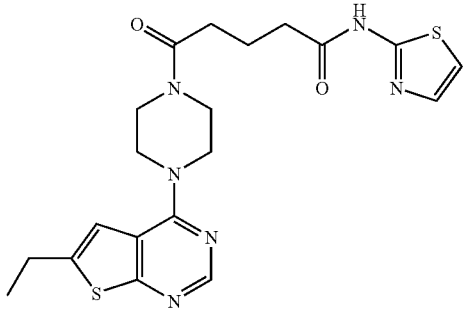

The title compound was obtained as a TFA salt by essentially following Example 5 except that 4-(thiazol-2-ylcarbamoyl)-butyric acid was used in place of 3,3,3-trifluoropropionic acid and MeCN in place of DMF in Step 2. ES-MS: (M+H)$^+$ 445

Example 423

Pyridine-2-carboxylic acid {4-[4-(6-ethyl-thieno[2,3-d]pyrimidin-4-yl)-piperazin-1-yl]-4-oxo-butyl}-amide

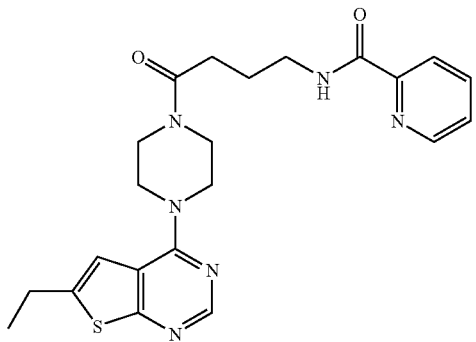

The title compound was obtained as a TFA salt by essentially following Example 5 except that 4-[(pyridine-2-carbonyl)-amino]-butyric acid was used in place of 3,3,3-trifluoropropionic acid and MeCN in place of DMF in Step 2. ES-MS: (M+H)$^+$ 439

Example 424

N-{4-[4-(6-Ethyl-thieno[2,3-d]pyrimidin-4-yl)-piperazin-1-yl]-4-oxo-butyl}-nicotinamide

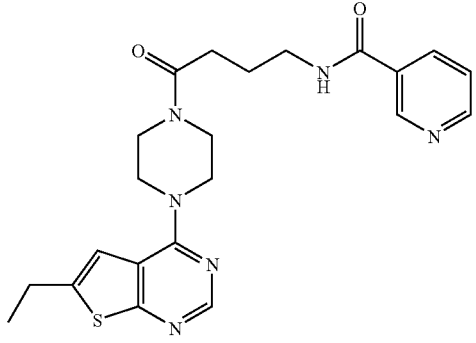

The title compound was obtained as a TFA salt by essentially following Example 5 except that 4-[(pyridine-3-carbonyl)-amino]-butyric acid was used in place of 3,3,3-trifluoropropionic acid and MeCN in place of DMF in Step 2. ES-MS: (M+H)$^+$ 439

Example 425

1-[4-(6-Ethyl-thieno[2,3-d]pyrimidin-4-yl)-piper-azin-1-yl]-5-pyridin-2-yl-pentane-1,5-dione

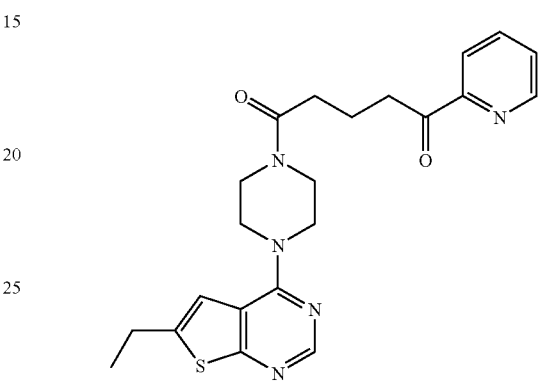

The title compound was obtained as a TFA salt by essentially following Example 5 except that 5-oxo-5-pyridin-2-yl-pentanoic acid was used in place of 3,3,3-trifluoropropionic acid and MeCN in place of DMF in Step 2. ES-MS: (M+H)$^+$ 424

Example 426

1-[4-(6-Ethyl-thieno[2,3-d]pyrimidin-4-yl)-piper-azin-1-yl]-5-pyridin-3-yl-pentane-1,5-dione

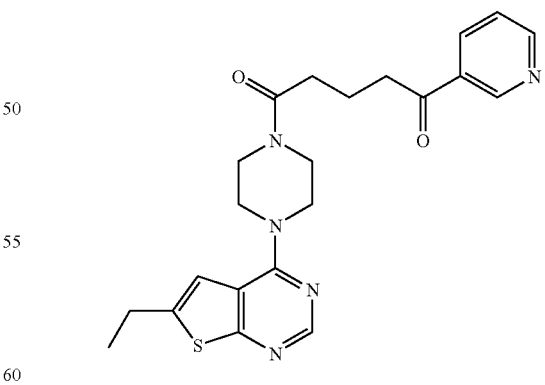

The title compound was obtained as a TFA salt by essentially following Example 5 except that 5-oxo-5-pyridin-3-yl-pentanoic acid was used in place of 3,3,3-trifluoropropionic acid and MeCN in place of DMF in Step 2. ES-MS: (M+H)$^+$ 424

Example 427

1-[4-(6-Ethyl-thieno[2,3-d]pyrimidin-4-yl)-piperazin-1-yl]-5-pyridin-4-yl-pentane-1,5-dione

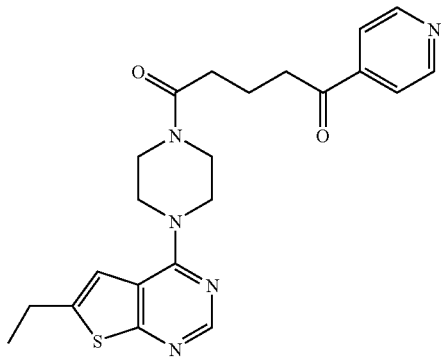

The title compound was obtained as a TFA salt by essentially following Example 5 except that 5-oxo-5-pyridin-4-yl-pentanoic acid was used in place of 3,3,3-trifluoropropionic acid and MeCN in place of DMF in Step 2. ES-MS: (M+H)+ 424

Example 428

1-[4-(6-Ethyl-thieno[2,3-d]pyrimidin-4-yl)-piperazin-1-yl]-4-(3-nitro-pyridin-2-ylamino)-butan-1-one

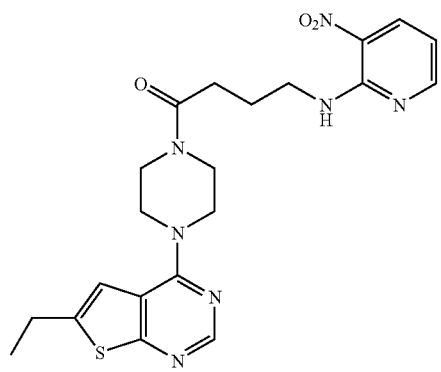

The title compound was obtained as a TFA salt by essentially following Example 5 except that 4-(3-nitro-pyridin-2-ylamino)-butyric acid was used in place of 3,3,3-trifluoropropionic acid and MeCN in place of DMF in Step 2. ES-MS: (M+H)+ 456

Example 429

1-[4-(6-Ethyl-thieno[2,3-d]pyrimidin-4-yl)-piperazin-1-yl]-4-(1-phenyl-1H-imidazol-2-ylsulfanyl)-butan-1-one

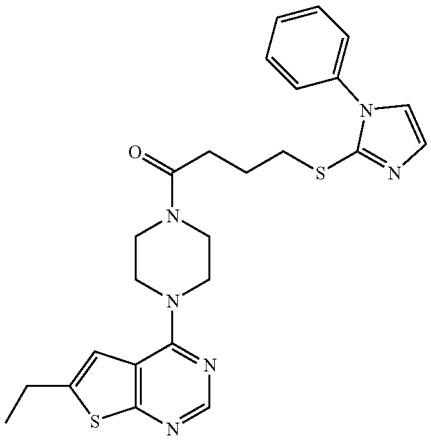

The title compound was obtained as a TFA salt by essentially following Example 5 except that 4-(1-phenyl-1H-imidazol-2-ylsulfanyl)-butyric acid was used in place of 3,3,3-trifluoropropionic acid and MeCN in place of DMF in Step 2. ES-MS: (M+H)+ 493

Example 430

1-[4-(6-Ethyl-thieno[2,3-d]pyrimidin-4-yl)-piperazin-1-yl]-4-(pyrimidin-2-ylamino)-butan-1-one Step 1:

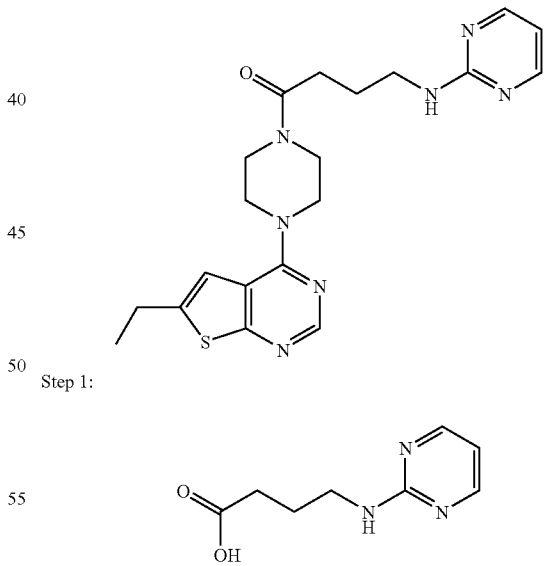

The target acid was obtained by essentially following Step 2 of Example 4 utilizing 4-(pyrimidin-2-ylamino)-butyric acid methyl ester. ES-MS: (M+H)+ 182

Step 2. The title compound was obtained as a TFA salt by essentially following Example 5 except that 4-(pyrimidin-2-ylamino)-butyric acid obtained in Step 1 of this example was used in place of 3,3,3-trifluoropropionic acid and MeCN in place of DMF in Step 2. ES-MS: (M+H)+ 412

Example 431

4-{2-[4-(6-Ethyl-thieno[2,3-d]pyrimidin-4-yl)-piperazin-1-yl]-2-oxo-1-phenyl-ethyl}-piperazine-1-carboxylic acid tert-butyl ester

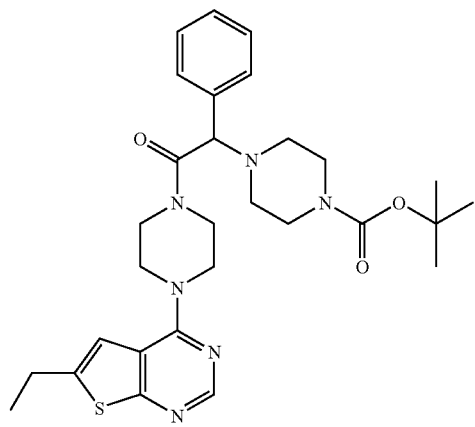

The title compound was obtained as a TFA salt by essentially following Example 5 except that 4-(carboxyphenyl-methyl)-piperazine-1-carboxylic acid tert-butyl ester was used in place of 3,3,3-trifluoropropionic acid and MeCN in place of DMF in Step 2. ES-MS: (M+H)$^+$ 551

Example 432

1-[4-(6-Ethyl-thieno[2,3-d]pyrimidin-4-yl)-piperazin-1-yl]-2-phenyl-2-piperazin-1-yl-ethanone

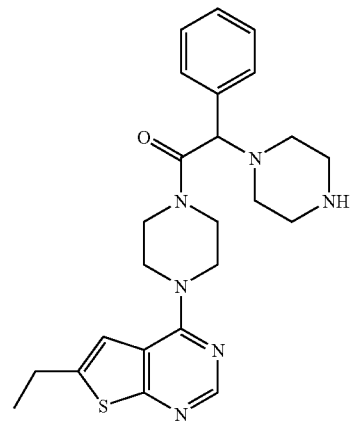

The title compound was obtained from 431 as a TFA salt by essentially following Step 1 of Example 2 and then purification using preparative RP-HPLC. ES-MS: (M+H)$^+$ 451

Example 433

3-[4-(6-Ethyl-thieno[2,3-d]pyrimidin-4-yl)-piperazine-1-carbonyl]-4-phenyl-pyrrolidine-1-carboxylic acid tert-butyl ester

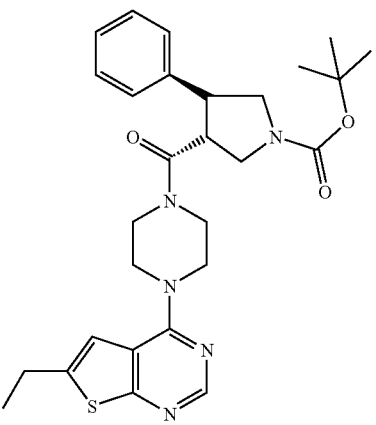

The title compound was obtained as a TFA salt by essentially following Example 5 except that 4-phenyl-pyrrolidine-1,3-dicarboxylic acid 1-tert-butyl ester was used in place of 3,3,3-trifluoropropionic acid and MeCN in place of DMF in Step 2. ES-MS: (M+H)$^+$ 522

Example 434

[4-(6-Ethyl-thieno[2,3-d]pyrimidin-4-yl)-piperazin-1-yl]-(4-phenyl-pyrrolidin-3-yl)-methanone

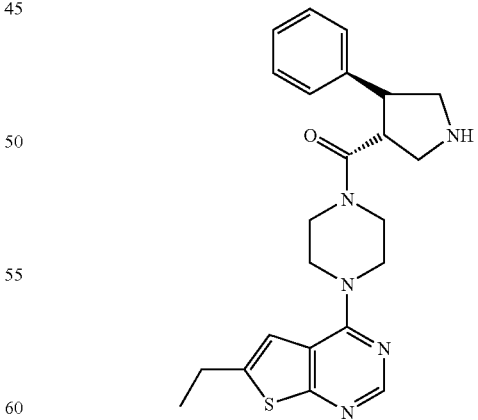

The title compound was obtained from 433 as a TFA salt by essentially following Step 1 of Example 2 and then purification using preparative RP-HPLC. ES-MS: (M+H)$^+$ 422

Example 435

[4-(6-Ethyl-thieno[2,3-d]pyrimidin-4-yl)-piperazin-1-yl]-(4-phenoxy-phenyl)-methanone

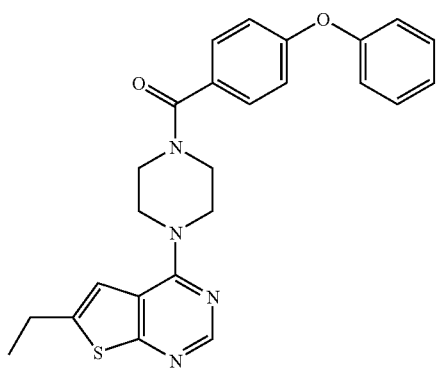

The title compound was obtained as a TFA salt by essentially following Example 5 except that 4-phenoxy-benzoic acid was used in place of 3,3,3-trifluoropropionic acid and MeCN in place of DMF in Step 2. ES-MS: (M+H)+ 445

Example 436

5-[4-(6-Ethyl-thieno[2,3-d]pyrimidin-4-yl)-piperazin-1-yl]-5-oxo-pentanoic acid (5-methyl-isoxazol-3-yl)-amide

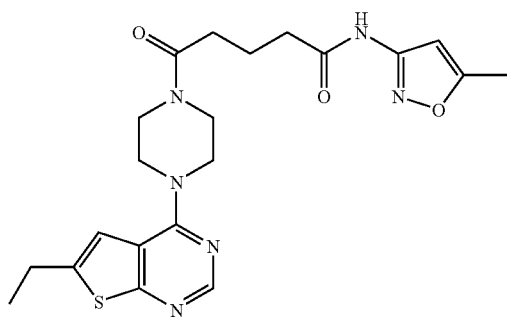

The title compound was obtained as a TFA salt by essentially following Example 5 except that 4-(5-methyl-isoxazol-3-ylcarbamoyl)-butyric acid was used in place of 3,3,3-trifluoropropionic acid and MeCN in place of DMF in Step 2. ES-MS: (M+H)+ 443

Example 437

[4-(6-Ethyl-thieno[2,3-d]pyrimidin-4-yl)-piperazin-1-yl]-(4-pyridin-4-yl-phenyl)-methanon

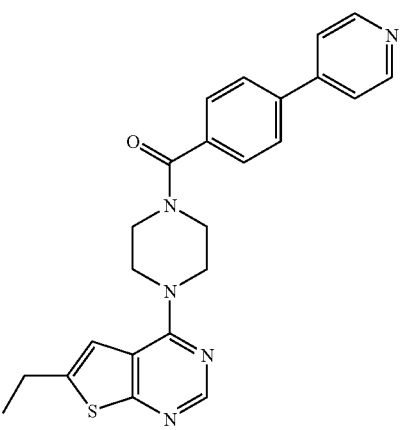

Step 1:

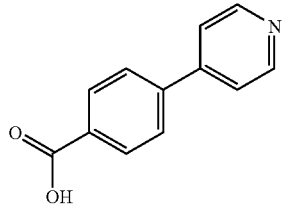

Concentrated $H_2SO_4$ (3.5 mL) was mixed with ice cold $H_2O$ (27 mL). Then 4-pyridin-4-yl-benzaldehyde (552 mg, 3 mmol) was dissolved in DCM (6 mL). The aldehyde solution was mixed with the $H_2SO_4$ at 0° C. and then $KMnO_4$ (480 mg, 3 mmol) was added slowly followed by vigorous stirring for 1.5 hrs. The solution was then lyophilized. After adding $H_2O$ (20 mL) and then 5 N NaOH (10 mL) to the residue, the solution was washed with DCM (20 mL). After addition of more 5 N NaOH (5 mL), a small amount of precipitate formed that was filtered and characterized as the desired acid (50 mg). The majority of the acid remained in the aqueous filtrate. ES-MS: (M+H)+ 200

Step 2. The title compound was obtained as a TFA salt by essentially following Example 5 except that the acid obtained in Step 1 of this example was used in place of 3,3,3-trifluoropropionic acid and MeCN in place of DMF in Step 2. ES-MS: (M+H)+ 430

Example 438

[4-(6-Ethyl-thieno[2,3-d]pyrimidin-4-yl)-piperazin-1-yl]-(4-pyridin-3-yl-phenyl)-methanon Step 1:

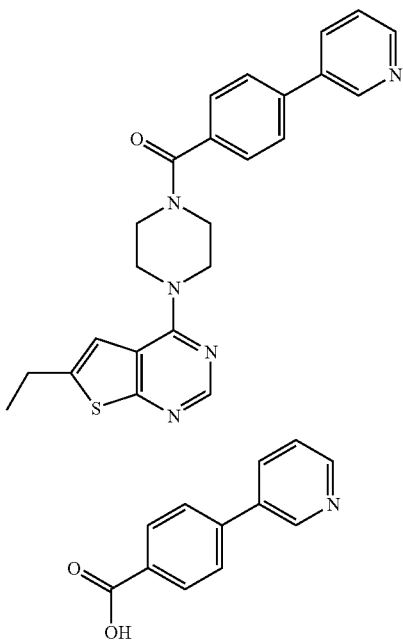

The target acid was obtained (50 mg) by essentially following Step 1 of Example 437 using 4-pyridin-3-yl-benzaldehyde in place of 4-pyridin-4-yl-benzaldehyde. ES-MS: (M+H)$^+$200

Step 2: The title compound was obtained as a TFA salt by essentially following Example 5 except that the acid obtained in Step 1 of this example was used in place of 3,3,3-trifluoropropionic acid and MeCN in place of DMF in Step 2. ES-MS: (M+H)$^+$ 430

Example 439

[4-(6-Ethyl-thieno[2,3-d]pyrimidin-4-yl)-piperazin-1-yl]-(4-pyridin-2-yl-phenyl)-methanon Step 1:

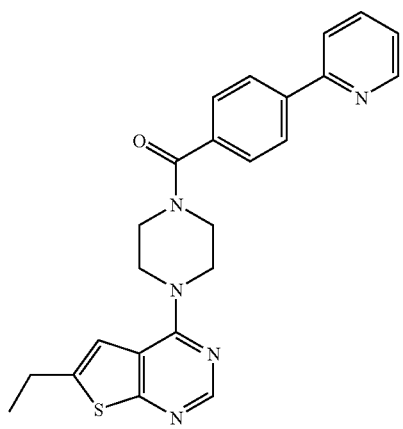

-continued

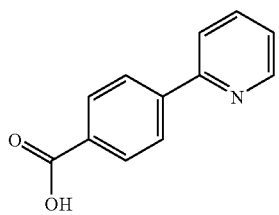

The target acid was obtained (50 mg) by essentially following Step 1 of Example 437 using 4-pyridin-2-yl-benzaldehyde in place of 4-pyridin-4-yl-benzaldehyde. ES-MS: (M+H)$^+$200

Step) 2. The title compound was obtained as a TFA salt by essentially following Example 5 except that the acid obtained in Step 1 of this example was used in place of 3,3,3-trifluoropropionic acid and MeCN in place of DMF in Step 2. ES-MS: (M+H)$^+$ 430

Example 440

1-[4-(6-Ethyl-thieno[2,3-d]pyrimidin-4-yl)-piperazin-1-yl]-5-tetrazol-1-yl-pentan-1-one

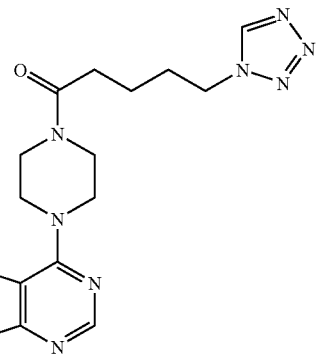

Treatment of the material from Example 5, Step 1 (46 mg, 0.14 mmol) with DIEA (0.25 mL) and then 5-bromovaleryl chloride (285 mg, 0.14 mmol) in DMF (1.5 mL) at rt for ½ hr provided the intermediate bromide. To this solution was then added 1H-tetrazole (15 mg, 0.21 mmol) followed by Cs$_2$CO$_3$ (46 mg) and then stirring over night. The resulting solution contained 2 isomers which were separated via prep RP-HPLC to afford the title compound (10 mg) as a TFA salt. ES-MS: (M+H)$^+$ 401

Example 441

1-[4-(6-Ethyl-thieno[2,3-d]pyrimidin-4-yl)-piperazin-1-yl]-5-tetrazol-2-yl-pentan-1-one

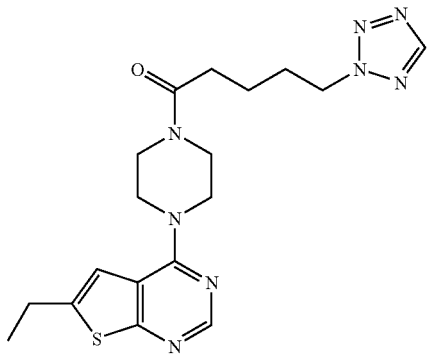

The title compound was obtained (12 mg) as a TFA salt by prep RP-HPLC from the mixture of 2 isomers from Example 440. ES-MS: (M+H)+ 401

Example 442

5-Bromo-1-[4-(6-ethyl-thieno[2,3-d]pyrimidin-4-yl)-piperazin-1-yl]-pentan-1-one

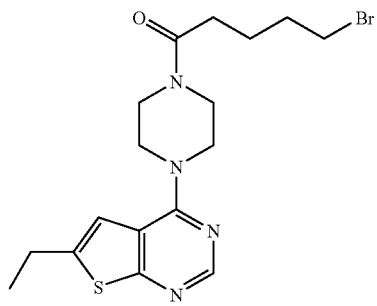

The title compound was obtained by essentially following Example 3 beginning with the material from Example 5, Step 1 (733 mg, 2.28 mmol) and 5-bromovaleryl chloride (455 mg) in place of phenylacetyl chloride. When the reaction was complete, brine was carefully added and the DCM washes (3×5 mL) were dried with MgSO4, filtered and stripped in vacuo to afford the desired bromide (0.9 gm). ES-MS: (M+H)+ 410/412

Example 443

1-[4-(6-Ethyl-thieno[2,3-d]pyrimidin-4-yl)-piperazin-1-yl]-5-[1,2,4]triazol-1-yl-pentan-1-one

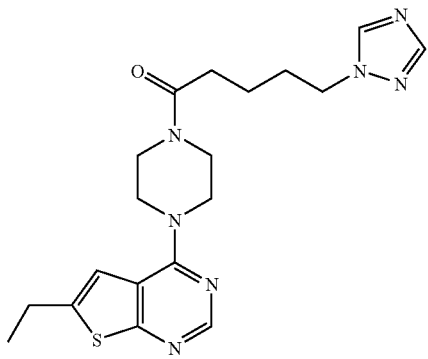

Compound 442 (88 mg, 0214 mmol) in DMF (2 mL) was treated with DIEA (0.3 mL) followed by 1,2,4-triazole (23 mg, 0.32 mmol) and then Cs2CO3 (76 mg) at rt. After stirring over night, the resulting solution was diluted with H2O and then purified via prep RP-HPLC to afford the title compound (33 mg) as a TFA salt. ES-MS: (M+H)+ 400

Example 444

1-[4-(6-Ethyl-thieno[2,3-d]pyrimidin-4-yl)-piperazin-1-yl]-5-[1,2,3]triazol-1-yl-pentan-1-one

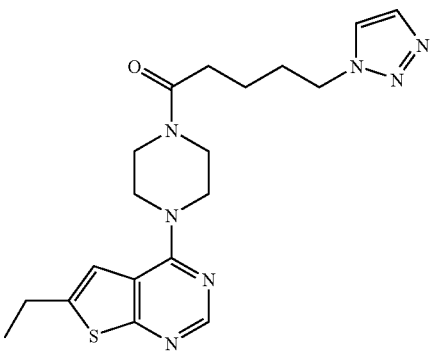

The title compound was obtained as a TFA salt by essentially following Example 443 except that 1,2,3-triazole was used instead of 1,2,4-triazole. ES-MS: (M+H)+ 400

Example 445

5-[4-(6-Ethyl-thieno[2,3-d]pyrimidin-4-yl)-piperazin-1-yl]-5-oxo-pentanoic acid (2-methyl-2H-pyrazol-3-yl)-amide

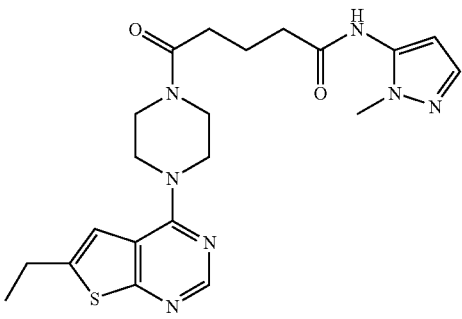

The title compound was obtained as a TFA salt by essentially following Example 5 except that 4-(2-methyl-2H-pyrazol-3-ylcarbamoyl)-butyric acid was used in place of 3,3,3-trifluoropropionic acid and MeCN in place of DMF in Step 2. ES-MS: (M+H)+ 442

Example 446

[4-(6-Ethyl-thieno[2,3-d]pyrimidin-4-yl)-piperazin-1-yl]-(1H-pyrrol-2-yl)-methanone

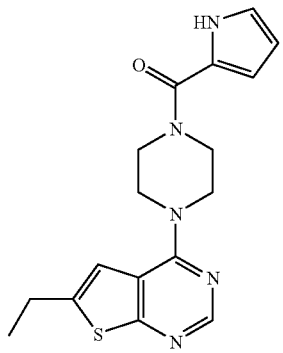

The title compound was obtained as a TFA salt by essentially following Example 5 except that 1H-pyrrole-2-carboxylic acid was used in place of 3,3,3-trifluoropropionic acid and MeCN in place of DMF in Step 2. ES-MS: (M+H)+ 342

Example 447

[4-(6-Ethyl-thieno[2,3-d]pyrimidin-4-yl)-piperazin 1-yl]-(1-methyl-1H-pyrrol-2-yl)-methanone

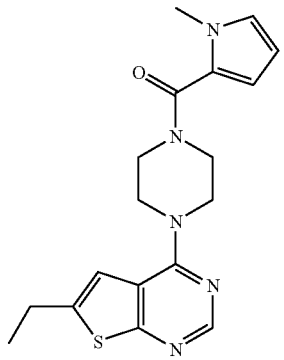

The title compound was obtained as a TFA salt by essentially following Example 5 except that 1-methyl-1H-pyrrole-2-carboxylic acid was used in place of 3,3,3-trifluoropropionic acid and MeCN in place of DMF in Step 2. ES-MS: (M+H)+ 356

Example 448

[4-(6-Ethyl-thieno[2,3-d]pyrimidin-4-yl)-piperazin-1-yl]-(1H-indol-3-yl)-methanone

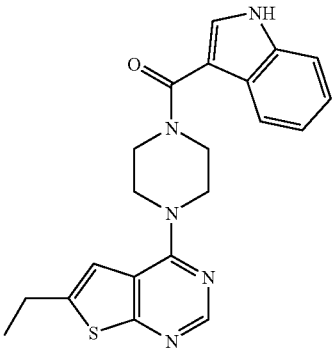

The title compound was obtained as a TFA salt by essentially following Example 5 except that 1H-indole-3-carboxylic acid was used in place of 3,3,3-trifluoropropionic acid and MeCN in place of DMF in Step 2. ES-MS: (M+H)+ 392

Example 449

[4-(6-Ethyl-thieno[2,3-d]pyrimidin-4-yl)-piperazin-1-yl]-thiophen-3-yl-methanone

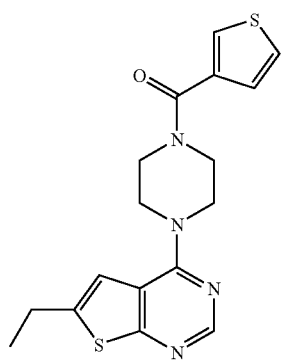

The title compound was obtained as a TFA salt by essentially following Example 5 except that thiophene-3-carboxylic acid was used in place of 3,3,3-trifluoropropionic acid and MeCN in place of DMF in Step 2. ES-MS: (M+H)+ 359

Example 450

[4-(6-Ethyl-thieno[2,3-d]pyrimidin-4-yl)-piperazin-1-yl]-pyrazin-2-yl-methanone

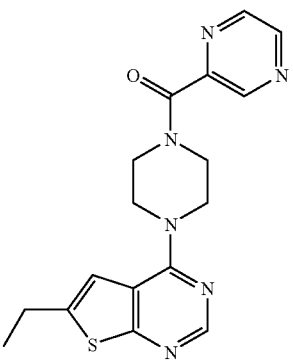

The title compound was obtained as a TFA salt by essentially following Example 5 except that pyrazine-2-carboxylic acid was used in place of 3,3,3-trifluoropropionic acid and MeCN in place of DMF in Step 2. ES-MS: (M+H)+ 355

Example 451

4-(3-Amino-pyridin-2-ylamino)-1-[4-(6-ethyl-thieno[2,3-d]pyrimidin-4-yl)-piperazin-1-yl]-butan-1-one

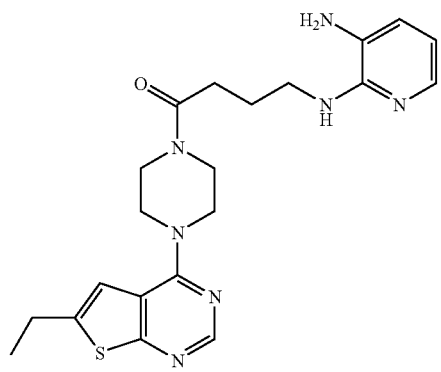

Compound 428 (20 mg, 0.044 mol) was mixed with SnCl$_2$—H$_2$O (60 mg, 0.27 mmol) in EtOH (2 mL) at rt. After 2 hr, EtOH (20 mL) was added and the yellow precipitate was filtered. The solvent was removed in vacuo, and the residue was purified via prep RP-HPLC to afford the desired amino compound. ES-MS: (M+H)$^+$ 426

Example 452

[4-(6-Ethyl-thieno[2,3-d]pyrimidin-4-yl)-piperazin-1-yl]-(2-phenyl-quinolin-4-yl)-methano

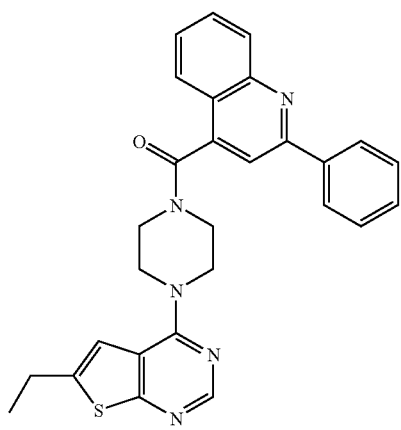

The title compound was obtained as a TFA salt by essentially following Example 5 except that 2-phenyl-quinoline-4-carboxylic acid was used in place of 3,3,3-trifluoropropionic acid and MeCN in place of DMF in Step 2. ES-MS: (M+H)$^+$ 480

Example 453

[4-(6-Ethyl-thieno[2,3-d]pyrimidin-4-yl)-piperazin-1-yl]-quinolin-2-yl-methanone

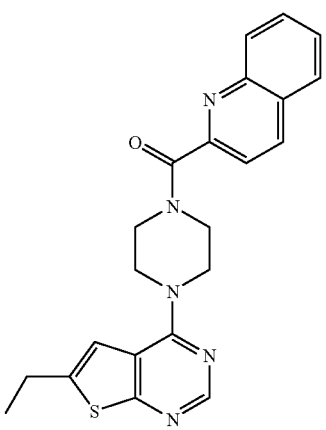

The title compound was obtained as a TFA salt by essentially following Example 5 except that quinoline-2-carboxylic acid was used in place of 3,3,3-trifluoropropionic acid and MeCN in place of DMF in Step 2. ES-MS: (M+H)$^+$ 404

Example 454

[4-(6-Ethyl-thieno[2,3-d]pyrimidin-4-yl)-piperazin-1-yl]-quinolin-3-yl-methanone

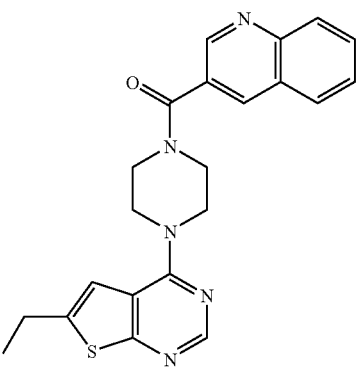

The title compound was obtained as a TFA salt by essentially following Example 5 except that quinoline-3-carboxylic acid was used in place of 3,3,3-trifluoropropionic acid and MeCN in place of DMF in Step 2. ES-MS: (M+H)$^+$ 404

Example 455

[4-(6-Ethyl-thieno[2,3-d]pyrimidin-4-yl)-piperazin-1-yl]-quinolin-4-yl-methanone

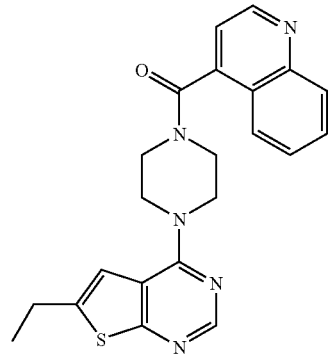

The title compound was obtained as a TFA salt by essentially following Example 5 except that quinoline-4-carboxylic acid was used in place of 3,3,3-trifluoropropionic acid and MeCN in place of DMF in Step 2. ES-MS: (M+H)+ 404

Example 456

[4-(6-Ethyl-thieno[2,3-d]pyrimidin-4-yl)-piperazin-1-yl]-quinoxalin-2-yl-methanone

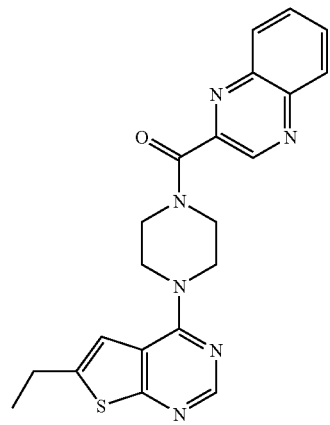

The title compound was obtained as a TFA salt by essentially following Example 5 except that quinoxaline-2-carboxylic acid was used in place of 3,3,3-trifluoropropionic acid and MeCN in place of DMF in Step 2. ES-MS: (M+H)+ 405

Example 457

[4-(6-Ethyl-thieno[2,3-d]pyrimidin-4-yl)-piperazin-1-yl]-isoquinolin-1-yl-methanone

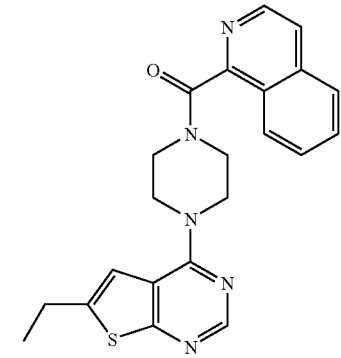

The title compound was obtained as a TFA salt by essentially following Example 5 except that isoquinoline-1-carboxylic acid was used in place of 3,3,3-trifluoropropionic acid and MeCN in place of DMF in Step 2. ES-MS: (M+H)+ 404

Example 458

[4-(6-Ethyl-thieno[2,3-(1]pyrimidin-4-yl)-piperazin-1-yl]-isoquinolin-3-yl-methanone

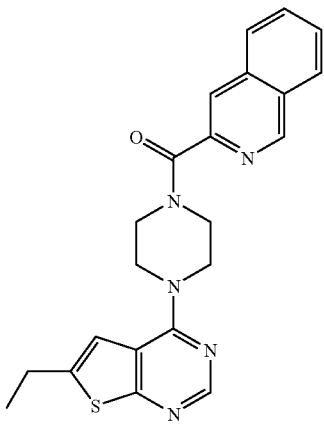

The title compound was obtained as a TFA salt by essentially following Example 5 except that isoquinoline-3-carboxylic acid was used in place of 3,3,3-trifluoropropionic acid and MeCN in place of DMF in Step 2. ES-MS: (M+H)+ 404

Example 459

Cinnolin-4-yl-[4-(6-ethyl-thieno[2,3-d]pyrimidin-4-yl)-piperazin-1-yl]-methanone

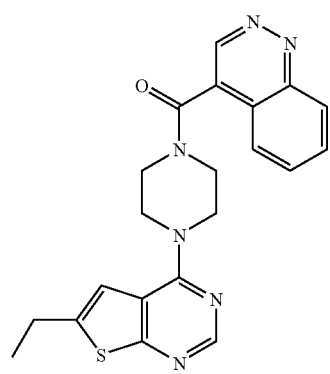

The title compound was obtained as a TFA salt by essentially following Example 5 except that cinnoline-4-carboxylic acid was used in place of 3,3,3-trifluoropropionic acid and MeCN in place of DMF in Step 2. ES-MS: (M+H)+ 405

Example 460

(2,3-Dihydro-1H-indol-2-y)-[4-(6-ethyl-thieno[2,3-d]pyrimidin-4-yl)-piperazin-1-yl]-methanone

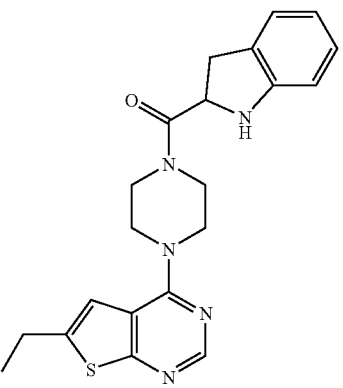

The title compound was obtained as a TFA salt by essentially following Example 5 except that 2,3-dihydro-1H-indole-2-carboxylic acid was used in place of 3,3,3-trifluoropropionic acid and MeCN in place of DMF in Step 2. ES-MS: (M+H)+ 394

Example 461

[4-(6-Ethyl-thieno[2,3-d]pyrimidin-4-yl)-piperazin-1-yl]-(1H-pyrazol-4-yl)-methanone

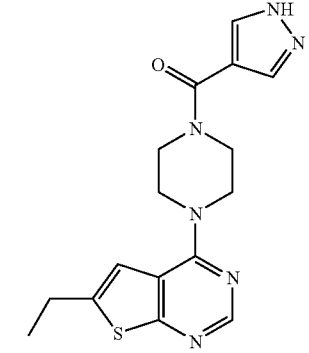

The title compound was obtained as a TFA salt by essentially following Example 5 except that 1H-pyrazole-4-carboxylic acid was used in place of 3,3,3-trifluoropropionic acid and MeCN in place of DMF in Step 2. ES-MS: (M+H)+ 343

Example 462

3-[4-(6-Ethyl-thieno[2,3-d]pyrimidin-4-yl)-piperazine-1-carbonyl]-benzonitrile

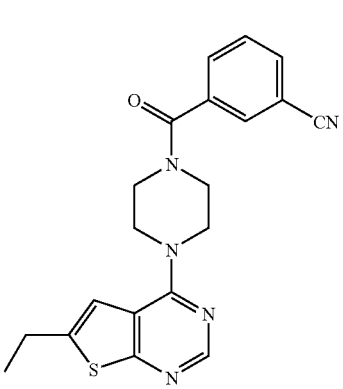

The title compound was obtained as a TFA salt by essentially following Example 3 beginning with the material from Example 5, Step 1 and 3-cyano-benzoyl chloride was used in place of phenylacetyl chloride. ES-MS: (M+H)+ 378

Example 463

4-[4-(6-Ethyl-thieno[2,3-d]pyrimidin-4-yl)-piperazine-1-carbonyl]-benzonitrile

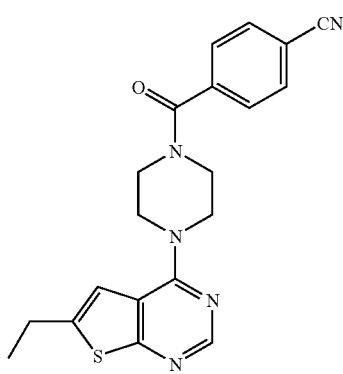

The title compound was obtained as a TFA salt by essentially following Example 3 beginning with the material from Example 5, Step 1 and 4-cyano-benzoyl chloride was used in place of phenylacetyl chloride. ES-MS: (M+H)$^+$ 378

Example 464

2-[4-(6-Ethyl-thieno[2,3-d]pyrimidin-4-yl)-piperazine-1-carbonyl]-benzonitrile

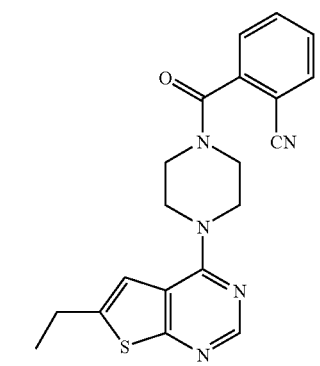

The title compound was obtained as a TFA salt by essentially following Example 5 except that 2-cyanobenzoic acid was used in place of 3,3,3-trifluoropropionic acid and MeCN in place of DMF in Step 2. ES-MS: (M+H)$^+$ 378

Example 465

[4-(6-Ethyl-thieno[2,3-d]pyrimidin-4-yl)-piperazin-1-yl]-(1H-indol-2-yl)-methanone

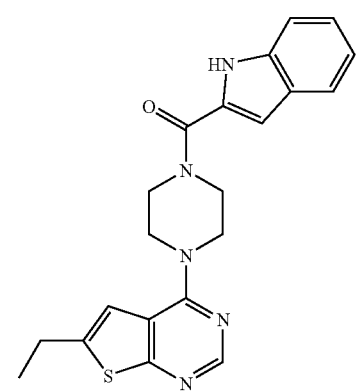

The title compound was obtained as a TFA salt by essentially following Example 5 except that 1H-indole-2-carboxylic acid was used in place of 3,3,3-trifluoropropionic acid and MeCN in place of DMF in Step 2. ES-MS: (M+H)$^+$ 392

Example 466

3-[4-(6-Ethyl-thieno[2,3-d]pyrimidin-4-yl)-piperazin-1-yl]-3-oxo-N-phenyl-propionamide

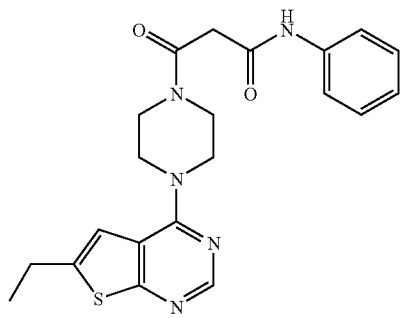

The title compound was obtained as a TFA salt by essentially following Example 5 except that N-phenyl-malonamic acid was used in place of 3,3,3-trifluoropropionic acid and MeCN in place of DMF in Step 2. ES-MS: (M+H)$^+$ 410

Example 467

N-Benzyl-3-[4-(6-ethyl-thieno[2,3-d]pyrimidin-4-yl)-piperazin-1-yl]-3-oxo-propionamide

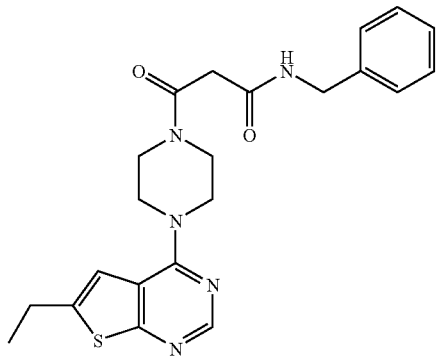

The title compound was obtained as a TFA salt by essentially following Example 5 except that N-benzyl-malonamic acid was used in place of 3,3,3-trifluoropropionic acid and MeCN in place of DMF in Step 2. ES-MS: (M+H)$^+$ 424

Example 468

1-[4-(6-Ethyl-thieno[2,3-d]pyrimidin-4-yl)-piperazin-1-yl]-2-thiophen-2-yl-ethanone

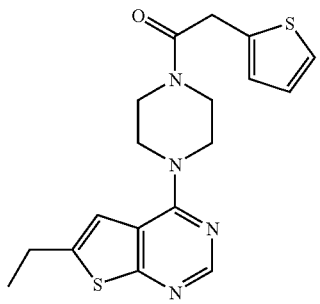

The title compound was obtained as a TFA salt by essentially following Example 3 beginning with the material from Example 5, Step 1 and thiophen-2-yl-acetyl chloride was used in place of phenylacetyl chloride. ES-MS: (M+H)$^+$ 373

Example 469

1-[4-(6-Ethyl-thieno[2,3-d]pyrimidin-4-yl)-piperazin-1-yl]-2-(1-methyl-1H-pyrrol-2-yl)-ethanone

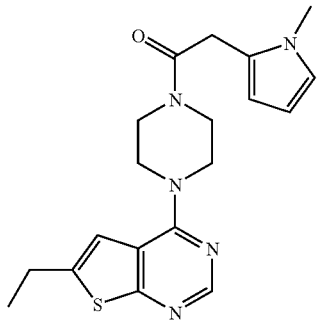

The title compound was obtained as a TFA salt by essentially following Example 5 except that (1-methyl-1H-pyrrol-2-yl)-acetic acid was used in place of 3,3,3-trifluoropropionic acid and MeCN in place of DMF in Step 2. ES-MS: (M+H)$^+$ 370

Example 470

[4-(6-Ethyl-thieno[2,3-d]pyrimidin-4-yl)-piperazin-1-yl]-(3-pyrazol-1-yl-phenyl)-methanon

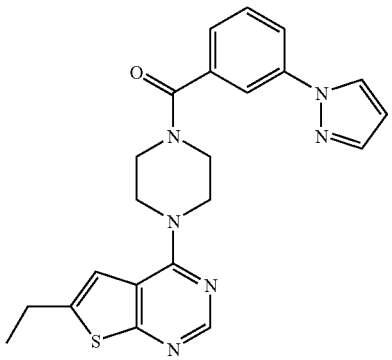

The title compound was obtained as a TFA salt by essentially following Example 5 except that 3-pyrazol-1-yl-benzoic acid was used in place of 3,3,3-trifluoropropionic acid and MeCN in place of DMF in Step 2. ES-MS: (M+H)$^+$ 419

Example 471

1-[4-(6-Ethyl-thieno[2,3-d]pyrimidin-4-yl)-piperazin-1-yl]-2-(5-methyl-1-phenyl-1H-pyrrol-2-yl)-ethanone

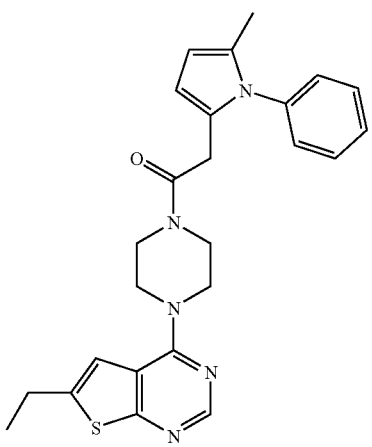

The title compound was obtained as a TFA salt by essentially following Example 5 except that (5-methyl-1-phenyl-1H-pyrrol-2-yl)-acetic acid was used in place of 3,3,3-trifluoropropionic acid and MeCN in place of DMF in Step 2. ES-MS: (M+H)$^+$ 446

Example 472

3-[4-(6-Ethyl-thieno[2,3-d]pyrimidin-4-yl)-piper-azin-1-yl]-3-oxo-N-pyridin-3-yl-propionamide Step 1:

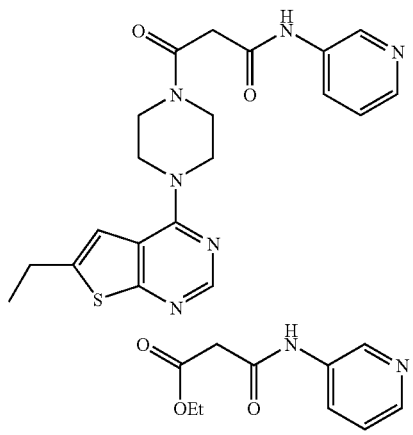

To 3-aminopyridine (95 mg, 1 mmol) in DCM (3 mL) at rt under argon was added ethylmalonyl chloride (0.128 mL) dropwise. After stirring over night, the solvent was evaporated and the residue was used in the next step without purification.

Step 2:

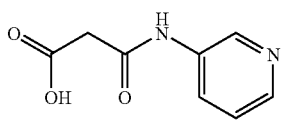

To the crude ester obtained in Step 1 was added EtOH (3 mL) and then 1N NaOH (2.5 mL). After stirring for 1.5 hrs, 1N HCl was added until the pH=1–2. The solution was washed with DCM (3×5 mL). The desired acid was still dissolved in the acidic aqueous layer, so it was lyophilized to afford the crude acid mixed with NaCl which was used in the next step without purification.

Step 3. The title compound was obtained (5.3 mg) as a TFA salt by essentially following Example 5 except that crude N-pyridin-3-yl-malonamic acid obtained in Step 2 of this example was used in place of 3,3,3-trifluoropropionic acid and MeCN in place of DMF in Step 2. ES-MS: (M+H)⁺ 411

Example 473

3-[4-(6-Ethyl-thieno[2,3-d]pyrimidin-4-yl)-piper-azin-1-yl]-N-methyl-3-oxo-propionamide Step 1:

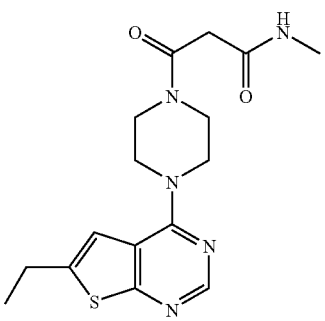

-continued

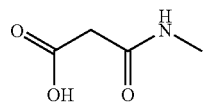

The target acid was obtained by essentially following Step 2 of Example 4 utilizing N-methyl-malonamic acid ethyl ester.

Step 2: The title compound was obtained as a TFA salt by essentially following Example 5 except that N-methyl-malonamic acid obtained in Step 1 of this example was used in place of 3,3,3-trifluoropropionic acid and MeCN in place of DMF in Step 2. ES-MS: (M+H)⁺ 362

Example 474

3-[4-(6-Ethyl-thieno[2,3-d]pyrimidin-4-yl)-pipera-zine-1-carbonyl]-piperidin-2-one Step 1:

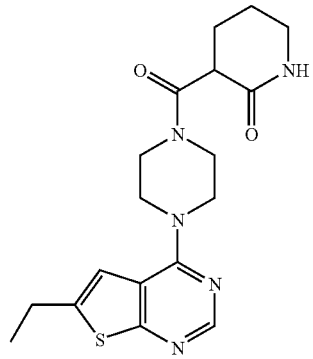

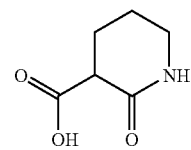

The target acid was obtained by essentially following Step 2 of Example 4 utilizing 2-oxo-piperidine-3-carboxylic acid ethyl ester.

Step 2. The title compound was obtained as a TFA salt by essentially following Example 5 except that 2-oxo-piperi-dine-3-carboxylic acid obtained in Step 1 of this example was used in place of 3,3,3-trifluoropropionic acid and MeCN in place of DMF in Step 2. ES-MS: (M+H)⁺ 374

Example 475

3-[4-(6-Ethyl-thieno[2,3-c]pyrimidin-4-yl)-piperazine-1-carbonyl]-4-phenyl-pyrrolidin-2-one

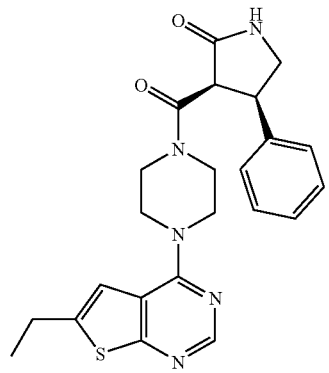

The title compound was obtained as a TFA salt by essentially following Example 5 except that 2-oxo-4-phenyl-pyrrolidine-3-carboxylic acid was used in place of 3,3,3-trifluoropropionic acid and MeCN in place of DMF in Step 2. Two diastereomers (see Example 476) were isolated from this reaction. The stereochemistry shown for both isomers has not been exactly determined. It is shown for illustrative purposes only. ES-MS: (M+H)$^+$436

Example 476

3-[4-(6-Ethyl-thieno[2,3-d]pyrimidin-4-yl)-piperazine-1-carbonyl]-4-phenyl-pyrrolidin-2-one

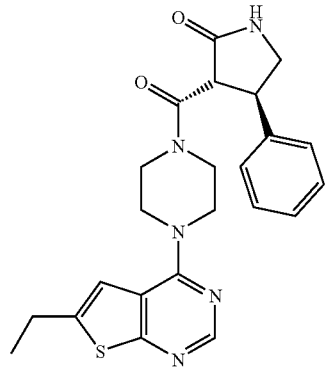

The title compound was obtained as a TFA salt by essentially following Example 5 except that 2-oxo-4-phenyl-pyrrolidine-3-carboxylic acid was used in place of 3,3,3-trifluoropropionic acid and MeCN in place of DMF in Step 2. Two diastereomers (see Example 475) were isolated from this reaction. The stereochemistry shown for both isomers has not been exactly determined. It is shown for illustrative purposes only. ES-MS: (M+H)$^+$436

Example 477

2-Benzenesulfonyl-1-[4-(6-ethyl-thieno[2,3-d]pyrimidin-4-yl)-piperazin-1-yl]-ethanone

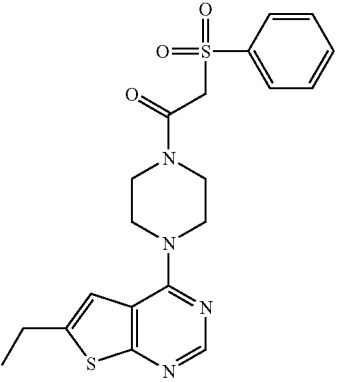

The title compound was obtained as a TFA salt by essentially following Example 5 except that benzenesulfonyl-acetic acid was used in place of 3,3,3-trifluoropropionic acid and MeCN in place of DMF in Step 2. ES-MS: (M+H)$^+$ 431

Example 478

1-[4-(6-Ethyl-thieno[2,3-d]pyrimidin-4-yl)-piperazin-1-yl]-2-methanesulfonyl-ethanone

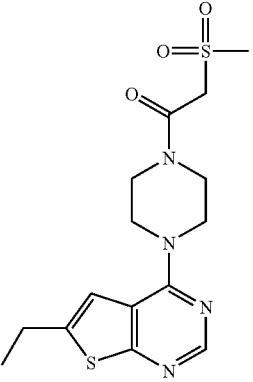

The title compound was obtained as a TFA salt by essentially following Example 5 except that methanesulfonyl-acetic acid was used in place of 3,3,3-trifluoropropionic acid and MeCN in place of DMF in Step 2. ES-MS: (M+H)$^+$ 369

Example 479

1-[4-(6-Ethyl-thieno[2,3-d]pyrimidin-4-yl)-piperazin-1-yl]-2-(3-methyl-isoxazol-5-yl)-ethanone

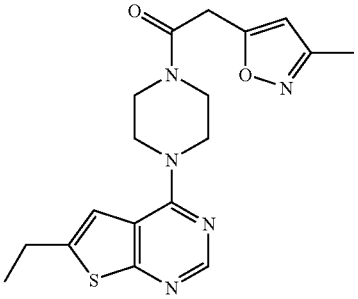

The title compound was obtained as a TFA salt by essentially following Example 5 except that (3-methylisoxazol-5-yl)-acetic acid was used in place of 3,3,3-trifluoropropionic acid and MeCN in place of DMF in Step 2. ES-MS: (M+H)+ 372

Example 480

N-Benzotriazol-1-yl-3-[4-(6-ethyl-thieno[2,3-d]pyrimidin-4-yl)-piperazin-1-yl]-3-oxo-propionamide Step 1:

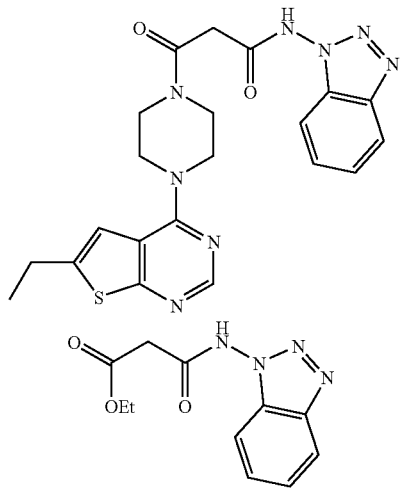

To 1-aminobenzotriazole (134 mg, 1 mmol) in DCM (4 mL) at rt under argon was added ethylmalonyl chloride (0.128 mL, 1 mmol) dropwise. After stirring ½ hr, more ethylmalonyl chloride (0.03 mL) was added. After another ½ hr, the precipitate that formed on initial addition of the ethylmalonyl chloride was filtered and the filtrate was evaporated and the residue was used in the next step without purification.

Step 1:

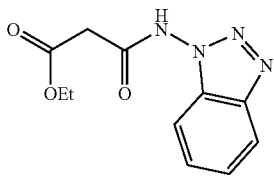

To the crude ester obtained in Step 1 was added EtOH (5 mL) and then 1N NaOH (4 mL). After stirring over night, 1 N HCl was added until the pH=1–2. The solution was washed with DCM (3×5 mL). The organic washes were dried, filtered and evaporated to afford the crude acid which was used in the next step without purification. ES-MS: (M+H)+206

Step 3: The title compound was obtained (13 mg) as a TFA salt by essentially following Example 5 except that crude N-benzotriazol-1-yl-malonamic acid obtained in Step 2 of this example was used in place of 3,3,3-trifluoropropionic acid and MeCN in place of DMF in Step 2. ES-MS: (M+H)+ 451

Example 481

Biphenyl-3-yl-[4-(6-ethyl-thieno[2,3-d]pyrimidin-4-yl)-piperazin-1-yl]-methanone

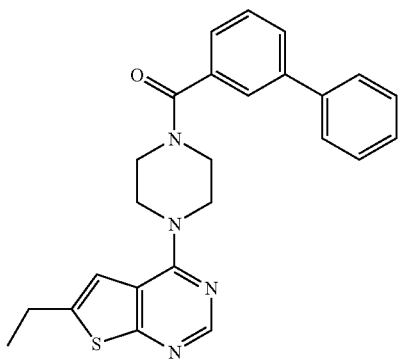

The title compound was obtained as a TFA salt by essentially following Example 5 except that biphenyl-3-carboxylic acid was used in place of 3,3,3-trifluoropropionic acid and MeCN in place of DMF in Step 2. ES-MS: (M+H)+ 429

Example 482

(1-Benzyl-1H-imidazol-4-yl)-[4-(6-ethyl-thieno[2,3-d]pyrimidin-4-yl)-piperazin-1-yl]-methanone

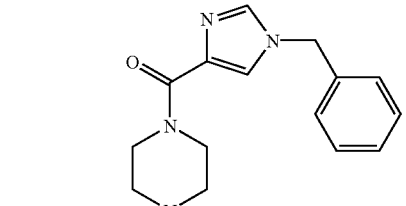

Step 1:

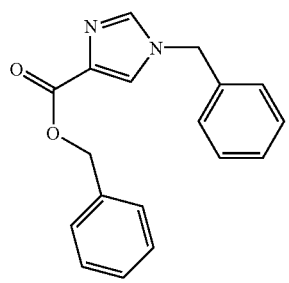

To 4-imidazolecarboxylic acid (200 mg, 1.8 mmol) in MeCN (10 mL) at rt under argon was added benzyl bromide (0.47 mL, 4 mmol) dropwise followed by Cs2CO3 (1.45 gm, 4.5 mmol). After stirring 2 days, the crude mixture was purified on prep RP-HPLC to give a 57% yield of the desired ester. ES-MS: (M+H)+ 293

Step 2:

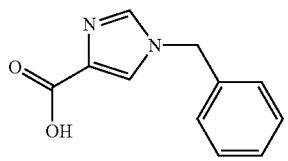

To the ester (88 mg) obtained in Step 1 was added dioxane (1.5 mL) and then 1N NaOH (1.5 mL). After stirring 2 hr, 1 N HCl was added until the pH=1–2. The solution was washed with DCM (3×5 mL). The desired acid was still dissolved in the aqueous layer, so it was lyophilized to afford the crude acid which was used in the next step without purification.

Step 3: The title compound was obtained as a TFA salt by essentially following Example 5 except that the acid obtained in Step 2 of this example was used in place of 3,3,3-trifluoropropionic acid and MeCN in place of DMF in Step 2. ES-MS: (M+H)$^+$ 433

Example 483

1-[4-(6-Ethyl-thieno[2,3-d]pyrimidin-4-yl)-piperazin-1-yl]-2-(3-pyrazol-1-yl-phenyl)-ethanone

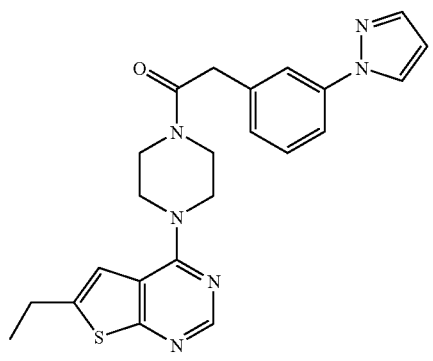

Step 1:

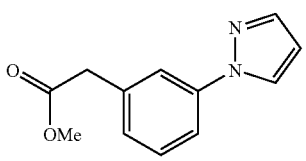

To methyl 3-iodophenylacetate (192 mg, 0.70 mmol) in dry dioxane (2 mL) at rt under argon was added pyrazole (57 mg, 0.84 mmol), CuI (3 mg), trans-1,2-diamino-cyclohexane (8 mg) and K$_2$CO$_3$ (192 mg, 1.4 mmol). The mixture was warmed to 80° C. and stirred for 4 days. The crude mixture was purified via prep RP-HPLC to give the desired ester. ES-MS: (M+H)$^+$ 293

Step 2:

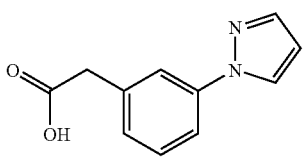

To the ester (88 mg) obtained in Step 1 was added dioxane (1.5 mL) and then 1N NaOH (1.5 mL). After stirring 2 hr, 1 N HCl was added until the pH=1–2. The solution was washed with DCM (3×5 mL). The desired acid was still dissolved in the aqueous layer, so it was lyophilized to afford the crude acid which was used in the next step without purification.

Step 3: The title compound was obtained as a TFA salt by essentially following Example 5 except that the acid obtained in Step 2 of this example was used in place of 3,3,3-trifluoropropionic acid and MeCN in place of DMF in Step 2. ES-MS: (M+H)$^+$ 433

Example 484

[4-(6-Ethyl-thieno[2,3-c]pyrimidin-4-yl)-piperazin-1-yl]-(3-tetrazol-1-yl-phenyl)-methanone

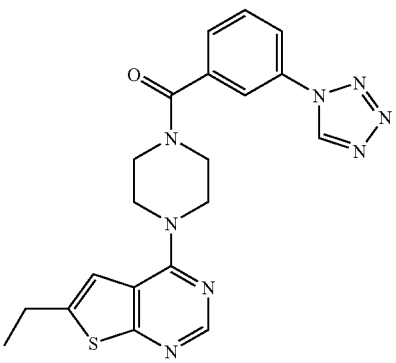

The title compound was obtained as a TFA salt by essentially following Example 5 except that 3-tetrazol-1-yl-benzoic acid was used in place of 3,3,3-trifluoropropionic acid and MeCN in place of DMF in Step 2. ES-MS: (M+H)$^+$ 420

Example 485

[4-(6-Ethyl-thieno[2,3-d]pyrimidin-4-yl)-piperazin-1-yl]-(4-tetrazol-1-yl-phenyl)-methanone

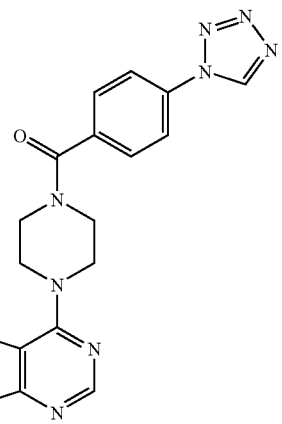

The title compound was obtained as a TFA salt by essentially following Example 5 except that 4-tetrazol-1-yl-benzoic acid was used in place of 3,3,3-trifluoropropionic acid and MeCN in place of DMF in Step 2. ES-MS: (M+H)$^+$ 420

Example 486

1-[4-(6-Ethyl-thieno[2,3-d]pyrimidin-4-yl)-piperazine-1-carbonyl]-cyclopropanecarboxylic Acid Amide

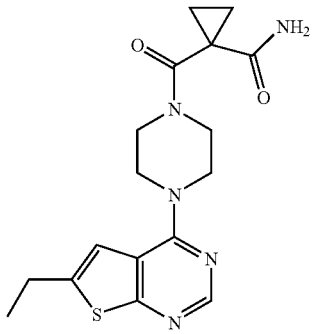

The title compound was obtained as a TFA salt by essentially following Example 5 except that 1-carbamoyl-cyclopropanecarboxylic acid was used in place of 3,3,3-trifluoropropionic acid and MeCN in place of DMF in Step 2. ES-MS: (M+H)$^+$ 360

Example 487

3-[4-(6-Ethyl-thieno[2,3-d]pyrimidin-4-yl)-piperazin-1-yl]-3-oxo-N-pyridin-4-ylmethyl-propionamide

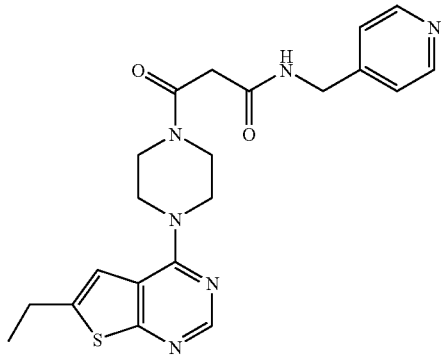

The title compound was obtained as a TFA salt by essentially following Example 5 except that acid 388 was used in place of 3,3,3-trifluoropropionic acid, C-pyridin-4-yl-methylamine was used in place of the material from Step 1 of Example 5, and MeCN in place of DMF in Step 2. ES-MS: (M+H)$^+$ 425

Example 488

3-[4-(6-Ethyl-thieno[2,3-d]pyrimidin-4-yl)-piperazin-1-yl]-3-oxo-N-pyridin-3-ylmethyl-propionamide

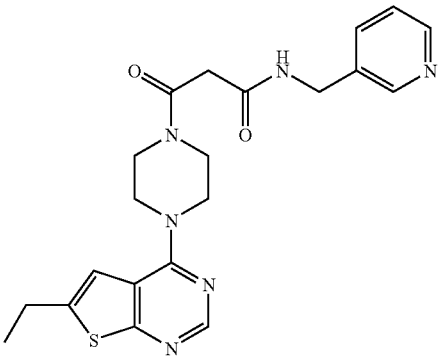

The title compound was obtained as a TFA salt by essentially following Example 5 except that acid 388 was used in place of 3,3,3-trifluoropropionic acid, C-pyridin-3-yl-methylamine was used in place of the material from Step 1 of Example 5, and MeCN in place of DMF in Step 2. ES-MS: (M+H)$^+$ 425

Example 489

3-[4-(6-Ethyl-thieno[2,3-c]pyrimidin-4-yl)-piperazin-1-yl]-3-oxo-N-pyridin-2-ylmethyl-propionamide

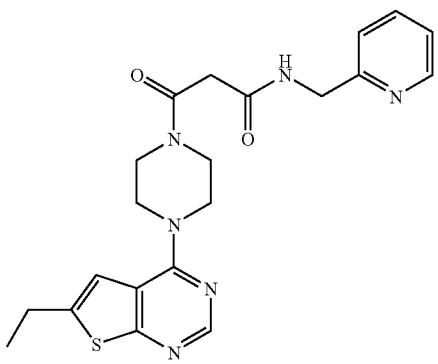

The title compound was obtained as a TFA salt by essentially following Example 5 except that acid 388 was used in place of 3,3,3-trifluoropropionic acid, C-pyridin-2-yl-methylamine was used in place of the material from Step 1 of Example 5, and MeCN in place of DMF in Step 2. ES-MS: (M+H)$^+$ 425.

It should be understood that the foregoing discussion, embodiments and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference.

What is claimed is:

1. A compound of formula II:

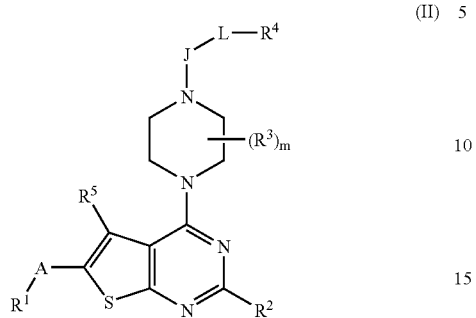

(II)

wherein
the subscript m is an integer of from 0 to 4;
$R^5$ is selected from the group consisting of H, $(C_1-C_6)$alkyl, $(C_3-C_7)$cycloalkyl and $-(CH_2)_{n1}-R^{11}$ wherein the subscript n1 is an integer of from 0 to 3 and $R^{11}$ is selected from the group consisting of $(C_1-C_6)$alkoxy, $(C_1-C_6)$alkylthio, mono- or di-$(C_1-C_6)$alkylamino, amino, phenyl, pyridyl, furanyl, pyrrolyl, imidazolyl, oxazolyl, isoxazolyl, triazolyl, tetrazolyl, thiazolyl, pyrazolyl, and thienyl, wherein each of the rings is optionally substituted with from 1 to 3 substituents selected from halogen, $N_3$, $NO_2$, CN, $(C_1-C_6)$alkyl, $OR^{12}$, $N(R^{12})_2$, $CO_2R^{12}$ and $CON(R^{12})_2$, wherein each $R^{12}$ is independently H or $(C_1-C_6)$alkyl;
J is selected from the group consisting of a direct link, C(O), C(S), C(NR9), S(O) and S(O)$_2$, wherein $R^9$ is selected from the group consisting of H, CN, $NO_2$ and $(C_1-C_6)$alkyl;
A is selected from the group consisting of a direct link, O, S, N—$R^{10}$, C(O) and CH(OH), wherein $R^{10}$ is selected from the group consisting of H, $(C_1-C_6)$alkyl and C(O)—$(C_1-C_6)$alkyl;
$R^1$ is selected from the group consisting of halo, CN, $NO_2$, $N_3$, $(C_1-C_6)$alkyl, $(C_3-C_7)$cycloalkyl, $-C(R^{13})=C(R^{13})_2$, $-C\equiv CR^{13}$ and $-(CH_2)_{n2}-R^{14}$; wherein each $R^{13}$ is independently selected from the group consisting of H, F, Cl, Br, CN, $(C_1-C_6)$alkyl, $(C_3-C_7)$cycloalkyl, $(CH_2)_{n2}-R^{14}$ and C(O)—$(CH_2)_2-R^{14}$; and wherein each subscript n2 is independently an integer of from 0 to 3 and each $R^{14}$ is independently selected from the group consisting of $(C_1-C_6)$alkoxy, $(C_1-C_6)$alkylthio, mono- or di-$(C_1-C_6)$alkylamino, amino, phenyl, pyridyl, furanyl, pyrrolyl, imidazolyl, oxazolyl, isoxazolyl, triazolyl, tetrazolyl, thiazolyl, pyrazolyl, and thienyl, wherein each of the rings is optionally substituted with from 1 to 3 substituents selected from halogen, $NO_2$, $N^3$, CN, $(C_1-C_6)$alkyl, $OR^{15}$, $N(R^{15})_2$, $CO_2R^{15}$ and $CON(R^{15})_2$, wherein each $R^{15}$ is independently H or $(C_1-C_6)$alkyl; and wherein any alkyl or cycloalkyl portions of $R^1$ are optionally substituted with from one to five F substituents;
$R^2$ is selected from the group consisting of H, CN, $NO_2$, $N_3$, $(C_1-C_6)$alkyl, $(C_3-C_7)$cycloalkyl, $-C(R^{16})=C(R^{16})_2$, $-C\equiv R^{16}$, $-C(O)-(CH_2)_{n3}-R^{17}$ and $-(CH_2)_{n3}-R^{17}$; wherein each $R^{16}$ is independently selected from the group consisting of H, F, Cl, Br, CN, $(C_1-C_6)$alkyl, $(CH_2)_{n3}-R^{17}$ and $-(CH_2)_{n3}-C(O)-R^{17}$; wherein the subscript n3 is an integer of from 0 to 3 and $R^{17}$ is selected from the group consisting of $(C_1-C_6)$alkoxy, $(C_1-C_6)$alkylthio, mono- or di-$(C_1-C_6)$alkylamino, amino, hydroxy, phenyl, pyridyl, furanyl, pyrrolyl, imidazolyl, oxazolyl, isoxazolyl, triazolyl, tetrazolyl, thiazolyl, pyrazolyl, and thienyl, wherein each of the rings is optionally substituted with from 1 to 3 substituents selected from halogen, $N_3$, $NO_2$, CN, $(C_1-C_6)$alkyl, $OR^{18}$, $N(R^{18})_2$, $CO_2R^{18}$ and $CON(R^{18})_2$, wherein each $R^{18}$ is independently H or $(C_1-C_6)$alkyl; and wherein any alkyl or cycloalkyl portions of $R^2$ are optionally substituted with from one to five F substituents;
each $R^3$ is independently selected from the group consisting of $(C_1-C_6)$alkyl, $(C_3-C_7)$cycloalkyl, $-(CH^2)_{n4}-R^{19}$ and $-C(O)-(CH_2)_{n4}-R^{19}$; wherein the subscript n4 is an integer of from 0 to 4 and $R^{19}$ is selected from the group consisting of $(C_1-C_6)$alkoxy, $(C_1-C_6)$alkylthio, mono- or di-$(C_1-C_6)$alkylamino, amino, phenyl, pyridyl, furanyl, pyrrolyl, imidazolyl, oxazolyl, isoxazolyl, triazolyl, tetrazolyl, thiazolyl, pyrazolyl, and thienyl, wherein each of the rings is optionally substituted with from 1 to 3 substituents selected from halogen, $N_3$, $NO_2$, CN, $(C_1-C_6)$alkyl, $OR^{20}$, $N(R^{20})_2$, $CO_2R^{20}$ and $CON(R^{20})_2$, wherein each $R^{20}$ is independently H or $(C_1-C_6)$alkyl; and wherein any alkyl or cycloalkyl portions of $R^3$ are optionally substituted with from one to five F substituents;
L is a direct link or a divalent linking group having a formula selected from the group consisting of

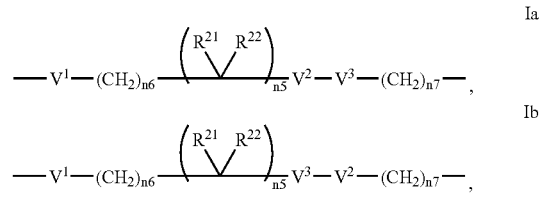

wherein
$V^1$ is selected from the group consisting of a direct link, O, S and $NR^{23}$,
$V^2$ is selected from the group consisting of a direct link, $-(CR^{24}=CR^{24})_{n8}-$, $-(C\equiv C)_{n8}-$, C(O), C(S), S(O), S(O)$_2$ and $C(NR^{23})$;
$V^3$ is selected from the group consisting of a direct link, O, S and $NR^{23}$;
the subscript n5 is an integer of from 0 to 2;
the subscripts n6 and n7 are each independently an integer of from 0 to 7;
the subscript n8 is an integer of from 1 to 2;
each $R^{23}$ is independently selected from the group consisting of H and $(C_1-C_6)$alkyl;
each $R^{24}$ independently selected from the group consisting of $(C_1-C_6)$alkyl, $(C_3-C_7)$ cycloalkyl, $(CH_2)_{n9}-R^{25}$ and $-(CO)-(CH_2)_{n9}-R^{25}$ wherein the subscript n9 is an integer of from 0 to 3 and $R^{25}$ is selected from the group consisting of $(C_1-C_6)$alkoxy, $(C_1-C_6)$alkylthio, mono- or di-$(C_1-C_6)$alkylamino, hydroxy, $NH_2$, phenyl, pyridyl, furanyl, pyrrolyl, imidazolyl, oxazolyl, isoxazolyl, triazolyl, tetrazolyl, thiazolyl, pyrazolyl, and thienyl, wherein each of the rings is optionally substituted with from 1 to 3 substituents selected from halogen, $N_3$, $NO_2$, CN, $(C_1-C_6)$alkyl, $OR^{26}$, $N(R^{26})_2$, $CO_2R^{26}$ and $CON(R^{26})_2$, wherein each $R^{26}$ is independently H or $(C_1-C_6)$alkyl;

each $R^{21}$ and $R^{22}$ is (i) independently selected from the group consisting of H, $(C_1-C_6)$alkyl, phenyl, pyridyl, furanyl, pyrrolyl, imidazolyl, oxazolyl, isoxazolyl, triazolyl, tetrazolyl, thiazolyl, pyrazolyl, and thienyl, wherein each of the rings is optionally substituted with from 1 to 3 substituents selected from halogen, $N_3$, $NO_2$, CN, $(C_1-C_6)$alkyl, $OR^{29}$, $N(R^{29})_2$, $CO_2R^{29}$ and $CON(R^{29})_2$, wherein each $R^{29}$ is independently H or $(C_1-C_6)$alkyl; or (ii) combined to form —$CH_2$—$(CH_2)_{n10}$—$CH_2$—; wherein the subscript n10 is an integer of from 0 to 4; and $R^4$ is a member selected from the group consisting of H, F, $CF_3$, CN, $N_3$, $NO_2$, $(C_1-C_6)$alkyl, amino, mono- or di-$(C_1-C_6)$alkylamino, $(C_3-C_7)$cycloalkyl, $(C_3-C_7)$heterocycloalkyl, heteroaryl, fused $(C_8-C_{10})$bicycloalkyl, fused $(C_8-C_{10})$bicycloalkaryl, aryl and fused bicycloaryl; wherein any alkyl group present in $R^4$ are unsubstituted, partially- or fully-substituted with F, and each of the rings is optionally substituted with from one to four substituents selected from halogen, $NO_2$, $N_3$, $SO_2NH2$, CN, $(C_1-C_6)$alkyl, $OR^{30}$, $N(R^{30})_2$, $CO_2R^{30}$ and $CON(R^{30})_2$, wherein each $R^{30}$ is independently H or $(C_1-C_6)$alkyl;

or a pharmaceutically acceptable salt or prodrug thereof.

2. A compound of claim 1, wherein A is a direct link and $R^1$ is selected from the group consisting of halo, CN, $NO_2$, $N_3$, $(C_1-C_6)$alkyl, $(C_3-C_7)$cycloalkyl, —$C(R^{13})$=$C(R^{13})_2$, —C≡$CR^{13}$ and —$(CH_2)_{n2}$—$R^{14}$; wherein each $R^{13}$ is independently selected from the group consisting of H, F, Cl, Br, CN, $(C_1-C_6)$alkyl, $(C_3-C_7)$cycloalkyl, $(CH_2)_2$—$R^{14}$ and C(O)—$(CH_2)_{n2}$—$R^{14}$; wherein each subscript n2 is independently an integer of from 0 to 3 and each $R^{14}$ is independently selected from the group consisting of $(C_1-C_6)$alkoxy, $(C_1-C_6)$alkylthio, mono- or di-$(C_1-C_6)$alkylamino, amino; and wherein any alkyl or cycloalkyl portions of $R^1$ are optionally substituted with from one to five F substituents.

3. A compound of claim 2, wherein $R^1$ is selected from the group consisting of $(C_1-C_6)$alkyl, $(C_3-C_7)$cycloalkyl, —$C(R^{13})$=$C(R^{13})_2$ and —C≡$CR^{13}$; wherein each $R^{13}$ is independently selected from the group consisting of H, $(C_1-C_6)$alkyl and $(C_3-C_7)$cycloalkyl; and wherein any alkyl or cycloalkyl portions of R are optionally substituted with from one to five F substituents.

4. A compound of claim 3, wherein $R^1$ is selected from the group consisting of ethyl, vinyl and acetylenyl.

5. A compound of claim 3, wherein m is an integer of from 0 to 2 and each $R^3$ is selected from the group consisting of $(C_1-C_6)$alkyl.

6. A compound of claim 5, wherein J is C(O).

7. A compound of claim 6, wherein L is a divalent linking group of formula Ia, wherein $V^1$ and $V^2$ are direct links, the subscripts n5 and n7 are 0, and the subscript n6 is an integer of from 1 to 6.

8. A compound of claim 7, wherein $V^3$ is O, S or $NR^{23}$.

9. A compound of claim 8, wherein $V^3$ is O and $R^4$ is selected from the group consisting of fused $(C_8-C_{10})$bicycloalkaryl, aryl and fused bicycloaryl.

10. A compound of claim 9, wherein $R^4$ is a fused bicycloaryl group selected from the group consisting of benzotriazolyl, benzimidazolyl, benzoxazolyl, benzisoxazolyl, benzothiazolyl and indazolyl.

11. A compound of claim 1, wherein J is C(O) or C(S), L is selected from formula Ia, and $R^4$ is a fused bicycloaryl group.

12. A compound of claim 1, wherein J is C(O), L is selected from formula Ia and Ib, and $R^4$ is a fused bicycloaryl group.

13. A compound of claim 1, wherein J is C(O), L is selected from formula Ia and Ib, and $R^4$ is a fused bicycloaryl group selected from the group consisting of benzotriazolyl, benzimidazolyl, benzoxazolyl, benzisoxazolyl, benzothiazolyl and indazolyl.

14. A composition for treating thrombosis in a mammal comprising a pharmaceutically acceptable excipient and a compound of claim 1.

15. A composition of claim 14, wherein said compound is present in an amount effective to inhibit platelet aggregation in a mammal.

16. A composition of claim 15, wherein said mammal is a human.

17. A composition of claim 16, wherein said platelet aggregation is platelet ADP-dependent aggregation.

18. A method of treating thrombosis or a thrombosis-related disorder, said method comprising administering to a mammalian subject in need thereof, an effective amount of a compound of claim 1.

19. A method in accordance with claim 18, wherein said subject is a human.

* * * * *